US009650656B2

(12) United States Patent
Li et al.

(10) Patent No.: US 9,650,656 B2
(45) Date of Patent: May 16, 2017

(54) BIOSYNTHETIC SYSTEMS PRODUCING FUNGAL INDOLE ALKALOIDS

(71) Applicants: THE REGENTS OF THE UNIVERSITY OF MICHIGAN, Ann Arbor, MI (US); COLORADO STATE UNIVERSITY RESEARCH FOUNDATION, Fort Collins, CO (US)

(72) Inventors: Shengying Li, Ann Arbor, MI (US); Krithika Anand Srinivasan, Ann Arbor, MI (US); Robert M. Williams, Fort Collins, CO (US); David H. Sherman, Ann Arbor, MI (US)

(73) Assignees: THE REGENTS OF THE UNIVERSITY OF MICHIGAN, Ann Arbor, MI (US); COLORADO STATE UNIVERSITY RESEARCH FOUNDATION, Fort Collins, CO (US)

( * ) Notice: Subject to any disclaimer, the term of this patent is extended or adjusted under 35 U.S.C. 154(b) by 44 days.

(21) Appl. No.: 14/390,360

(22) PCT Filed: Apr. 3, 2013

(86) PCT No.: PCT/US2013/035131
§ 371 (c)(1),
(2) Date: Oct. 2, 2014

(87) PCT Pub. No.: WO2013/152110
PCT Pub. Date: Oct. 10, 2013

(65) Prior Publication Data

US 2015/0044735 A1 Feb. 12, 2015

Related U.S. Application Data

(60) Provisional application No. 61/622,265, filed on Apr. 10, 2012, provisional application No. 61/620,176, filed on Apr. 4, 2012.

(51) Int. Cl.

| | |
|---|---|
| ***C12P 5/00*** | (2006.01) |
| ***C12P 17/18*** | (2006.01) |
| ***C07G 5/00*** | (2006.01) |
| ***C12N 15/52*** | (2006.01) |
| ***C12N 9/04*** | (2006.01) |
| ***C12N 9/02*** | (2006.01) |
| ***C12N 9/10*** | (2006.01) |
| ***C12N 9/00*** | (2006.01) |

(52) U.S. Cl.
CPC ................ *C12P 17/18* (2013.01); *C07G 5/00* (2013.01); *C12N 9/0006* (2013.01); *C12N 9/0071* (2013.01); *C12N 9/1085* (2013.01); *C12N 9/93* (2013.01); *C12N 15/52* (2013.01); *C12P 5/007* (2013.01); *C12Y 114/14001* (2013.01); *C12Y 205/01* (2013.01); *C12Y 603/02* (2013.01)

(58) Field of Classification Search
None
See application file for complete search history.

(56) References Cited

U.S. PATENT DOCUMENTS

2007/0218461 A1 9/2007 Bryan et al.

OTHER PUBLICATIONS

Ngo et al. In the Protein Folding Problem and Tertiary Structure Prediction, 1994, Merz et al. (ed.), Birkhauser, Boston, MA, pp. 433 and 492-495.*
Li et al. (Genbank Accession AGA37267.1 Dec. 22, 2012).*
Anzai et al., Functional analysis of MycCl and MycG, cytochrome P450 enzymes involved in biosynthesis of mycinamicin macrolide antibiotics, Chem. Biol., 15(9):950-9 (2008).
Baba et al., Improvement of compactin (ML-236B) production by genetic engineering in compactin high-producing Penicillium citrinum, Appl. Microbiol. Biotechnol., 83(4):697-704 (2009).
Balibar et al., Terrequinone A biosynthesis through L-tryptophan oxidation, dimerization and bisprenylation, Nat. Chem. Biol., 3(9):584-92 (2007).
Baltz, New genetic methods to improve secondary metabolite production in Streptomyces, J. Ind. Microbiol. Biotechnol. 20, 360-363 (1998).
Birch et al., The brevianamides: a new class of fungal alkaloid, J. Chem. Soc. Chem. Commun., 644-5 (1969).
Buntin et al., Biosynthesis of thuggacins in myxobacteria: comparative cluster analysis reveals basis for natural product structural diversity, Chem. Biol., 17(4):342-56 (2010).
Cane et al., Harnessing the biosynthetic code: combinations, permutations, and mutations, Science, 282(5386):63-8 (1998).
Carlson et al., Identification of the tirandamycin biosynthetic gene cluster from *Streptomyces* sp. 307-9, Chembiochem., 11(4):564-72 (2010).

(Continued)

*Primary Examiner* — Richard Hutson
(74) *Attorney, Agent, or Firm* — Marshall, Gerstein & Borun LLP

(57) ABSTRACT

The biosynthesis of fungal bicyclo[2.2.2]diazaoctane indole alkaloids with a wide spectrum of biological activities have attracted increasing interest. Their intriguing mode of assembly has long been proposed to feature a non-ribosomal peptide synthetase, a presumed intramolecular Diels-Alderase, a variant number of prenyltransferases, and a series of oxidases responsible for the diverse tailoring modifications of their cyclodipeptide-based structural core. Until recently, the details of these biosynthetic pathways have remained largely unknown due to lack of information on the fungal derived biosynthetic gene clusters. Herein, we report a comparative analysis of four natural product metabolic systems of a select group of bicyclo[2.2.2]diazaoctane indole alkaloids including (+)/(−)-notoamide, paraherquamide and malbrancheamide, in which we propose an enzyme for each step in the biosynthetic pathway based on deep annotation and on-going biochemical studies.

10 Claims, 13 Drawing Sheets

(56) References Cited

OTHER PUBLICATIONS

Carlson et al., Tirandamycin biosynthesis is mediated by co-dependent oxidative enzymes, Nat. Chem., 3(8):628-33 (2011).
Cheng et al., Enzymatic total synthesis of enterocin polyketides, Nat. Chem. Biol., 3(9):557-8 (2007).
Database GenBank JQ708193.1, Malbranchea aurantiaca strain RRC1813 malbrancheamide biosynthetic gene cluster, partial sequence, Dec. 22, 2012.
Database GenBank JQ708195.1, Penicillium fellutanum strain ATCC 20841 paraherquamide biosynthetic gene cluster, partial sequence, Dec. 22, 2012.
Ding et al., Detection of VM55599 and preparaherquamide from Aspergillus japonicus and Penicillium fellutanum: biosynthetic implications, J. Nat. Prod., 71(9):1574-8 (2008).
Ding et al., Premalbrancheamide: synthesis, isotopic labeling, biosynthetic incorporation, and detection in cultures of Malbranchea aurantiaca, Org. Lett., 10(21):4863-6 (2008).
Ding et al.,Genome-based characterization of two prenylation steps in the assembly of the stephacidin and notoamide anticancer agents in a marine-derived *Aspergillus* sp, J. Am. Chem. Soc., 132(36):12733-40 (2010).
Dong et al., Tryptophan 7-halogenase (PrnA) structure suggests a mechanism for regioselective chlorination, Science, 309(5744):2216-9 (2005).
Figueroa et al., Malbrancheamide B, a novel compound from the fungus Malbranchea aurantiaca, Nat. Prod. Res., 22(8):709-14 (2008).
Finefield et al., Biosynthetic studies of the notoamides: isotopic synthesis of stephacidin A and incorporation into notoamide B and sclerotiamide, Org. Lett., 13915):3802-5 (2011).
Galm et al., Comparative analysis of the biosynthetic gene clusters and pathways for three structurally related antitumor antibiotics: bleomycin, tallysomycin, and zorbamycin, J. Nat. Prod., 74(3):526-36 (2011).
Galm et al., Expression of biosynthetic gene clusters in heterologous hosts for natural product production and combinatorial biosynthesis, Expert. Opin. Drug Discov., 1 5):409-37 (2006).
Greshock et al., A concise, biomimetic total synthesis of stephacidin A and notoamide B, Angew. Chem. Int. Ed. Engl., 46(13):2262-5 (2007).
Greshock et al., Isolation, structure elucidation, and biomimetic total synthesis of versicolamide B, and the isolation of antipodal (−)-stephacidin A and (+)-notoamide B from Aspergillus versicolor NRRL 35600, Angew. Chem. Int. Ed. Engl., 47(19):3573-7 (2008).
Grubbs et al., A concise total synthesis of the notoamides C and D, Angew. Chem. Int. Ed. Engl., 46(13):2257-61 (2007).
Gu et al., Metamorphic enzyme assembly in polyketide diversification, Nature, 459(7247):731-5 (2009).
Hausinger, FeII/alpha-ketoglutarate-dependent hydroxylases and related enzymes, Crit. Rev. Biochem. Mol. Biol., 39(1):21-68 (2004).
Hawkins et al., Next-generation genomics: an integrative approach, Nat. Rev. Genet., 11(7):476-86 (2010).
Hewitson et al., Oxidation by 2-oxoglutarate oxygenases: non-haem iron systems in catalysis and signalling, Philos. Trans A Math Phys. Eng. Sci., 363(1829):807-28 (2005).
International Preliminary Report on Patentability, International Application No. PCT/US2013/035131, Oct. 7, 2014.
International Search Report and Written Opinion, International Application No. PCT/US2013/035131, mailed Jul. 18, 2013.
Kato et al., Identification of cytochrome P450s required for fumitremorgin biosynthesis in Aspergillus fumigatus, Chembiochem., 10(5):920-8 (2009).
Kato et al., Notoamides A-D: prenylated indole alkaloids isolated from a marine-derived fungus, *Aspergillus* sp, Angew. Chem. Int. Ed. Engl., 46(13):2254-6 (2007).
Keating et al., Chain termination steps in nonribosomal peptide synthetase assembly lines: directed acyl-S-enzyme breakdown in antibiotic and siderophore biosynthesis, Chembiochem., 2(2):99-107 (2001).
Kittendorf et al., The methymycin/pikromycin pathway: a model for metabolic diversity in natural product biosynthesis, Bioorg. Med. Chem., 17(6):2137-46 (2009).
LeGoff et al., From hydrogenases to noble metal-free catalytic nanomaterials for H2 production and uptake, Science, 326(5958):1384-7 (2009).
Li et al., Biochemical characterization of NotB as an FAD-dependent oxidase in the biosynthesis of notoamide indole alkaloids, J. Am. Chem. Soc., 134(2):788-91 (2012).
Li et al., Drug discovery and natural products: end of an era or an endless frontier?, Science, 325(5937):161-5 (2009).
Li et al., Genome mining and biosynthesis of fumitremorgin-type alkaloids in ascomycetes, J. Antibiot. (Tokyo), 64(1):45-9 (2011).
Li et al., Rational strain improvement for enhanced clavulanic acid production by genetic engineering of the glycolytic pathway in Streptomyces clavuligerus, Metab. Eng., 8(3):240-52 (2006).
Liesch et al., Novel antinematodal and antiparasitic agents from Penicillium charlesii. II. Structure determination of paraherquamides B, C, D, E, F, and G, J. Antibiot. (Tokyo), 43(11):1380-6 (1990).
Luesch et al., Biosynthesis of 4-methylproline in cyanobacteria: cloning of nosE and nosF genes and biochemical characterization of the encoded dehydrogenase and reductase activities, J. Org. Chem., 68(1):83-91 (2003).
Martinez-Luis et al., Malbrancheamide, a new calmodulin inhibitor from the fungus Malbranchea aurantiaca, Tetrahedron, 62(8): 1817-22 (2006).
Metzker, Sequencing technologies—the next generation, Nat. Rev. Genet., 11(1):31-46 (2010).
Miller et al., Biomimetic total synthesis of malbrancheamide and malbrancheamide B, J. Org. Chem., 73(8):3116-9 (2008).
Neumann et al., A flavin-dependent halogenase catalyzes the chlorination step in the biosynthesis of Dictyostelium differentiation-inducing factor 1, Proc. Natl. Acad. Sci. USA, 107(13):5798-803 (2010).
Newman et al., Natural products as sources of new drugs over the last 25 years, J. Nat. Prod., 70(3):461-77 (2007).
Noh et al., Isolation and genetic manipulation of the antibiotic down-regulatory gene, wblA ortholog for doxorubicin-producing Streptomyces strain improvement, Appl. Microbiol. Biotechnol., 86(4):1145-53 (2010).
Oliynyk et al., Analysis of the biosynthetic gene cluster for the polyether antibiotic monensin in Streptomyces cinnamonensis and evidence for the role of monB and monC genes in oxidative cyclization, Mol. Microbiol., 49(5):1179-90 (2003).
Ondeyka et al., Novel antinematodal and antiparasitic agents from Penicillium charlesii. I. Fermentation, isolation and biological activity, J. Antibiot., 43(11):1375-9 (1990).
Peant et al., Comparative analysis of the exopolysaccharide biosynthesis gene clusters from four strains of Lactobacillus rhamnosus, Microbiology, 151 (Pt. 6):1839-51 (2005).
Pollier et al., Combinatorial biosynthesis in plants: a (p)review on its potential and future exploitation, Nat. Prod. Rep., 28(12):1897-916 (2011).
Qian-Cutrone et al., Stephacidin A and B: two structurally novel, selective inhibitors of the testosterone-dependent prostate LNCaP cells, J. Am. Chem. Soc., 124(49):14556-7 (2002).
Que et al., Biologically inspired oxidation catalysis, Nature, 455(7211):333-40 (2008).
Ryan et al., Biosynthetic gene cluster for the cladoniamides, bis-indoles with a rearranged scaffold, PLoS One, 6(8):e23694 (2011).
Sanchez et al., Combinatorial biosynthesis of antitumor indolocarbazole compounds, Proc. Natl. Acad. Sci. USA, 102(2):461-6 (2005).
Schuster, Next-generation sequencing transforms today's biology, Nat. Methods, 5(1):16-8 (2008).
Shaffer, Next-generation sequencing outpaces expectations, Nat. Biotechnol., 25(2):149 (2007).

(56) References Cited

OTHER PUBLICATIONS

Steffan et al., FtmOx1, a non-heme Fe(II) and alpha-ketoglutarate-dependent dioxygenase, catalyses the endoperoxide formation of verruculogen in Aspergillus fumigatus, Org. Biomol. Chem., 7(19):4082-7 (2009).
Steyn, Austamide, a new toxic metabolite from aspergillus ustus, Tetrahedron Lett., 12(36):3331-4 (1971).
Stocking et al., Chemistry and biology of biosynthetic Diels-Alder reactions, Angew. Chem. Int. Ed. Engl., 42(27):3078-115 (2003).
Stocking et al., Studies on the biosynthesis of paraherquamide. Construction of the amino acid framework, Tetrahedron, 57(25):5303-20 (2001).
Stocking et al., Studies on the Biosynthesis of Paraherquamide: Synthesis and Incorporation of a Hexacyclic Indole Derivative as an Advanced Metabolite This work was supported by the National Institutes of Health (Grant No. CA70375 to R.M.W.). We wish to acknowledge the American Chemical Society Division of Organic Chemistry Fellowship (sponsored by SmithKline Beecham) and the Pharmacia-Upjohn Company for financial support (to E.M.S.). Mass spectra were obtained on instruments supported by the National Institutes of Health Shared Instrumentation Grant (No. GM49631). We also wish to thank Professor Dean Crick of the Department of Microbiology at Colorado State University for helpful discussions. J.F.S.-C. thanks the DGICYT of Spain for a research grant (project No. PB98-1438), Angew. Chem. Int. Ed. Engl., 40(7):1296-8 (2001).
Stocking et al., Total Synthesis of VM55599. Utilization of an Intramolecular Diels-Alder Cycloaddition of Potential Biogenetic Relevance, J. Am. Chem. Soc., 122(8):1675-83 (2000).
Strohl, Biochemical engineering of natural product biosynthesis pathways, Metab. Eng., 3(1):4-14 (2001).
Sunderhaus et al., Studies on the Biosynthesis of the Stephacidin and Notoamide Natural Products: A Stereochemical and Genetic Conundrum, Isr. J. Chem., 51(3):442-52 (2011).
Tang et al., Cloning and heterologous expression of the epothilone gene cluster, Science, 287(5453):640-2 (2000).
Treangen et al., Repetitive DNA and next-generation sequencing: computational challenges and solutions, Nat. Rev. Genet., 13(1):36-46 (2011).
Tsukamoto et al., Isolation of notoamide E, a key precursor in the biosynthesis of prenylated indole alkaloids in a marine-derived fungus, *Aspergillus* sp, J. Am. Chem. Soc., 131(11):3834-5 (2009).
van Pee et al., Flavin-dependent halogenases involved in secondary metabolism in bacteria, Appl. Mlcrobiol. Biotechnol., 70(6):631-41 (2006).
Walsh, Combinatorial biosynthesis of antibiotics: challenges and opportunities, Chembiochem., 3(2-3):125-34 (2002).
Watts et al., Current and emerging approaches for natural product biosynthesis in microbial cells, Adv. Synth. Catalysis, 347(7-8):927-40 (2005).
Watts et al., Utilizing DART mass spectrometry to pinpoint halogenated metabolites from a marine invertebrate-derived fungus, J. Org. Chem., 76(15):6201-8 (2011).
Whyte et al., Sclerotiamide: a new member of the paraherquamide class with potent antiinsectan activity from the sclerotia of Aspergillus sclerotiorum, J. Nat. Prod., 59(11):1093-5 (1996).
Williams et al., Asymmetric, stereocontrolled total synthesis of paraherquamide A, J. Am. Chem. Soc., 125(40):12172-8 (2003).
Williams et al., Paraherquamides, brevianamides, and asperparalines: laboratory synthesis and biosynthesis. An interim report, Acc. Chem. Res., 36(2):127-39 (2003).
Xue et al., A gene cluster for macrolide antibiotic biosynthesis in Streptomyces venezuelae: architecture of metabolic diversity, Proc. Natl. Acad. Sci. USA, 95(21):12111-6 (1998).
Yamazaki et al., the structure of paraherquamide, a toxic metabolite from penicillium paraherquei, Tetrahedron Lett., 22(2):135-6 (1981).
Zeng et al., A novel fungal flavin-dependent halogenase for natural product biosynthesis, Chembiochem., 11(15):2119-23 (2010).
Zhang et al., Methods and options for the heterologous production of complex natural products, Nat. Prod. Rep., 28(1):125-51 (2011).

* cited by examiner

| SEQ ID NO: | PN = polynucleotide | SEQ ID NO: | PP = polypeptide |
|---|---|---|---|
| 1 | Malbrancheamide biosynthetic gene cluster. | | |
| 2 | MalA PN<br>Falvin-dependent halogenase | 3 | MalA PP |
| 4 | MalB PN<br>Prenyltransferase | 5 | MalB PP |
| 6 | MalC PN<br>Short chain dehydrogenase | 7 | MalC PP |
| 8 | MalD PN<br>Negative regulator | 9 | MalD PP |
| 10 | MalE PN<br>Prenyltransferase | 11 | MalE PP |
| 12 | MalF PN<br>Oxidoreductase | 13 | MalF PP |
| 14 | MalG PN<br>NRPS | 15 | MalG PP |
| | | | |
| 16 | notoamide biosynthetic gene cluster PN | | |
| 17 | NotA PN<br>Negative regulator | 18 | NotA PP |
| 19 | NotB PN<br>FAD monooxygenase | 20 | NotB PP |
| 21 | NotC PN<br>Prenyltransferase | 22 | NotC PP |
| 23 | NotD PN<br>Oxidoreductase | 24 | NotD PP |
| 25 | NotE PN<br>NRPS | 26 | NotE PP |

FIGURE 7A

| SEQ ID NO: | PN = polynucleotide | SEQ ID NO: | PP = polypeptide |
|---|---|---|---|
| 27 | NotF PN<br>Prenyltransferase | 28 | NotF PP |
| 29 | NotG PN<br>P450 monooxygenase | 30 | NotG PP |
| 31 | NotH PN<br>P450 monooxygenase | 32 | NotH PP |
| 33 | NotI PN<br>FAD monooxygenase | 34 | NotI PP |
| 35 | NotJ PN<br>Unknown | 36 | NotJ PP |
| 37 | NotK PN<br>Nucleoside transport | 38 | NotK PP |
| 39 | NotL PN<br>Transcription factor | 40 | NotL PP |
| 41 | NotM PN<br>Unknown | 42 | NotM PP |
| 43 | NotN PN<br>Unknown | 44 | NotN PP |
| 45 | NotO PN<br>Unknown | 46 | NotO PP |
| 47 | NotP PN<br>Short chain dehydrogenase | 48 | NotP PP |
| 49 | NotQ PN<br>Transcription factor | 50 | NotQ PP |
| 51 | NotR PN<br>Unknown | 52 | NotR PP |

FIGURE 7B

| SEQ ID NO: | PN = polynucleotide | SEQ ID NO: | PP = polypeptide |
|---|---|---|---|
| 53 | Paraherquamide biosynthetic gene cluster. PN | | |
| 54 | phqA PN Prenyltransferase | 55 | phqA PP |
| 56 | phqB PN NRPS | 57 | phqB PP |
| 58 | phqC PN 2OG-Fe(II)-oxygenase | 59 | phqC PP |
| 60 | phqD PN Pyrroline-5-carboxylate reductase | 61 | phqD PP |
| 62 | PhqE PN Short chain dehydrogenase | 63 | phqE PP |
| 64 | phqF PN Efflux pump | 65 | phqF PP |
| 66 | phqG PN Negative regulator | 67 | phqG pp |
| 68 | phqD2 PN Oxidoreductase | 69 | phqD2 PP |
| 70 | phqI PN Prenyltransferase | 71 | phqI PP |
| 72 | phqJ PN Prenyltransferase | 73 | phqJ PP |
| 74 | PhqK PN FAD monooxygenase | 75 | PhqK PP |
| 76 | phqL PN P450 monooxygenase | 77 | phqL PP |
| 78 | phqM PN P450 monooxygenase | 79 | phqM PP |

FIGURE 7C

| SEQ ID NO: | PN = polynucleotide | SEQ ID NO: | PP = polypeptide |
|---|---|---|---|
| 80 | phqN PN<br>Methyltransferase | 81 | phqN PP |
| 82 | phqO PN<br>P450 monooxygenase | 83 | phqO PP |

FIGURE 7D

BIOSYNTHETIC SYSTEMS PRODUCING FUNGAL INDOLE ALKALOIDS

PRIORITY CLAIM

This application claims priority benefit of U.S. Provisional Patent Application No. 61/620,176, filed Apr. 4, 2012, and U.S. Provisional Application No. 61/622,265, filed Apr. 10, 2012, the disclosures of which are incorporated in their entireties herein.

STATEMENT OF GOVERNMENT INTEREST

This invention was made with government support under Grant Number R01 CA070375. Awarded by the National Institutes of Health (NIH). The government has certain rights in the invention.

INCORPORATION BY REFERENCE

This application contains, as a separate part of disclosure, a Sequence Listing in computer-readable form (filename: 46904PCT_SeqListing.txt; created Mar. 27, 2013; 446,686 bytes—ASCII text file) which is incorporated herein by reference in its entirety.

BACKGROUND

Natural products continue to be a rich source of clinical drugs for treatment of human and animal diseases.[1,2] With respect to drug development, advanced understanding of their biosynthesis is significant for rational strain improvement efforts. This includes genetic manipulation (e.g. gene knock-out, knock-in, and whole gene cluster amplification) of the key biosynthetic and regulatory genes in order to increase the yield of pharmaceuticals to a desired level.[3-6] Knowledge on biosynthesis is also valuable for guiding generation of novel natural product analogs as new drug candidates by metabolic engineering, mutasynthesis and allied approaches.[7-11] In addition, biochemical characterization of diverse biosynthetic enzymes continues to reveal new catalytic mechanisms that inspire inventions of novel chemical and biological catalysts in organic chemistry for production of fine-chemical and medicinal agents.[12,13]

Elucidation of the biosynthetic pathway of a particular natural product or a family of natural products first requires identification of the gene cluster encoding its production.[14-16] Next, the combined genetic (in vivo) and biochemical characterization (in vitro) of each individual biosynthetic enzyme provides important information, including enzyme substrate specificity, co-factor requirements, and the precise order of multiple biosynthetic steps.[17,18] With this information available, it becomes possible to reconstitute the entire biosynthetic pathway in a heterologous host[19-21] or in a multi-component in vitro reaction.[22,23]

Across all microbes, plants and animals that generate natural products, it is particularly challenging to elucidate a biosynthetic pathway completely when unprecedented steps are involved, or precedent knowledge of biosynthetic origin is limited or non-existent. Conventionally, the hunting for such enzymes catalyzing these unusual biotransformations via unexplored mechanisms depends on implementing reasonable biosynthetic principles, and the scanning of the activity of all possible candidate enzymes against all hypothetical substrates.[18,24,25] Thus, the entire process can require prolonged and intensive efforts, especially for those complex natural products assembled by a large number of biosynthetic enzymes.

Due to the discovery of natural products from different microorganisms bearing the same unique structural core, but varying from one another in their tailoring groups, opportunities for facile identification of unique enzymes arise. In this scenario comparative bioinformatic analysis suggests that homologous genes can be linked to formation of a common structural core, whereas cluster-specific genes provide the basis for structural differences.[26-29] Recent advances in whole genome sequencing technology have made this approach rapid and cost-effective.[30-34] Thus, identification of biosynthetic gene clusters for structurally related natural products from different microorganisms has become practical for comparative analysis of these systems. Deep annotation provides adequate information to develop hypotheses regarding key gene(s) and their protein products. This in turn guides experimental strategies to explore unusual biotransformation(s) of interest using genetic and/or biochemical approaches. Although considerable information can be gleaned from biosynthetic pathway mining and annotation, putative biochemical function can only be verified by analysis of the gene product in vitro using natural or suitable model substrates.

DESCRIPTION OF THE DRAWINGS

FIGS. 7A-7C—Sequence Table showing correlation between sequence identification numbers and specific open reading frames.

SUMMARY OF THE INVENTION

Figure 1A:
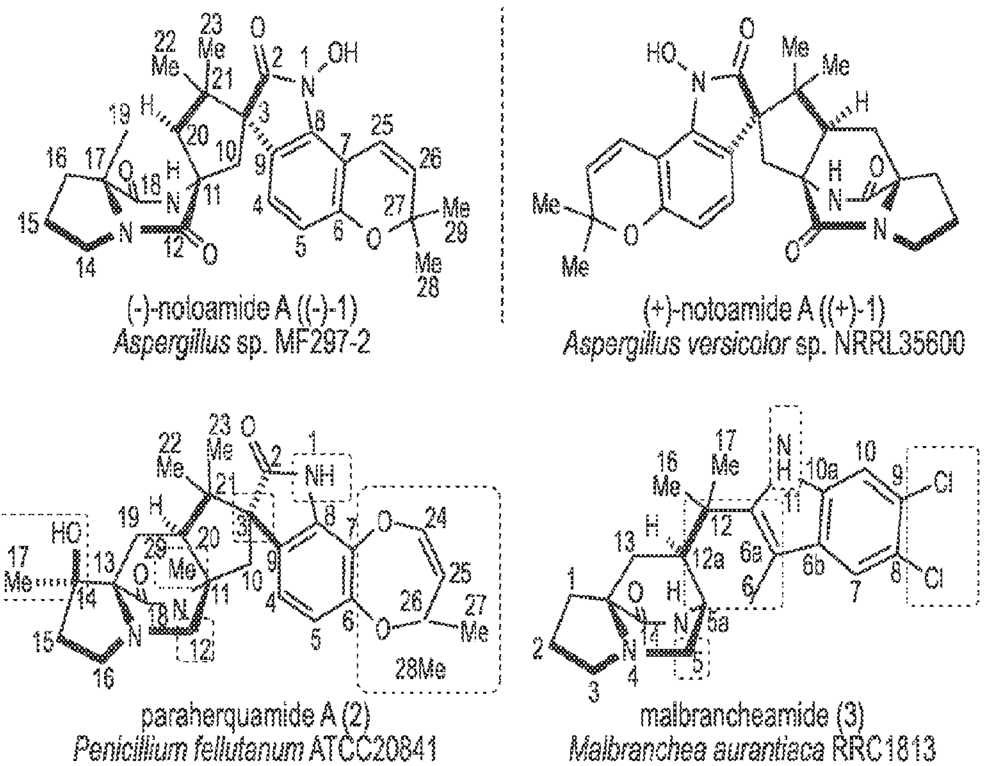
FIG. 1 (A) Structures of (±)-notoamide A ((±)-1), paraherquamide A (2), and malbrancheamide (3). The unique structural features in 2 and 3 compared to 1 are highlighted in dashed boxes; (B) Proposed formation of the antipodal bicyclo[2.2.2]diazaoctane ring systems.

The disclosure provides a host cell that produces a prenylated indole alkaloid.

The disclosure provides a host cell transformed with one or more polynucleotides selected from the group consisting of: a polynucleotide encoding SEQ ID NO: 3 or a protein 98% or more, 97% or more, 96% or more, 95% or more, 90% or more, 85% or more, 80% or more, or 75% or more identical to SEQ ID NO: 3 having MalA activity; a polynucleotide encoding SEQ ID NO: 5 or a protein 98% or more, 97% or more, 96% or more, 95% or more, 90% or more, 85% or more, 80% or more, or 75% or more identical to SEQ ID NO: 5 having MalB activity; a polynucleotide encoding SEQ ID NO: 7 or a protein 98% or more, 97% or more, 96% or more, 95% or more, 90% or more, 85% or more, 80% or more, or 75% or more identical to SEQ ID NO: 7 having MalC activity; a polynucleotide encoding SEQ ID NO: 9 or a protein 98% or more, 97% or more, 96% or more, 95% or more, 90% or more, 85% or more, 80% or more, or 75% or more identical to SEQ ID NO: 9 having MalD activity; a polynucleotide encoding SEQ ID NO: 11 or a protein 98% or more, 97% or more, 96% or more, 95% or more, 90% or more, 85% or more, 80% or more, or 75% or more identical to SEQ ID NO: 11 having MalE activity; a polynucleotide encoding SEQ ID NO: 13 or a protein 98% or more, 97% or more, 96% or more, 95% or more, 90% or more, 85% or more, 80% or more, or 75% or more identical to SEQ ID NO: 13 having MalF activity, and a polynucleotide encoding SEQ ID NO: 15 or a protein 98% or more, 97% or more, 96% or more, 95% or more, 90% or more, 85% or more, 80% or more, or 75% or more identical to SEQ ID NO: 15 having MalG activity.

The disclosure further provides a host cell transformed with one or more polynucleotides selected from the group consisting of: a polynucleotide encoding SEQ ID NO: 18 or a protein 98% or more, 97% or more, 96% or more, 95% or more, 90% or more, 85% or more, 80% or more, or 75% or more identical to SEQ ID NO: 18 having NotA activity; a polynucleotide encoding SEQ ID NO: 20 or a protein 98% or more, 97% or more, 96% or more, 95% or more, 90% or more, 85% or more, 80% or more, or 75% or more identical to SEQ ID NO: 20 having NotB activity; a polynucleotide encoding SEQ ID NO: 22 or a protein 98% or more, 97% or more, 96% or more, 95% or more, 90% or more, 85% or more, 80% or more, or 75% or more identical to SEQ ID NO: 22 having NotC activity; a polynucleotide encoding SEQ ID NO: 24 or a protein 98% or more, 97% or more, 96% or more, 95% or more, 90% or more, 85% or more, 80% or more, or 75% or more identical to SEQ ID NO: 24 having NotD activity; a polynucleotide encoding SEQ ID NO: 26 or a protein 98% or more, 97% or more, 96% or more, 95% or more, 90% or more, 85% or more, 80% or more, or 75% or more identical to SEQ ID NO: 26 having NotE activity; a polynucleotide encoding SEQ ID NO: 28 or a protein 98% or more, 97% or more, 96% or more, 95% or more, 90% or more, 85% or more, 80% or more, or 75% or more identical to SEQ ID NO: 28 having NotF activity; a polynucleotide encoding SEQ ID NO: 30 or a protein 98% or more, 97% or more, 96% or more, 95% or more, 90% or more, 85% or more, 80% or more, or 75% or more identical to SEQ ID NO: 30 having NotG activity; a polynucleotide encoding SEQ ID NO: 32 or a protein 98% or more, 97% or more, 96% or more, 95% or more, 90% or more, 85% or more, 80% or more, or 75% or more identical to SEQ ID NO: 32 having NotH activity; a polynucleotide encoding SEQ ID NO: 34 or a protein 98% or more, 97% or more, 96% or more, 95% or more, 90% or more, 85% or more, 80% or more, or 75% or more identical to SEQ ID NO: 34 having NotI activity; a polynucleotide encoding SEQ ID NO: 36 or a protein 98% or more, 97% or more, 96% or more, 95% or more, 90% or more, 85% or more, 80% or more, or 75% or more identical to SEQ ID NO: 36 having NotJ activity; a polynucleotide encoding SEQ ID NO: 38 or a protein 98% or more, 97% or more, 96% or more, 95% or more, 90% or more, 85% or more, 80% or more, or 75% or more identical to SEQ ID NO: 38 having NotK activity; a polynucleotide encoding SEQ ID NO: 40 or a protein 98% or more, 97% or more, 96% or more, 95% or more, 90% or more, 85% or more, 80% or more, or 75% or more identical to SEQ ID NO: 40 having NotL activity; a polynucleotide encoding SEQ ID NO: 42 or a protein 98% or more, 97% or more, 96% or more, 95% or more, 90% or more, 85% or more, 80% or more, or 75% or more identical to SEQ ID NO: 42 having NotM activity; a polynucleotide encoding SEQ ID NO: 44 or a protein 98% or more, 97% or more, 96% or more, 95% or more, 90% or more, 85% or more, 80% or more, or 75% or more identical to SEQ ID NO: 44 having NotN activity; a polynucleotide encoding SEQ ID NO: 46 or a protein 98% or more, 97% or more, 96% or more, 95% or more, 90% or more, 85% or more, 80% or more, or 75% or more identical to SEQ ID NO: 46 having NotO activity; a polynucleotide encoding SEQ ID NO: 48 or a protein 98% or more, 97% or more, 96% or more, 95% or more, 90% or more, 85% or more, 80% or more, or 75% or more identical to SEQ ID NO: 48 having NotP activity; a polynucleotide encoding SEQ ID NO: 50 or a protein 98% or more, 97% or more, 96% or more, 95% or more, 90% or more, 85% or more, 80% or more, or 75% or more identical to SEQ ID NO: 50 having NotQ activity, and a polynucleotide encoding SEQ ID NO: 52 or a protein 98% or more, 97% or more, 96% or more, 95% or more, 90% or more, 85% or more, 80% or more, or 75% or more identical to SEQ ID NO: 52 having NotR activity.

The disclosure further provides a host cell transformed with one or more polynucleotides selected from the group consisting of: a polynucleotide encoding SEQ ID NO: 55 or a protein 98% or more, 97% or more, 96% or more, 95% or more, 90% or more, 85% or more, 80% or more, or 75% or more identical to SEQ ID NO: 55 having phqA activity; a polynucleotide encoding SEQ ID NO: 57 or a protein 98% or more, 97% or more, 96% or more, 95% or more, 90% or more, 85% or more, 80% or more, or 75% or more identical to SEQ ID NO: 57 having phqB activity; a polynucleotide encoding SEQ ID NO: 59 or a protein 98% or more, 97% or more, 96% or more, 95% or more, 90% or more, 85% or more, 80% or more, or 75% or more identical to SEQ ID NO: 59 having phqC activity; a polynucleotide encoding SEQ ID NO: 61 or a protein 98% or more, 97% or more, 96% or more, 95% or more, 90% or more, 85% or more, 80% or more, or 75% or more identical to SEQ ID NO: 61 having phqD activity; a polynucleotide encoding SEQ ID NO: 63 or a protein 98% or more, 97% or more, 96% or more, 95% or more, 90% or more, 85% or more, 80% or more, or 75% or more identical to SEQ ID NO: 63 having phqE activity; a polynucleotide encoding SEQ ID NO: 65 or a protein 98% or more, 97% or more, 96% or more, 95% or more, 90% or more, 85% or more, 80% or more, or 75% or more identical to SEQ ID NO: 65 having phqF activity; a polynucleotide encoding SEQ ID NO: 67 or a protein 98% or more, 97% or more, 96% or more, 95% or more, 90% or more, 85% or more, 80% or more, or 75% or more identical to SEQ ID NO: 67 having phqG activity; a polynucleotide encoding SEQ ID NO: 69 or a protein 98% or more, 97% or more, 96% or more, 95% or more, 90% or more, 85% or more, 80% or more, or 75% or more identical to SEQ ID NO: 69 having phD2 activity; a polynucleotide encoding SEQ ID NO: 71 or a protein 98% or more, 97% or more, 96% or more, 95% or more, 90% or more, 85% or more, 80% or more, or 75% or more identical to SEQ ID NO: 71 having phqI activity; a polynucleotide encoding SEQ ID NO: 73 or a protein 98% or more, 97% or more, 96% or more, 95% or more, 90% or more, 85% or more, 80% or more, or 75% or more identical to SEQ ID NO: 73 having phqJ activity; a polynucleotide encoding SEQ ID NO: 75 or a protein 98% or more, 97% or more, 96% or more, 95% or more, 90% or more, 85% or more, 80% or more, or 75% or more identical to SEQ ID NO: 75 having phqK activity; a polynucleotide encoding SEQ ID NO: 77 or a protein 98% or more, 97% or more, 96% or more, 95% or more, 90% or more, 85% or more, 80% or more, or 75% or more identical to SEQ ID NO: 77 having phqL activity; a polynucleotide encoding SEQ ID NO: 79 or a protein 98% or more, 97% or more, 96% or more, 95% or more, 90% or more, 85% or more, 80% or more, or 75% or more identical to SEQ ID NO: 79 having phqM activity; a polynucleotide encoding SEQ ID NO: 81 or a protein 98% or more, 97% or more, 96% or more, 95% or more, 90% or more, 85% or more, 80% or more, or 75% or more identical to SEQ ID NO: 81 having phqN activity, and a polynucleotide encoding SEQ ID NO: 83 or a protein 98% or more, 97% or more, 96% or more, 95% or more, 90% or more, 85% or more, 80% or more, or 75% or more identical to SEQ ID NO: 83 having phqO activity.

The disclosure also provides a host cell transformed with one or more polynucleotides selected from the group consisting of: a polynucleotide encoding SEQ ID NO: 3 or a protein 98% or more, 97% or more, 96% or more, 95% or more, 90% or more, 85% or more, 80% or more, or 75% or more identical to SEQ ID NO: 3 having MalA activity, a polynucleotide encoding SEQ ID NO: 5 or a protein 98% or more, 97% or more, 96% or more, 95% or more, 90% or more, 85% or more, 80% or more, or 75% or more identical to SEQ ID NO: 5 having MalB activity; a polynucleotide encoding SEQ ID NO: 7 or a protein 98% or more, 97% or more, 96% or more, 95% or more, 90% or more, 85% or more, 80% or more, or 75% or more identical to SEQ ID NO: 7 having MalC activity; a polynucleotide encoding SEQ ID NO: 9 or a protein 98% or more, 97% or more, 96% or more, 95% or more, 90% or more, 85% or more, 80% or more, or 75% or more identical to SEQ D NO: 9 having MalD activity; a polynucleotide encoding SEQ ID NO: 11 or a protein 98% or more, 97% or more, 96% or more, 95% or more, 90% or more, 85% or more, 80% or more, or 75% or more identical to SEQ ID NO: 11 having MalE activity; a polynucleotide encoding SEQ ID NO: 13 or a protein 98% or more, 97% or more, 96% or more, 95% or more, 90% or more, 85% or more, 80% or more, or 75% or more identical to SEQ ID NO: 13 having MalF activity; a polynucleotide encoding SEQ ID NO: 15 or a protein 98% or more, 97% or more, 96% or more, 95% or more, 90% or more, 85% or more, 80% or more, or 75% or more identical to SEQ ID NO: 15 having MalG activity; a polynucleotide encoding SEQ ID NO: 18 or a protein 98% or more, 97% or more, 96% or more, 95% or more, 90% or more, 85% or more, 80% or more, or 75% or more identical to SEQ ID NO: 18 having NotA activity; a polynucleotide encoding SEQ ID NO: 20 or a protein 98% or more, 97% or more, 96% or more, 95% or more, 90% or more, 85% or more, 80% or more, or 75% or more identical to SEQ ID NO: 20 having NotB activity; a polynucleotide encoding SEQ ID NO: 22 or a protein 98% or more, 97% or more, 96% or more, 95% or more, 90% or more, 85% or more, 80% or more, or 75% or more identical to SEQ ID NO: 22 having NotC activity; a polynucleotide encoding SEQ ID NO: 24 or a protein 98% or more, 97% or more, 96% or more, 95% or more, 90% or more, 85% or more, 80% or more, or 75% or more identical to SEQ ID NO: 24 having NotD activity; a polynucleotide encoding SEQ ID NO: 26 or a protein 98% or more, 97% or more, 96% or more, 95% or more, 90% or more, 85% or more, 80% or more, or 75% or more identical to SEQ ID NO: 26 having NotE activity; a polynucleotide encoding SEQ ID NO: 28 or a protein 98% or more, 97% or more, 96% or more, 95% or more, 90% or more, 85% or more, 80% or more, or 75% or more identical to SEQ ID NO: 28 having NotF activity; a polynucleotide encoding SEQ ID NO: 30 or a protein 98% or more, 97% or more, 96% or more, 95% or more, 90% or more, 85% or more, 80% or more, or 75% or more identical to SEQ ID NO: 30 having NotG activity; a polynucleotide encoding SEQ ID NO: 32 or a protein 98% or more, 97% or more, 96% or more, 95% or more, 90% or more, 85% or more, 80% or more, or 75% or more identical to SEQ ID NO: 32 having NotH activity; a polynucleotide encoding SEQ ID NO: 34 or a protein 98% or more, 97% or more, 96% or more, 95% or more, 90% or more, 85% or more, 80% or more, or 75% or more identical to SEQ ID NO: 34 having NotI activity; a polynucleotide encoding SEQ ID NO: 36 or a protein 98% or more, 97% or more, 96% or more, 95% or more, 90% or more, 85% or more, 80% or more, or 75% or more identical to SEQ ID NO: 36 having NotJ activity; a polynucleotide encoding SEQ ID NO: 38 or a protein 98% or more, 97% or more, 96% or more, 95% or more, 90% or more, 85% or more, 80% or more, or 75% or more identical to SEQ ID NO: 38 having NotK activity; a polynucleotide encoding SEQ ID NO: 40 or a protein 98% or more, 97% or more, 96% or more, 95% or more, 90% or more, 85% or more, 80% or more, or 75% or more identical to SEQ ID NO: 40 having NotL activity; a polynucleotide encoding SEQ ID NO: 42 or a protein 98% or more, 97% or more, 96% or more, 95% or more, 90% or more, 85% or more, 80% or more, or 75% or more identical to SEQ ID NO: 42 having NotM activity; a polynucleotide encoding SEQ ID NO: 44 or a protein 98% or more, 97% or more, 96% or more, 95% or more, 90% or more, 85% or more, 80% or more, or 75% or more identical to SEQ ID NO: 44 having NotN activity; a polynucleotide encoding SEQ ID NO: 46 or a protein 98% or more, 97% or more, 96% or more, 95% or more, 90% or more, 85% or more, 80% or more, or 75% or more identical to SEQ ID NO: 46 having NotO activity; a polynucleotide encoding SEQ ID NO: 48 or a protein 98% or more, 97% or more, 96% or more, 95% or more, 90% or more, 85% or more, 80% or more, or 75% or more identical to SEQ ID NO: 48 having NotP activity; a polynucleotide encoding SEQ ID NO: 50 or a protein 98% or more, 97% or more, 96% or more, 95% or more, 90% or more, 85% or more, 80% or more, or 75% or more identical to SEQ ID NO: 50 having NotQ activity; a polynucleotide encoding SEQ ID NO: 52 or a protein 98% or more, 97% or more, 96% or more, 95% or more, 90% or more, 85% or more, 80% or more, or 75% or more identical to SEQ ID NO: 52 having NotR activity; a polynucleotide encoding SEQ ID NO: 55 or a protein 98% or more, 97% or more, 96% or more, 95% or more, 90% or more, 85% or more, 80% or more, or 75% or more identical to SEQ ID NO: 55 having phqA activity; a polynucleotide encoding SEQ ID NO: 57 or a protein 98% or more, 97% or more, 96% or more, 95% or more, 90% or more, 85% or more, 80% or more, or 75% or more identical to SEQ ID NO: 57 having phqB activity; a polynucleotide encoding SEQ ID NO: 59 or a protein 98% or more, 97% or more, 96% or more, 95% or more, 90% or more, 85% or more, 80% or more, or 75% or more identical to SEQ ID NO: 59 having phqC activity; a polynucleotide encoding SEQ ID NO: 61 or a protein 98% or more, 97% or more, 96% or more, 95% or more, 90% or more, 85% or more, 80% or more, or 75% or more identical to SEQ ID NO: 61 having phqD activity; a polynucleotide encoding SEQ ID NO: 63 or a protein 98% or more, 97% or more, 96% or more, 95% or more, 90% or more, 85% or more, 80% or more, or 75% or more identical to SEQ ID NO: 63 having phqE activity; a polynucleotide encoding SEQ ID NO: 65 or a protein 98% or more, 97% or more, 96% or more, 95% or more, 90% or more, 85% or more, 80% or more, or 75% or more identical to SEQ ID NO: 65 having phqF activity; a polynucleotide encoding SEQ ID NO: 67 or a protein 98% or more, 97% or more, 96% or more, 95% or more, 90% or more, 85% or more, 80% or more, or 75% or more identical to SEQ ID NO: 67 having phqG activity; a polynucleotide encoding SEQ ID NO: 69 or a protein 98% or more, 97% or more, 96% or more, 95% or more, 90% or more, 85% or more, 80% or more, or 75% or more identical to SEQ ID NO: 69 having phD2 activity; a polynucleotide encoding SEQ ID NO: 71 or a protein 98% or more, 97% or more, 96% or more, 95% or more, 90% or more, 85% or more, 80% or more, or 75% or more identical to SEQ ID NO: 71 having phqI activity; a polynucleotide encoding SEQ ID NO: 73 or a protein 98% or more, 97% or more, 96% or more, 95% or more, 90% or more, 85% or more, 80% or more, or 75% or more identical to SEQ ID NO: 73 having phqJ activity; a polynucleotide encoding SEQ ID NO: 75 or a protein 98% or more, 97% or more, 96% or more, 95% or more, 90% or more, 85% or more, 80% or more, or 75% or more identical to SEQ ID NO: 75 having phqK activity; a polynucleotide encoding SEQ ID NO: 77 or a protein 98% or more, 97% or more, 96% or more, 95% or more, 90% or more, 85% or more, 80% or more, or 75% or more identical to SEQ ID NO: 77 having phqL activity; a polynucleotide encoding SEQ ID NO: 79 or a protein 98% or more, 97% or more, 96% or more, 95% or more, 90% or more, 85% or more, 80% or more, or 75% or more identical to SEQ ID NO: 79 having phqM activity; a polynucleotide encoding SEQ ID NO: 81 or a protein 98% or more, 97% or more, 96% or more, 95% or more, 90% or more, 85% or more, 80% or more, or 75% or more identical to SEQ ID NO: 81 having phqN activity, and a polynucleotide encoding SEQ ID NO: 83 or a protein 98% or more, 97% or more, 96% or more, 95% or more, 90% or more, 85% or more, 80% or more, or 75% or more identical to SEQ ID NO: 83 having phqO activity.

The disclosure also provides a MalA protein having the amino acid sequence set out in SEQ ID NO: 3 or a protein 98% or more, 97% or more, 96% or more, 95% or more, 90% or more, 85% or more, 80% or more, or 75% or more identical to SEQ ID NO: 3 having MalA activity.

The disclosure also provides a MalB protein having the amino acid sequence set out in SEQ ID NO: 5 or a protein 98% or more, 97% or more, 96% or more, 95% or more, 90% or more, 85% or more, 80% or more, or 75% or more identical to SEQ ID NO: 5 having EtuA2 activity.

The disclosure also provides a MalC protein having the amino acid sequence set out in SEQ ID NO: 7 or a protein 98% or more, 97% or more, 96% or more, 95% or more, 90% or more, 85% or more, 80% or more, or 75% or more identical to SEQ ID NO: 7 having MalC activity.

The disclosure also provides a MalD protein having the amino acid sequence set out in SEQ ID NO: 9 or a protein 98% or more, 97% or more, 96% or more, 95% or more, 90% or more, 85% or more, 80% or more, or 75% or more identical to SEQ ID NO: 9 having MalD activity.

The disclosure also provides a MalE protein having the amino acid sequence set out in SEQ ID NO: 11 or a protein 98% or more, 97% or more, 96% or more, 95% or more, 90% or more, 85% or more, 80% or more, or 75% or more identical to SEQ ID NO: 11 having MalE activity.

The disclosure also provides a MalF protein having the amino acid sequence set out in SEQ ID NO: 13 or a protein 98% or more, 97% or more, 96% or more, 95% or more, 90% or more, 85% or more, 80% or more, or 75% or more identical to SEQ ID NO: 13 having MalF activity.

The disclosure also provides a MalG protein having the amino acid sequence set out in SEQ ID NO: 15 or a protein 98% or more, 97% or more, 96% or more, 95% or more, 90% or more, 85% or more, 80% or more, or 75% or more identical to SEQ ID NO: 15 having MalG activity.

The disclosure also provides a NoA protein having the amino acid sequence set out in SEQ ID NO: 18 or a protein 98% or more, 97% or more, 96% or more, 95% or more, 90% or more, 85% or more, 80% or more, or 75% or more identical to SEQ ID NO: 18 having NotA activity.

The disclosure also provides a NotB protein having the amino acid sequence set out in SEQ ID NO: 20 or a protein 98% or more, 97% or more, 96% or more, 95% or more, 90% or more, 85% or more, 80% or more, or 75% or more identical to SEQ ID NO: 20 having NotB activity.

The disclosure also provides a NotC protein having the amino acid sequence set out in SEQ ID NO: 22 or a protein 98% or more, 97% or more, 96% or more, 95% or more, 90% or more, 85% or more, 80% or more, or 75% or more identical to SEQ ID NO: 22 having NotC activity.

The disclosure also provides a NotD protein having the amino acid sequence set out in SEQ ID NO: 24 or a protein 98% or more, 97% or more, 96% or more, 95% or more, 90% or more, 85% or more, 80% or more, or 75% or more identical to SEQ ID NO: 24 having NotD activity.

The disclosure also provides a NotE protein having the amino acid sequence set out in SEQ ID NO: 26 or a protein 98% or more, 97% or more, 96% or more, 95% or more, 90% or more, 85% or more, 80% or more, or 75% or more identical to SEQ ID NO: 26 having NotE activity.

The disclosure also provides a NotF protein having the amino acid sequence set out in SEQ ID NO: 28 or a protein 98% or more, 97% or more, 96% or more, 95% or more, 90% or more, 85% or more, 80% or more, or 75% or more identical to SEQ ID NO: 28 having NotF activity.

The disclosure also provides a NotG protein having the amino acid sequence set out in SEQ ID NO: 30 or a protein 98% or more, 97% or more, 96% or more, 95% or more, 90% or more, 85% or more, 80% or more, or 75% or more identical to SEQ ID NO: 30 having NotG activity.

The disclosure also provides a NotH protein having the amino acid sequence set out in SEQ ID NO: 32 or a protein 98% or more, 97% or more, 96% or more, 95% or more, 90% or more, 85% or more, 80% or more, or 75% or more identical to SEQ ID NO: 32 having NotH activity.

The disclosure also provides a NotI protein having the amino acid sequence set out in SEQ ID NO: 34 or a protein 98% or more, 97% or more, 96% or more, 95% or more, 90% or more, 85% or more, 80% or more, or 75% or more identical to SEQ ID NO: 34 having NotI activity.

The disclosure also provides a NotJ protein having the amino acid sequence set out in SEQ ID NO: 36 or a protein 98% or more, 97% or more, 96% or more, 95% or more, 90% or more, 85% or more, 80% or more, or 75% or more identical to SEQ ID NO: 36 having NotJ activity The disclosure also provides a NotK protein having the amino acid sequence set out in SEQ ID NO: 38 or a protein 98% or more, 97% or more, 96% or more, 95% or more, 90% or more, 85% or more, 80% or more, or 75% or more identical to SEQ ID NO: 38 having NotK activity The disclosure also provides a NotL protein having the amino acid sequence set out in SEQ ID NO: 40 or a protein 98% or more, 97% or more, 96% or more, 95% or more, 90% or more, 85% or more, 80% or more, or 75% or more identical to SEQ ID NO: 40 having NotL activity.

The disclosure also provides a NotM protein having the amino acid sequence set out in SEQ ID NO: 42 or a protein 98% or more, 97% or more, 96% or more, 95% or more, 90% or more, 85% or more, 80% or more, or 75% or more identical to SEQ ID NO: 42 having NotM activity.

The disclosure also provides a NotN protein having the amino acid sequence set out in SEQ ID NO: 44 or a protein 98% or more, 97% or more, 96% or more, 95% or more, 90% or more, 85% or more, 80% or more, or 75% or more identical to SEQ ID NO: 44 having NotN activity.

The disclosure also provides a NotO protein having the amino acid sequence set out in SEQ ID NO: 46 or a protein 98% or more, 97% or more, 96% or more, 95% or more, 90% or more, 85% or more, 80% or more, or 75% or more identical to SEQ ID NO: 46 having EtuT activity.

The disclosure also provides a NotP protein having the amino acid sequence set out in SEQ ID NO: 48 or a protein 98% or more, 97% or more, 96% or more, 95% or more, 90% or more, 85% or more, 80% or more, or 75% or more identical to SEQ ID NO: 48 having NotP activity.

The disclosure also provides a NotQ protein having the amino acid sequence set out in SEQ ID NO: 50 or a protein 98% or more, 97% or more, 96% or more, 95% or more, 90% or more, 85% or more, 80% or more, or 75% or more identical to SEQ ID NO: 50 having NotQ activity.

The disclosure also provides a NotR protein having the amino acid sequence set out in SEQ ID NO: 52 or a protein 98% or more, 97% or more, 96% or more, 95% or more, 90% or more, 85% or more, 80% or more, or 75% or more identical to SEQ ID NO: 52 having NotR activity.

The disclosure also provides a phqA protein having the amino acid sequence set out in SEQ ID NO: 55 or a protein 98% or more, 97% or more, 96% or more, 95% or more, 90% or more, 85% or more, 80% or more, or 75% or more identical to SEQ ID NO: 24 having phqA activity.

The disclosure also provides a phqB protein having the amino acid sequence set out in SEQ ID NO: 57 or a protein 98% or more, 97% or more, 96% or more, 95% or more, 90% or more, 85% or more, 80% or more, or 75% or more dentical to SEQ ID NO: 57 having phqB activity.

The disclosure also provides a phqC protein having the amino acid sequence set out in SEQ ID NO: 59 or a protein 98% or more, 97% or more, 96% or more, 95% or more, 90% or more, 85% or more, 80% or more, or 75% or more identical to SEQ ID NO: 59 having phqC activity.

The disclosure also provides a phqD protein having the amino acid sequence set out in SEQ ID NO: 61 or a protein 98% or more, 97% or more, 96% or more, 95% or more, 90% or more, 85% or more, 80% or more, or 75% or more identical to SEQ ID NO: 61 having phqD activity.

The disclosure also provides a phqE protein having the amino acid sequence set out in SEQ ID NO: 63 or a protein 98% or more, 97% or more, 96% or more, 95% or more, 90% or more, 85% or more, 80% or more, or 75% or more identical to SEQ ID NO: 63 having phqE activity.

The disclosure also provides a phqF protein having the amino acid sequence set out in SEQ ID NO: 65 or a protein 98% or more, 97% or more, 96% or more, 95% or more, 90% or more, 85% or more, 80% or more, or 75% or more identical to SEQ ID NO: 65 having phqF activity.

The disclosure also provides a phqG protein having the amino acid sequence set out in SEQ ID NO: 67 or a protein 98% or more, 97% or more, 96% or more, 95% or more, 90% or more, 85% or more, 80% or more, or 75% or more identical to SEQ ID NO: 67 having phqH activity The disclosure also provides a phqH protein having the amino acid sequence set out in SEQ ID NO: 69 or a protein 98% or more, 97% or more, 96% or more, 95% or more, 90% or more, 85% or more, 80% or more, or 75% or more identical to SEQ ID NO: 69 having phqH activity The disclosure also provides a phqI protein having the amino acid sequence set out in SEQ ID NO: 71 or a protein 98% or more, 97% or more, 96% or more, 95% or more, 90% or more, 85% or more, 80% or more, or 75% or more identical to SEQ ID NO: 71 having phqI activity.

The disclosure also provides a phqJ protein having the amino acid sequence set out in SEQ ID NO: 73 or a protein 98% or more, 97% or more, 96% or more, 95% or more, 90% or more, 85% or more, 80% or more, or 75% or more identical to SEQ ID NO: 73 having phqJ activity.

The disclosure also provides a phqK protein having the amino acid sequence set out in SEQ ID NO: 75 or a protein 98% or more, 97% or more, 96% or more, 95% or more, 90% or more, 85% or more, 80% or more, or 75% or more identical to SEQ ID NO: 75 having phqK activity.

The disclosure also provides a phqL protein having the amino acid sequence set out in SEQ ID NO: 77 or a protein 98% or more, 97% or more, 96% or more, 95% or more, 90% or more, 85% or more, 80% or more, or 75% or more identical to SEQ ID NO: 77 having phqL activity.

The disclosure also provides a phqM protein having the amino acid sequence set out in SEQ ID NO: 79 or a protein 98% or more, 97% or more, 96% or more, 95% or more, 90% or more, 85% or more, 80% or more, or 75% or more identical to SEQ ID NO: 79 having phqM activity.

The disclosure also provides a phqN protein having the amino acid sequence set out in SEQ ID NO: 81 or a protein 98% or more, 97% or more, 96% or more, 95% or more, 90% or more, 85% or more, 80% or more, or 75% or more identical to SEQ ID NO: 81 having phqN activity.

The disclosure also provides a phqO protein having the amino acid sequence set out in SEQ ID NO: 83 or a protein 98% or more, 97% or more, 96% or more, 95% or more, 90% or more, 85% or more, 80% or more, or 75% or more identical to SEQ ID NO: 83 having phqO activity.

The disclosure also provides a polynucleotide set out in SEQ ID NO: 2 or a polynucleotide 98% or more, 97% or more, 96% or more, 95% or more, 90% or more, 85% or more, 80% or more, or 75% or more homologous thereto.

The disclosure also provides a polynucleotide set out in SEQ ID NO: 4 or a polynucleotide 98% or more, 97% or more, 96% or more, 95% or more, 90% or more, 85% or more, 80% or more, or 75% or more homologous thereto.

The disclosure also provides a polynucleotide set out in SEQ ID NO: 6 or a polynucleotide 98% or more, 97% or more, 96% or more, 95% or more, 90% or more, 85% or more, 80% or more, or 75% or more homologous thereto.

The disclosure also provides a polynucleotide set out in SEQ ID NO: 8 or a polynucleotide 98% or more, 97% or more, 96% or more, 95% or more, 90% or more, 85% or more, 80% or more, or 75% or more homologous thereto.

The disclosure also provides a polynucleotide set out in SEQ ID NO: 10 or a polynucleotide 98% or more, 97% or more, 96% or more, 95% or more, 90% or more, 85% or more, 80% or more, or 75% or more homologous thereto.

The disclosure also provides a polynucleotide set out in SEQ ID NO: 12 or a polynucleotide 98% or more, 97% or more, 96% or more, 95% or more, 90% or more, 85% or more, 80% or more, or 75% or more homologous thereto.

The disclosure also provides a polynucleotide set out in SEQ ID NO: 14 or a polynucleotide 98% or more, 97% or more, 96% or more, 95% or more, 90% or more, 85% or more, 80% or more, or 75% or more homologous thereto.

The disclosure also provides a polynucleotide set out in SEQ ID NO: 17 or a polynucleotide 98% or more, 97% or more, 96% or more, 95% or more, 90% or more, 85% or more, 80% or more, or 75% or more homologous thereto.

The disclosure also provides a polynucleotide set out in SEQ ID NO: 19 or a polynucleotide 98% or more, 97% or more, 96% or more, 95% or more, 90% or more, 85% or more, 80% or more, or 75% or more homologous thereto.

The disclosure also provides a polynucleotide set out in SEQ ID NO: 21 or a polynucleotide 98% or more, 97% or more, 96% or more, 95% or more, 90% or more, 85% or more, 80% or more, or 75% or more homologous thereto.

The disclosure also provides a polynucleotide set out in SEQ ID NO: 23 or a polynucleotide 98% or more, 97% or more, 96% or more, 95% or more, 90% or more, 85% or more, 80% or more, or 75% or more homologous thereto.

The disclosure also provides a polynucleotide set out in SEQ ID NO: 25 or a polynucleotide 98% or more, 97% or more, 96% or more, 95% or more, 90% or more, 85% or more, 80% or more, or 75% or more homologous thereto.

The disclosure also provides a polynucleotide set out in SEQ ID NO: 27 or a polynucleotide 98% or more, 97% or more, 96% or more, 95% or more, 90% or more, 85% or more, 80% or more, or 75% or more homologous thereto.

The disclosure also provides a polynucleotide set out in SEQ ID NO: 29 or a polynucleotide 98% or more, 97% or more, 96% or more, 95% or more, 90% or more, 85% or more, 80% or more, or 75% or more homologous thereto.

The disclosure also provides a polynucleotide set out in SEQ ID NO: 31 or a polynucleotide 98% or more, 97% or more, 96% or more, 95% or more, 90% or more, 85% or more, 80% or more, or 75% or more homologous thereto.

The disclosure also provides a polynucleotide set out in SEQ ID NO:33 or a polynucleotide 98% or more, 97% or more, 96% or more, 95% or more, 90% or more, 85% or more, 80% or more, or 75% or more homologous thereto.

The disclosure also provides a polynucleotide set out in SEQ ID NO:35 or a polynucleotide 98% or more, 97% or more, 96% or more, 95% or more, 90% or more, 85% or more, 80% or more, or 75% or more homologous thereto.

The disclosure also provides a polynucleotide set out in SEQ ID NO:37 or a polynucleotide 98% or more, 97% or more, 96% or more, 95% or more, 90% or more, 85% or more, 80% or more, or 75% or more homologous thereto.

The disclosure also provides a polynucleotide set out in SEQ ID NO: 39 or a polynucleotide 98% or more, 97% or more, 96% or more, 95% or more, 90% or more, 85% or more, 80% or more, or 75% or more homologous thereto.

The disclosure also provides a polynucleotide set out in SEQ ID NO: 41 or a polynucleotide 98% or more, 97% or more, 96% or more, 95% or more, 90% or more, 85% or more, 80% or more, or 75% or more homologous thereto.

The disclosure also provides a polynucleotide set out in SEQ ID NO: 43 or a polynucleotide 98% or more, 97% or more, 96% or more, 95% or more, 90% or more, 85% or more, 80% or more, or 75% or more homologous thereto.

The disclosure also provides a polynucleotide set out in SEQ ID NO: 45 or a polynucleotide 98% or more, 97% or more, 96% or more, 95% or more, 90% or more, 85% or more, 80% or more, or 75% or more homologous thereto.

The disclosure also provides a polynucleotide set out in SEQ ID NO: 47 or a polynucleotide 98% or more, 97% or more, 96% or more, 95% or more, 90% or more, 85% or more, 80% or more, or 75% or more homologous thereto.

The disclosure also provides a polynucleotide set out in SEQ ID NO: 49 or a polynucleotide 98% or more, 97% or more, 96% or more, 95% or more, 90% or more, 85% or more, 80% or more, or 75% or more homologous thereto.

The disclosure also provides a polynucleotide set out in SEQ ID NO: 51 or a polynucleotide 98% or more, 97% or more, 96% or more, 95% or more, 90% or more, 85% or more, 80% or more, or 75% or more homologous thereto.

The disclosure also provides a polynucleotide set out in SEQ ID NO: 54 or a polynucleotide 98% or more, 97% or more, 96% or more, 95% or more, 90% or more, 85% or more, 80% or more, or 75% or more homologous thereto.

The disclosure also provides a polynucleotide set out in SEQ ID NO: 56 or a polynucleotide 98% or more, 97% or more, 96% or more, 95% or more, 90% or more, 85% or more, 80% or more, or 75% or more homologous thereto.

The disclosure also provides a polynucleotide set out in SEQ ID NO: 58 or a polynucleotide 98% or more, 97% or more, 96% or more, 95% or more, 90% or more, 85% or more, 80% or more, or 75% or more homologous thereto.

The disclosure also provides a polynucleotide set out in SEQ ID NO: 60 or a polynucleotide 98% or more, 97% or more, 96% or more, 95% or more, 90% or more, 85% or more, 80% or more, or 75% or more homologous thereto.

The disclosure also provides a polynucleotide set out in SEQ ID NO: 62 or a polynucleotide 98% or more, 97% or more, 96% or more, 95% or more, 90% or more, 85% or more, 80% or more, or 75% or more homologous thereto.

The disclosure also provides a polynucleotide set out in SEQ ID NO: 64 or a polynucleotide 98% or more, 97% or more, 96% or more, 95% or more, 90% or more, 85% or more, 80% or more, or 75% or more homologous thereto.

The disclosure also provides a polynucleotide set out in SEQ ID NO: 66 or a polynucleotide 98% or more, 97% or more, 96% or more, 95% or more, 90% or more, 85% or more, 80% or more, or 75% or more homologous thereto.

The disclosure also provides a polynucleotide set out in SEQ ID NO:68 or a polynucleotide 98% or more, 97% or more, 96% or more, 95% or more, 90% or more, 85% or more, 80% or more, or 75% or more homologous thereto.

The disclosure also provides a polynucleotide set out in SEQ ID NO: 70 or a polynucleotide 98% or more, 97% or more, 96% or more, 95% or more, 90% or more, 85% or more, 80% or more, or 75% or more homologous thereto.

The disclosure also provides a polynucleotide set out in SEQ ID NO: 72 or a polynucleotide 98% or more, 97% or more, 96% or more, 95% or more, 90% or more, 85% or more, 80% or more, or 75% or more homologous thereto.

The disclosure also provides a polynucleotide set out in SEQ ID NO: 74 or a polynucleotide 98% or more, 97% or more, 96% or more, 95% or more, 90% or more, 85% or more, 80% or more, or 75% or more homologous thereto.

The disclosure also provides a polynucleotide set out in SEQ ID NO: 76 or a polynucleotide 98% or more, 97% or more, 96% or more, 95% or more, 90% or more, 85% or more, 80% or more, or 75% or more homologous thereto.

The disclosure also provides a polynucleotide set out in SEQ ID NO: 78 or a polynucleotide 98% or more, 97% or more, 96% or more, 95% or more, 90% or more, 85% or more, 80% or more, or 75% or more homologous thereto.

The disclosure also provides a polynucleotide set out in SEQ ID NO: 80 or a polynucleotide 98% or more, 97% or more, 96% or more, 95% or more, 90% or more, 85% or more, 80% or more, or 75% or more homologous thereto.

The disclosure also provides a polynucleotide set out in SEQ ID NO: 82 or a polynucleotide 98% or more, 97% or more, 96% or more, 95% or more, 90% or more, 85% or more, 80% or more, or 75% or more homologous thereto.

The disclosure also provides a polynucleotide encoding a protein of any one of the polynucleotides of the disclosure.

The disclosure also provides an expression vector comprising a polynucleotide of the disclosure.

The disclosure also provides a host cell transformed with an expression vector of the disclosure or a polynucleotide of the disclosure.

The disclosure also provides a method for producing prenylated indole alkaloid or a metabolic intermediate for producing a prenylated indole alkaloid comprising the step of growing a host cell of the disclosure under conditions to express the protein encoded by the transformed polynucleotide and producing a prenylated indole alkaloid or the metabolic intermediate for producing a prenylated indole alkaloid. In various aspects, the method further comprises the step of isolating the prenylated indole alkaloid or the metabolic intermediate of the prenylated indole alkaloid. In various aspects, the host cell is a prokaryote. In various aspects, the host cell is selected from the group consisting of *E. coli, Streptomyces lavendulae, Myxococcus xanthus*, and *Pseudomonas fluorescens.*

DESCRIPTION OF THE INVENTION

"Sequence identity" means that two amino acid or polynucleotide sequences are identical over a region of comparison, such as a region of at least about 250 residues or bases. Optionally, the region of identity spans at least about 100-500 residues or bases, and spans the active domain of the polypeptide. Several methods of conducting sequence alignment are known in the art and include, for example, the homology alignment algorithm (Needleman & Wunsch, *J. Mol. Biol.,* 48, 443 (1970)); the local homology algorithm (Smith & Waterman, *Adv. Appl. Math.,* 2, 482 (1981)); and the search for similarity method (Pearson & Lipman, *Proc. Natl. Acad. Sci. USA,* 85, 2444 (1988)). Preferably, the algorithm used to determine percent sequence identity and sequence similarity is the BLAST algorithm (Altschul et al., *J. Mol. Biol.,* 215, 403-410 (1990); Henikoff & Henikoff. *Proc. Natl. Acad. Sci. USA,* 89, 10915 (1989); Karlin & Altschul, *Proc. Natl. Acad. Sci. USA,* 90, 5873-5787 (1993)). Software for performing BLAST analyses is publicly available through the National Center for Biotechnology Information. Other examples of alignment software, including GAP, BESTFIT, FASTA, PILEUP, and TFASTA provided by Wisconsin Genetics Software Package (Genetics Computer Group, 575 Science Dr., Madison, Wis.), and CLUSTALW (Thompson et al., *Nuc. Acids Res.,* 22, 4673-4680 (1994); are known in the art. The degree of homology (percent identity) between a native and a mutant sequence may be determined, for example, by comparing the two sequences using computer programs commonly employed for this purpose. Briefly, the GAP program defines identity as the number of aligned symbols (i.e., nucleotides or amino acids) which are identical, divided by the total number of symbols in the shorter of the two sequences. The default parameters for the GAP program include: (1) a unary comparison matrix (containing a value of 1 for identities and 0 for non-identities) for nucleotides, and the weighted comparison matrix of Gribskov and Burgess, Nucl. Acids Res. 14:6745, 1986, as described by Schwartz and Dayhoff, eds., Atlas of Protein Sequence and Structure, National Biomedical Research Foundation, pp. 353-358, 1979; (2) a penalty of 3.0 for each gap and an additional 0.10 penalty for each symbol in each gap; and (3) no penalty for end gaps.

Alterations of the native amino acid sequence may be accomplished by any of a number of known techniques. Mutations can be introduced at particular loci by synthesizing oligonucleotides containing a mutant sequence, flanked by restriction sites enabling ligation to fragments of the native sequence. Following ligation, the resulting reconstructed sequence encodes an analog having the desired amino acid insertion, substitution, or deletion.

Alternatively, oligonucleotide-directed site-specific mutagenesis procedures can be employed to provide an altered gene having particular codons altered according to the substitution, deletion, or insertion required. Techniques for making such alterations include those disclosed by Walder et al. (Gene 42:133, 1986); Bauer et al. (Gene 37:73, 1985); Craik (BioTechniques, January 1985, 12-19); Smith et al. (Genetic Engineering: Principles and Methods, Plenum Press, 1981); and U.S. Pat. Nos. 4,518,584 and 4,737,462, which are incorporated by reference herein.

The disclosure provides an example of the comparative analysis of biosynthetic gene clusters (mined from the whole genome) and pathways for structurally related fungal indole alkaloids bearing the unusual bicyclo[2.2.2]diazaoctane core, including the anticancer agents (−)-notoamide A ((−)-1) and (+)-notoamide A ((+)-1),[35,36] the anthelmintic paraherquamide A (2),[37-39] and the calmodulin-inhibitor malbrancheamide[40-42] (3) (FIG. 1A) produced by *Aspergillus* sp. MF297-2,[43] *Aspergillus versicolor* NRRL35600, *Penicillium fellutanum* ATCC20841, and *Malbranchea aurantiaca* RRC1813, respectively. These fungal natural products are assembled from an L-tryptophan, a second cyclic amino acid residue, and one or two isoprene units through biosynthetic pathways that are proposed to feature an intriguing intramolecular Diels Alderase (IMDAse), and a number of unique enantiomerically selective enzymes.[44-49] The diverse bioactivities of this natural product family suggests that elucidation of their biosynthesis could direct future structural diversification via biosynthetic engineering, thereby leading to enhanced biological activities.

This comparative analysis provides significant insights into a number of intriguing biosynthetic questions: (1) which enzyme in each pathway is likely responsible for the formation of the bicyclo[2.2.2]diazaoctane core via the proposed intramolecular [4+2] Diels-Alder (IMDA) cyclization; (2) which enzyme in the pathway of 1 and 2 installs the spiro-oxindole functionality via a putative epoxide-initiated Pinacol-type rearrangement; and (3) what genetic difference controls formation of the dioxopiperazine in 1 versus the monooxopiperazine in 2 and 3.

Figure 1B:
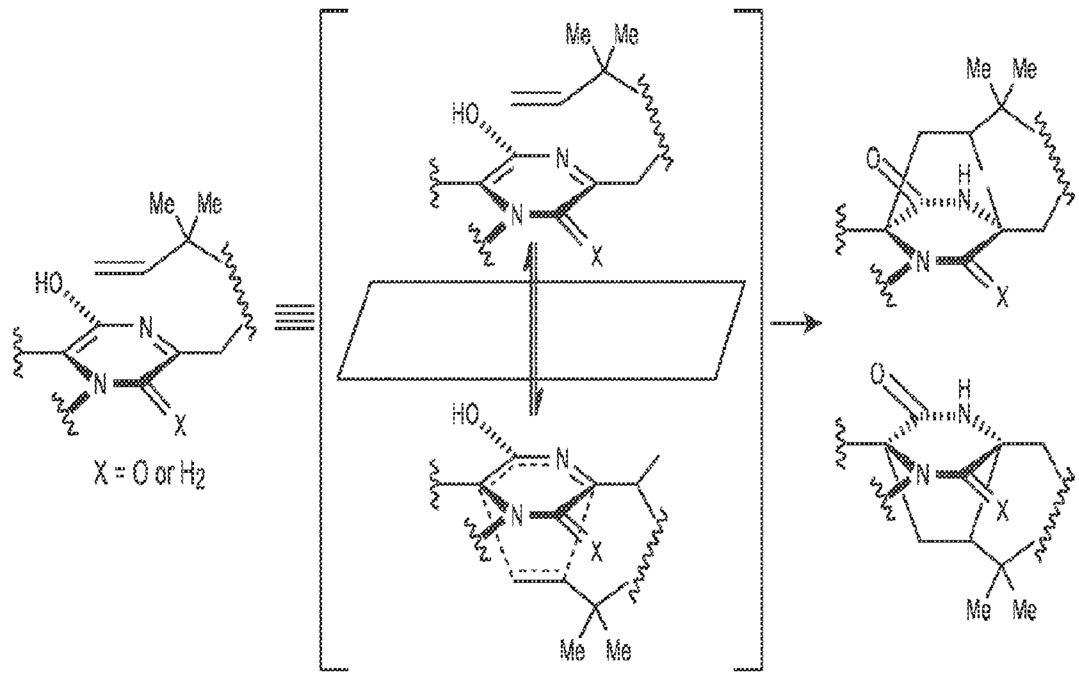

The most significant structural similarity between 1-3 is the bicyclo[2.2.2]diazaoctane core (FIG. 1A). Biosynthetically, this unique structural moiety was proposed to arise from a [4+2] IMDA reaction (FIG. 1B).[44,46] This presumed cycloaddition reaction is also believed to catalyze the first enantiodivergent step in an otherwise common biosynthetic pathway from *Aspergillus* sp. MF297-2 and *A. versicolor* NRRL35600, leading to formation of (−)-1 and (+)-1, respectively, together with several other enantiomeric metabolites (FIG. 3).[47] Currently, it remains unknown whether a specific IMDAse indeed exists in these biosynthetic pathways. However, if it does exist, one would expect its encoding gene should be present in all four gene clusters. Second, the spiro-oxindole is absent in 3, suggesting the responsible enzyme is likely absent from the pathway for 3, and present in those for 1 and 2. Third, a specific reductase responsible for reducing the tryptophan carbonyl group would be expected in the gene cluster of 2 and 3, but not 1. This genetic difference would account for the lack of the second amide carbonyl group in the piperazine ring of 2 and 3. Finally, the different hydroxylation status of the indole amide, distinct aromatic decoration among 1-3, together with other unique structural features including the tailoring of the proline moiety and N-methylation in 2, are also expected to be reflected at the genetic level.

The following examples are provided to illustrate particular embodiments of the present invention, and are not to be construed as limiting the scope of the invention.

EXAMPLE 1

The genomes of *A. versicolor* NRRL35600, *P. fellutanum* ATCC20841, and *M. aurantiaca* RRC1813A harboring not', phq, and mal gene clusters, respectively were sequenced to approximately 99, 84, and 181 times coverage of their estimated genome size (35 Mb), using the Illumina Solexa technology (Genome Analyzer IIx).

Figure 2:
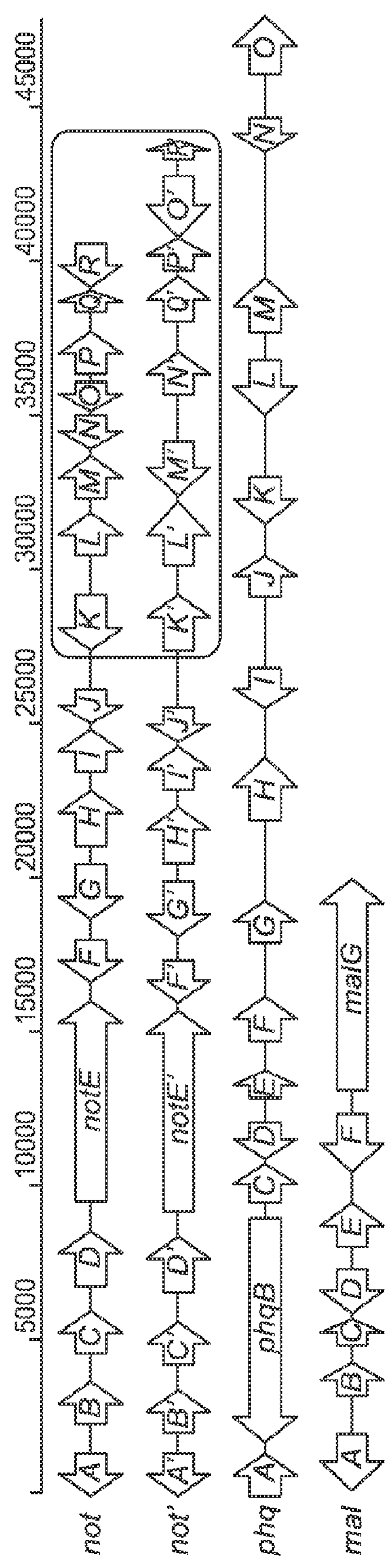
FIG. 2—The (−)-notoamide A (not), (+)-notoamide A (not'), paraherquamide (phq), and malbrancheamide (mal) biosynthetic gene clusters identified from genome sequencing and bioinformatic mining of *Aspergillus* sp. MF297-2, *Aspergillus versicolor* NRRL35600, *P. fellutanum* ATCC20841, and *M. aurantiaca* RRC1813, respectively. Homology of open reading frames across gene clusters is shown by same colored arrows. The not and not' genes in the red box are unlikely involved in notoamide biosynthesis.

First, the key biosynthetic gene notE' (Table 1) encoding a non-ribosomal peptide synthetase (NRPS) was mined from the genome sequences using the notE DNA sequence from the reported not gene cluster[43] as a probe for homologous genes. NotE', which shows 79% identity and 86% similarity to NotE at the amino acid (AA) level, was predicted to be a bimodular NRPS with the A-T-C-A-T-C (A: adenylation, T: thiolation, C: condensation) domain organization using the PKS/NRPS Analyzer. Genome walking from notE' toward 5' and 3' ends identified another nine genes (notA'-J', Table 1 and FIG. 2) that display high AA sequence similarity (>70%) with corresponding gene products of the not gene cluster. Notably, the overall nucleotide identity between notA'-J' (25,440 bp) and notA-J (26,210 bp) is 71%, which is not surprising since both metabolic pathways are responsible for assembling "identical", yet antipodal compounds. In addition to the high sequence similarity, the genetic architecture (i.e. order and direction of genes) within this region is identical in the two clusters (FIG. 2). The pattern of the exon/intron arrangement in the corresponding genes is also highly similar to each other (see Supplementary Information). In contrast, the sequence similarity is reduced drastically and the gene architecture differs after notK'/notK (Table 1, FIG. 2), strongly suggesting the previously assigned not gene cluster (notA-R) probably ends at notJ.

At the genetic level, it is not possible to glean the key differences that account for production of antipodal notoamide metabolites, suggesting that subtle active site sequence variation in those enantiomerically selective enzymes play a critical role in the control of absolute chirality. This requires direct biochemical analysis of the key notoamide biosynthetic enzymes, including structural biology efforts, which is currently ongoing in our laboratories.

Second, the paraherquamide (phq) gene cluster (47,884 bp) was identified from the partially assembled *P. fellutanum* genome by using a select group of not genes including the NRPS gene notE, the prenyltransferase genes notC and notF, and the P450 monooxygenase gene notG as in silico probes.[43] Fifteen genes were identified that are likely involved in paraherquamide biosynthesis. The largest number of biosynthetic genes among the four studied metabolic pathways is consistent with 2 as the most complex structure compared to 1 and 3. Comparative bioinformatic analysis demonstrates that nine (phqA, B, F, G, H, J, K, L, and M) out of fifteen total phq genes are homologous to corresponding not genes (Table 1), although their homology is significantly lower than that between not and not' genes. Notably, the bimodular phqB NRPS gene is different from notE in that a reductase (R) domain is located at its carboxy terminus instead of a condensation (C) domain, which is found in notE and notE'. This difference is significant because the reductase (vs condensation) domain is presumed to account for the presence of the monooxopiperazine in 2 (vs dioxopiperazine in 1) (see below).[50] Among the remaining six cluster-specific genes, phqC shows high sequence similarity to 2-oxoglutarate (2OG) and Fe(II) dependent oxygenases.[51,52] The phqD and phqE genes, which putatively encoding a pyrroline-5-carboxylate reductase and a short chain dehydrogenase, respectively, might be involved in the formation of the β-methyl-proline starter unit. The phqI gene that encodes the third prenyltransferase in phq is unique as it is free of introns, and therefore, distinct from the single intron-containing prenyltransferase genes phqA/notC and phqJ/notF. It is worth noting that the presence of three prenyltransferase genes is inconsistent with the two isoprene groups incorporated into the structure of 2. Thus, it is of special interest to examine whether the third prenyltransferase gene is redundant or plays an alternative, and as yet unknown function in the biosynthesis of 2. Furthermore, phqN is predicted to function as a methyltransferase, likely responsible for the N-methylation in 2. Finally, the phqO P450 gene with a unique exon/intron organization pattern is hypothesized to catalyze the C14 hydroxylation of the β-methyl-proline moiety.

Third, the seven-gene containing mal gene cluster (20179 bp) was mined from the genome of *Malbranchea aurantiaca* RRC1813A using phqB as an in silico probe to identify the metabolic system for 3. It has the smallest size among gene clusters of 1-3, which is consistent with the simplest structure and corresponding biosynthetic pathway. The genes malB, malD, malE, malF, and malG are common to the four gene clusters. Thus, except for the regulatory gene of malD (homologous to notA, notA' and phqG), the remaining four biosynthetic genes (and their homologues in not, not' and phq) are possibly responsible for installing the shared structural features of 1-3. This strongly suggests that the hypothetical Diels Alderase (if extant) should be represented by one of these four gene products (see below). Interestingly, the mal genes show greater sequence similarity to phq genes than not (or not') genes, perhaps indicating their closer evolutionary relationship. Similar to PhqB, the NRPS MalG harbors a reductase domain at its carboxy terminus, which is consistent with the monooxopiperazine moiety in 3. Again, the apparent redundancy of the second prenyltransferase (3 only contains one isoprene group) is difficult to rationalize, but genetic disruption or RNA silencing (malB or malE) efforts are likely to shed light on the individual role of these enzymes. Finally, it is evident that the flavin-dependent halogenase MalA is likely involved in the introduction of one or both chlorine atoms in the biosynthesis of 3.

EXAMPLE 2

Since the discovery of the biosynthetic gene cluster of (−)-1 from marine *Aspergillus* sp. MF297-2, in vitro biochemical characterization of the reverse prenyltransferase NotF using the NRPS (NotE) product brevianamide F[53] (4) as substrate and the normal prenyltransferase NotC using 6-hydroxy-deoxybrevianamide E (6) as substrate has partially established the early steps of the notoamide pathway leading to notoamide S (7) (FIG. 3).[43] The P450 monooxygenase NotG is likely catalyzing the C6 indole hydroxylation since its close homologue FtmC (59%/72% identity/similarity) in fumitremorgin biosynthesis had been characterized to hydroxylate the analogous aromatic C—H bond in the indole ring of tryprostatin B,[54,55] which is structurally similar to deoxybrevianamide E (5).[56]

As the proposed pivotal branching point in notoamide biosynthesis,[47,57,58] 7 can be diverted to notoamide E (8) through an oxidative pyran ring closure putatively catalyzed by either NotH P450 monooxygenase (based on precedented examples of pyran ring formation from the epoxide intermediate generated by P450 enzymes[59]), or the NotD oxidoreductase. This step would be followed by an indole 2,3-epoxidation-initiated Pinacol-like rearrangement catalyzed by NotB FAD monooxygenase (FMO) leading to the formation of notoamide C (9) and notoamide D (10).[58] Notably, notB (or notB') is only observed in the not (or not') gene cluster, consistent with the fact that this branching pathway leading to natural products 9 and 10 is only observed in notoamide biosynthesis.

Figure 3A:
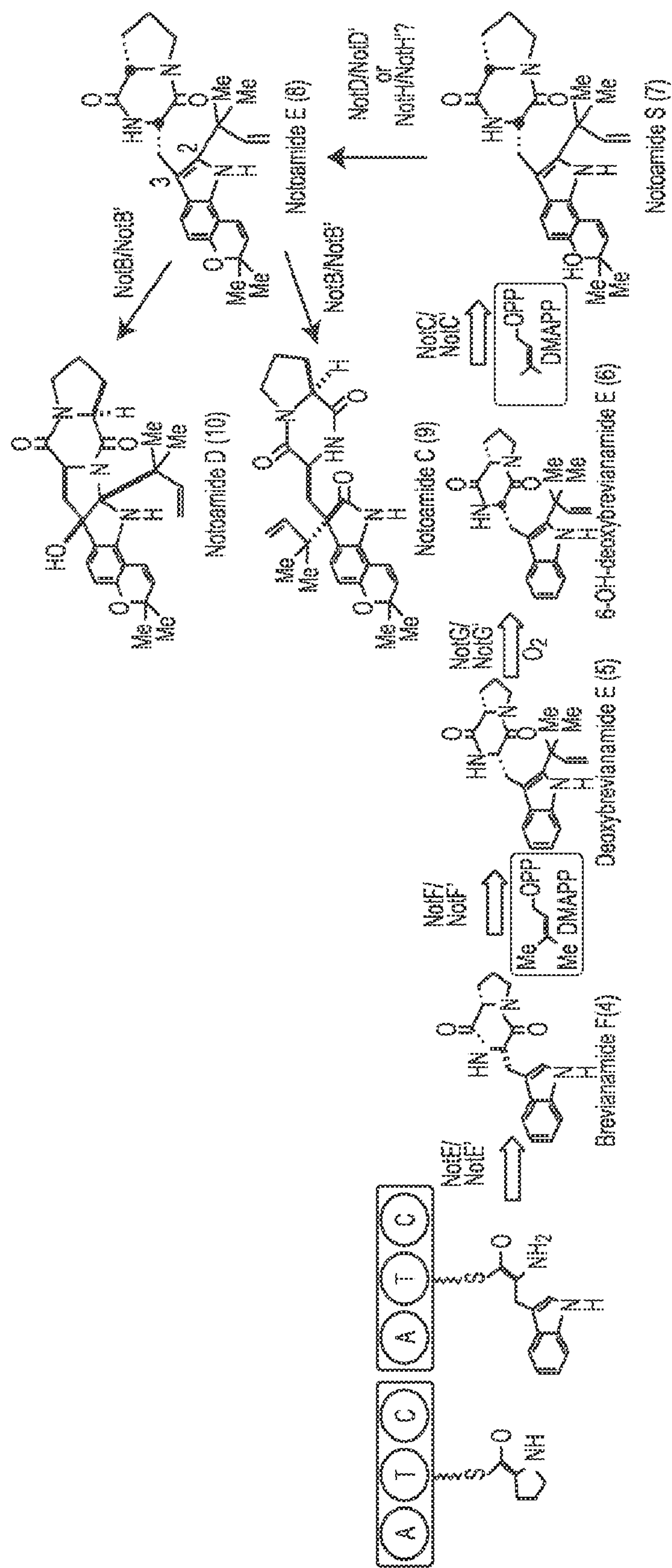
FIG. 3—Proposed biosynthetic pathway for antipodal notoamide metabolites.
Figure 3B:
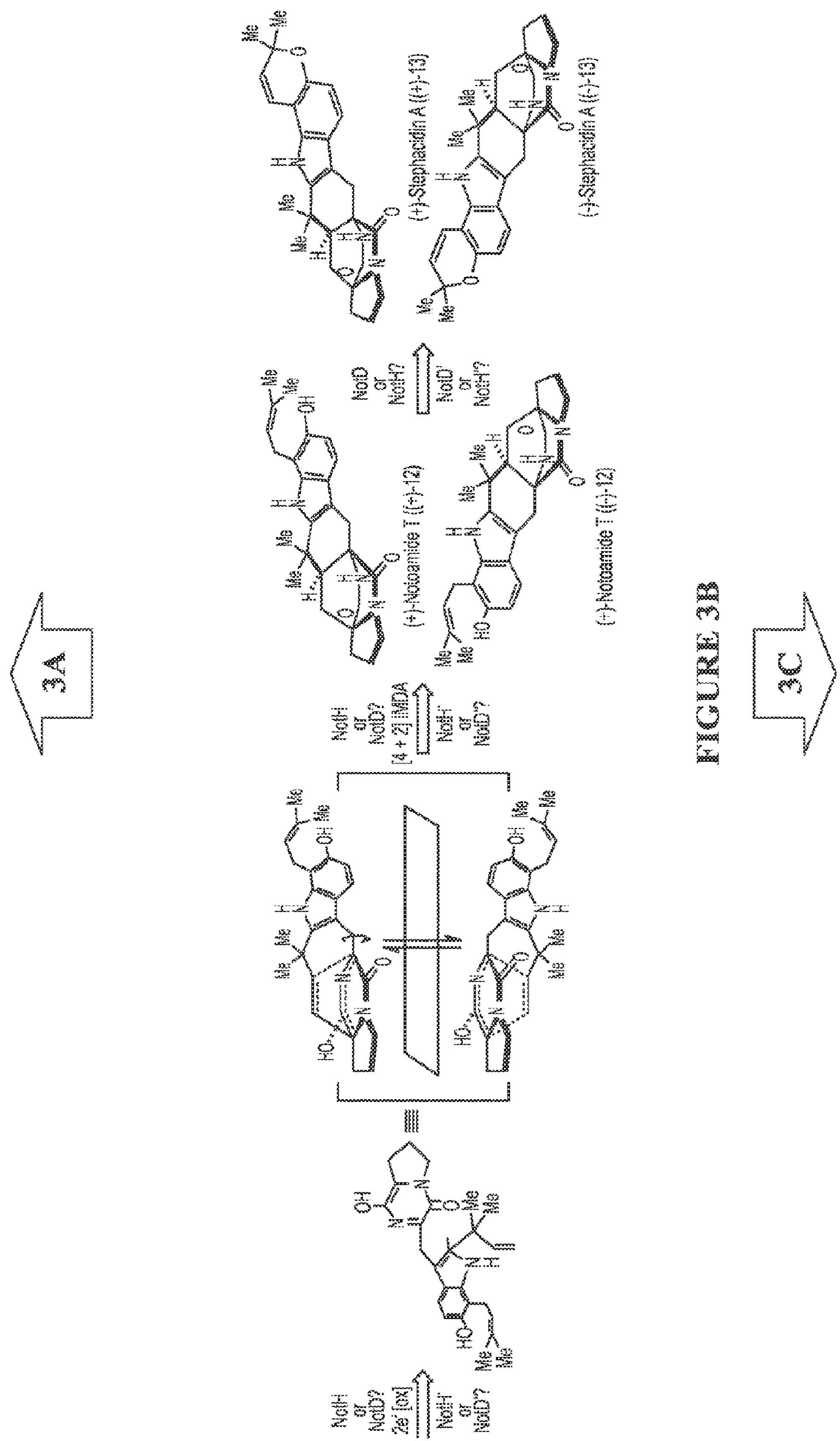
Figure 3C:
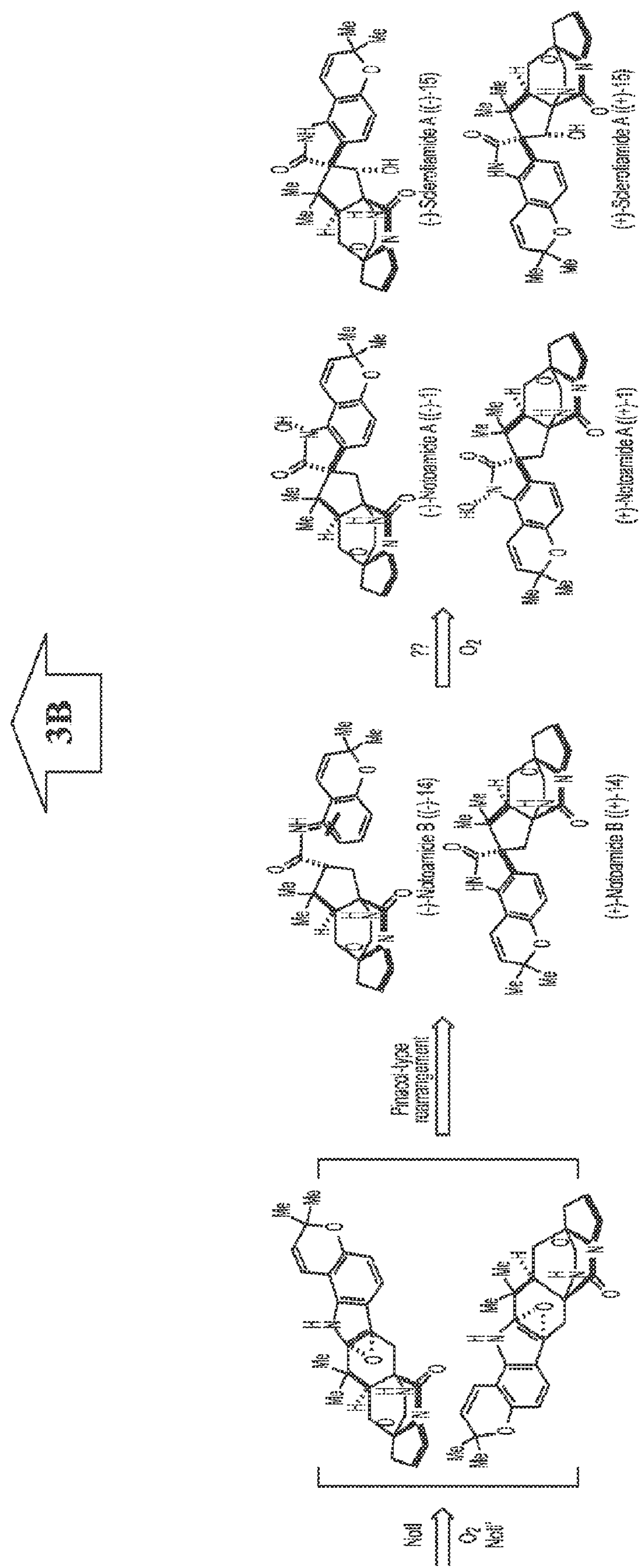

On the other hand, extensive precursor feeding and incorporation studies using stable isotopically labeled intermediates have supported 7 as the substrate for the hypothetical IMDA.[47] As a working hypothesis, a two-electron oxidation catalyzed by an oxidase would give rise to the achiral azadiene intermediate (11), which may immediately undergo a spontaneous stereoselective [4+2] IMDA cyclization in the active site of the same oxidase, yielding either (+)-notoamide T ((+)-12) in *Aspergillus* sp. MF297-2 or (−)-notoamide T ((−)-12) in *A. versicolor*. The opposing conformation (endo/exo) assumed by achiral 11 presumably determined by the scaffolding of each putative Diels-Alderase might account for the enantio-divergence at this key step. The five oxidases encoded by the not gene cluster, include FMO NotB and NotI, P450 enzymes NotG and NotH, and the FAD-dependent oxidoreductase NotD. NotB was recently identified as the notoamide E oxidase.[58] NotI is highly similar to NotB with 42% protein sequence identity and 59% similarity, and is predicted to catalyze a similar conversion from (+)-stephacidin A[60] ((+)-13) to (−)-notoamide B ((−)-14) via the 2,3-epoxidation of (+)-13 followed by a Pinacol-type rearrangement. Thus, if the putative function of NotG (see above) is correct, NotH (or NotD) is likely the bifunctional oxidase that also functions as the IMDAse responsible for generation of (+)-12. To generate antipodal (−)-12, NotH' (or NotD') is expected to catalyze a Diels Alder reaction leading to the opposite stereochemistry. Currently, this hypothesis is being tested in our laboratories through in vitro characterization of NotH/NotH' (or NotD/NotD'). With comparative analysis of four gene clusters (Table 1), it appears that NotD/NotD' is more likely to serve as the IMDAse since its homologs (PhqH and MalF) are present in all clusters. This hypothesis is based on the assumption that these four biosynthetic pathways use the same type of protein scaffolding enzyme to catayze the [4+2] cyclo addition. However, we have recently begun to challenge this assumption (see below). Presently, the possibility that NotH/NotH' functions as the IMDAse in notoamide biosynthesis cannot be excluded. Once its identity is determined, the final oxidase NotD (or NotH) will likely be found to catalyze the oxidative pyran ring formation (FIG. 3).

Another important fact of these two related notoamide pathways is that enzymes catalyzing the biosynthetic steps after formation of 12 must also be enantiomerically and diastereochemically selective. Specifically, in previous precursor incorporation studies of racemic $^{13}C$-labeled (±)-13 with *Aspergillus* sp. MF297-2 and *A. versicolor*,[61] it was ascertained that only one enantiomer of 13 can be processed (currently presumed by NotI and NotI') to form downstream products. Understanding the subtle differences between these two enzymes will likely provide significant insights into how related enzymes have evolved to adopt opposing enantiomeric selectivity.

Finally, it remains unclear which enzyme could be responsible for the final hydroxylation steps leading to notoamide A (1) and sclerotiamide[62] (15) since all five oxidative enzymes in the not(') gene cluster has been assigned a putative function. It is possible that 1 and 15 are opportunistically produced upon the activity of unknown oxidases whose genes reside outside of the defined notoamide gene cluster. Alternatively, the possibility that a not oxidase may possess bi-functionality cannot be excluded.

EXAMPLE 3

Figure 4A:
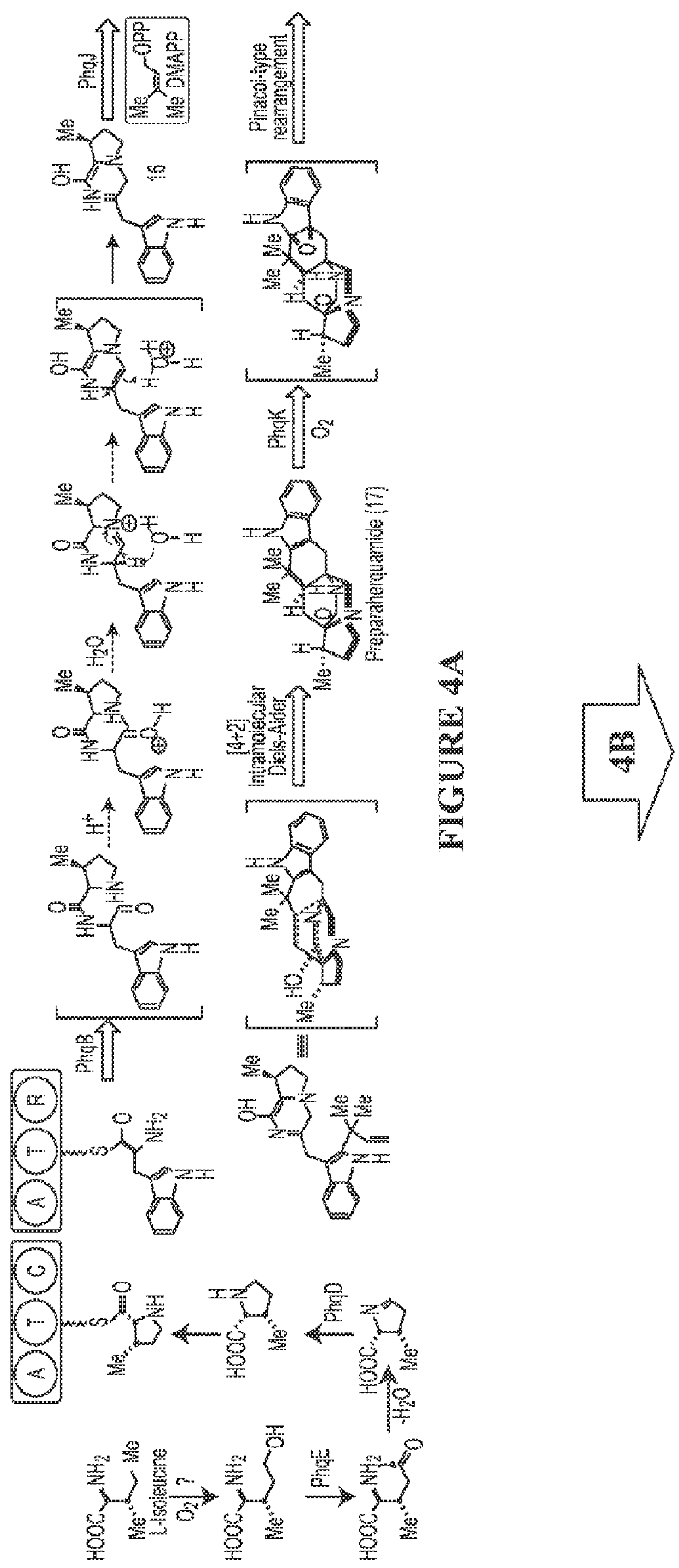
FIG. 4—Proposed biosynthetic pathway for paraherquamide A.
Figure 4B:
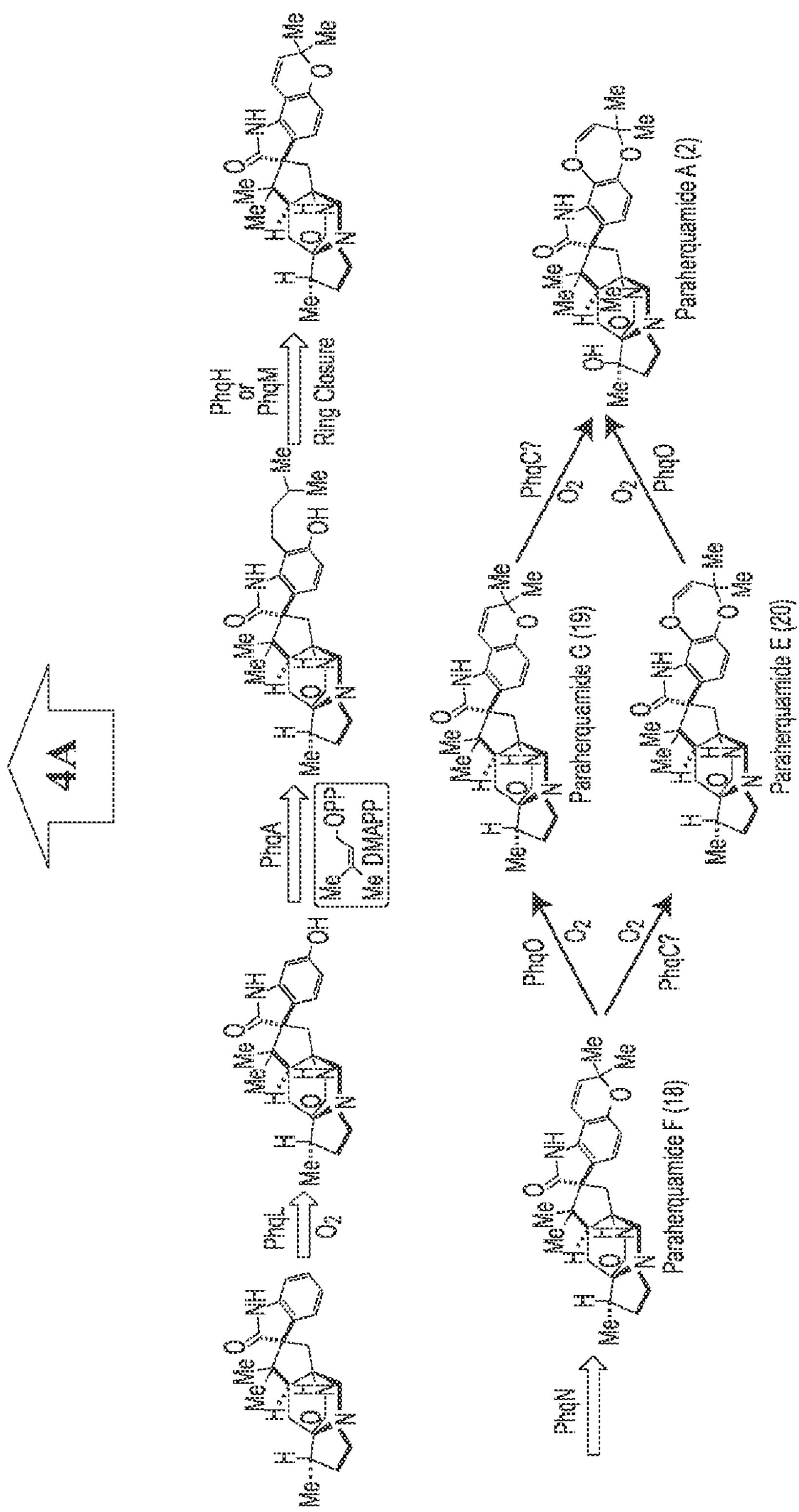

Previous feeding studies demonstrated that L-isoleucine is the precursor to the β-methyl-β-hydroxy proline moiety in 2.[45,63] Identification of the pyrroline-5-carboxylate reductase PhqD and the short chain dehydrogenase PhqE from phq cluster suggests a reasonable pathway from L-isoleucine to β-methyl proline (FIG. 4). Similar to the partially identified biosynthesis of 4-methyl proline in cyanobacterial *Nostoc* sp.,[64] PhqE presumably oxidizes the terminally hydroxylated L-isoleucine (by an unknown enzyme) to the corresponding aldehyde. Spontaneous cyclization and dehydration would yield the 4-methyl pyrolline-5-carboxylic acid, which is then reduced by PhqD leading to the β-methyl proline precursor.

The presence of a C-terminal NAD(P)-dependent reductase domain in the bimodular paraherquamide NRPS (A-T-C-A-T-R) clearly indicates that the mechanism for dipeptide release by PhqB must be different from the final condensation domain of NotE (FIG. 3).[50] What likely occurs is that the PhqB R domain utilizes NADPH for hydride transfer to reduce the thioester bond of the T domain-tethered linear dipeptide to a hemithioaminal intermediate, which spontaneously cleaves the C—S bond to release the aldehyde product. Subsequently, the acid-activated aldehyde is intramolecularly trapped by the nucleophilic amine from the adjacent amino acid to form a hemiaminal intermediate, which then undergoes a spontaneous dehydration and double bond rearrangement leading to formation of the monooxopiperazine intermediate 16 (likely existing as the enol form) prior to all other biosynthetic steps. This hypothesis is in good agreement with previous observations[65,66] that the dioxopiperazine analog of preparaherquamide (17) cannot be incorporated into 2 by *P. fellutanum* since all substrates for downstream enzymes should bear the monooxopiperazine ring system. In this scheme (FIG. 4), formation of the diene in 16 is achieved by a reductive process, as opposed to the $2e^-$ oxidation step proposed in the notoamide biosynthetic pathway (FIG. 3). If this is correct, in contrast to an oxidase (NotH/NotH' or NotD/NotD') proposed to be the Diels Alderase in notoamide biosynthesis, the reverse prenyltransferase (proposed to be PhqJ) might act as the scaffold for an IMDA reaction after introduction of the reverse prenyl group to 16. In this proposed route, the terminal double bond of the isoprene group would become the dienophile to react with the azadiene in the prenyltransferase active site, thus resulting in formation of the [2.2.2]diazaoctane intermediate 17.

Following formation of 17, the pyran ring formation is proposed to be installed by PhqA prenyltransferase (22% identical to NotC), PhqL (29% identical to NotG) and PhqH oxidoreductase (34% identical to NotD) (or PhqM P450 enzymes (15% identical to NotH)). The FMO PhqK (32% identical to NotI) is likely responsible for generation of the spiro-oxindole, and the N-methylation is likely mediated by the PhqN methyltransferase leading to the isolable natural product paraherquamide F[38,67] (18). However, the order of these biosynthetic steps cannot be predicted without further in vivo genetic studies and/or in vitro biochemical analysis.

In late-stage paraherquamide biosynthesis, the third P450 monooxygenase PhqO is probably responsible for the C14 hydroxylation, transforming 18 to paraherquamide G[38,67] (19), and paraherquamide E[38,67] (20) to the final product 2. However, expansion from the 6-membered ring pyran (in 18 and 19) to the 7-membered dioxepin ring (in 2 and 20) represents a poorly understood but intriguing process. Possibly, phqC that encodes a 2OG-Fe(II)-oxygenase is involved in this ring expansion, which is consistent with previous reports showing this class of enzyme functioning as an expandase.[68]

Finally, the biosynthetic genes, including phqI as well as phqM (or phqH, the one uninvolved in the pyran ring formation), do not have a clearly prescribed role and appear to be redundant.

EXAMPLE 4

Except for using L-proline instead of β-methyl proline as the starter unit, the biosynthetic route through premalbrancheamide (21) (FIG. 5) is proposed to parallel that of paraherquamide biosynthesis through 17 (FIG. 4). Mediated by NRPS MalG (A-T-C-A-T-R, 37% identical to PhqB) and prenyltransferase MalE (36%/34% identical to NotF/PhqJ), 21 is produced with its structure slightly different from 17 in lacking the C1 methyl group.

Subsequently, the halogenase MalA presumably chlorinates the C9 position (malbrancheamide numbering) first to afford the isolable natural product malbrancheamide B (22), which could be further chlorinated by MalA at C8 leading to the final product malbrancheamide (3). This putative pathway is partially supported by the previous feeding study showing that the $^{13}C$ labeled 21 can be incorporated into 22 by *M. aurantiaca*.[69] Lack of observed $^{13}C$ labeled 3 from the fermentation broth was interpreted to suggest that the second chlorination might be too slow to incorporate detectable levels of $^{13}C$ material from 22 to 3. Notably, the order of these two chlorinations seems unexchangeable since the C8-monochloro regioisomer of 22 (C9-monochlorinated) was not detected as a natural product despite considerable effort.[42] It is also possible that the dichloro species, malbrancheamide, arises from a pre-halogenated tryptophan-based assembly.

Blast sequence analysis revealed significant homology of MalA to the family of flavin-dependent tryptophan halogenases.[70-73] This result suggests two alternative malbrancheamide biosynthetic pathways. First, MalA could chlorinate tryptophan at C4 and C5 (tryptophan numbering) sequentially prior to being loaded onto the second T domain of MalG. Then, both monochlorinated and dichlorinated tryptophan could be processed by subsequent assembly enzymes, thereby respectively leading to 22 and 3 in parallel. Second, MalA might only monochlorinate the C4 position of tryptophan, resulting in 22. Then, 22 is converted into 3 by either MalA or another unidentified halogenase that resides outside mal. To test these hypotheses, it would be the best to conduct in vitro functional analysis of purified MalA against selected substrates such as L-tryptophan and 22. Alternatively, whether or not the $^{13}C$ labeled 22 can be incorporated into 3 in an in vivo precursor feeding study would also provide useful information about the timing of the two chlorination steps in malbrancheamide biosynthesis.

According to the proposed malbrancheamide biosynthetic pathway (FIG. 5), only three enzymes are required to assemble the final product 3. Inactivation of these seemingly redundant genes including malB, malC, and malF (Table 1) is currently underway. Interestingly, the MalC short chain dehydrogenase related to PhqE, which is presumed to participate in preparation of β-methyl proline starter unit in paraherquamide biosynthesis (see above), is present in the mal gene cluster although apparently unnecessary for malbrancheamide biosynthesis. This implies that malC, together with other redundant genes, might be residuals from ancestral or a horizontally transferred gene cluster (e.g. one analogous to phq). The evolving biosynthetic gene cluster not only recruits new genes, but also eliminates or retains unused genes when facing a diverse living environment and selection pressure during its evolutionary history.[24]

Recently, a novel malbrancheamide-type natural product named spiromalbramide (23) (FIG. 5) was isolated from a marine invertebrate-derived *Malbranchea graminicola* fungal strain.[74] This new derivative contains the spiro-oxindole moiety that is found in notoamides and paraherquamides, but is absent from malbrancheamides. Based on the comparative analysis of not, not', phq, and mal gene cluster, we are now capable of predicting that an FMO gene homologous to notI, notI' or phqK should reside in the uncharacterized biosynthetic gene cluster of 23. So far, the Solexa genome sequencing of *M. graminicola* has been completed. This prediction will be tested in the near future as soon as the biosynthetic gene cluster is mined and annotated from genome sequences.

EXAMPLE 5

In principle, the shared genes from different clusters are responsible for assembling the common structural core among similar natural products. The cluster-specific gene products are presumed to modify these structures by a series of variant tailoring steps, thereby leading to structural diversification. However, it is noteworthy that the redundant genes and multifunctional genes could complicate comparative analysis of gene clusters. Therefore, conclusions can only be unambiguously drawn after genetic and/or biochemical confirmation of enzymatic activities.

Figure 5:
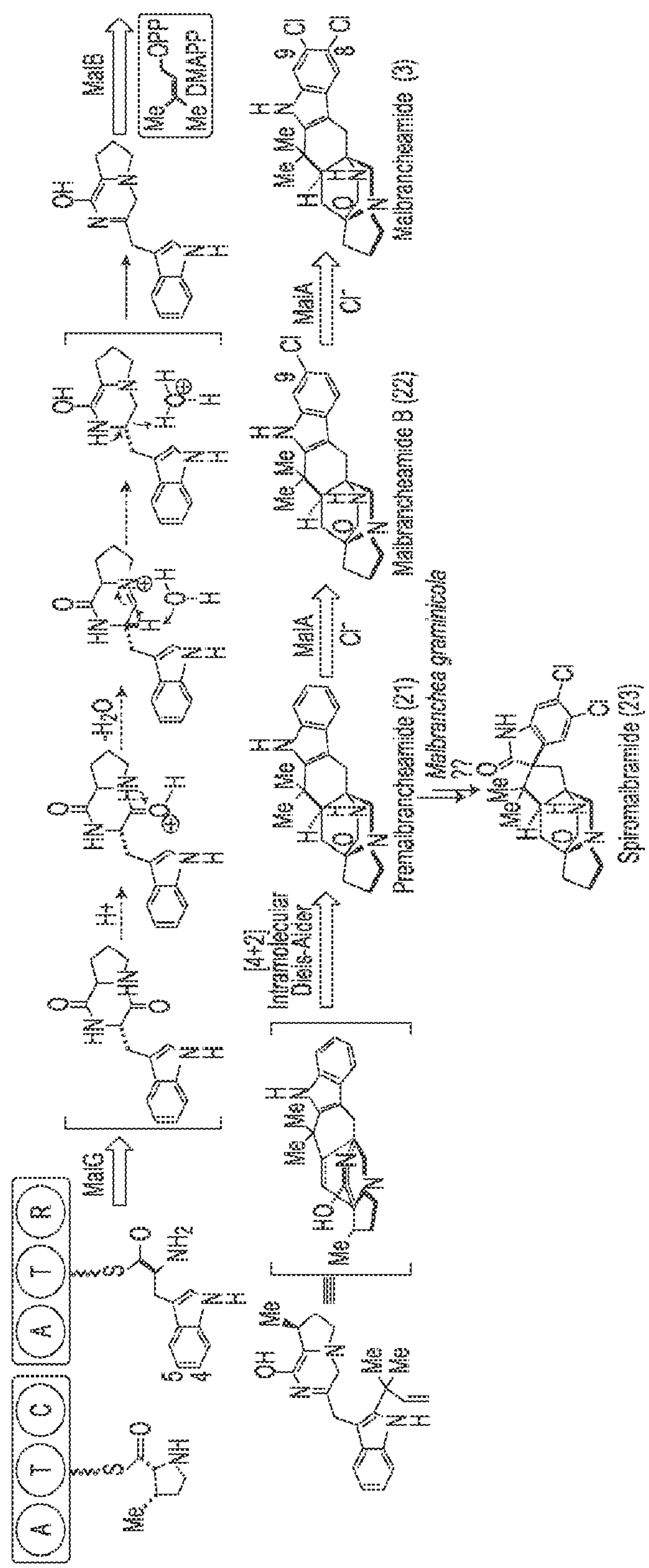
FIG. 5—Proposed biosynthetic pathway for malbrancheamide natural products.

Following these simple but logical principles, we performed a comparative analysis wasperformed for four related gene clusters including not, not', phq, and mal, based on the proposed complete biosynthetic pathways for (+)/(−)-notoamides, paraherquamides, and malbrancheamides with a biosynthetic enzyme assigned for each individual step (FIG. 3-5). For example, the function of the not-specific gene notB can be readily connected to the pathway specific transformation from notoamide E (8) to notoamide C (9) and D (10). This was recently confirmed by in vitro characterization of NotB FMO enzyme.[58]

Figure 6:
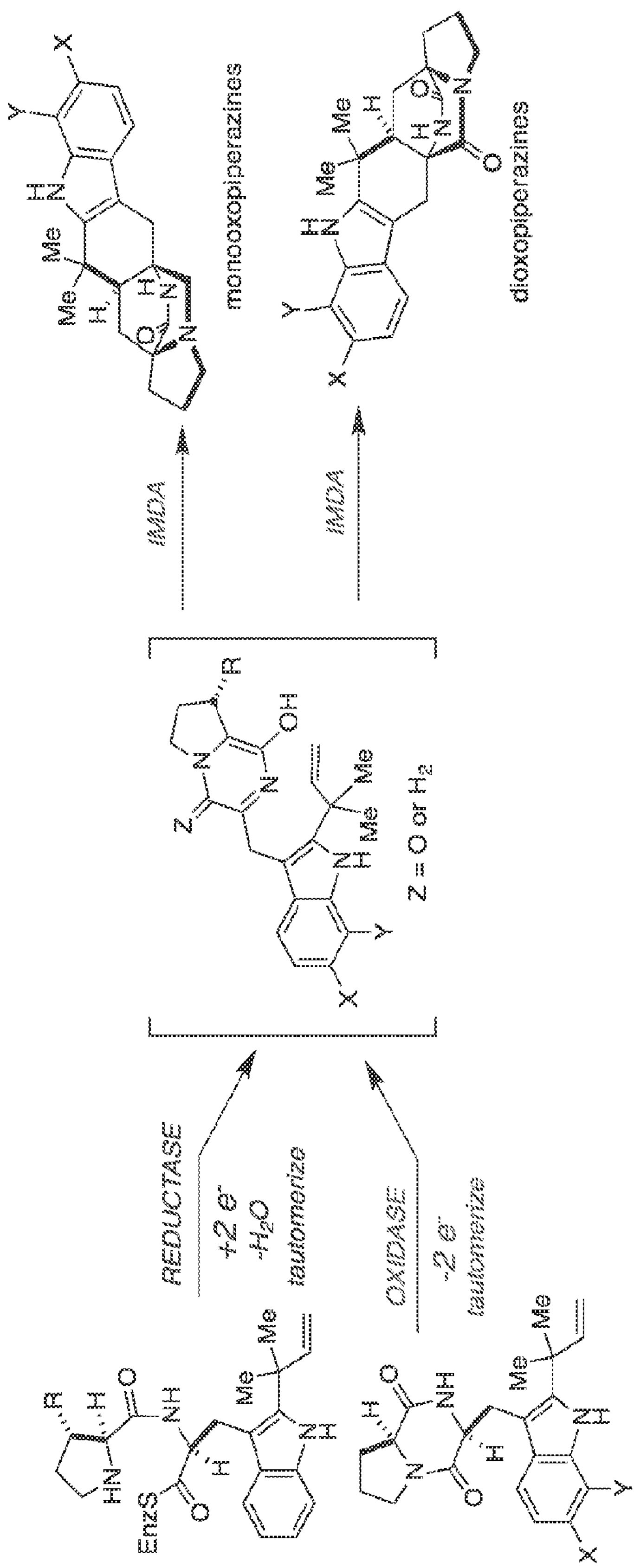
FIG. 6—Summary of divergent NRPS strategies that culminate in the formation of structurally related bicyclo [2.2.2]diazaoctane ring systems in distinct oxidation states.

Furthermore, detailed comparative analysis resulted in nomination of the oxidases NotH and NotH' (or NotD and NotD'), and the prenyltransferases PhqJ and MalE as putative Diels-Alderases to catalyze the distinctive IMDA reactions for these pathways. Next, comparative functional analysis of these enzymes in vitro will enable us to test this long standing hypothesis regarding the existence of a Diels-Alderase in the biosynthesis of fungal indole alkaloids with the bicyclo[2.2.2]diazaoctane core. It is striking that Nature has conscripted two evolutionarily related gene cluster paradigms, to construct the novel bicyclo[2.2.2]diazaoctane ring system by vastly different mechanistic protocols (FIG. 6). In one instance, for the notoamides, the net transformation from the NRPS-loaded dipeptide to the bicyclo[2.2.2]diazaoctane core, a net two-electron oxidation is required to reach the key, putative azadiene species required for the proposed IMDA construction. In the other, the paraherquamide and malbrancheamide systems, the NRPS-loaded dipeptide substrate is cleaved in a net two-electron reduction, that we speculate cyclizes and dehydrates to the related (reduced) azadiene species for the homologous IMDA construction. This insight was most readily presented to us, by the analysis of the respective gene cluster annotations, and has provided a very satisfying level of corroboration with labeled precursor incorporation experiments that at first, seemed incongruous. We expect that the tremendous insights that the bioinformatics analyses have provided in these systems, will render understanding the possible biogenesis of these and related natural products more efficient, congruent and intellectually satisfying.

The foregoing description and examples have been set forth merely to illustrate the invention and are not intended to be limiting. Since modifications of the described embodiments incorporating the spirit and substance of the invention may occur to persons skilled in the art, the invention should be construed broadly to include all variations within the scope of the appended claims and equivalents thereof.

REFERENCES

1. J. W.-H. Li and J. C. Vederas, *Science,* 2009, 325, 161.
2. D. J. Newman and G. M. Cragg, *J. Nat. Prod.,* 2007, 70, 461.
3. R. Li and C. A. Townsend, *Metab. Eng.,* 2006, 8, 240.
4. R. H. Baltz, *J. Ind. Microbiol. Biotechnol.,* 1998, 20, 360.
5. S. Baba, Y. Abe, T. Suzuki, C. Ono, K. Iwamoto, T. Nihira and M. Hosobuchi, *Appl.*
Microbiol. Biotechnol., 2009, 83, 697.
6. J.-H. Noh, S.-H. Kim, H.-N. Lee, S. Y. Lee and E.-S. Kim, *Appl. Microbiol. Biotechnol.,* 2010, 86, 1145.
7. W. R. Strohl, *Metab. Eng.,* 2001, 3, 4.
8. D. E. Cane, C. T. Walsh and C. Khosla, *Science,* 1998, 282, 63.
9. C. T. Walsh, *ChemBioChem,* 2002, 3, 125.
10. C. Sanchez, L. Zhu, A. F. Brana, A. P. Salas, J. Rohr, C. Mendez and J. A. Salas, *Proc. Natl. Acad. Sci. U.S.A.,* 2005, 102, 461.
11. J. Pollier, T. Moses and A. Goossens, *Nat. Prod. Rep.,* 2011, 28, 1897.
12. J. L. Que and W. B. Tolman, *Nature,* 2008, 455, 333.
13. A. L. Goff, V. Artero, B. Jousselme, P. D. Tran, N. Guillet, R. Métayé, A. Fihri, S. Palacin and M. Fontecave, *Science,* 2009, 326, 1384.
14. K. T. Watts, B. N. Mijts and C. Schmidt-Dannert, *Adv. Synth. Catal.,* 2005, 347, 927.
15. Y. Xue, L. Zhao, H.-w. Liu and D. H. Sherman, *Proc. Natl. Acad. Sci. U.S.A.,* 1998, 95, 12111.
16. J. C. Carlson, J. L. Fortman, Y. Anzai, S. Li, D. A. Burr and D. H. Sherman, *ChemBioChem,* 2010, 11, 564.
17. J. D. Kittendorf and D. H. Sherman, *Bioorg. Med. Chem.,* 2009, 17, 2137.
18. J. C. Carlson, S. Li, S. S. Gunatilleke, Y. Anzai, D. A. Burr, L. M. Podust and D. H. Sherman, *Nat. Chem.,* 2011, 3, 628.
19. H. Zhang, B. A. Boghigian, J. Armando and B. A. Pfeifer, *Nat. Prod. Rep.,* 2011, 28, 125.
20. U. Galm and B. Shen, *Expert Opin. Drug. Discov.,* 2006, 1, 409.
21. L. Tang, S. Shah, L. Chung, J. Carney, L. Katz, C. Khosla and B. Julien, *Science,* 2000, 287, 640.
22. Q. Cheng, L. Xiang, M. Izumikawa, D. Meluzzi and B. S. Moore, *Nat. Chem. Biol.,* 2007, 3, 557.

23. C. J. Balibar, A. R. Howard-Jones and C. T. Walsh, *Nat. Chem. Biol.,* 2007, 3, 584.
24. L. Gu, B. Wang, A. Kulkarni, T. W. Geders, R. V. Grindberg, L. Gerwick, K. Hakansson, P. Wipf, J. L. Smith, W. H. Gerwick and D. H. Sherman, *Nature,* 2009, 459, 731.
25. Y. Anzai, S. Li, M. R. Chaulagain, K. Kinoshita, J. Montgomery and D. H. Sherman, *Chem. Biol.,* 2008, 15, 950.
26. U. Galm, E. Wendt-Pienkowski, L. Wang, S.-X. Huang, C. Unsin, M. Tao, J. M. Coughlin and B. Shen, *J. Nat. Prod.,* 2011, 74, 526.
27. B. Peant, G. LaPointe, C. Gilbert, D. Atlan, P. Ward and D. Roy, *Microbiology,* 2005, 151, 1839.
28. K. S. Ryan, *PLoS One,* 2011, 6, e23694.
29. K. Buntin, H. Irschik, K. J. Weissman, E. Luxenburger, H. Blöcher and R. Müller, *Chem. Biol.,* 2010, 17, 342.
30. R. D. Hawkins, G. C. Hon and B. Ren, *Nat. Rev. Genet.,* 2010, 11, 476.
31. M. L. Metzker, *Nat. Rev. Genet.,* 2010, 11, 31.
32. T. J. Treangen and S. L. Salzberg, *Nat. Rev. Genet.,* 2012, 13, 36.
33. C. Shaffer, *Nat. Biotechnol.,* 2007, 25, 149.
34. S. C. Schuster, *Nat. Methods,* 2008, 5, 16.
35. H. Kato, T. Yoshida, T. Tokue, Y. Nojiri, H. Hirota, T. Ohta, R. M. Williams and S. Tsukamoto, *Angew. Chem. Intl. Ed.,* 2007, 46, 2254.
36. T. J. Greshock, A. W. Grubbs, P. Jiao, D. T. Wicklow, J. B. Gloer and R. M. Williams, *Angew. Chem. Intl. Ed.,* 2008, 47, 3573.
37. M. Yamazaki, E. Okuyama, M. Kobayashi and H. Inoue, *Tetrahedron Lett.,* 1981, 22, 135.
38. J. G. Ondeyka, R. T. Goegelman, J. M. Schaeffer, L. Kelemen and L. Zitano, *J. Antibiot.,* 1990, 43, 1375.
39. R. M. Williams, J. Gao, H. Tsujishima and R. J. Cox, *J. Am. Chem. Soc.,* 2003, 125, 12172.
40. S. Martinez-Luis, R. Rodriguez, L. Acevedo, M. C. Gonzalez, A. Lira-Rocha and R. Mata, *Tetrahedron,* 2006, 62, 1817.
41. M. Figueroa, M. C. Gonzalez and R. Mata, *Nat. Prod. Res.,* 2008, 22, 709.
42. K. A. Miller, T. R. Welch, T. J. Greshock, Y. Ding, D. H. Sherman and R. M. Williams, *J. Org. Chem.,* 2008, 73, 3116.
43. Y. Ding, J. R. deWet, J. Cavalcoli, S. Li, T. J. Greshock, K. A. Miller, J. M. Finefield, J. D. Sunderhaus, T. J. McAfoos, S. Tsukamoto, R. M. Williams and D. H. Sherman, *J. Am. Chem. Soc.,* 2010, 132, 12733.
44. R. M. Williams and R. J. Cox, *Acc. Chem. Res.,* 2003, 36, 127.
45. E. M. Stocking, J. F. Sanz-Cervera, C. J. Unkefer and R. M. Williams, *Tetrahedron,* 2001, 57, 5303.
46. E. M. Stocking and R. M. Williams, *Angew. Chem. Intl. Ed.,* 2003, 42, 3078.
47. J. D. Sunderhaus, D. H. Sherman and R. M. Williams, *Isr. J. Chem.,* 2011, 51, 442.
48. A. W. Grubbs, G. D. I. Artman, S. Tsukamoto and R. M. Williams, *Angew. Chem. Intl. Ed.,* 2007, 46, 2257.
49. T. J. Greshock, A. W. Grubbs, S. Tsukamoto and R. M. Williams, *Angew. Chem. Intl. Ed.,* 2007, 46, 2262.
50. T. A. Keating, D. E. Ehmann, R. M. Kohli, C. G. Marshall, J. W. Trauger and C. T. Walsh, *ChemBioChem,* 2001, 2, 99.
51. N. Steffan, A. Grundmann, S. Afiyatullov, H. Ruan and S.-M. Li, *Org. Biomol. Chem.,* 2009, 7, 4082.
52. R. P. Hausinger, *Crit. Rev. Biochem. Mol. Biol.,* 2004, 39, 21.

53. A. J. Birch and J. J. Wright, *J. Chem. Soc. Chem. Commun.*, 1969, 644.

54. S.-M. Li, *J. Antibiot.*, 2011, 64, 45.

55. N. Kato, H. Suzuki, H. Takagi, H. Kakeya, M. Uramoto, T. Usui, S. Takahashi, Y. Sugimoto and H. Osada, *ChemBioChem*, 2009, 10, 920.

56. P. S. Steyn, *Tetrahedron Lett.*, 1971, 12, 3331.

57. S. Tsukamoto, H. Kato, T. J. Greshock, H. Hirota, T. Ohta and R. M. Williams, *J. Am. Chem. Soc.*, 2009, 131, 3834.

58. S. Li, J. M. Finefield, J. D. Sunderhaus, T. J. McAfoos, R. M. Williams and D. H. Sherman, *J. Am. Chem. Soc.*, 2012, 134, 788.

59. M. Oliynyk, C. B. W. Stark, A. Bhatt, M. A. Jones, Z. A. Hugher-Thomas, C. Wilkinson, Z. Oliynyk, Y. Demydchuk, J. Staunton and P. F. Leadlay, *Mol. Microbiol.*, 2003, 49, 1179.

60. J. Qian-Cutrone, S. Huang, Y. Z. Shu, D. Vyas, C. Fairchild, A. Menendez, K. Krappitz, R. Dalterio, S. E. Klohr and Q. Gao, *J. Am. Chem. Soc.*, 2002, 124, 14556.

61. J. M. Finefield, H. Kato, T. J. Greshock, D. H. Sherman, S. Tsukamoto and R. M. Williams, *Org. Lett.*, 2011, 13, 3802.

62. C. Authrine and J. B. Gloer, *J. Nat. Prod.*, 1996, 59, 1093.

63. E. M. Stocking, J. F. Sanz-Cervera and R. M. Williams, *J. Am. Chem. Soc.*, 2000, 122, 1675.

64. H. Luesch, D. Hoffmann, J. M. Hevel, J. E. Becker, T. Golakoti and R. E. Moore, *J. Org. Chem.*, 2002, 68, 83.

65. Y. Ding, S. Gruschow, T. J. Greshock, J. M. Finefield, D. H. Sherman and R. M. Williams, *J. Nat. Prod.*, 2008, 71, 1574.

66. E. M. Stocking, J. F. Sanz-Cervera and R. M. Williams, *Angew. Chem. Intl. Ed.*, 2001, 40, 1296.

67. J. M. Liesch and C. F. Wichmann, *J. Antibiot.*, 1990, 43, 1380.

68. K. S. Hewitson, N. Granatino, R. W. D. Welford, M. A. McDonough and C. J. Schofield, *Phil. Trans. R. Soc. A*, 2005, 363, 807.

69. Y. Ding, T. J. Greshock, K. A. Miller, D. H. Sherman and R. M. Williams, *Org. Lett.*, 2008, 10, 4863.

70. K. H. vanPee and E. P. Patallo, *Appl. Microbiol. Biotechnol.*, 2006, 70, 631.

71. J. Zeng and J. Zhan, *ChemBioChem*, 2010, 11, 2119.

72. C. S, Neumann, C. T. Walsh and R. R. Kay, *Proc. Natl. Acad. Sci. U.S.A.*, 2010, 107, 5798.

73. C. Dong, S. Flecks, S. Unversucht, C. Haupt, K. H. vanPee and J. H. Naismith, *Science*, 2005, 309, 2216.

74. K. R. Watts, S. T. Loveridge, K. Tenney, J. Media, F. A. Valeriote and P. Crews, *J. Org. Chem.*, 2011, 76, 6201.

TABLE 1

Comparative analysis* of gene clusters of not, not', phq, and mal

| Not proteins (AA) | Function | Not' proteins (AA) | Function (% identity to corresponding Not protein) | Phq proteins (AA) | Function (% identity to corresponding Not protein) | Mal proteins (AA) | Function (% identity to corresponding Not/Phq protein) |
|---|---|---|---|---|---|---|---|
| NotA (339) | Negative regulator | NotA' (334) | Negative regulator (70% NotA) | PhqA (405) | Prenyltransferase (22% NotC) | MalA (667) | Halogenase (—/—) |
| NotB (456) | FAD monooxygenase | NotB' (455) | FAD monooxygenase (88% NotB) | PhqB (2449) | NRPS [A-T-C-A-T-R] (26% NotE) | MalB (369) | Prenyltransferase (28% NotC/34% PhqA) |
| NotC (427) | Prenyltransferase | NotC' (426) | Prenyltransferase (87% NotC) | PhqC (353) | 2OG-Fe(II)-oxygenase (—) | MalC (264) | Short chain dehydrogenase (—/52% PhqE) |
| NotD (621) | Oxidoreductase | NotD' (612) | Oxidoreductase (80% NotD) | PhqD (322) | Pyrroline-5-carboxylate reductase (—) | MalD (336) | Negative regulator (36% NotA/55% PhqG) |
| NotE (2241) | NRPS [A-T-C-A-T-C] | NotE' (2225) | NRPS [A-T-C-A-T-C] (79% NotE) | PhqE (265) | Short chain dehydrogenase (—) | MalE (438) | Prenyltransferase (36% NotF/34% PhqJ) |
| NotF (453) | Prenyltransferase | NotF' (435) | Prenyltransferase (79% NotF) | PhqF (411) | Efflux pump (18% NotK) | MalF (590) | Oxidoreductase (37% NotD/39% PhqH) |
| NotG (544) | P450 monooxygenase | NotG' (544) | P450 monooxygenase (87% NotG) | PhqG (338) | Negative regulator (34% NotA) | MalG (2345) | NRPS [A-T-C-A-T-R] (27% NotE/37% PhqB) |
| NotH (502) | P450 monooxygenase | NotH' (499) | P450 monooxygenase (84% NotH) | PhqH (602) | Oxidoreductase (34% NotD) | | |
| NotI (434) | FAD monooxygenase | NotI' (433) | FAD monooxygenase (85% NotI) | PhqI (462) | Prenyltransferase (—) | | |
| NotJ (371) | Unknown | NotJ' (362) | Unknown (80% NotJ) | PhqJ (406) | Prenyltransferase (32% NotF) | | |
| NotK (564) | Efflux pump | NotK' (577) | Efflux pump (14% NotK) | PhqK (459) | FAD monooxygenase (32% NotI) | | |
| NotL (484) | Transcriptional activator | NotL' (620) | Transcriptional factor (15% NotL) | PhqL (563) | P450 monooxygenase (29% NotG) | | |
| NotM (402) | Unknown | NotM' (454) | Unknown (—) | PhqM (536) | P450 monooxygenase (15% NotH) | | |
| NotN (340) | Dehydrogenase | NotN' (416) | Unknown (—) | PhqN (326) | Methyltransferase | | |
| NotO (331) | Short-chain dehydrogenase | NotO' (462) | Unknown (—) | PhqO (451) | P450 monooxygenase (—) | | |

TABLE 1-continued

| Comparative analysis* of gene clusters of not, not', phq, and mal | | | | | | | |
|---|---|---|---|---|---|---|---|
| Not proteins (AA) | Function | Not' proteins (AA) | Function (% identity to corresponding Not protein) | Phq proteins (AA) | Function (% identity to corresponding Not protein) | Mal proteins (AA) | Function (% identity to corresponding Not/Phq protein) |
| NotP (322) | Unknown | NotP' (292) | Unknown (—) | | | | |
| NotQ (152) | Unknown | NotQ' (506) | Transcription factor | | | | |
| NotR (461) | Transcriptional coactivator | NotR' (172) | Unknown | | | | |

*Genes were predicted using the FGENESH-M tool. Functions of gene products were predicted using BLAST search.

What is claimed is:

1. A protein in the prenylated indole alkaloid pathway, wherein the protein is a MalG protein having an amino acid sequence that is 98% or more identical to SEQ. ID NO: 15, comprises at least one amino acid substitution, insertion or deletion relative to SEQ ID NO: 15 and has MalG activity.

2. The MalG protein of claim 1 further comprising a chlorinated tryptophan loaded onto the second thiolation (T) domain of the protein.

3. A polynucleotide encoding a protein in the prenylated indole alkaloid pathway, wherein the polynucleotide encodes a MalG protein having an amino acid sequence that is 98% or more identical to SEQ ID NO: 15, comprises at least one amino acid substitution, insertion or deletion relative to SEQ ID NO:15 and has MalG activity.

4. A host cell transformed with the polynucleotide of claim 3.

5. An expression vector comprising the polynucleotide of claim 3.

6. A host cell transformed with the expression vector of claim 5.

7. A method for producing prenylated indole alkaloid or a metabolic intermediate for producing a prenylated indole alkaloid comprising the step of growing a host cell comprising the polynucleotide of claim 3 under conditions to express the protein and producing a prenylated indole alkaloid or the metabolic intermediate for producing a prenylated indole alkaloid.

8. The method of claim 7 further comprising the step of isolating the prenylated indole alkaloid or the metabolic intermediate of the prenylated indole alkaloid.

9. The method of claim 8 wherein the host cell is a prokaryote.

10. The method of claim 9 wherein the host cell is selected from the group consisting of *Escherichia coli, Streptomyces lavendulae, Myxococcus xanthus*, and *Pseudomonas fluorescens*.

* * * * *

UNITED STATES PATENT AND TRADEMARK OFFICE
CERTIFICATE OF CORRECTION

PATENT NO. : 9,650,656 B2
APPLICATION NO. : 14/390360
DATED : May 16, 2017
INVENTOR(S) : Shengying Li et al.

It is certified that error appears in the above-identified patent and that said Letters Patent is hereby corrected as shown below:

On the Title Page

At item (57), Line 13, “select” should be -- selected --.

In the Claims

At Column 311, Line 4, “SEQ.” should be -- SEQ --.

Signed and Sealed this
Eighth Day of May, 2018

Andrei Iancu
*Director of the United States Patent and Trademark Office*

SEQUENCE LISTING

```
<160> NUMBER OF SEQ ID NOS: 83

<210> SEQ ID NO 1
<211> LENGTH: 20179
<212> TYPE: DNA
<213> ORGANISM: Malbranchea aurantiaca RRC1813

<400> SEQUENCE: 1

ctatgcagct ggcctggtag gggttggtag ctttaactcc ttcgaggggt cgtatttagg     60

cgcagtattc caggcagcgt aaagtaacgc ttcttcttct gcggtcagcg gggggatcaaa    120

ggtaacggcc gtttgcggct cggtgcccag aagaccgcat gagtggcact ttttccaatc    180

tgggcggagt tggagccatg ccccgcaacc cgagcattgt ctcgtataga tgtccctgct    240

tgtcttccct tcgacgaaat tcaaagaccg atcgaaagag cgcaggatcg catcccaccg    300

gagactgaag tcgtctgcgg ccacggcagc acttttaatt cggttcgaaa acgcaagcaa    360

ctcatcaacc atcgcatcgg gaagtcgctc atcgaggggg acggtttcga tatgctcaat    420

gcatttctgt gcgacttgtt gatattcagg caccatggct ccccaaaccc atttaatcgc    480

gtaatgtgcg aaggtttcaa tgttaacatc tgacaaatat cgctctatgc cagcgaaaaa    540

ctgccagagg catgccacct ggggacctaa acgtgtatcg cgataacaga cgtagttaaa    600

tcgattcatt tgctcgagtg ccggaactag ggacttgcaa taatcgtcat atgggaccag    660

taattttcga atagaggact ccgccgcatc tgcaggcgca cttttcccaa tctccacaat    720

tcggtgcgaa agctgtgcgg cccatgttga agtcgacatg ccaacattaa tccccggaga    780

atagagcggg ttggtgaaac cacaggcatc accaatggca agccagccag gtccagaaac    840

cactggagac tggtatgcca gcgtcttacg gatgaaccat gtggtcccag ggccataaag    900

attttcaata agctcaaagt ttgacatgaa ctgctgaagc agctcatact tctgaacaaa    960

gtagttgaat ttttgctctg cctcacgggt cccataggct gagagatctt ccgggtactt   1020

gacatcattg cgcacggcaa agccaatact tgtcacccac tgaaacttga gcccaaacat   1080

cctggcaagc tcttcagaac tcgggagttc atcaccaggt actccggcgt cagcgcattc   1140

gagtatgtat gtcaccatat ccatcaagtt cgctatgagg ctcccttccc aagagggtag   1200

acgaataacc cagacccaac cttccggaaa acacaggtgg tttgtgtgat caccttcata   1260

gagatcaaag ggaatcttgc tctcatcctt tggggcagtg aaataacccc agaaggcgtt   1320

gcagttccat ccatcgaatc ggtgtcgggg ggctttcttg gagcaaaatt ggcggaagcg   1380

gcctgttgcg tcaacgaaga gggctgaatc tattgtcttg ggtgtgctat catatttgcc   1440

ccgggagact gcgatcttgt tgccctggcc accccccttgg accaccgtgc ttttaaaatc   1500
```

```
cacctcccgg ccgtgataga cattgactcc atttcgttgc gcaagaattg taaagagcag   1560
ctcgctcatt ggccgctcaa tctgtaaact ggctaatacc aaacctggag ccccaacact   1620
gcagaagtct gtgtactgcc cctggttctc tcgatcaaga aagtaaaagc acagcccatc   1680
cttgagtccg aatagtcgaa ggaggtatgc cgcggagatg ccgtggagtt tgcaccaggt   1740
gtaaaagata ggtagagtgc tctcgccaat cttgtaacca ggcctagtgt tcttctcaat   1800
aacggagatc ttgaggttgt tcggtttata ctttgaagcg tgaagggcat agatcagacc   1860
atggatacca gcaccgccca ccaccacatc cgattcatct gggagctcag atccagtagg   1920
attattggag ttgagaatct cagcgtcgct gagattgcct gccgcagccc tctcggtaaa   1980
cgtatacttt ggtgtcggcg ccatggtgtt caaggcaaac gaggataatt aaaatgttcg   2040
gatttagtta gagcggataa aagatgctta ataggaataa acctgggccg caattgaccc   2100
cttcggtgtt gcctttataa attatgctct gatggaggaa tgtcagagtc ttcctcctgt   2160
cctctttagt ccgcctgata acccaaacag aacactcatg gccctggctg ggtcctgtgg   2220
cagggactgg aaggcgcaaa acggcccaag agaaggttgg gatcatctcc ctgcacactc   2280
tgccggagtg gattcagccc gcaccatcca aagtgaggcg cctgcctacc cagctgtgtt   2340
cttcccttga cggagaaagc tctccgagtc aggcggcccc ccgtttctga agtcgagaaa   2400
gagtttgggt aaccaccgac tccacaacgt gaatggatga gcaggctggt tgaaaattgg   2460
gtatccgtct gcataagaat caggtcgatc gaacatgata tggctccaga tttcttcgtg   2520
tccacgtctc gtgaccggta tttcctcggg accaacaccg cccggatttc tagccagtct   2580
ctggcagaat ttgggtccag gctggaccaa gatcctttga tggcctgttc aacatcaatt   2640
cttcagagtt cagagagctc agaaagcggt ggatatgaca cagatggagt ggccatcggg   2700
atctactgat cttcgtcctt cgcccgcgcc gatgatgata tctgagattc caataaaggg   2760
gcgttgactg aggctggaac agcgtcctgg actgctcatc aatccggaat gttcagcttg   2820
gtgatgggta gtgatagtta atgctaaata ctaattacct tagcacggat ttggtccgcg   2880
cagttctgtt gatgacggcc ccaggggttg aaggagcccc ttacgggcag accggagcaa   2940
caagtatatt gcagcgatat ccctcccaca tccatcttga tagtcacata tagtttgctc   3000
tcttttgttt accctaatgt catctgctga ttcaactctc ccatttcagc atgatgcctt   3060
cacaaagccc atatcatgct ctcagtagat acttttcttt cccaaaccgt gaccaccagg   3120
cctggtggac gggaaagggc cctcttctcg ggaatatgct cgcggatgct ggatacccgg   3180
aacaacagca gtaccagtat ctcaccttat tcaacttgca tcttatccca gccttgggac   3240
cgtccgaaag ccacggtgca ggcatcgacg gagcagaatg gaaatcgctc ctgtcgggtt   3300
ctgggaagct cgagtttagc atgacatacc gaaaatcggc ggtttcgttg cgcattgcct   3360
ttgagccgac gagcttgctt gcgggtacga agaaggatgt gtttaataaa cggcgcacgc   3420
aacagctcct gggtgatctt gagagacttg acatcgacat cgacacggtg ttgtatcatc   3480
ctttatttga taccctggtg gtgtccgatg aagaagaggc agcgttgcaa aacgctggga   3540
ctgtgattcc cgactcgtct aggacacagc agctgctcgc tttgaatttg attgaaggga   3600
atgttagagc tgatctctat gtctatcctt acgtcaaggc gcttgccact ggaaccgcaa   3660
gttcgacgct tttgtgggca gccgtgaaga agatagatcg gtataacaga tttcgggatg   3720
cgttgtcaat cctgaaaggc tactttgaaa catatccgtc ctcaactaca aacccgatgt   3780
ttctctcaag tgacctcgcc gcaccaagga acgctttctg ccgtctcttc ttttccgaaa   3840
```

```
cgaatttcag ttgggagaga gtgcaacatc tatggaccct cgggggaacg ttaagcgata   3900
agccaactct caaaggtttg gaacttgcaa aaatcctctg ggacattttg ggaatttcca   3960
cagcgccggc atccccagac tcatttcctc ttctattcac attcgaactt cgtccggaac   4020
agccatacct gcgacaaaaa ctcggcatcc cagtctctgg gttgacggag agcgcaatcg   4080
cgaatgcttg cgtcgctttt tttgaacgtt tgggctggga tgaccatgca gcttcctatc   4140
gaaccaactt gtcagcttac tagtgagtct ccctttctgt tgtccattga atgcctcgaa   4200
ttaatgcccg ctttttcaag cccggaccaa gacctcaaca agccgcttgg caaacaggcc   4260
tggcttgctt tctcctatgt tagcgaagaa ggcccaagct tgacggtaca ccactattaa   4320
tcaggcgcgc tgcttggaga actgatcccc gcggatgatg agtttcgttt ggtcagaata   4380
gaggagtaag atttttaaa cgtctaagtt gtgtcacaag ggcaaagtcc gacgatagcc   4440
ttgtgctgtg ttgcagagcc gaataaaatt atacgcaaaa tgacaggagc attggccgtc   4500
aatatcaatc catcttttgc attggtagaa gtaggccaat ggaaacatgc cgtccatttc   4560
tttttttct caagactacg aagggagaag actttgctag agctccggcc caggcaatcg   4620
gagtatgtat gcttcgggac tggatttcat caatgccgcc cggattgaaa gaaaaaatcc   4680
gccgagcatg ttgaacccac atccacccgg tcaaaactgc aagcctcggc gcgatacatg   4740
aaagtgtgct tgcgaaaggg tccagaaatg agaaactgcc ttatccatct cccacttctg   4800
gtcttgctcc cctacttatc ataatttttt cttcacctag tccttcaagc tccttttcct   4860
gttccccaac ccgactggga tcaagatggc acctaccagg agatctagag acctacttcg   4920
cgggaagaat gtcctcatta tcggtggaac atctgggatt ggttttgccg tggcccagct   4980
ggtgatagag cacggagcca tggcatgcat cgcgggctcc aatccaacaa agttgggaaa   5040
ggctcttgat gccctgaagc aacacccaga ccgcgaccct atagctattg tccagagtgc   5100
gacgtgtgac cttttcgacg tacccaatct tgaacagaac ctcgacaatc tcctcaagct   5160
ggcggccggt gattcgaaaa tccatcacat cgtcttcacc gccgcagaca tggtgcagcc   5220
tccgcctctg gcgtcagtca cgattgagca gatccagcgc gttggcacga ttcgatttac   5280
agcaccgatg ctggtcgcca aattgcttcc gaaatacatg gagctctgcc ctgaaaattc   5340
gtataccttg accagcggat cgcatgcaaa acagcccgat ccgggatgga gtcttgttac   5400
gggatactgc ggcggcgtag agggtttgat gaggggcctg gcggttgaca tgatgcccct   5460
gcgagtcaat gttgtgtcgc ccggcgctgt tctcacgccc gttttgcggg atatcctggg   5520
ggactcgttg gagatagcgc tcgatgcggc gagaaagaag tcgactaccg gaaggattgc   5580
acggccagag gacgttgcgg aggcatatct ttacattatg aaggatcaga atattactgg   5640
cactgtcttg gagaccagtg cggggatgct tttgcgctga agagccccca tctgcagcgg   5700
tgcgttttac tttcggagta taggaatcag ttgtagccag ttacttgctc agtaattgaa   5760
tatggacagc aatagtctca tttaatctcc atatctcaaa agtcgctcaa tatagatacc   5820
tagggagtca ggatattcag ttggatgacc atttcgactt gaccaacgca aaacacaaca   5880
gtttttatta ggagagtccg acagtgggta cggtctctac atagctaata ccgtattcaa   5940
tttggtaacc gtctctccca ttgtttgtgg atccaatcct tgaaggctgt caatgacccg   6000
tccgtaactc cctgagcaag cttcgcctcc ttcttcagag ttgttgcagt gtcaatttca   6060
ctttcatcag gcacgaacca tttcccgcca ttcgaataca ttgagtgaaa gatcgcgcgc   6120
atctcttctc gacagctcgt gccgtcgagg ggaatgtcca cccacgattt cagtctcacg   6180
tagcgcgcct tctctccggt aactgtaatc caatcccacc gtcagtaagt cctctccatc   6240
```

```
tcgaagcccg aaaaatcgat tcggaggaaa tgaatacatg ctgtgccggt ttacgtacct   6300
tccatgaaat cctccaccat tttttcaaat gaaatcagtt cgcttgatcc ctgaattgtt   6360
ttgagatgat aggaatccgg atccagaaaa atgccatgga caatgtcacc aaagtcgtct   6420
tcaacgctca cccagggcat cctctcatca ccaccataag gaggagtcgc aagaagatat   6480
tcgccggtat cacgcttgaa ccaagggaaa ccaccgagag attgacagaa cgactccgca   6540
aggaacgctt ccataaacga tgctggcacg ataggtgtga aagtttggaa gccctttctt   6600
ctcccatatt gttccacgta gtacttgcct acgcaagacg gtcaacattt aggccgaagc   6660
atgggtcatg ggactgttgc ttgagtgaac agaaatatcc ccttactttc aaagccctca   6720
ctgtggactc tgccatttgt gtacttgcaa aggttgaggc cagaactata cacgacgtgt   6780
ttcactccag cttctttcgt ggcgtcgagg acggttgaac caaggtcata atcgctacgg   6840
ccaccgggga ttttataaat ctatcaagtg tcaataagat cagtctcatt cagccatctt   6900
tgaggacagg ggctagaaaa aactagctta cttcttcgtc agaattagta ttaacaaatg   6960
caccccagct acccataaaa gcactgacag tctccgactt gttgaagccg tctgctttga   7020
ctaactctgc gccgagtttg gcacatgctt gggctttctc cgaagtaggg tctcgggtga   7080
tgactcgaac atggaacagt ttgtctttgt gtgccagtaa tgatcggacg acactactgc   7140
cttggtttcc tttgattgga aatcgggctc tacgttagct agactaataa atcagacatg   7200
tagtcgacgg gggattgctt tacgcaccag taccaccaaa aactgtgaca agtctctttc   7260
ctgtatccat tgttccagtt ttctgtgata gatgtttttc tcttgaatcc aggcgtcaac   7320
gtgcaacaat tcgctgcctt cttggtgcga gttctgagaa ggactcgagt gcccagctta   7380
aaaagcattt ttcccaatgg agtccataag acacaaaacg acttatcaga tggcgcatct   7440
gattgatttt ccaaccggga tgaccttcac tagtcctgat cgaaatagct acctagttag   7500
ggtactgcgg acggtttcca aacacacagg ttgggatgag aatacttggg acttgggtaa   7560
actggagaat tatgactggt gccacctaat ccggatcgct agctggttag gaacaccttg   7620
catccggtgt aacgtttgaa gatcctgagg ctaattcagg tctcatggct ggcacctcgg   7680
acctggcccg tcctgtaatt gtccccattt gttcgatcca cgggaaggaa atccatacag   7740
actctgtgcc cgatttccta gcatcgtcac ctgtgacctt atctcacctg gctgctgatt   7800
gccccgtaaa agcgactgcc caaaattgga ctccctgctg agagaagcgg ggctagtaat   7860
atgttcagag cggtttcaaa aaacccataa gacctacagg agaatcaaaa agcctcaaag   7920
tcagggccga gtggtagata ctctgcctga ttcacctttg atcttccgcc catcatatcc   7980
ctatatcaca acttagcaga cctgttcata gtccgagctc ttccaggtag ataaagacga   8040
cagaaaatga cagcaggtcc gatgggaaac aaaagcacgt cagatattga cagtgtgctg   8100
gtatataagt cgctttcacg atatctcaag ttctcggaga acgaggaagg ttggtggcat   8160
aaaacagcgc ctctgctcaa caaaatattg gccgctgcga aatacgatgt gcatctccag   8220
tatcgatatc tggtattcta ctatgccgct tgcgtttctg ccctgggacc ttatcctcag   8280
cgattctcga gttccatcac ccgaagcggc ctcccagtcg aattcagcgt caactatcaa   8340
aacaattcga aaccgatcgt gcgcatcgga tacgaaccga tcagtcactt gagcggaacc   8400
gaacgcgacc cttacaacca taagacggct tccgagatag tcgctaccct ctcaaagatc   8460
caacccgact ttgacccacg gcttttcaac tactttgtcc atcagctgag cgtcaacaaa   8520
gccgagtccg atgtattaaa tggtgccaat gtcgaaggta gcgagatgaa atctcaaact   8580
```

```
gcctttggat ttgacttggt caacggagag atctctgtca aggggtatgc ttttcccgcc   8640
atgaaatgtc aggtatcgca acagtctctt tcacaattgc tcaaggcggc aattaatggc   8700
ttgaaaggcg agttcgactg tgcctttggc ctcgtcgatg agtatatgga gcgttgtggc   8760
gggtacaacc aattctcgtt tgtctcctgg gattgcgtcg ttcctgcgaa gtcccgcttc   8820
aaggtctatg gagtccacaa cgatgtaacc tggaaaaaga tcgaagatat ctggacactc   8880
gggggccaag ctaccagcgg aaatgtcacc aagggcctgg agttgttgaa ggaattgtgg   8940
acactgattg acttggacga aggtgaacgt gggtacacgg gacgttttga cgatgcgaac   9000
gacaatggga gcaatatcca gagtccaatg gtgtggaatt atgaactcag gcccaacaat   9060
ccatggccgt tggcaaagtt ctactttccg gtgcacgggg aaaacgacat gaagattgtg   9120
aaaggcttag cccgattctt cgagaatcgg ggttggactg agctggcccg atcctacgtt   9180
cagacggtgt cctccttctt gtaagtcctc tatgccaact cactccaatt cgcgctccta   9240
gcattggatc cgagtaccat gagtgatggc agaaataact aacgggttct gagtagtcct   9300
gatcgagacc tgaatcaaac gcagcgcctg gtatcgtgga tttcattcgc ctacactgaa   9360
aagactgggg tatacctgag tgtttactac cattcttcag ccgattatct atggatatcc   9420
gagtctgggg aaaagagagg tcaaggagat ggtgcttgac tctagtcttg gatattcgac   9480
tgtctcgtgc gagaaattat cccagccagg ccggactaac gtgcgagtta tcgggttgtc   9540
ctctagaata agtttatcga ggcttttttt tcggtttccg tagtcaagaa aatgtcccca   9600
agaactttca cccgtattct gtgtagtgga catccattgg agcatgctgg gtcgaaaact   9660
tcgtagctac cgatgtgttg tgaagtcggt cggaagacca gtgccaacca gcggttagtt   9720
accacttttg gcttctctga aagatagcca aatattgtaa gaaatggagt ggcaatctag   9780
tgctatgctc cggacttcgt acggagttgt gtatttcgat tttgagtttc cgaacgggca   9840
acctaggcgc cccaaaaacg agctacagct ggaagaaaat gtttgatccc agggtgcgaa   9900
acagatttgt gacacataag ccactgggcg atttttgaat ctggctacaa tcgtgatgcc   9960
attcgaacaa aagctctgat tctgcaatgt gggcttctgg cgcctggtgc cggtctggaa  10020
gagctgctgc agacttcagc tcctcacagc ccgtatccat atgctttcgg tcagctggag  10080
cccgcgcatg gaagcatggc gccttgccga atgtccatct tgtattacac acgatatttc  10140
gataacaact gcccatcttt tggacagcca acgaccaacg ataaatgagt ctgatgtaat  10200
tctagcccgg gacagaagcc tcaggcgatg gaggtcatat ttcaggaaca ttaagccgct  10260
catatctgcc actggctacc gagacggtga gagatccgag ttcaatttgg gggcccgaac  10320
ccttaccgtt ccgacgatgg gcacgcaaca tgaggtaaaa gggaagcggg accgacactt  10380
tcaggcttga ttaagtgaag ccgaccagag agtatggaga tccattctgg ataatgcaaa  10440
gcgaccctcg ctcgattcaa aacctggcca aagcatgcca tagtccactg tcggccctcg  10500
tgcacattcc ctcatcgtcc cagcgttcac ttcccactcc gactctggta atgaacagat  10560
cctctggatc ccatgctcgc tttactttca agagccggtc gtagttcttc ccccagaatg  10620
aatcctggaa gtaaacttca ttgggataag ccactgcaag ataagccccc tttcgaccac  10680
cctcgagaga acgaagtcgg ggcaattgat cattctccaa ttcgctctca atggatttga  10740
gggtttctaa tgtgtatcct ggaggcactc cacgaccgac tgtgagtgaa agaagagcag  10800
atcgccagtc tggatggaca gcactgttga ttcgattttt gttgttcaca acctggccgc  10860
caccaaaagc gtccacgcta aacgatgatc caggacccaa ccgtaggtcc gacaaggcgc  10920
tggtcacttt ggcagggccg tccttggatg cgacaagatc ataagacagg aacacgctgc  10980
```

```
ctgggatcac actgatgcca gccaaatcga cgcctttggg ggctgcgaga aagcggctga  11040
ggttgccctg gaagtcatgg gacaatttaa aggggatacc gaagtcatcc aaagcgcgct  11100
ggagtgcaag tagtgaaact gcaccctttt tgttaaaggt atatccttcg aatgaggcag  11160
aagccccgcc cgtggaggaa gcaggaagaa ctatcatacg ggcagaattg ccggcatccg  11220
taagctcagg taggattgaa agcacggttt tgacaccagc ccaaaatatt gcatccgccg  11280
agggggtatt gatttgaatc ccggtcaccg tagccggaag gtcagcgaac gcgcggagtg  11340
taacagaagt gatgacacca aatgtaccgc cacctcctcc acggactgcc cagaatagat  11400
cctcattttg atattggttg gcaatgatat gactgccctg accgccaaac aaaacaaaag  11460
aatgttagtg atgcctcaat agttggactt ccacacaatt gactctggat atgaacctac  11520
atcggcggtc acgatttcca cctgaagaac atggtcggag ccgaggcctt tcgatggact  11580
caatattccc atcccaccgc tctggatgaa gccacccgcg atgccaacag tactgcaggc  11640
ccccccgagt acaacaaatc ctttctcaga gccagtagcg tagagctcgc ctgtgagaat  11700
gcccgctcct atagtgactg cggggcccat gggctcagcg gatccctgag taataaaggg  11760
cacgaaattt tccgtgtaat tgatgccctt caacccactt gtaagaattt gcagggaacc  11820
aggggcactg gatcgccctg ccatatcgtg accagtgttg cgaacgacta ggcgtaggtt  11880
tcgatgtttt gcgaaggaga ctgcctgttg aacctgcttt gtcgactcaa ccgccgcaga  11940
gtacagtggt atacgtccct gagcgcaacc atcgacagct tcgcgtacaa tctgacaact  12000
ctggtttttc tcaggccagc tttcccagct cacgagctgt agggattcta aacaataaat  12060
cagccgaaga gccaggtgct cagaaagata tatatcaaca taccgggatg gtcaacacgc  12120
caggaagagt tatgggtcat cgcaagcact tcgtcacatt tctccttgtg gtaggccgat  12180
tgctgacatg gaagcccaac aggcctcaga tgacgtagct tgccatcgat tgattgattc  12240
aatgatgacc actcagcggt agtaggccaa caagcatctt cttgacgaca acggcaaatc  12300
gtgctcctcc gttgggtttg gatgccaatt gctaggataa gcagggcgaa agtggcagtg  12360
tatttcattg ctggcaacat cactgacact tgtacggata gtctgaagag gagttaaaaa  12420
gaattttgaa ggaagcagtt caatcgcaga gcagacctct tctcaccttg cacaatcttg  12480
caaggtggga aaagaatcat tgagggaaac aggagcagtt ggtaccggta gctgcaacgt  12540
cccacaaggg accaatctcc ttaccaggaa acgagtcaag cgaaatcttg gagacgaaag  12600
attcgtacag ccgccaactc cccccactgc ggcccggtga actttgcgat tcagcttcct  12660
aataagatcc cgactaactt aaagtctaga tgtagtgatt aggtgagatt ttatgatcat  12720
gcatgattgg cggtcaaaat gttgcctctg tctatcaata ttagcatcca cactgcctgg  12780
ccgacaatga tcgtctggcg caataactta ccaaaccacc cacttagata ccggacactg  12840
gaggcgggtt tgtccgaagg ctgcctgaac tcatgaagtc ggagatatat attatgcact  12900
tttatattct gaccgtgtgt tgcttaaatg tcatccatat cccaagccat acctgtccga  12960
agttaataat cgcacctggg catcgaaaag aaaaacttac tcatcgacaa tggtccaacg  13020
gcaactcata tctaaacggc tcgggctcct atccatggat ggagctcatg agccaacaga  13080
acgtcttcgt atattgtcga gaacgagatg cccgtttcaa tcaaacccta gcttggactt  13140
catgtctgat gatccgcttc tgtcgtcccc aacagaggca atatgtttga atcattcagt  13200
gacagacctc cggctggctg cggcactgaa gctgagctgg acatttctct tggctcatta  13260
ctctggatcc agcgaaatac cgcttgatat ccgactcgaa tataggtata ttgatggaag  13320
```

```
cgaaacgaat ttcgagccat tcgacgcgac attcgaggtc gacaaaaagt ctctgatcga  13380
ggactccatc ggcatgatcc aaaacatgct cacaccgtcg acacgcccac acagcctgag  13440
taatggaata aattcgtctc agagcgacaa acatgtacca gaggcccagg tctcattcac  13500
cttcagcagt ggttcacgac ctgtgcttga aaaaggtgcc acaactcggt atgccgccac  13560
tgtcttggaa ttagagtgct tgcaggggct gaagaaggaa tacctttgcc ggatcaactt  13620
caacaggatg atgtggaacg tggaagaggc gacgggaatt ctgcgccaat tccgccatat  13680
tgcccaacag atcgtttcag cagatgtctg tgccacactc agccaaatca acttgatgtg  13740
tgagtccgat atcgaacaac tcaaacgttg gaactcaact gtccccgatc cggtgcttgc  13800
ctgcatacac gagttgtttt ctgagcaagc aaaaaagaat cccacggcaa ccgccgtaca  13860
aacgagtgaa ggaagcttcg actacgggcg tcttgatgaa ctgtcttctg ccttagcatg  13920
ccacctgagt tccaacggtc tgacaagagg aacacccgtc ccactcctct tcgacaagtc  13980
catgtggatg gttgtggcca ctcttgccgt gctcaaggca ggtgccactt gtgttagcat  14040
ctgtacagga cttcccacga aggctataga agacatactt gagcaaaccg ctgcgcagct  14100
cgtccttgtc tccgaatcac aaggcttaag attaagcgaa acccgaaccc aggttgtttc  14160
cgacaaaaca atgcagatat ggcacaccat gtctggcaaa ccagaacttc ctcaatccga  14220
ccctacggac ctagcgtgca tcatattcac gtccggaagc acgggaaagc caaagggaat  14280
tatgctggac cacatagctt tggttaccag tataaggaat cacggcccta gtttggggat  14340
ttcctccagt tcgcgtgctc ttcagttctc gtcctacgct ttcgacatga gcttttatga  14400
gacgtacacc acgctattgt ctggaggctg catttgcatc ccttccgaga ccgaaaggct  14460
caacagtctg cctcaattta tctgcgacca caatgttaac tgggcgtttt taaccccgtc  14520
agtgctacga gattttcacc ctagtgagtt tccatccctc aggacactcg ccaccggagg  14580
ggagcccgtt ggagcggaca tcgcgaacga atgggcagga agactgcaac ttttcaacct  14640
gtggggtcca gcagaggcaa caatatgcgc gaccggacca atattgccag gcgtctggat  14700
acccgggaca tttggcaaag ctgtgggctg cattgcatgg atcacacagg cagagaaccc  14760
ggatgagctg gttcctattg gggcggtggg tgaggtgctg atcgagggtc ccgtgctggc  14820
tcaaggttac tcgggggacg ttgaaaagac gaaggcttcc ttcattccgt ttcccaagtg  14880
gagagaaagg ttcgaactga caccgcgagg acgggtactt ttcagaactg gagaccttgc  14940
tcagtacaat ccagacggta caatacggta tgttggaagg atggggaccg tagttaaagt  15000
cggcggccaa cgagtggaca tcgacgcggt tgaatatgca ttgcgccgga tcgatcggtc  15060
ttctcacata gcggtcgagg cagtcgaact agagaaagaa actggtcagg gacctacttt  15120
gatcgcgttc ctgtctagcg atatgaatgg agtgtccgga tctgaaaaga aacggtgctg  15180
ttcaatcgac cctggatccc gttcctggga agcctgggca aatattgcaa tacgtctcca  15240
ggacactctc gctggagtat tgccacggta tatgatcccc catttattca tcccagtttc  15300
aacgattcca accaccccaa gcggcaaagc caacaaacgc cagttgcaag ctcttgtcct  15360
gggccaatcc aaggcacacc tcctgcagtt gtgccgacag cggtcgccag atgcctcata  15420
cccagagcag catctcactg agaatgagac actgttacgt ttgttagtga gtgacgtgct  15480
tgggattgat agggatcacg tcgcaatgaa ctcaaggttt tttcaccttg gggcgactc  15540
ccttgcagct gtgaagctgg ttgcactcgc tcgacaacag ggtattcagt taaaggtcga  15600
agcaatcctt caatcttgta gccttcgcga agctgctgga accatgatct ctgctggtga  15660
aaagcagaaa ttgcagtcaa agacatcatt cgccattaac aaatgcgatg acaaacttgg  15720
```

```
gctacttgaa gaagcgacgg tccagtgcgg aatttcagag tccgatatcg aggagatata  15780
ccccagtacg ccgttgcagg aagggcttat aaccgtaact tcaacttttt cagcatcgaa  15840
gccgtatgtc gacaaaatcc tcttcacttt gtcagccaca gcagatttgg accgtgtgcg  15900
agacgcatgg aaccacgtcg tcgccgcgaa tgatatcttg agatcccgca tcatcctatc  15960
tccggcaggc aaagcgttca atgttgtggt cagatcagaa ccatcctggc aatattacaa  16020
gactgtccag cagtacctgg agaacgacaa tgcgcaagac atgactttcg gaaaagagct  16080
catcacgttc aacctcatag caagccatga tcaatctgct tccgcccggt ccattgggat  16140
aacaatacat cacgctctgt acgacaattg gactgtctcc ctgctgcaca agcaggccga  16200
ggatgcatat cgtggagaac ttgttgagcc atgctcattt tcgacatttt cccactatgt  16260
ccttcaacag agccctgata ttaacaaaga gttttggcgc aagcaatttt tagatttgag  16320
ggcgggtacc tttcctgagc tgccgtcatc tgattatgta cctcgtgcaa actcatcgtc  16380
tcagcacctg tacaaggggc agcatcaacg cagagatttt agcatggcaa caaatatcca  16440
gctcgcttgg gcgctcctgc tctctcttta cacgaattcc cccgatgtcg tttatggtct  16500
tgttgtcaat gggcgtatgg ccccgatgcc gggggtcggg ggattagttg gcccaacgat  16560
tgctactgtc cccttccgaa caaccgtgga gaggagtatg agcgtccagg ccgccttaga  16620
ggccattcag aagcgggttc tgtcaatagt ccctttcgaa caaaccggtc tgcaaaacat  16680
tgcgcgaatg gggggaaggcc ctaaaactgc ctgtaacttc caaaacctcc tagtgataca  16740
acaggacctt gagtttaagg gcgaagggat attctgccgg agacaaaact tggtcggagc  16800
ggtaaacaat ttcccaggat atgggattat acttctctgt agtgcgacgg agcatggatg  16860
ggcatttgaa atactctata gtaactcatt aattccagaa acccgcgcac gtcggattct  16920
cctgcagctg gaccacctgc ttcggcaact cgaggttgac ccataccgac aactggctca  16980
actggagctc ctctgtccat cagataaaag caaactaaca tcctggaaca cccagttgcc  17040
cattcgagta aacgcgtgta tccccgaagt cttcggagcg caatgccttg tccggagcga  17100
gcgcactgca gtgtccgcct gggatgggag cctttcgtat agggagctcg atcgattttc  17160
ttcgatagta gcaaggcatc tccaagcggt gggggttgga aagggaacta ttacacctat  17220
cctgtttgaa aagtcgcggt gggtggttgt cgccatgctg gccgtgctca agaccggagc  17280
ggccttcgtc atgctagata caaaccagcc cctgcaaaga aagcaaggta tctgccgtgc  17340
agtcagggct accaccatcg ctacgtctgc ttcgtgcgcc catgagagca aagttctggc  17400
gaactcgata tatgttctcg acgaagcgag catcacaaag accgacacaa atcaattcct  17460
tcccctcgtg gaggtttccc ccaacgatct cgcgtacgtc gtcttcactt ctggctcaac  17520
cggagaaccc aaaggcgtcc tgatcgagca tgcgtcgtct tgctcggcat caagggctca  17580
agccgcgaaa ttgggtatct cgccggattc tcgggtgctc caactctcat cttatacctt  17640
tgactcgttc gcagttgaga ttctcgcgtc tctattggct ggatgctgca tttgcatccc  17700
gtcggaaagc gagagcagca acgatattgc cggtgccgtt cggcgatttt cagcgacatg  17760
gctatgcatc acaccctctg tattgggatt aaccaaccca gatgaagttc ccagcctcaa  17820
gaccgtcgtt gccgtgggag agtcagcccg accgagccag atcagactct ggtcgacaag  17880
agtgaatttt atctgcggat atggaccttc cgaatgctca acgggtgctt cagcacagct  17940
gatacggtct gcaggctctg acccccgtat catcggttcc ggcatgggct cctgtctgtg  18000
ggtagcccac acagatgatc acaatgtcct ggtgcctatt ggtgccatcg gtgaacttct  18060
```

```
catccagggt ccaatcgtgg ggagaggcta catgaattca cccgaaaaga cgcgagcggc  18120
ctttctcgag agcacagctt ggattccaga gtttagacag gttgccacag aacgttttta  18180
caaaaccggg gacttggtcc gtcaaaatga ggatggatcg atcgtctatc tcgggagaaa  18240
gaaccgagag gtaaaacttc gaggccagag actagatctt gaagaagtcg agaaccagct  18300
ttcagcagca ctagaaatgg acattaatat agtggctgaa gttgtgaagc ccaaaggagt  18360
cgattcccag ccggtactta ttgcattttt ccaggttgtg gcagatgtgg aactccggtc  18420
tgacaatatt acattcctcg agttaaatcc ggatatcggc cttcggctcc tggatgcgga  18480
agagaaattg cggaaaatcc ttccccctgt aatgatacct tctgtatatc tacaggttca  18540
aagaatgcct ctcacaatgt cggggaagat gaaccgacag gccttgcgga ataaagcatc  18600
caccagaact ctctcgcagc tcttctcgtc tggctcggtc agacacgagg acgattatct  18660
cacacttcaa cctcacgaaa gcactgccct tttcgtttgc caagcaatct gcggcattat  18720
gagagacaaa attgacgata ccaagacctt gattgcaggg aaaaatgtca atctatccag  18780
gacaggaatg gactccatcg atgccatgat gctcgctcgc acaatttcgc ggcatttcgg  18840
catcacccta tcgatacgtg catttttagg tagcagcgta accgtccgtg atatcgccag  18900
gctcattgaa ggggttaaga gtgaggataa tctctcacaa ttcgatctct atgccaagta  18960
cgagtccatt tgggaagagt tgcgaggcgt ggtcaggggt ttgaccccgt cggacaagcc  19020
tcaactctgc gacaagacgc ccgctgggat gagcgtcttc ttaaccggcg gaacagggtt  19080
tctgggaaca catattcttc gacagatctt gcaagatcca cgtgtcgagc tcgtgacagt  19140
cctcacacga gctgagtcac cggcccatgc cttgtccaaa attgtcgagt ctgcgaaaat  19200
tgcgcaatgg tggcaggagt cgtaccggaa ccgaattgat gcatgggtag gagatttggc  19260
ccggccacgt ctaggtctgt ctgatgatca ttgggctaga ctctgcgggt atggcgagca  19320
caaattcacc tcgatcattc ataacggggc cgcggtacac tggggatacg acttcgaaaa  19380
gttgaagcct gtaaacgtga tgagcacgtt ttggcttctt gtttcgctct tcatagctgg  19440
ccctttggtt aatttcacgt atgtgtcggc attgttgccg gaatgcgatg gactcacaga  19500
ccgtgagatt gcactcaaaa cctccgatga tggctacagt cagaccaaat acgtgtccga  19560
gcttctggtt aagaatttta aggagcagct ctgtaacaac ccgatcgcga ttgttcgccc  19620
agggttactg atcggatcgg ctgaacacgg tgtggccaac gtcggtgact acttatggcg  19680
cgttgtctcc agtgcgtttt ccgtcggggc ttatatttcg gagaaaggag acgcgtggat  19740
ctatatcgca gccgtcgatt gggttgccaa tcaagttatc cgggaagccc tatatgagag  19800
taccactgac cttcgaataa tcaatgtaac ggatggtctg acagtgaaag agttttggag  19860
agcgattcag attgcgtcgc cccgtcaatt gaatgctctc caatccgaag actggctctc  19920
tttgatccgt cagcagctgg atgtcacggg aaagtcccat ccgctatggc cggtaatttc  19980
tttcctggag tccagtaaag gctgccttgg gttttcgcat aacctcccgc cccaggcaca  20040
ctcactttcc tccatgatca tcactgcgtt gattaaaaac gtgcggtatc tggcctcgct  20100
ggggttggtt tcgtggacca cgaccggctc taactgcgat cactcagttc aacagcgtat  20160
ttttagacgc gtcctgtga                                                20179
```

<210> SEQ ID NO 2
<211> LENGTH: 1980
<212> TYPE: DNA
<213> ORGANISM: Malbranchea aurantiaca RRC1813

<400> SEQUENCE: 2

```
tggtagcttt aactccttcg aggggtcgta tttaggcgca gtattccagg cagcgtaaag     60
taacgcttct tcttctgcgg tcagcggggg atcaaaggta acggccgttt gcggctcggt    120
gcccagaaga ccgcatgagt ggcacttttt ccaatctggg cggagttgga gccatgcccc    180
gcaacccgag cattgtctcg tatagatgtc cctgcttgtc ttcccttcga cgaaattcaa    240
agaccgatcg aaagagcgca ggatcgcatc ccaccggaga ctgaagtcgt ctgcggccac    300
ggcagcactt ttaattcggt tcgaaaacgc aagcaactca tcaaccatcg catcgggaag    360
tcgctcatcg agggggacgg tttcgatatg ctcaatgcat ttctgtgcga cttgttgata    420
ttcaggcacc atggctcccc aaacccattt aatcgcgtaa tgtgcgaagg tttcaatgtt    480
aacatctgac aaatatcgct ctatgccagc gaaaaactgc cagaggcatg ccacctgggg    540
acctaaacgt gtatcgcgat aacagacgta gttaaatcga ttcatttgct cgagtgccgg    600
aactagggac ttgcaataat cgtcatatgg gaccagtaat tttcgaatag aggactccgc    660
cgcatctgca ggcgcacttt tcccaatctc cacaattcgg tgcgaaagct gtgcggccca    720
tgttgaagtc gacatgccaa cattaatccc cggagaatag agcgggttgg tgaaaccaca    780
ggcatcacca atggcaagcc agccaggtcc agaaaccact ggagactggt atgccagcgt    840
cttacggatg aaccatgtgg tcccagggcc ataaagattt tcaataagct caaagtttga    900
catgaactgc tgaagcagct catacttctg aacaaagtag ttgaattttt gctctgcctc    960
acgggtccca taggctgaga gatcttccgg gtacttgaca tcattgcgca cggcaaagcc   1020
aatacttgtc acccactgaa acttgagccc aaacatcctg gcaagctctt cagaactcgg   1080
gagttcatca ccaggtactc cggcgtcagc gcattcgagt atgtatgtca ccatatccat   1140
caagttcgct atgaggctcc cttcccaaga gggtagacga ataacccaga cccaaccttc   1200
cggaaaacac aggtggtttg tgtgatcacc ttcatagaga tcaaagggaa tcttgctctc   1260
atcctttggg gcagtgaaat aaccccagaa ggcgttgcag ttccatccat cgaatcggtg   1320
tcgggggggct ttcttggagc aaaattggcg gaagcggcct gttgcgtcaa cgaagagggc   1380
tgaatctatt gtcttgggtg tgctatcata tttgccccgg gagactgcga tcttgttgcc   1440
ctggccaccc ccttggacca ccgtgctttt aaaatccacc tcccggccgt gatagacatt   1500
gactccattt cgttgcgcaa gaattgtaaa gagcagctcg ctcattggcc gctcaatctg   1560
taaactggct aataccaaac ctggagcccc aacactgcag aagtctgtgt actgcccctg   1620
gttctctcga tcaagaaagt aaaagcacag cccatccttg agtccgaata gtcgaaggag   1680
gtatgccgcg gagatgccgt ggagtttgca ccaggtgtaa aagataggta gagtgctctc   1740
gccaatcttg taaccaggcc tagtgttctt ctcaataacg gagatcttga ggttgttcgg   1800
tttatacttt gaagcgtgaa gggcatagat cagaccatgg ataccagcac cgcccaccac   1860
cacatccgat tcatctggga gctcagatcc agtaggatta ttggagttga gaatctcagc   1920
gtcgctgaga ttgcctgccg cagccctctc ggtaaacgta tactttggtg tcggcgccat   1980
```

<210> SEQ ID NO 3
<211> LENGTH: 660
<212> TYPE: PRT
<213> ORGANISM: Malbranchea aurantiaca RRC1813

<400> SEQUENCE: 3

```
Met Ala Pro Thr Pro Lys Tyr Thr Phe Thr Glu Arg Ala Ala Ala Gly
1               5                   10                  15

Asn Leu Ser Asp Ala Glu Ile Leu Asn Ser Asn Asn Pro Thr Gly Ser
```

```
            20                  25                  30

Glu Leu Pro Asp Glu Ser Asp Val Val Val Gly Gly Ala Gly Ile His
        35                  40                  45

Gly Leu Ile Tyr Ala Leu His Ala Ser Lys Tyr Lys Pro Asn Asn Leu
    50                  55                  60

Lys Ile Ser Val Ile Glu Lys Asn Thr Arg Pro Gly Tyr Lys Ile Gly
65                  70                  75                  80

Glu Ser Thr Leu Pro Ile Phe Tyr Thr Trp Cys Lys Leu His Gly Ile
                85                  90                  95

Ser Ala Ala Tyr Leu Leu Arg Leu Phe Gly Leu Lys Asp Gly Leu Cys
            100                 105                 110

Phe Tyr Phe Leu Asp Arg Glu Asn Gln Gly Gln Tyr Thr Asp Phe Cys
        115                 120                 125

Ser Val Gly Ala Pro Gly Leu Val Leu Ala Ser Leu Gln Ile Glu Arg
    130                 135                 140

Pro Met Ser Glu Leu Leu Phe Thr Ile Leu Ala Gln Arg Asn Gly Val
145                 150                 155                 160

Asn Val Tyr His Gly Arg Glu Val Asp Phe Lys Ser Thr Val Val Gln
                165                 170                 175

Gly Gly Gly Gln Gly Asn Lys Ile Ala Val Ser Arg Gly Lys Tyr Asp
            180                 185                 190

Ser Thr Pro Lys Thr Ile Asp Ser Ala Leu Phe Val Asp Ala Thr Gly
        195                 200                 205

Arg Phe Arg Gln Phe Cys Ser Lys Lys Ala Pro Arg His Arg Phe Asp
    210                 215                 220

Gly Trp Asn Cys Asn Ala Phe Trp Gly Tyr Phe Thr Ala Pro Lys Asp
225                 230                 235                 240

Glu Ser Lys Ile Pro Phe Asp Leu Tyr Glu Gly Asp His Thr Asn His
                245                 250                 255

Leu Cys Phe Pro Glu Gly Trp Val Trp Val Ile Arg Leu Pro Ser Trp
            260                 265                 270

Glu Gly Ser Leu Ile Ala Asn Leu Met Asp Met Val Thr Tyr Ile Leu
        275                 280                 285

Glu Cys Ala Asp Ala Gly Val Pro Gly Asp Glu Leu Pro Ser Ser Glu
    290                 295                 300

Glu Leu Ala Arg Met Phe Gly Leu Lys Phe Gln Trp Val Thr Ser Ile
305                 310                 315                 320

Gly Phe Ala Val Arg Asn Asp Val Lys Tyr Pro Glu Asp Leu Ser Ala
                325                 330                 335

Tyr Gly Thr Arg Glu Ala Glu Gln Lys Phe Asn Tyr Phe Val Gln Lys
            340                 345                 350

Tyr Glu Leu Leu Gln Gln Phe Met Ser Asn Phe Glu Leu Ile Glu Asn
        355                 360                 365

Leu Tyr Gly Pro Gly Thr Thr Trp Phe Ile Arg Lys Thr Leu Ala Tyr
    370                 375                 380

Gln Ser Pro Val Val Ser Gly Pro Gly Trp Leu Ala Ile Gly Asp Ala
385                 390                 395                 400

Cys Gly Phe Thr Asn Pro Leu Tyr Ser Pro Gly Ile Asn Val Gly Met
                405                 410                 415

Ser Thr Ser Thr Trp Ala Ala Gln Leu Ser His Arg Ile Val Glu Ile
            420                 425                 430

Gly Lys Ser Ala Pro Ala Asp Ala Ala Glu Ser Ser Ile Arg Lys Leu
        435                 440                 445
```

-continued

Leu Val Pro Tyr Asp Asp Tyr Cys Lys Ser Leu Val Pro Ala Leu Glu
450 455 460

Gln Met Asn Arg Phe Asn Tyr Val Cys Tyr Arg Asp Thr Arg Leu Gly
465 470 475 480

Pro Gln Val Ala Cys Leu Trp Gln Phe Phe Ala Gly Ile Glu Arg Tyr
485 490 495

Leu Ser Asp Val Asn Ile Glu Thr Phe Ala His Tyr Ala Ile Lys Trp
500 505 510

Val Trp Gly Ala Met Val Pro Glu Tyr Gln Gln Val Ala Gln Lys Cys
515 520 525

Ile Glu His Ile Glu Thr Val Pro Leu Asp Glu Arg Leu Pro Asp Ala
530 535 540

Met Val Asp Glu Leu Leu Ala Phe Ser Asn Arg Ile Lys Ser Ala Ala
545 550 555 560

Val Ala Ala Asp Asp Phe Ser Leu Arg Trp Asp Ala Ile Leu Arg Ser
565 570 575

Phe Asp Arg Ser Leu Asn Phe Val Glu Gly Lys Thr Ser Arg Asp Ile
580 585 590

Tyr Thr Arg Gln Cys Ser Gly Cys Gly Ala Trp Leu Gln Leu Arg Pro
595 600 605

Asp Trp Lys Lys Cys His Ser Cys Gly Leu Leu Gly Thr Glu Pro Gln
610 615 620

Thr Ala Val Thr Phe Asp Pro Pro Leu Thr Ala Glu Glu Glu Ala Leu
625 630 635 640

Leu Tyr Ala Ala Trp Asn Thr Ala Pro Lys Tyr Asp Pro Ser Lys Glu
645 650 655

Leu Lys Leu Pro
660

<210> SEQ ID NO 4
<211> LENGTH: 810
<212> TYPE: DNA
<213> ORGANISM: Malbranchea aurantiaca RRC1813

<400> SEQUENCE: 4
attgcctttg agccgacgag cttgcttgcg ggtacgaaga aggatgtgtt taataaacgg 60
cgcacgcaac agctcctggg tgatcttgag agacttgaca tcgacatcga cacggtgttg 120
tatcatcctt tatttgatac cctggtggtg tccgatgaag aagaggcagc gttgcaaaac 180
gctgggactg tgattcccga ctcgtctagg acacagcagc tgctcgcttt gaatttgatt 240
gaagggaatg ttagagctga tctctatgtc tatccttacg tcaaggcgct tgccactgga 300
accgcaagtt cgacgctttt gtgggcagcc gtgaagaaga tagatcggta taacagattt 360
cgggatgcgt tgtcaatcct gaaaggctac tttgaaacat atccgtcctc aactacaaac 420
ccgatgtttc tctcaagtga cctcgccgca ccaaggaacg ctttctgccg tctcttcttt 480
tccgaaacga atttcagttg ggagagagtg caacatctat ggaccctcgg gggaacgtta 540
agcgataagc caactctcaa aggtttggaa cttgcaaaaa tcctctggga cattttggga 600
atttccacag cgccggcatc cccagactca tttcctcttc tattcacatt cgaacttcgt 660
ccggaacagc catacctgcg acaaaaactc ggcatcccag tctctgggtt gacggagagc 720
gcaatcgcga atgcttgcgt cgcttttttt gaacgtttgg gctgggatga ccatgcagct 780
tcctatcgaa ccaacttgtc agcttactag 810

<210> SEQ ID NO 5
<211> LENGTH: 369
<212> TYPE: PRT
<213> ORGANISM: Malbranchea aurantiaca RRC1813

<400> SEQUENCE: 5

```
Met Pro Ser Gln Ser Pro Tyr His Ala Leu Ser Arg Tyr Phe Ser Phe
1               5                   10                  15

Pro Asn Arg Asp His Gln Ala Trp Trp Thr Gly Lys Gly Pro Leu Leu
            20                  25                  30

Gly Asn Met Leu Ala Asp Ala Gly Tyr Pro Glu Gln Gln Gln Tyr Gln
        35                  40                  45

Tyr Leu Thr Leu Phe Asn Leu His Leu Ile Pro Ala Leu Gly Pro Ser
    50                  55                  60

Glu Ser His Gly Ala Gly Ile Asp Gly Ala Glu Trp Lys Ser Leu Leu
65                  70                  75                  80

Ser Gly Ser Gly Lys Leu Glu Phe Ser Met Thr Tyr Arg Lys Ser Ala
                85                  90                  95

Val Ser Leu Arg Ile Ala Phe Glu Pro Thr Ser Leu Leu Ala Gly Thr
            100                 105                 110

Lys Lys Asp Val Phe Asn Lys Arg Arg Thr Gln Gln Leu Leu Gly Asp
        115                 120                 125

Leu Glu Arg Leu Asp Ile Asp Ile Asp Thr Val Leu Tyr His Pro Leu
    130                 135                 140

Phe Asp Thr Leu Val Val Ser Asp Glu Glu Glu Ala Ala Leu Gln Asn
145                 150                 155                 160

Ala Gly Thr Val Ile Pro Asp Ser Ser Arg Thr Gln Gln Leu Leu Ala
                165                 170                 175

Leu Asn Leu Ile Glu Gly Asn Val Arg Ala Asp Leu Tyr Val Tyr Pro
            180                 185                 190

Tyr Val Lys Ala Leu Ala Thr Gly Thr Ala Ser Ser Thr Leu Leu Trp
        195                 200                 205

Ala Ala Val Lys Lys Ile Asp Arg Tyr Asn Arg Phe Arg Asp Ala Leu
    210                 215                 220

Ser Ile Leu Lys Gly Tyr Phe Glu Thr Tyr Pro Ser Ser Thr Thr Asn
225                 230                 235                 240

Pro Met Phe Leu Ser Ser Asp Leu Ala Ala Pro Arg Asn Ala Phe Cys
                245                 250                 255

Arg Leu Phe Phe Ser Glu Thr Asn Phe Ser Trp Glu Arg Val Gln His
            260                 265                 270

Leu Trp Thr Leu Gly Gly Thr Leu Ser Asp Lys Pro Thr Leu Lys Gly
        275                 280                 285

Leu Glu Leu Ala Lys Ile Leu Trp Asp Ile Leu Gly Ile Ser Thr Ala
    290                 295                 300

Pro Ala Ser Pro Asp Ser Phe Pro Leu Leu Phe Thr Phe Glu Leu Arg
305                 310                 315                 320

Pro Glu Gln Pro Tyr Leu Arg Gln Lys Leu Gly Ile Pro Val Ser Gly
                325                 330                 335

Leu Thr Glu Ser Ala Ile Ala Asn Ala Cys Val Ala Phe Phe Glu Arg
            340                 345                 350

Leu Gly Trp Asp Asp His Ala Ala Ser Tyr Arg Thr Asn Leu Ser Ala
        355                 360                 365

Tyr
```

<210> SEQ ID NO 6
<211> LENGTH: 795
<212> TYPE: DNA
<213> ORGANISM: Malbranchea aurantiaca RRC1813

<400> SEQUENCE: 6

```
atggcaccta ccaggagatc tagagaccta cttcgcggga agaatgtcct cattatcggt     60
ggaacatctg ggattggttt tgccgtggcc cagctggtga tagagcacgg agccatggca    120
tgcatcgcgg gctccaatcc aacaaagttg ggaaaggctc ttgatgccct gaagcaacac    180
ccagaccgcg accctatagc tattgtccag agtgcgacgt gtgacctttt cgacgtaccc    240
aatcttgaac agaacctcga caatctcctc aagctggcgg ccggtgattc gaaaatccat    300
cacatcgtct tcaccgccgc agacatggtg cagcctccgc ctctggcgtc agtcacgatt    360
gagcagatcc agcgcgttgg cacgattcga tttacagcac cgatgctggt cgccaaattg    420
cttccgaaat acatggagct ctgccctgaa aattcgtata ccttgaccag cggatcgcat    480
gcaaaacagc ccgatccggg atggagtctt gttacgggat actgcggcgg cgtagagggt    540
ttgatgaggg gcctggcggt tgacatgatg cccctgcgag tcaatgttgt gtcgcccggc    600
gctgttctca cgcccgtttt gcgggatatc ctgggggact cgttggagat agcgctcgat    660
gcggcgagaa agaagtcgac taccggaagg attgcacggc cagaggacgt tgcggaggca    720
tatctttaca ttatgaagga tcagaatatt actggcactg tcttggagac cagtgcgggg    780
atgcttttgc gctga                                                     795
```

<210> SEQ ID NO 7
<211> LENGTH: 264
<212> TYPE: PRT
<213> ORGANISM: Malbranchea aurantiaca RRC1813

<400> SEQUENCE: 7

```
Met Ala Pro Thr Arg Arg Ser Arg Asp Leu Leu Arg Gly Lys Asn Val
1               5                   10                  15

Leu Ile Ile Gly Gly Thr Ser Gly Ile Gly Phe Ala Val Ala Gln Leu
            20                  25                  30

Val Ile Glu His Gly Ala Met Ala Cys Ile Ala Gly Ser Asn Pro Thr
        35                  40                  45

Lys Leu Gly Lys Ala Leu Asp Ala Leu Lys Gln His Pro Asp Arg Asp
    50                  55                  60

Pro Ile Ala Ile Val Gln Ser Ala Thr Cys Asp Leu Phe Asp Val Pro
65                  70                  75                  80

Asn Leu Glu Gln Asn Leu Asp Asn Leu Leu Lys Leu Ala Ala Gly Asp
                85                  90                  95

Ser Lys Ile His His Ile Val Phe Thr Ala Ala Asp Met Val Gln Pro
            100                 105                 110

Pro Pro Leu Ala Ser Val Thr Ile Glu Gln Ile Gln Arg Val Gly Thr
        115                 120                 125

Ile Arg Phe Thr Ala Pro Met Leu Val Ala Lys Leu Leu Pro Lys Tyr
    130                 135                 140

Met Glu Leu Cys Pro Glu Asn Ser Tyr Thr Leu Thr Ser Gly Ser His
145                 150                 155                 160

Ala Lys Gln Pro Asp Pro Gly Trp Ser Leu Val Thr Gly Tyr Cys Gly
                165                 170                 175

Gly Val Glu Gly Leu Met Arg Gly Leu Ala Val Asp Met Met Pro Leu
            180                 185                 190
```

```
Arg Val Asn Val Val Ser Pro Gly Ala Val Leu Thr Pro Val Leu Arg
        195                 200                 205

Asp Ile Leu Gly Asp Ser Leu Glu Ile Ala Leu Asp Ala Ala Arg Lys
    210                 215                 220

Lys Ser Thr Thr Gly Arg Ile Ala Arg Pro Glu Asp Val Ala Glu Ala
225                 230                 235                 240

Tyr Leu Tyr Ile Met Lys Asp Gln Asn Ile Thr Gly Thr Val Leu Glu
                245                 250                 255

Thr Ser Ala Gly Met Leu Leu Arg
            260
```

<210> SEQ ID NO 8
<211> LENGTH: 821
<212> TYPE: DNA
<213> ORGANISM: Malbranchea aurantiaca RRC1813

<400> SEQUENCE: 8

```
tcaatttggt aaccgtctct cccattgttt gtggatccaa tccttgaagg ctgtcaatga      60

cccgtccttc catgaaatcc tccaccattt tttcaaatga aatcagttcg cttgatccct     120

gaattgtttt gagatgatag gaatccggat ccagaaaaat gccatggaca atgtcaccaa     180

agtcgtcttc aacgctcacc cagggcatcc tctcatcacc accataagga ggagtcgcaa     240

gaagatattc gccggtatca cgcttgaacc aagggaaacc accgagagat tgacagaacg     300

actccgcaag gaacgcttcc ataaacgatg ctggcacgat aggtgtgaaa gtttggaagc     360

cctttcttct cccatattgt tccacgtagt acttgcatcc ccttactttc aaagccctca     420

ctgtggactc tgccatttgt gtacttgcaa aggttgaggc cagaactata cacgacgtgt     480

ttcactccag cttctttcgt ggcgtcgagg acggttgaac caaggtcata atcgctacgg     540

ccaccgggga ttttataaat ttcttcgtca gaattagtat taacaaatgc accccagcta     600

cccataaaag cactgacagt ctccgacttg ttgaagccgt ctgctttgac taactctgcg     660

ccgagtttgg cacatgcttg ggctttctcc gaagtagggt ctcgggtgat gactcgaaca     720

tggaacagtt tgtctttgtg tgccagtaat gatcggacga cactactgcc ttggtttcca     780

gtaccaccaa aaactgtgac aagtctcttt cctgtatcca t                         821
```

<210> SEQ ID NO 9
<211> LENGTH: 336
<212> TYPE: PRT
<213> ORGANISM: Malbranchea aurantiaca RRC1813

<400> SEQUENCE: 9

```
Met Asp Thr Gly Lys Arg Leu Val Thr Val Phe Gly Gly Thr Gly Asn
1               5                   10                  15

Gln Gly Ser Ser Val Val Arg Ser Leu Leu Ala His Lys Asp Lys Leu
            20                  25                  30

Phe His Val Arg Val Ile Thr Arg Asp Pro Thr Ser Glu Lys Ala Gln
        35                  40                  45

Ala Cys Ala Lys Leu Gly Ala Glu Leu Val Lys Ala Asp Gly Phe Asn
    50                  55                  60

Lys Ser Glu Thr Val Ser Ala Phe Met Gly Ser Trp Gly Ala Phe Val
65                  70                  75                  80

Asn Thr Asn Ser Asp Glu Glu Ile Tyr Lys Ile Pro Gly Gly Arg Ser
                85                  90                  95

Asp Tyr Asp Leu Gly Ser Thr Val Leu Asp Ala Thr Lys Glu Ala Gly
```

```
            100                 105                 110

Val Lys His Val Val Tyr Ser Ser Gly Leu Asn Leu Cys Lys Tyr Thr
        115                 120                 125

Asn Gly Arg Val His Ser Glu Gly Phe Glu Ser Lys Tyr Tyr Val Glu
    130                 135                 140

Gln Tyr Gly Arg Arg Lys Gly Phe Gln Thr Phe Thr Pro Ile Val Pro
145                 150                 155                 160

Ala Ser Phe Met Glu Ala Phe Leu Ala Glu Ser Phe Cys Gln Ser Leu
                165                 170                 175

Gly Gly Phe Pro Trp Phe Lys Arg Asp Thr Gly Glu Tyr Leu Leu Ala
            180                 185                 190

Thr Pro Pro Tyr Gly Gly Asp Glu Arg Met Pro Trp Val Ser Val Glu
        195                 200                 205

Asp Asp Phe Gly Asp Ile Val His Gly Ile Phe Leu Asp Pro Asp Ser
    210                 215                 220

Tyr His Leu Lys Thr Ile Gln Gly Ser Ser Glu Leu Ile Ser Phe Glu
225                 230                 235                 240

Lys Met Val Glu Asp Phe Met Glu Val Thr Gly Glu Lys Ala Arg Tyr
                245                 250                 255

Val Arg Leu Lys Ser Trp Val Asp Ile Pro Leu Asp Gly Thr Ser Cys
            260                 265                 270

Arg Glu Glu Met Arg Ala Ile Phe His Ser Met Tyr Ser Asn Gly Gly
        275                 280                 285

Lys Trp Phe Val Pro Asp Glu Ser Glu Ile Asp Thr Ala Thr Thr Leu
    290                 295                 300

Lys Lys Glu Ala Lys Leu Ala Gln Gly Val Thr Asp Gly Ser Leu Thr
305                 310                 315                 320

Ala Phe Lys Asp Trp Ile His Lys Gln Trp Glu Arg Arg Leu Pro Asn
                325                 330                 335


<210> SEQ ID NO 10
<211> LENGTH: 1217
<212> TYPE: DNA
<213> ORGANISM: Malbranchea aurantiaca RRC1813

<400> SEQUENCE: 10

aaggttggtg gcataaaaca gcgcctctgc tcaacaaaat attggccgct gcgaaatacg      60

atgtgcatct ccagtatcga tatctggtat tctactatgc cgcttgcgtt tctgccctgg     120

gaccttatcc tcagcgattc tcgagttcca tcacccgaag cggcctccca gtcgaattca     180

gcgtcaacta tcaaaacaat tcgaaaccga tcgtgcgcat cggatacgaa ccgatcagtc     240

acttgagcgg aaccgaacgc gacccttaca accataagac ggcttccgag atagtcgcta     300

ccctctcaaa gatccaaccc gactttgacc cacggctttt caactacttt gtccatcagc     360

tgagcgtcaa caaagccgag tccgatgtat taaatggtgc caatgtcgaa ggtagcgaga     420

tgaaatctca aactgccttt ggatttgact tggtcaacgg agagatctct gtcaaggggt     480

atgcttttcc cgccatgaaa tgtcaggtat cgcaacagtc tctttcacaa ttgctcaagg     540

cggcaattaa tggcttgaaa ggcgagttcg actgtgcctt tggcctcgtc gatgagtata     600

tggagcgttg tggcgggtac aaccaattct cgtttgtctc ctgggattgc gtcgttcctg     660

cgaagtcccg cttcaaggtc tatggagtcc acaacgatgt aacctggaaa aagatcgaag     720

atatctggac actcgggggc caagctacca gcggaaatgt caccaagggc ctggagttgt     780

tgaaggaatt gtggacactg attgacttgg acgaaggtga acgtgggtac acgggacgtt     840
```

```
ttgacgatgc gaacgacaat gggagcaata tccagagtcc aatggtgtgg aattatgaac    900

tcaggcccaa caatccatgg ccgttggcaa agttctactt tccggtgcac ggggaaaacg    960

acatgaagat tgtgaaaggc ttagcccgat tcttcgagaa tcggggttgg actgagctgg   1020

cccgatccta cgttcagacg gtgtcctcct tctttcctga tcgagacctg aatcaaacgc   1080

agcgcctggt atcgtggatt tcattcgcct acactgaaaa gactggggta tacctgagtg   1140

tttactacca ttcttcagcc gattatctat ggatatccga gtctggggaa aagagaggtc   1200

aaggagatgg tgcttga                                                  1217
```

<210> SEQ ID NO 11
<211> LENGTH: 438
<212> TYPE: PRT
<213> ORGANISM: Malbranchea aurantiaca RRC1813

<400> SEQUENCE: 11

```
Met Thr Ala Gly Pro Met Gly Asn Lys Ser Thr Ser Asp Ile Asp Ser
1               5                   10                  15

Val Leu Val Tyr Lys Ser Leu Ser Arg Tyr Leu Lys Phe Ser Glu Asn
            20                  25                  30

Glu Glu Gly Trp Trp His Lys Thr Ala Pro Leu Leu Asn Lys Ile Leu
        35                  40                  45

Ala Ala Ala Lys Tyr Asp Val His Leu Gln Tyr Arg Tyr Leu Val Phe
    50                  55                  60

Tyr Tyr Ala Ala Cys Val Ser Ala Leu Gly Pro Tyr Pro Gln Arg Phe
65                  70                  75                  80

Ser Ser Ser Ile Thr Arg Ser Gly Leu Pro Val Glu Phe Ser Val Asn
                85                  90                  95

Tyr Gln Asn Asn Ser Lys Pro Ile Val Arg Ile Gly Tyr Glu Pro Ile
            100                 105                 110

Ser His Leu Ser Gly Thr Glu Arg Asp Pro Tyr Asn His Lys Thr Ala
        115                 120                 125

Ser Glu Ile Val Ala Thr Leu Ser Lys Ile Gln Pro Asp Phe Asp Pro
    130                 135                 140

Arg Leu Phe Asn Tyr Phe Val His Gln Leu Ser Val Asn Lys Ala Glu
145                 150                 155                 160

Ser Asp Val Leu Asn Gly Ala Asn Val Glu Gly Ser Glu Met Lys Ser
                165                 170                 175

Gln Thr Ala Phe Gly Phe Asp Leu Val Asn Gly Glu Ile Ser Val Lys
            180                 185                 190

Gly Tyr Ala Phe Pro Ala Met Lys Cys Gln Val Ser Gln Gln Ser Leu
        195                 200                 205

Ser Gln Leu Leu Lys Ala Ala Ile Asn Gly Leu Lys Gly Glu Phe Asp
    210                 215                 220

Cys Ala Phe Gly Leu Val Asp Glu Tyr Met Glu Arg Cys Gly Gly Tyr
225                 230                 235                 240

Asn Gln Phe Ser Phe Val Ser Trp Asp Cys Val Val Pro Ala Lys Ser
                245                 250                 255

Arg Phe Lys Val Tyr Gly Val His Asn Asp Val Thr Trp Lys Lys Ile
            260                 265                 270

Glu Asp Ile Trp Thr Leu Gly Gly Gln Ala Thr Ser Gly Asn Val Thr
        275                 280                 285

Lys Gly Leu Glu Leu Leu Lys Glu Leu Trp Thr Leu Ile Asp Leu Asp
    290                 295                 300
```

```
Glu Gly Glu Arg Gly Tyr Thr Gly Arg Phe Asp Asp Ala Asn Asp Asn
305                 310                 315                 320

Gly Ser Asn Ile Gln Ser Pro Met Val Trp Asn Tyr Glu Leu Arg Pro
                325                 330                 335

Asn Asn Pro Trp Pro Leu Ala Lys Phe Tyr Phe Pro Val His Gly Glu
            340                 345                 350

Asn Asp Met Lys Ile Val Lys Gly Leu Ala Arg Phe Phe Glu Asn Arg
        355                 360                 365

Gly Trp Thr Glu Leu Ala Arg Ser Tyr Val Gln Thr Val Ser Ser Phe
    370                 375                 380

Phe Pro Asp Arg Asp Leu Asn Gln Thr Gln Arg Leu Val Ser Trp Ile
385                 390                 395                 400

Ser Phe Ala Tyr Thr Glu Lys Thr Gly Val Tyr Leu Ser Val Tyr Tyr
                405                 410                 415

His Ser Ser Ala Asp Tyr Leu Trp Ile Ser Glu Ser Gly Glu Lys Arg
            420                 425                 430

Gly Gln Gly Asp Gly Ala
        435
```

<210> SEQ ID NO 12
<211> LENGTH: 1673
<212> TYPE: DNA
<213> ORGANISM: Malbranchea aurantiaca RRC1813

<400> SEQUENCE: 12

```
tcaaaacctg gccaaagcat gccatagtcc actgtcggcc ctcgtgcaca ttccctcatc      60

gtcccagcgt tcacttccca ctccgactct ggtaatgaac agatcctctg gatcccatgc     120

tcgctttact ttcaagagcc ggtcgtagtt cttcccccag aatgaatcct ggaagtaaac     180

ttcattggga taagccactg caagataagc cccctttcga ccaccctcga gagaacgaag     240

tcggggcaat tgatcattct ccaattcgct ctcaatggat ttgagggttt ctaatgtgta     300

tcctggaggc actccacgac cgactgtgag tgaaagaaga gcagatcgcc agtctggatg     360

gacagcactg ttgattcgat ttttgttgtt cacaacctgg ccgccaccaa aagcgtccac     420

gctaaacgat gatccaggac ccaaccgtag gtccgacaag gcgctggtca ctttggcagg     480

gccgtccttg gatgcgacaa gatcataaga caggaacacg ctgcctggga tcacactgat     540

gccagccaaa tcgacgcctt tgggggctgc gagaaagcgg ctgaggttgc cctggaagtc     600

atgggacaat ttaaagggga taccgaagtc atccaaagcg cgctggagtg caagtagtga     660

aactgcaccc tttttgttaa aggtatatcc ttcgaatgag gcagaagccc cgcccgtgga     720

ggaagcagga agaactatca tacgggcaga attgccggca tccgtaagct caggtaggat     780

tgaaagcacg gttttgacac cagcccaaaa tattgcatcc gccgaggggg tattgatttg     840

aatcccggtc accgtagccg gaaggtcagc gaacgcgcgg agtgtaacag aagtgatgac     900

accaaatgta ccgccacctc ctccacggac tgcccagaat agatcctcat tttgatattg     960

gttggcaatg atatgactgc catcggcggt cacgatttcc acctgaagaa catggtcgga    1020

gccgaggcct ttcgatggac tcaatattcc catcccaccg ctctggatga agccacccgc    1080

gatgccaaca gtactgcagg cccccccgag tacaacaaat cctttctcag agccagtagc    1140

gtagagctcg cctgtgagaa tgcccgctcc tatagtgact gcggggccca tgggctcagc    1200

ggatccctga gtaataaagg gcacgaaatt ttccgtgtaa ttgatgccct tcaacccact    1260

tgtaagaatt tgcagggaac caggggcact ggatcgccct gccatatcgt gaccagtgtt    1320
```

```
gcgaacgact aggcgtaggt ttcgatgttt tgcgaaggag actgcctgtt gaacctgctt   1380

tgtcgactca accgccgcag agtacagtcg ggatggtcaa cacgccagga agagttatgg   1440

gtcatcgcaa gcacttcgtc acatttctcc ttgtggtagg ccgattgctg acatggaagc   1500

ccaacaggcc tcagatgacg tagcttgcca tcgattgatt gattcaatga tgaccactca   1560

gcggtagtag gccaacaagc atcttcttga cgacaacggc aaatcgtgct cctccgttgg   1620

gtttggatgc caattgctag gataagcagg gcgaaagtgg cagtgtattt cat          1673


<210> SEQ ID NO 13
<211> LENGTH: 590
<212> TYPE: PRT
<213> ORGANISM: Malbranchea aurantiaca RRC1813

<400> SEQUENCE: 13

Met Lys Tyr Thr Ala Thr Phe Ala Leu Leu Ile Leu Ala Ile Gly Ile
1               5                   10                  15

Gln Thr Gln Arg Arg Ser Thr Ile Cys Arg Cys Arg Gln Glu Asp Ala
            20                  25                  30

Cys Trp Pro Thr Thr Ala Glu Trp Ser Ser Leu Asn Gln Ser Ile Asp
        35                  40                  45

Gly Lys Leu Arg His Leu Arg Pro Val Gly Leu Pro Cys Gln Gln Ser
    50                  55                  60

Ala Tyr His Lys Glu Lys Cys Asp Glu Val Leu Ala Met Thr His Asn
65                  70                  75                  80

Ser Ser Trp Arg Val Asp His Pro Glu Ser Leu Gln Leu Val Ser Trp
                85                  90                  95

Glu Ser Trp Pro Glu Lys Asn Gln Ser Cys Gln Ile Val Arg Glu Ala
            100                 105                 110

Val Asp Gly Cys Ala Gln Gly Arg Ile Pro Leu Tyr Ser Ala Ala Val
        115                 120                 125

Glu Ser Thr Lys Gln Val Gln Gln Ala Val Ser Phe Ala Lys His Arg
    130                 135                 140

Asn Leu Arg Leu Val Val Arg Asn Thr Gly His Asp Met Ala Gly Arg
145                 150                 155                 160

Ser Ser Ala Pro Gly Ser Leu Gln Ile Leu Thr Ser Gly Leu Lys Gly
                165                 170                 175

Ile Asn Tyr Thr Glu Asn Phe Val Pro Phe Ile Thr Gln Gly Ser Ala
            180                 185                 190

Glu Pro Met Gly Pro Ala Val Thr Ile Gly Ala Gly Ile Leu Thr Gly
        195                 200                 205

Glu Leu Tyr Ala Thr Gly Ser Glu Lys Gly Phe Val Val Leu Gly Gly
    210                 215                 220

Ala Cys Ser Thr Val Gly Ile Ala Gly Gly Phe Ile Gln Ser Gly Gly
225                 230                 235                 240

Met Gly Ile Leu Ser Pro Ser Lys Gly Leu Gly Ser Asp His Val Leu
                245                 250                 255

Gln Val Glu Ile Val Thr Ala Asp Gly Ser His Ile Ile Ala Asn Gln
            260                 265                 270

Tyr Gln Asn Glu Asp Leu Phe Trp Ala Val Arg Gly Gly Gly Gly Gly
        275                 280                 285

Thr Phe Gly Val Ile Thr Ser Val Thr Leu Arg Ala Phe Ala Asp Leu
    290                 295                 300

Pro Ala Thr Val Thr Gly Ile Gln Ile Asn Thr Pro Ser Ala Asp Ala
```

```
305                 310                 315                 320

Ile Phe Trp Ala Gly Val Lys Thr Val Leu Ser Ile Leu Pro Glu Leu
                325                 330                 335

Thr Asp Ala Gly Asn Ser Ala Arg Met Ile Val Leu Pro Ala Ser Ser
            340                 345                 350

Thr Gly Gly Ala Ser Ala Ser Phe Glu Gly Tyr Thr Phe Asn Lys Lys
        355                 360                 365

Gly Ala Val Ser Leu Leu Ala Leu Gln Arg Ala Leu Asp Asp Phe Gly
    370                 375                 380

Ile Pro Phe Lys Leu Ser His Asp Phe Gln Gly Asn Leu Ser Arg Phe
385                 390                 395                 400

Leu Ala Ala Pro Lys Gly Val Asp Leu Ala Gly Ile Ser Val Ile Pro
                405                 410                 415

Gly Ser Val Phe Leu Ser Tyr Asp Leu Val Ala Ser Lys Asp Gly Pro
            420                 425                 430

Ala Lys Val Thr Ser Ala Leu Ser Asp Leu Arg Leu Gly Pro Gly Ser
        435                 440                 445

Ser Phe Ser Val Asp Ala Phe Gly Gly Gly Gln Val Val Asn Asn Lys
    450                 455                 460

Asn Arg Ile Asn Ser Ala Val His Pro Asp Trp Arg Ser Ala Leu Leu
465                 470                 475                 480

Ser Leu Thr Val Gly Arg Gly Val Pro Pro Gly Tyr Thr Leu Glu Thr
                485                 490                 495

Leu Lys Ser Ile Glu Ser Glu Leu Glu Asn Asp Gln Leu Pro Arg Leu
            500                 505                 510

Arg Ser Leu Glu Gly Gly Arg Lys Gly Ala Tyr Leu Ala Val Ala Tyr
        515                 520                 525

Pro Asn Glu Val Tyr Phe Gln Asp Ser Phe Trp Gly Lys Asn Tyr Asp
    530                 535                 540

Arg Leu Leu Lys Val Lys Arg Ala Trp Asp Pro Glu Asp Leu Phe Ile
545                 550                 555                 560

Thr Arg Val Gly Val Gly Ser Glu Arg Trp Asp Asp Glu Gly Met Cys
                565                 570                 575

Thr Arg Ala Asp Ser Gly Leu Trp His Ala Leu Ala Arg Phe
            580                 585                 590
```

<210> SEQ ID NO 14
<211> LENGTH: 7038
<212> TYPE: DNA
<213> ORGANISM: Malbranchea aurantiaca RRC1813

<400> SEQUENCE: 14

```
atgtctgatg atccgcttct gtcgtcccca acagaggcaa tatgtttgaa tcattcagtg      60

acagacctcc ggctggctgc ggcactgaag ctgagctgga catttctctt ggctcattac     120

tctggatcca gcgaaatacc gcttgatatc cgactcgaat ataggtatat tgatggaagc     180

gaaacgaatt tcgagccatt cgacgcgaca ttcgaggtcg acaaaaagtc tctgatcgag     240

gactccatcg gcatgatcca aaacatgctc acaccgtcga cacgcccaca cagcctgagt     300

aatggaataa attcgtctca gagcgacaaa catgtaccag aggcccaggt ctcattcacc     360

ttcagcagtg gttcacgacc tgtgcttgaa aaaggtgcca caactcggta tgccgccact     420

gtcttggaat tagagtgctt gcaggggctg aagaaggaat acctttgccg gatcaacttc     480

aacaggatga tgtggaacgt ggaagaggcg acgggaattc tgcgccaatt ccgccatatt     540
```

```
gcccaacaga tcgtttcagc agatgtctgt gccacactca gccaaatcaa cttgatgtgt    600
gagtccgata tcgaacaact caaacgttgg aactcaactg tccccgatcc ggtgcttgcc    660
tgcatacacg agttgttttc tgagcaagca aaaaagaatc ccacggcaac cgccgtacaa    720
acgagtgaag gaagcttcga ctacgggcgt cttgatgaac tgtcttctgc cttagcatgc    780
cacctgagtt ccaacggtct gacaagagga acacccgtcc cactcctctt cgacaagtcc    840
atgtggatgg ttgtggccac tcttgccgtg ctcaaggcag gtgccacttg tgttagcatc    900
tgtacaggac ttcccacgaa ggctatagaa gacatacttg agcaaaccgc tgcgcagctc    960
gtccttgtct ccgaatcaca aggcttaaga ttaagcgaaa cccgaaccca ggttgtttcc   1020
gacaaaacaa tgcagatatg gcacaccatg tctggcaaac cagaacttcc tcaatccgac   1080
cctacggacc tagcgtgcat catattcacg tccggaagca cgggaaagcc aaagggaatt   1140
atgctggacc acatagcttt ggttaccagt ataaggaatc acggccctag tttggggatt   1200
tcctccagtt cgcgtgctct tcagttctcg tcctacgctt tcgacatgag cttttatgag   1260
acgtacacca cgctattgtc tggaggctgc atttgcatcc cttccgagac cgaaaggctc   1320
aacagtctgc ctcaatttat ctgcgaccac aatgttaact gggcgttttt aaccccgtca   1380
gtgctacgag attttcaccc tagtgagttt ccatccctca ggacactcgc caccggaggg   1440
gagcccgttg gagcggacat cgcgaacgaa tgggcaggaa gactgcaact tttcaacctg   1500
tggggtccag cagaggcaac aatatgcgcg accggaccaa tattgccagg cgtctggata   1560
cccgggacat ttggcaaagc tgtgggctgc attgcatgga tcacacaggc agagaacccg   1620
gatgagctgg ttcctattgg ggcggtgggt gaggtgctga tcgagggtcc cgtgctggct   1680
caaggttact cgggggacgt tgaaaagacg aaggcttcct tcattccgtt tcccaagtgg   1740
agagaaaggt tcgaactgac accgcgagga cgggtacttt tcagaactgg agaccttgct   1800
cagtacaatc cagacggtac aatacggtat gttggaagga tggggaccgt agttaaagtc   1860
ggcggccaac gagtggacat cgacgcggtt gaatatgcat tgcgccggat cgatcggtct   1920
tctcacatag cggtcgaggc agtcgaacta gagaaagaaa ctggtcaggg acctactttg   1980
atcgcgttcc tgtctagcga tatgaatgga gtgtccggat ctgaaaagaa acggtgctgt   2040
tcaatcgacc ctggatcccg ttcctgggaa gcctgggcaa atattgcaat acgtctccag   2100
gacactctcg ctggagtatt gccacggtat atgatccccc atttattcat cccagtttca   2160
acgattccaa ccaccccaag cggcaaagcc aacaaacgcc agttgcaagc tcttgtcctg   2220
ggccaatcca aggcacacct cctgcagttg tgccgacagc ggtcgccaga tgcctcatac   2280
ccagagcagc atctcactga gaatgagaca ctgttacgtt tgttagtgag tgacgtgctt   2340
gggattgata gggatcacgt cgcaatgaac tcaaggtttt ttcaccttgg gggcgactcc   2400
cttgcagctg tgaagctggt tgcactcgct cgacaacagg gtattcagtt aaaggtcgaa   2460
gcaatccttc aatcttgtag ccttcgcgaa gctgctggaa ccatgatctc tgctggtgaa   2520
aagcagaaat tgcagtcaaa gacatcattc gccattaaca aatgcgatga caaacttggg   2580
ctacttgaag aagcgacggt ccagtgcgga atttcagagt ccgatatcga ggagatatac   2640
cccagtacgc cgttgcagga agggcttata accgtaactt caactttttc agcatcgaag   2700
ccgtatgtcg acaaaatcct cttcactttg tcagccacag cagatttgga ccgtgtgcga   2760
gacgcatgga accacgtcgt cgccgcgaat gatatcttga gatcccgcat catcctatct   2820
ccggcaggca aagcgttcaa tgttgtggtc agatcagaac catcctggca atattacaag   2880
actgtccagc agtacctgga gaacgacaat gcgcaagaca tgactttcgg aaaaagagctc  2940
```

```
atcacgttca acctcatagc aagccatgat caatctgctt ccgcccggtc cattgggata   3000
acaatacatc acgctctgta cgacaattgg actgtctccc tgctgcacaa gcaggccgag   3060
gatgcatatc gtggagaact tgttgagcca tgctcatttt cgacattttc ccactatgtc   3120
cttcaacaga gccctgatat taacaaagag ttttggcgca agcaattttt agatttgagg   3180
gcgggtacct ttcctgagct gccgtcatct gattatgtac ctcgtgcaaa ctcatcgtct   3240
cagcacctgt acaaggggca gcatcaacgc agagatttta gcatggcaac aaatatccag   3300
ctcgcttggg cgctcctgct ctctctttac acgaattccc ccgatgtcgt ttatggtctt   3360
gttgtcaatg ggcgtatggc cccgatgccg gggtcgggg gattagttgg cccaacgatt    3420
gctactgtcc ccttccgaac aaccgtggag aggagtatga gcgtccaggc cgccttagag   3480
gccattcaga agcgggttct gtcaatagtc cctttcgaac aaaccggtct gcaaaacatt   3540
gcgcgaatgg gggaaggccc taaaactgcc tgtaacttcc aaaacctcct agtgatacaa   3600
caggaccttg agtttaaggg cgaaggata ttctgccgga gacaaaactt ggtcggagcg    3660
gtaaacaatt tcccaggata tgggattata cttctctgta gtgcgacgga gcatggatgg   3720
gcatttgaaa tactctatag taactcatta attccagaaa cccgcgcacg tcggattctc   3780
ctgcagctgg accacctgct tcggcaactc gaggttgacc cataccgaca actggctcaa   3840
ctggagctcc tctgtccatc agataaaagc aaactaacat cctggaacac ccagttgccc   3900
attcgagtaa acgcgtgtat ccccgaagtc ttcggagcgc aatgccttgt ccggagcgag   3960
cgcactgcag tgtccgcctg ggatgggagc ctttcgtata gggagctcga tcgattttct   4020
tcgatagtag caaggcatct ccaagcggtg gggttggaa agggaactat tacacctatc    4080
ctgtttgaaa agtcgcggtg ggtggttgtc gccatgctgg ccgtgctcaa gaccggagcg   4140
gccttcgtca tgctagatac aaaccagccc ctgcaaagaa agcaaggtat ctgccgtgca   4200
gtcagggcta ccaccatcgc tacgtctgct tcgtgcgccc atgagagcaa agttctggcg   4260
aactcgatat atgttctcga cgaagcgagc atcacaaaga ccgacacaaa tcaattcctt   4320
cccctcgtgg aggtttcccc caacgatctc gcgtacgtcg tcttcacttc tggctcaacc   4380
ggagaaccca aaggcgtcct gatcgagcat gcgtcgtctt gctcggcatc aagggctcaa   4440
gccgcgaaat tgggtatctc gccggattct cgggtgctcc aactctcatc ttatacettt   4500
gactcgttcg cagttgagat tctcgcgtct ctattggctg gatgctgcat ttgcatcccg   4560
tcggaaagcg agagcagcaa cgatattgcc ggtgccgttc ggcgattttc agcgacatgg   4620
ctatgcatca caccctctgt attgggatta accaacccag atgaagttcc cagcctcaag   4680
accgtcgttg ccgtgggaga gtcagcccga ccgagccaga tcagactctg gtcgacaaga   4740
gtgaatttta tctgcggata tggaccttcc gaatgctcaa cgggtgcttc agcacagctg   4800
atacggtctg caggctctga cccccgtatc atcggttccg gcatgggctc ctgtctgtgg   4860
gtagcccaca cagatgatca caatgtcctg gtgcctattg gtgccatcgg tgaacttctc   4920
atccagggtc caatcgtggg gagaggctac atgaattcac ccgaaaagac gcgagcggcc   4980
tttctcgaga gcacagcttg gattccagag tttagacagg ttgccacaga acgtttttac   5040
aaaaccgggg acttggtccg tcaaaatgag gatggatcga tcgtctatct cgggagaaag   5100
aaccgagagg taaaacttcg aggccagaga ctagatcttg aagaagtcga gaaccagctt   5160
tcagcagcac tagaaatgga cattaatata gtggctgaag ttgtgaagcc caaaggagtc   5220
gattcccagc cggtacttat tgcatttttc caggttgtgg cagatgtgga actccggtct   5280
```

```
gacaatatta cattcctcga gttaaatccg gatatcggcc ttcggctcct ggatgcggaa   5340

gagaaattgc ggaaaatcct tcccccctgta atgatacctt ctgtatatct acaggttcaa   5400

agaatgcctc tcacaatgtc ggggaagatg aaccgacagg ccttgcggaa taaagcatcc   5460

accagaactc tctcgcagct cttctcgtct ggctcggtca gacacgagga cgattatctc   5520

acacttcaac ctcacgaaag cactgccctt ttcgtttgcc aagcaatctg cggcattatg   5580

agagacaaaa ttgacgatac caagaccttg attgcaggga aaaatgtcaa tctatccagg   5640

acaggaatgg actccatcga tgccatgatg ctcgctcgca caatttcgcg gcatttcggc   5700

atcaccctat cgatacgtgc atttttaggt agcagcgtaa ccgtccgtga tatcgccagg   5760

ctcattgaag ggttaagag tgaggataat ctctcacaat tcgatctcta tgccaagtac   5820

gagtccattt gggaagagtt gcgaggcgtg gtcaggggtt tgaccccgtc ggacaagcct   5880

caactctgcg acaagacgcc cgctgggatg agcgtcttct taaccggcgg aacagggttt   5940

ctgggaacac atattcttcg acagatcttg caagatccac gtgtcgagct cgtgacagtc   6000

ctcacacgag ctgagtcacc ggcccatgcc ttgtccaaaa ttgtcgagtc tgcgaaaatt   6060

gcgcaatggt ggcaggagtc gtaccggaac cgaattgatg catgggtagg agatttggcc   6120

cggccacgtc taggtctgtc tgatgatcat tgggctagac tctgcgggta tggcgagcac   6180

aaattcacct cgatcattca taacggggcc gcggtacact ggggatacga cttcgaaaag   6240

ttgaagcctg taaacgtgat gagcacgttt tggcttcttg tttcgctctt catagctggc   6300

cctttggtta atttcacgta tgtgtcggca ttgttgccgg aatgcgatgg actcacagac   6360

cgtgagattg cactcaaaac ctccgatgat ggctacagtc agaccaaata cgtgtccgag   6420

cttctggtta agaattttaa ggagcagctc tgtaacaacc cgatcgcgat tgttcgccca   6480

gggttactga tcggatcggc tgaacacggt gtggccaacg tcggtgacta cttatggcgc   6540

gttgtctcca gtgcgttttc cgtcggggct tatatttcgg agaaaggaga cgcgtggatc   6600

tatatcgcag ccgtcgattg ggttgccaat caagttatcc gggaagccct atatgagagt   6660

accactgacc ttcgaataat caatgtaacg gatggtctga cagtgaaaga gttttggaga   6720

gcgattcaga ttgcgtcgcc ccgtcaattg aatgctctcc aatccgaaga ctggctctct   6780

ttgatccgtc agcagctgga tgtcacggga aagtcccatc cgctatggcc ggtaatttct   6840

ttcctggagt ccagtaaagg ctgccttggg ttttcgcata acctcccgcc ccaggcacac   6900

tcactttcct ccatgatcat cactgcgttg attaaaaacg tgcggtatct ggcctcgctg   6960

gggttggttt cgtggaccac gaccggctct aactgcgatc actcagttca acagcgtatt   7020

tttagacgcg tcctgtga                                                 7038
```

```
<210> SEQ ID NO 15
<211> LENGTH: 2345
<212> TYPE: PRT
<213> ORGANISM: Malbranchea aurantiaca RRC1813

<400> SEQUENCE: 15

Met Ser Asp Asp Pro Leu Leu Ser Ser Pro Thr Glu Ala Ile Cys Leu
1               5                   10                  15

Asn His Ser Val Thr Asp Leu Arg Leu Ala Ala Ala Leu Lys Leu Ser
            20                  25                  30

Trp Thr Phe Leu Leu Ala His Tyr Ser Gly Ser Ser Glu Ile Pro Leu
        35                  40                  45

Asp Ile Arg Leu Glu Tyr Arg Tyr Ile Asp Gly Ser Glu Thr Asn Phe
    50                  55                  60
```

```
Glu Pro Phe Asp Ala Thr Phe Glu Val Asp Lys Lys Ser Leu Ile Glu
65                  70                  75                  80

Asp Ser Ile Gly Met Ile Gln Asn Met Leu Thr Pro Ser Thr Arg Pro
                85                  90                  95

His Ser Leu Ser Asn Gly Ile Asn Ser Ser Gln Ser Asp Lys His Val
            100                 105                 110

Pro Glu Ala Gln Val Ser Phe Thr Phe Ser Ser Gly Ser Arg Pro Val
        115                 120                 125

Leu Glu Lys Gly Ala Thr Thr Arg Tyr Ala Ala Thr Val Leu Glu Leu
    130                 135                 140

Glu Cys Leu Gln Gly Leu Lys Lys Glu Tyr Leu Cys Arg Ile Asn Phe
145                 150                 155                 160

Asn Arg Met Met Trp Asn Val Glu Glu Ala Thr Gly Ile Leu Arg Gln
                165                 170                 175

Phe Arg His Ile Ala Gln Gln Ile Val Ser Ala Asp Val Cys Ala Thr
            180                 185                 190

Leu Ser Gln Ile Asn Leu Met Cys Glu Ser Asp Ile Glu Gln Leu Lys
        195                 200                 205

Arg Trp Asn Ser Thr Val Pro Asp Pro Val Leu Ala Cys Ile His Glu
    210                 215                 220

Leu Phe Ser Glu Gln Ala Lys Lys Asn Pro Thr Ala Thr Ala Val Gln
225                 230                 235                 240

Thr Ser Glu Gly Ser Phe Asp Tyr Gly Arg Leu Asp Glu Leu Ser Ser
                245                 250                 255

Ala Leu Ala Cys His Leu Ser Ser Asn Gly Leu Thr Arg Gly Thr Pro
            260                 265                 270

Val Pro Leu Leu Phe Asp Lys Ser Met Trp Met Val Val Ala Thr Leu
        275                 280                 285

Ala Val Leu Lys Ala Gly Ala Thr Cys Val Ser Ile Cys Thr Gly Leu
    290                 295                 300

Pro Thr Lys Ala Ile Glu Asp Ile Leu Glu Gln Thr Ala Ala Gln Leu
305                 310                 315                 320

Val Leu Val Ser Glu Ser Gln Gly Leu Arg Leu Ser Glu Thr Arg Thr
                325                 330                 335

Gln Val Val Ser Asp Lys Thr Met Gln Ile Trp His Thr Met Ser Gly
            340                 345                 350

Lys Pro Glu Leu Pro Gln Ser Asp Pro Thr Asp Leu Ala Cys Ile Ile
        355                 360                 365

Phe Thr Ser Gly Ser Thr Gly Lys Pro Lys Gly Ile Met Leu Asp His
    370                 375                 380

Ile Ala Leu Val Thr Ser Ile Arg Asn His Gly Pro Ser Leu Gly Ile
385                 390                 395                 400

Ser Ser Ser Ser Arg Ala Leu Gln Phe Ser Ser Tyr Ala Phe Asp Met
                405                 410                 415

Ser Phe Tyr Glu Thr Tyr Thr Thr Leu Leu Ser Gly Gly Cys Ile Cys
            420                 425                 430

Ile Pro Ser Glu Thr Glu Arg Leu Asn Ser Leu Pro Gln Phe Ile Cys
        435                 440                 445

Asp His Asn Val Asn Trp Ala Phe Leu Thr Pro Ser Val Leu Arg Asp
    450                 455                 460

Phe His Pro Ser Glu Phe Pro Ser Leu Arg Thr Leu Ala Thr Gly Gly
465                 470                 475                 480
```

```
Glu Pro Val Gly Ala Asp Ile Ala Asn Glu Trp Ala Gly Arg Leu Gln
                485                 490                 495

Leu Phe Asn Leu Trp Gly Pro Ala Glu Ala Thr Ile Cys Ala Thr Gly
            500                 505                 510

Pro Ile Leu Pro Gly Val Trp Ile Pro Gly Thr Phe Gly Lys Ala Val
        515                 520                 525

Gly Cys Ile Ala Trp Ile Thr Gln Ala Glu Asn Pro Asp Glu Leu Val
    530                 535                 540

Pro Ile Gly Ala Val Gly Glu Val Leu Ile Glu Gly Pro Val Leu Ala
545                 550                 555                 560

Gln Gly Tyr Ser Gly Asp Val Glu Lys Thr Lys Ala Ser Phe Ile Pro
                565                 570                 575

Phe Pro Lys Trp Arg Glu Arg Phe Glu Leu Thr Pro Arg Gly Arg Val
            580                 585                 590

Leu Phe Arg Thr Gly Asp Leu Ala Gln Tyr Asn Pro Asp Gly Thr Ile
        595                 600                 605

Arg Tyr Val Gly Arg Met Gly Thr Val Val Lys Val Gly Gly Gln Arg
    610                 615                 620

Val Asp Ile Asp Ala Val Glu Tyr Ala Leu Arg Arg Ile Asp Arg Ser
625                 630                 635                 640

Ser His Ile Ala Val Glu Ala Val Glu Leu Glu Lys Glu Thr Gly Gln
                645                 650                 655

Gly Pro Thr Leu Ile Ala Phe Leu Ser Ser Asp Met Asn Gly Val Ser
            660                 665                 670

Gly Ser Glu Lys Lys Arg Cys Cys Ser Ile Asp Pro Gly Ser Arg Ser
        675                 680                 685

Trp Glu Ala Trp Ala Asn Ile Ala Ile Arg Leu Gln Asp Thr Leu Ala
    690                 695                 700

Gly Val Leu Pro Arg Tyr Met Ile Pro His Leu Phe Ile Pro Val Ser
705                 710                 715                 720

Thr Ile Pro Thr Thr Pro Ser Gly Lys Ala Asn Lys Arg Gln Leu Gln
                725                 730                 735

Ala Leu Val Leu Gly Gln Ser Lys Ala His Leu Leu Gln Leu Cys Arg
            740                 745                 750

Gln Arg Ser Pro Asp Ala Ser Tyr Pro Glu Gln His Leu Thr Glu Asn
        755                 760                 765

Glu Thr Leu Leu Arg Leu Leu Val Ser Asp Val Leu Gly Ile Asp Arg
    770                 775                 780

Asp His Val Ala Met Asn Ser Arg Phe Phe His Leu Gly Gly Asp Ser
785                 790                 795                 800

Leu Ala Ala Val Lys Leu Val Ala Leu Ala Arg Gln Gln Gly Ile Gln
                805                 810                 815

Leu Lys Val Glu Ala Ile Leu Gln Ser Cys Ser Leu Arg Glu Ala Ala
            820                 825                 830

Gly Thr Met Ile Ser Ala Gly Glu Lys Gln Lys Leu Gln Ser Lys Thr
        835                 840                 845

Ser Phe Ala Ile Asn Lys Cys Asp Asp Lys Leu Gly Leu Leu Glu Glu
    850                 855                 860

Ala Thr Val Gln Cys Gly Ile Ser Glu Ser Asp Ile Glu Glu Ile Tyr
865                 870                 875                 880

Pro Ser Thr Pro Leu Gln Glu Gly Leu Ile Thr Val Thr Ser Thr Phe
                885                 890                 895

Ser Ala Ser Lys Pro Tyr Val Asp Lys Ile Leu Phe Thr Leu Ser Ala
```

-continued

```
            900                 905                 910

Thr Ala Asp Leu Asp Arg Val Arg Asp Ala Trp Asn His Val Val Ala
        915                 920                 925

Ala Asn Asp Ile Leu Arg Ser Arg Ile Ile Leu Ser Pro Ala Gly Lys
    930                 935                 940

Ala Phe Asn Val Val Val Arg Ser Glu Pro Ser Trp Gln Tyr Tyr Lys
945                 950                 955                 960

Thr Val Gln Gln Tyr Leu Glu Asn Asp Asn Ala Gln Asp Met Thr Phe
                965                 970                 975

Gly Lys Glu Leu Ile Thr Phe Asn Leu Ile Ala Ser His Asp Gln Ser
            980                 985                 990

Ala Ser Ala Arg Ser Ile Gly Ile  Thr Ile His His Ala  Leu Tyr Asp
        995                 1000                1005

Asn Trp  Thr Val Ser Leu Leu  His Lys Gln Ala Glu  Asp Ala Tyr
    1010                1015                1020

Arg Gly  Glu Leu Val Glu Pro  Cys Ser Phe Ser Thr  Phe Ser His
    1025                1030                1035

Tyr Val  Leu Gln Gln Ser Pro  Asp Ile Asn Lys Glu  Phe Trp Arg
    1040                1045                1050

Lys Gln  Phe Leu Asp Leu Arg  Ala Gly Thr Phe Pro  Glu Leu Pro
    1055                1060                1065

Ser Ser  Asp Tyr Val Pro Arg  Ala Asn Ser Ser Ser  Gln His Leu
    1070                1075                1080

Tyr Lys  Gly Gln His Gln Arg  Arg Asp Phe Ser Met  Ala Thr Asn
    1085                1090                1095

Ile Gln  Leu Ala Trp Ala Leu  Leu Leu Ser Leu Tyr  Thr Asn Ser
    1100                1105                1110

Pro Asp  Val Val Tyr Gly Leu  Val Val Asn Gly Arg  Met Ala Pro
    1115                1120                1125

Met Pro  Gly Val Gly Gly Leu  Val Gly Pro Thr Ile  Ala Thr Val
    1130                1135                1140

Pro Phe  Arg Thr Thr Val Glu  Arg Ser Met Ser Val  Gln Ala Ala
    1145                1150                1155

Leu Glu  Ala Ile Gln Lys Arg  Val Leu Ser Ile Val  Pro Phe Glu
    1160                1165                1170

Gln Thr  Gly Leu Gln Asn Ile  Ala Arg Met Gly Glu  Gly Pro Lys
    1175                1180                1185

Thr Ala  Cys Asn Phe Gln Asn  Leu Leu Val Ile Gln  Gln Asp Leu
    1190                1195                1200

Glu Phe  Lys Gly Glu Gly Ile  Phe Cys Arg Arg Gln  Asn Leu Val
    1205                1210                1215

Gly Ala  Val Asn Asn Phe Pro  Gly Tyr Gly Ile Ile  Leu Leu Cys
    1220                1225                1230

Ser Ala  Thr Glu His Gly Trp  Ala Phe Glu Ile Leu  Tyr Ser Asn
    1235                1240                1245

Ser Leu  Ile Pro Glu Thr Arg  Ala Arg Arg Ile Leu  Leu Gln Leu
    1250                1255                1260

Asp His  Leu Leu Arg Gln Leu  Glu Val Asp Pro Tyr  Arg Gln Leu
    1265                1270                1275

Ala Gln  Leu Glu Leu Leu Cys  Pro Ser Asp Lys Ser  Lys Leu Thr
    1280                1285                1290

Ser Trp  Asn Thr Gln Leu Pro  Ile Arg Val Asn Ala  Cys Ile Pro
    1295                1300                1305
```

```
Glu Val  Phe Gly Ala Gln Cys  Leu Val Arg Ser Glu  Arg Thr Ala
    1310                 1315                 1320

Val Ser  Ala Trp Asp Gly Ser  Leu Ser Tyr Arg Glu  Leu Asp Arg
    1325                 1330                 1335

Phe Ser  Ser Ile Val Ala Arg  His Leu Gln Ala Val  Gly Val Gly
    1340                 1345                 1350

Lys Gly  Thr Ile Thr Pro Ile  Leu Phe Glu Lys Ser  Arg Trp Val
    1355                 1360                 1365

Val Val  Ala Met Leu Ala Val  Leu Lys Thr Gly Ala  Ala Phe Val
    1370                 1375                 1380

Met Leu  Asp Thr Asn Gln Pro  Leu Gln Arg Lys Gln  Gly Ile Cys
    1385                 1390                 1395

Arg Ala  Val Arg Ala Thr Thr  Ile Ala Thr Ser Ala  Ser Cys Ala
    1400                 1405                 1410

His Glu  Ser Lys Val Leu Ala  Asn Ser Ile Tyr Val  Leu Asp Glu
    1415                 1420                 1425

Ala Ser  Ile Thr Lys Thr Asp  Thr Asn Gln Phe Leu  Pro Leu Val
    1430                 1435                 1440

Glu Val  Ser Pro Asn Asp Leu  Ala Tyr Val Val Phe  Thr Ser Gly
    1445                 1450                 1455

Ser Thr  Gly Glu Pro Lys Gly  Val Leu Ile Glu His  Ala Ser Ser
    1460                 1465                 1470

Cys Ser  Ala Ser Arg Ala Gln  Ala Ala Lys Leu Gly  Ile Ser Pro
    1475                 1480                 1485

Asp Ser  Arg Val Leu Gln Leu  Ser Ser Tyr Thr Phe  Asp Ser Phe
    1490                 1495                 1500

Ala Val  Glu Ile Leu Ala Ser  Leu Leu Ala Gly Cys  Cys Ile Cys
    1505                 1510                 1515

Ile Pro  Ser Glu Ser Glu Ser  Ser Asn Asp Ile Ala  Gly Ala Val
    1520                 1525                 1530

Arg Arg  Phe Ser Ala Thr Trp  Leu Cys Ile Thr Pro  Ser Val Leu
    1535                 1540                 1545

Gly Leu  Thr Asn Pro Asp Glu  Val Pro Ser Leu Lys  Thr Val Val
    1550                 1555                 1560

Ala Val  Gly Glu Ser Ala Arg  Pro Ser Gln Ile Arg  Leu Trp Ser
    1565                 1570                 1575

Thr Arg  Val Asn Phe Ile Cys  Gly Tyr Gly Pro Ser  Glu Cys Ser
    1580                 1585                 1590

Thr Gly  Ala Ser Ala Gln Leu  Ile Arg Ser Ala Gly  Ser Asp Pro
    1595                 1600                 1605

Arg Ile  Ile Gly Ser Gly Met  Gly Ser Cys Leu Trp  Val Ala His
    1610                 1615                 1620

Thr Asp  Asp His Asn Val Leu  Val Pro Ile Gly Ala  Ile Gly Glu
    1625                 1630                 1635

Leu Leu  Ile Gln Gly Pro Ile  Val Gly Arg Gly Tyr  Met Asn Ser
    1640                 1645                 1650

Pro Glu  Lys Thr Arg Ala Ala  Phe Leu Glu Ser Thr  Ala Trp Ile
    1655                 1660                 1665

Pro Glu  Phe Arg Gln Val Ala  Thr Glu Arg Phe Tyr  Lys Thr Gly
    1670                 1675                 1680

Asp Leu  Val Arg Gln Asn Glu  Asp Gly Ser Ile Val  Tyr Leu Gly
    1685                 1690                 1695
```

-continued

```
Arg Lys  Asn Arg Glu Val Lys  Leu Arg Gly Gln Arg  Leu Asp Leu
    1700                 1705                 1710

Glu Glu  Val Glu Asn Gln Leu  Ser Ala Ala Leu Glu  Met Asp Ile
    1715                 1720                 1725

Asn Ile  Val Ala Glu Val Val  Lys Pro Lys Gly Val  Asp Ser Gln
    1730                 1735                 1740

Pro Val  Leu Ile Ala Phe Phe  Gln Val Val Ala Asp  Val Glu Leu
    1745                 1750                 1755

Arg Ser  Asp Asn Ile Thr Phe  Leu Glu Leu Asn Pro  Asp Ile Gly
    1760                 1765                 1770

Leu Arg  Leu Leu Asp Ala Glu  Glu Lys Leu Arg Lys  Ile Leu Pro
    1775                 1780                 1785

Pro Val  Met Ile Pro Ser Val  Tyr Leu Gln Val Gln  Arg Met Pro
    1790                 1795                 1800

Leu Thr  Met Ser Gly Lys Met  Asn Arg Gln Ala Leu  Arg Asn Lys
    1805                 1810                 1815

Ala Ser  Thr Arg Thr Leu Ser  Gln Leu Phe Ser Ser  Gly Ser Val
    1820                 1825                 1830

Arg His  Glu Asp Asp Tyr Leu  Thr Leu Gln Pro His  Glu Ser Thr
    1835                 1840                 1845

Ala Leu  Phe Val Cys Gln Ala  Ile Cys Gly Ile Met  Arg Asp Lys
    1850                 1855                 1860

Ile Asp  Asp Thr Lys Thr Leu  Ile Ala Gly Lys Asn  Val Asn Leu
    1865                 1870                 1875

Ser Arg  Thr Gly Met Asp Ser  Ile Asp Ala Met Met  Leu Ala Arg
    1880                 1885                 1890

Thr Ile  Ser Arg His Phe Gly  Ile Thr Leu Ser Ile  Arg Ala Phe
    1895                 1900                 1905

Leu Gly  Ser Ser Val Thr Val  Arg Asp Ile Ala Arg  Leu Ile Glu
    1910                 1915                 1920

Gly Val  Lys Ser Glu Asp Asn  Leu Ser Gln Phe Asp  Leu Tyr Ala
    1925                 1930                 1935

Lys Tyr  Glu Ser Ile Trp Glu  Glu Leu Arg Gly Val  Val Arg Gly
    1940                 1945                 1950

Leu Thr  Pro Ser Asp Lys Pro  Gln Leu Cys Asp Lys  Thr Pro Ala
    1955                 1960                 1965

Gly Met  Ser Val Phe Leu Thr  Gly Gly Thr Gly Phe  Leu Gly Thr
    1970                 1975                 1980

His Ile  Leu Arg Gln Ile Leu  Gln Asp Pro Arg Val  Glu Leu Val
    1985                 1990                 1995

Thr Val  Leu Thr Arg Ala Glu  Ser Pro Ala His Ala  Leu Ser Lys
    2000                 2005                 2010

Ile Val  Glu Ser Ala Lys Ile  Ala Gln Trp Trp Gln  Glu Ser Tyr
    2015                 2020                 2025

Arg Asn  Arg Ile Asp Ala Trp  Val Gly Asp Leu Ala  Arg Pro Arg
    2030                 2035                 2040

Leu Gly  Leu Ser Asp Asp His  Trp Ala Arg Leu Cys  Gly Tyr Gly
    2045                 2050                 2055

Glu His  Lys Phe Thr Ser Ile  Ile His Asn Gly Ala  Ala Val His
    2060                 2065                 2070

Trp Gly  Tyr Asp Phe Glu Lys  Leu Lys Pro Val Asn  Val Met Ser
    2075                 2080                 2085

Thr Phe  Trp Leu Leu Val Ser  Leu Phe Ile Ala Gly  Pro Leu Val
```

```
    2090                2095                2100

Asn Phe  Thr Tyr Val Ser Ala  Leu Leu Pro Glu Cys  Asp Gly Leu
    2105                2110                2115

Thr Asp  Arg Glu Ile Ala Leu  Lys Thr Ser Asp Asp  Gly Tyr Ser
    2120                2125                2130

Gln Thr  Lys Tyr Val Ser Glu  Leu Leu Val Lys Asn  Phe Lys Glu
    2135                2140                2145

Gln Leu  Cys Asn Asn Pro Ile  Ala Ile Val Arg Pro  Gly Leu Leu
    2150                2155                2160

Ile Gly  Ser Ala Glu His Gly  Val Ala Asn Val Gly  Asp Tyr Leu
    2165                2170                2175

Trp Arg  Val Val Ser Ser Ala  Phe Ser Val Gly Ala  Tyr Ile Ser
    2180                2185                2190

Glu Lys  Gly Asp Ala Trp Ile  Tyr Ile Ala Ala Val  Asp Trp Val
    2195                2200                2205

Ala Asn  Gln Val Ile Arg Glu  Ala Leu Tyr Glu Ser  Thr Thr Asp
    2210                2215                2220

Leu Arg  Ile Ile Asn Val Thr  Asp Gly Leu Thr Val  Lys Glu Phe
    2225                2230                2235

Trp Arg  Ala Ile Gln Ile Ala  Ser Pro Arg Gln Leu  Asn Ala Leu
    2240                2245                2250

Gln Ser  Glu Asp Trp Leu Ser  Leu Ile Arg Gln Gln  Leu Asp Val
    2255                2260                2265

Thr Gly  Lys Ser His Pro Leu  Trp Pro Val Ile Ser  Phe Leu Glu
    2270                2275                2280

Ser Ser  Lys Gly Cys Leu Gly  Phe Ser His Asn Leu  Pro Pro Gln
    2285                2290                2295

Ala His  Ser Leu Ser Ser Met  Ile Ile Thr Ala Leu  Ile Lys Asn
    2300                2305                2310

Val Arg  Tyr Leu Ala Ser Leu  Gly Leu Val Ser Trp  Thr Thr Thr
    2315                2320                2325

Gly Ser  Asn Cys Asp His Ser  Val Gln Gln Arg Ile  Phe Arg Arg
    2330                2335                2340

Val Leu
    2345


<210> SEQ ID NO 16
<211> LENGTH: 43815
<212> TYPE: DNA
<213> ORGANISM: Aspergillus versicolor NRRL35600

<400> SEQUENCE: 16

ctagagcagc ggtgccacat gcttttcaaa ccactcgaca agagttatga gtttacggtc      60

gctggggtct ttgccctggg cctcagcagc ctttgccttc aaagtggccg agatgtccgt     120

tgaaatgggc tcatcgccaa aatacttgcc attggtaaat ttgccaaact tgaagattgc     180

aaggctttct ttcccgtggt gagaatcgcc aaagtgagct tcccagtctg taactggtat     240

gtatcgtgcc ttttggccag tggctaatgc atggaccgat gttagacgac agaccaggaa     300

ccagaaaagg gatggcatac ctgattggaa agcatcgatc atctctggat aggtgcgaat     360

gtcactgaca gtcggaacga ctcgtccgtt atagtcctct ggcgtgagga agatgccatg     420

tacaatgtcg ccaaaatcgt cttcgagcga tatccaagga aggggcatat cggtatgggt     480

gccccatcgc ggaagacgga gtgtgcggaa tttatcctca tcctcgaaat aaggaaagcc     540
```

```
tccaagagcg tgcgcgtact cctgtcctcg aaagacatcc atgtaccaac cttggtatag    600
agggcagacg gtgtcaaagt gccccgaact cgcagcatac cgctcgattt tcgacttctc    660
tgggcagtat tagcgatgca gctggacgtg cgaccagagg gggtgcaaca taccatcagc    720
tgcctcgata atcgcctggc cattggtgaa gcttgatgtg tcaacaaacg acgagtagac    780
gaggtgtttg acagtgccag cctggataat cccatcgata atgatctttc caaggtcgaa    840
ttcggttgga tgattggcat cccaaaagca ctgcctgcgt tagatagcta gatcgaattc    900
gctggactcg caccttttct cttaccggat cgtccgagtt ggtgttgaca aaggccgccc    960
acgatccaga aaacgctgcc accatctgct ccttcttcca tccatccccc tggacaatct   1020
cagcgccgag gtcggccagg gcctttgccg cctcagattc aggcttccgg gtaattgctc   1080
ggactttgaa tgcattgttc ttcagcaagg accggaccac ggggccgccc tgggcacccg   1140
tcgcgccata cactgttatg gttctgcggt tggtattggt catcttggat gtaatgagcg   1200
agacattggt ccgctgcatt tagggtgagg gtgctccctt atataggatc gtggccgtgt   1260
cgcgttggca ttgggcacca ctgcatccat cattggtcgt gagtgatgtc aacagacatg   1320
gaattaggtg ccatatcaca tggcttacct tgaggggcag aaggaatgga ggttcttaga   1380
gcattatcga gtaaatgtag tggctgaagc gagccaggct acccctcctt cacccttgct   1440
ggacaccgat cgagcaagta tgagcaaggg tggaatgcgc tatagacagg gcctgggcac   1500
cgcctggatg acgaaggctg cctgccacgt cagcgccatg gcacttggtg atcctctgct   1560
gatgcatatg caagccatat tcggatacct ccagtgagaa tgcaggtggc tcatccagtc   1620
ccagcgatac gggggaccga agggctgcca tctcgtttta atacaatatg cagaagtgac   1680
acgacatttg accaaggctc cattctaatg aaccaccacg tctttcctgc tccctcgggt   1740
ctttcaaccc cccctttcaa tcatctacac catgacaaaa agccagacca acccacgggg   1800
accagccata ttgtccccgg cagatctgac tgtgattatt gtcggtctag gaatcgccgg   1860
gctcactgct gccattgaat gtcaccgaaa gggatacact gttattggcc tcgagaagaa   1920
gccagatgcc aaccaactag gtgggttact ctgggctaat agatcaagac cccgtgctaa   1980
tcgtccccct tatgctaggt gatatcatcg ggctaagcgg caatagcatg aggattctgg   2040
cagagtggaa caatggctct ctcgcgcatt tgatagacga cgacatcacc tgcgatgtga   2100
ccgcactgga gcttttcgac gccgaggggc atcgcaaact tgcgatgccg tacaatgcta   2160
ataatcccat ccagggatat ctgttccggc gaacagggct tcttaccagc ttgtgccact   2220
atgctagcca gctgggaatt gatctccgct tcggagttac cgtggacgac tactgggaaa   2280
cagacagcaa tgccggcgta tatgccaaca acgagaagat cacaggcgac tgcgtggttg   2340
cagccgacgg attccacagc aaggccaggg gaatcattac cggagaaaac cctgagccga   2400
aggacattgg ggttgtcgcc tacaggtcca ttttcgatgc caatgcgatt gcggacgtgc   2460
cagaggcgca gtggatattg aagaacgcac aaacagcgga tattttccac tcctattacg   2520
gtaaagacac catggtagcg attgggacgg cagccagggg ccgctacgtg cactggggct   2580
gcgcggttcg tgtatgtcat gatcccttcc agagaatgag cggctctaaa aaatgaattg   2640
actggcaggg cgctttggag gagaagtatg aagcctggat gcaacctgct ccccccgatc   2700
ccatcctgaa atgtctggag agctggccgg tggggagcaa gcttgcagct ggtatcgcga   2760
gaactccacc ggggaagtgt ttccagcagt ccctccgtgc aatgccgccg ttgaagagat   2820
gggtgtcaac tggagggagg atgattgtca ttggtgatgc agcacattcc tttctccctt   2880
acgccggcca ggggggcaac caagcaattg aggatgcagc ggttttgggt atctgtctgg   2940
```

```
agcttgcggg cacatcaaat gtgccactag ccctgcgtgt tgtggaaaaa ctccggttag   3000
tcgtcctctc ccctctagat ttattctgcc gatggcccat catccgacta tatactgagt   3060
tggtaattgc aatagacaca agcgagtatc gctcatccag aaaggttctg cggaggcagg   3120
agactctttc ctcaatgccg cctgggagag tgacaacgca gcagaaaagc caacggcatt   3180
cacacatcag gcctgggttt acgcgcataa ctgcgtggac cacgcgtatg aacagttcaa   3240
tgctgccgcc gaagctgtta tgaatggctg ggaatatact ccaacaaata tcccagcaaa   3300
cggcaaattc cgtcaagaag agggaaacat atagtgtgta gttgctgttg gacagctcat   3360
agtcgggcta tactcaaagg aaatgactac aatgtgtgct ggatcccaat ggacgtgtgc   3420
ttgaagatca gcggatgccg agattagacg acgcaaagat atgtgcaaaa tagggatagt   3480
agagagaaaa gctggctgcc accgaagggg catgtatgtg aacaatgctg tgaaaccgta   3540
cttcctttca aggggtcgca gacctaagac gggcaggcga agtcgtcagc cgtccgctat   3600
accatgatat atccaagttg agcaccaatg ttcgttatga taggacgtga taaagcgtgc   3660
tcgtggtagt gtgagtcgag gaatcctcag cggacaacag catatggtgg catggatgga   3720
ccggaacata atttggacaa ttgcaccatg aaatccatga tggagggatc cggatgactg   3780
gagtttgaac ccacgagcat aacccttact aactcaaagg caaggggcac acatgcgagt   3840
gaggtcgagg cttcagctcg agtgagggcc agccacgact cggggtcgag ggccactttt   3900
cctagtatac ccaatacaag atcgcccact gagcacagat tctcaaagtc atgcgatcgt   3960
atatattcag ccgtcgcatg aaggaaatca agagaggaga gacattgctg accagtaagg   4020
gggcatgtat gacgtggatc aagcagaatc cgactcggac gaatcagtga aggagaggct   4080
cgtataggtc gtacaaggag aatgtgcaat gggcaagggc catttgaatt gctggttctg   4140
ttcatatagc ggatagtcag acaaggtatc gcctgggaaa cgtttccgat agtctatttc   4200
tgtttgactg gcactgcaag ctatatacta tcatggctat tgaagaatct ccaacatacg   4260
ctgagccggg accatacgaa gccctgagcc ggttctcttc acttactcgc gaggaccacc   4320
gaaaatggtg ggaacacaca ggccctgtac tggagaaggt cttgaaagac tccggatatg   4380
agctccaaag ccagtacaca tatctatact ttgtccagca acatctcgtt ccataccttg   4440
ggacattccc caccaggggt gaagacgagc atcgctggca gagcaatctg acccccctaca  4500
aggttcccta cgagttgagc tggaatattt caaacaaagt ggtcagaatc tcatgggatc   4560
cggtctgcga tgcatctggg accgaggccg atgctttcaa taagaaggca atccacgact   4620
gcactcgtca aatcgcccag ctaagcaaca ccattgtcct cgaccggtac agaattcttc   4680
accaggagct ggtcatctca gaccaagaag aacaggaact ccttcgccgc gatgacctac   4740
caaagtccgg cagaggacaa cataacttgg ccgtggattt ccagaatgga ggcatagccc   4800
tgaaagtcta cttttatcct tacatgaaat tcctagcgac tggatctccg gttgagcaac   4860
tctttttcgc tgccattgaa aagataggca ccgcagatat tcaagagcct gtgaagatgc   4920
tgagatgctt cctgagcccg agctttgacg acggcaagcc ctctgttgat caaaaggtgt   4980
ttcctagcct cctcgcctgc gacctgtgcg accccagcaa gagtcgcatc aagtactatg   5040
tgatcgacaa atgggtgaag tgggagcgaa tagcaagcct gtggacgatc ggtggccggc   5100
gcctcgaaga cccctcttgc gccaaaggtc tggccctgct caaggaactg tgggatcttt   5160
tggcaatccc agaaggcgac cgtggagata tatggcctaa cctcgtcctt ggacaacctc   5220
cgacgcatct gatgacgacg atggccaact atacgttgtc gcccgcgagt cgtttccccg   5280
```

```
agcctcaagt gtacctgacc acgtttggaa tgaacgacat ggcaatcatg gatgccttga   5340
cagcctttta tgagcgtgct ggccttaccg acatggccaa gtcgtataaa aagaacgtcc   5400
agtcgtacta gtaagttggg cccttcccga tgatatccgg cttggatctt ggaggaaaac   5460
tgaccattcc tgctctacag tcccaatctc gatctcagcc aaacaaactg ggtgcacgag   5520
gccatttcat tttcgtatcg gaattcgaag ccatacctca gcgtgtacta ttccccttc    5580
tgagcggcga ctacaggcaa aggatggtgc ggagagtccc cagtaaacca aacagtattc   5640
ttgagaatgt ataagtctgt gttggcctat aaggggttat attatgaaga cgggcatgag   5700
ggcctataga aatgaatgca tcttcttttt tcgttgttcg gttccatcgg cacggtatat   5760
gagagctcca tccggaccgt gccctacatc cttccctata acgtagacat ctctttttcg   5820
ggagactcag gcataactgc cctccggaat ggatatttcc gccctgagta taatgacgga   5880
agccaggcct ttagcagaaa gaggttcact gccccttggc tgtcaagctt tactaaatgt   5940
gagtggcgcc accatcagga atgcgcctag catttcaata taaacaatct ttatcatcct   6000
cctctggttg aaactgcaat cacgtctcgc ctgcatttgc aggcttctag acaacgtgat   6060
cggtatgctt tagtcaaccc attctgctaa ccatctgagg tactcgaggg gtacagcggt   6120
caaccgaaca atccagacct atccagagaa tcctccctag ggtactgagc tccttgcata   6180
tagcggaaat ttccaacttt cccaggcaaa cgagtgtacg gagtcccttg tacgacaagc   6240
ctcctaccgc cggggttgcc acagaattac gaccagggtt gcgaattgta aggggatttg   6300
ggaaaccccg tttttttttt tttctttctc tttttccttt ttcttttcag ggccctgtgg   6360
ataagagtcc acccatcata caaggaatgc tcacgtccag gacgtctctt catcctccaa   6420
gagtccactc gatgagctac tgtcacaatg cgtgatattc gagagcttct gcttgtgctt   6480
ttcacatctt gccttgcact gggctccgtt ccttctagct tcgatggcga tcggtattgt   6540
cggtgtcaac caggagaggc ttgttggccg tctcttgcag attggcaggc cctgaacatg   6600
tcaatacagg gtaccctcgt tgaggtcagg ccaattggac acgtttgcca tgagcctaca   6660
tataacaagg cggactgtga gcgggtatcc aagttgtcgt caaatgggac gtggagagca   6720
agccagccag gtaagccagc cgcaccttca aaatgtcctt gactcaaaga aagcccatcc   6780
caggtgcaca acaggagcat gcatgggagg tttccctgtc acgaaatgag agctgttatg   6840
ttggtcccgc caatcctgcc gagccatgcg gccagggccg tatcccgcga tactcggcta   6900
tggtagagac caccgaacag gcgcagaagg caatcaggtt cgccagggag agacggcttc   6960
gtcttgtcat caagaacacg ggccatgatt ccgggggggcg ctccagtgcg gtggattcgt   7020
ttcagatcct cacacagcgg ctaaaagata ttagcttcat cgaggaattc acgccgactc   7080
tcgcggagac aagggggccc agtgtcagga tcggagcggg agtcctgacg aaagagctct   7140
atgccgtcgc ggatgagcac ggctatacgg ctatgggtgg cgagtgcgca acagtcgggg   7200
tggccggagg atacatccaa gggggggcg tgtcgacggc gctgacaccc atgatgggcc    7260
tggccgcaga cctggtgcag gagtttgagg tgatcagtgc ggaggtatac tctgcccctt   7320
ggcctttctg tccagcatcc agctattaac gtcaatattc ttttcatagg gcagccttgt   7380
catagcaaac gaatttcaaa accaggacct cttctgggct ctccgcgggg gcggcggagg   7440
gacagttgga ctggtgacaa gcatcacaat gcctgtcttc ggcgcgattc cggcaaatat   7500
atcagagttg tcgtttgaaa gccagcaacc cgatgaagcc ttctggaccg ccgtaaagga   7560
gatgatctat gtcacacgcg atataaccac tggggggaac tcgggtcagt attgggttgg   7620
tcgcggtccc acggggagct atttcgtccg acaaacactg ttctttctag gcgagacaga   7680
```

```
catagagccg gcagacaaga tgggaagcct cctccgtgtc cttcaggatc aagagattgc   7740
ctttcgtttc aatgtgacgg catacccccg gctgagttct tttcttgcga ttccccaagg   7800
cgagttcgtg ggtgggatcg cattccacca ggaaaacatc ctaattcccc aggggtttta   7860
cgactcccct gaaggcccgg cacagctggt cgaccgcctc gcggaagtta aattgaatcc   7920
aggtgatatg tgggtggcta atacgctggg cggacaggtg atggccaaca aggatgtgga   7980
taacgccatg cactccggct ggcggacggc gtctgttctg ctggtgggaa atcggatctt   8040
cgagccagcg ttaaagtcac agcttgatgt gcaggagcgc ttgacggcgg ttgaagggcc   8100
tcttttacac tccatcggac agccggctcc tgaggccata tacttgaatg aggcggacgc   8160
agacctcgag aactggcagg actggttttg ggcgagaaag tacgcccgtc tccgcgatat   8220
caagagcaaa tgggatcctg acgatctgtt tctcgtgagg catggggtag gaagtgagga   8280
ctgggatgag gacggcatgt gtcgcatgca gctgtcaccg caagaatgcc cggtgagaga   8340
acactcacgg tgcacctgta aattcttcga atgcgcaatg ttgcatgtgc ccgggttgct   8400
ataggtagtc gattaactag tccgaggctt tccagtagat cgcctggtat ttctttactc   8460
cattgaaact ggcttgtggg atggaagtta tgatggtctt gggagcgtgt aatgtacgaa   8520
tatcaaaccg cataccctaa gggattatct ccaatgatat caagccagct ccatgactca   8580
ggcacgagag ccaagatgga tatgtatagt attccagagc gtctaatcag cggaggagac   8640
aggacgtact ggcatcagtt tacctgaata gctgacctca ggctttgcca cagcccagaa   8700
cacccaataa gcaagccgag acatggaacc cttcatctcg atgggtcaag tgaaccaacg   8760
tgctatgacc tctgctgact gtgaagaagg acaaggccct tgccttgctg cccgagttcg   8820
cctggtactt ttcaaattcc tgtcgccccc agcgtaacct ttgcgcccgt tgtactacac   8880
ggataaatga cgcgactaca cccttcctgg cccaggccga gtaggcatgt aaggggcgta   8940
gctgatcaag aagcctctgg ttgtttagtt gtttccgccc agtagtcctt ggattgtggg   9000
ccgtttgcct aactggagag ccgttctccg tgggcgtgga taataaaaga aggccgtagg   9060
gcccgcgaga ggtggcacat gcgtgaaaac caagtataag acatggattc aacacaaatt   9120
acagagtcaa atcgagagtg cagtgtgctc cagggcaagc tggccactga gacagtcaga   9180
gagtcactct cttcgtctcc ctcgccattg ccttccctcg cctctcctgt ctcctctggc   9240
tctgaacctc cagcatttgg agagacgcag ccccagagcc gggattccac cctgttattt   9300
aacgcccaag tgcccgagtt ctgggagaca tgtgtacacg acgtaatcca ggaaaggtgt   9360
aaggaagcgc cgcaatcaac agcagtggcg gcttgggacg ggtcctttac gtacggtgaa   9420
ttggacgacc tttccaatcg cctggcgtca gccttgacct tactgggcgt caaggccgaa   9480
acgttcgtcc caatatgcat ggagaaatcg cggtgggcga cagtcgcggt gttgggagtg   9540
atgaaggccg gtggcgcgtt caccctgctc gatgcatcat accctctgcc ccggctaaag   9600
acaatttgcc aggagctgtc cagtctcgtg gttctctcct ccactgccca gtccgagcgc   9660
tgcacgcagc tggcgaatat gattgttgta gagcacctgt gccgagcgtg gcaccctgtt   9720
gctcacacca cccagtcccc ggccactgtc tgcccttcga acgccctata tgtgtccttt   9780
acctccggat cgaccggccg gccgaagggg gtcctgattg aacatcgggc atacagctca   9840
ggcgcccgag agcatctaaa ggccttccga atcgaccaga cctcccgggt cctgcagttc   9900
tcctcgtacg cctttgacgt cagcatcatg gagacgctta gcacgctgat ggcgggtggc   9960
tgcctctgcg tgctggggga tgcccaacgc tcggacgtct gcttgtttgc tgcggcggtc  10020
```

-continued

```
gacgagttcc aagttagcca tgctctactg acgccgtcgt ttgcacggac ggtgccgtgg  10080
gagaacgtga ggcacctcca gacactggtc ctcggcgggg aggaaatgcg agtttcggac  10140
gcagcaatgt gcgtggagcg aggagtcaga ctgatcaatg cctacggcac agctgaatgc  10200
tcggtgaatg ccacggcacg gcccggggtc cagcctgggg ataatctcag caccatcggg  10260
caccccacgg gagcggtagc ctggctcatc gacccggacg acccggagac gccgataggg  10320
cccgggatgg aaggggagct gctcctggaa gggccgattg tgggccgtgg gtatttgaac  10380
aacccggccg cgactgcagc ggcgtttata ggccccccaa agtggctgca gcagctccgg  10440
aagacggact accagcacca gctgtatcgg acgggggacc tcgcggtgca ggacagcact  10500
ggggccttga tgctccttgg ccgcagggac gggcagctga agatccgagg ccagcgggtg  10560
gaggtggccg aaatagaaca gcatattgac cgcgtgctgg ccgcagtgaa ggaggtgatt  10620
gttgagaagg tgacccccga gtgcgagcag cgagaaatcc taatggcgtt cgtccagact  10680
ggggcgactt cacaggcttg gactgagggc tcgcccttgt ttctgcctcc agggccaacc  10740
tccgtacaag aatttaggac agcccagagc cagctgcgcg ggcagctccc cagctacatg  10800
gtccctacca ttttcatcgg tgttgctgca gtcccacgaa ccgcctctgg caagatggat  10860
cgccggctac tgcgagtgac cgctgggcgc ttgtcgagag aagagctgca ggcgttcacc  10920
ggctcacccg ttgacagtcg ctctcctacc actgcgactg agctcatgtt gcaacgactg  10980
tatgcagagg tgctcgaact gcctaccacg agcatcagca tggaggactc cttcgtgcgc  11040
ctcggtgggg actccatcat ggctgtccga ctgctggggg ccgctcggcg ggcagggctt  11100
gtgttagaca tcggcgatgt gcttgggacg gcacggctgg aggagcaagc gcaacgagct  11160
accccctatga cagagggaac agcatgtgag acctacatcc ccttctcggc gctgggaagc  11220
cggtatatga accgcgagga agtgctgcgc ctagcggcag agcagtgcgg gacctcccta  11280
tctgagattg aagatatata cccatgtacg ccgctgcagg aaggaatgtt ggcgttggca  11340
tccagtcaga cctggatgta cgtcggccat attgtctttg gactaccgga gggcgtcgac  11400
gtctcccgat tcaaggccgc gtggcagtcc acggcagata cgactcccat cctgcgcacg  11460
cgcatcatcg agacaccaca gggactcttg caggtggtgc ttcgaggcag cctggtctgg  11520
gaaacctaca acgagccgcc agacgcgtgc gtagccgatg gggctccca gatcgggtcc  11580
cccggtgcac cgctgatgcg ctttgctcta ggggatgggg atcatcgtga tgaatttgtc  11640
ctcaccgtcc accatgcagt atgggatgcc tggtcgatgc gcctgatcca cgatgcagtc  11700
gaacggtcct tccagggcga gcaggtaaag aaacagccgt tccacccgtt catccagcac  11760
ctgcagcaag ttgacggcgg aatggacgaa ttctggcgca ccgaactggc caacctggag  11820
gcggtcccat tcccagctct gccatcgact cactaccggc catcacccac ggcgatgctg  11880
cggcacaccg tggagaagat cgagatttgt gcgccgcgca gccacacaat ggccagctac  11940
atccacttgg cctggtcgct actggtggcg cactatacag attcgacaga ggctgtgtac  12000
ggtgccacca tgagcggccg caatgcccct gtagaagcta ttaatgagct ggcagggccc  12060
accattgcta cggtgcctgt gagagtccac gtccgaccgg aggataccat ctcggcggcg  12120
ctggagcaga tccagtcttg catggtgcgc atggtcccgc atgagcaagc cgggctcctt  12180
cgtattgcaa agaccagctc ggatgctgcc agggcgtgcg ccttccagag ccacctgaac  12240
atccaagtcg tcgagcccga gcggcgcctg ttccctgtca ggcggggaat cgccagcacc  12300
ggcatggacc tgacacggtt ctccagctac gccctcaatc tgatgctact gctaagcccc  12360
gacaatacta gcgtcatcgt gaatattgcg tacgaccccc aagtgttgag tgcgtgggag  12420
```

```
gtctaccgga tgatccacca gtgggagcat atcctgcgcc aagtttgccg agagccgact  12480

gggtctctcc aggagctcga cttggccagt ccactagatc aggatctgct gagggtatgg  12540

aatgcaaaga caccggccgt ggaccggcgc tgcttgcacg atctcgtgct ggcccaggcg  12600

atgcagcagc cttcacgaca ggctgtgtcc gcgtgggacg gtggattcac gtacggcgag  12660

ctggcccatc tgtcctcgaa ctttgcccgg ctgctcagtc tatttgcagt ggggcgcggg  12720

tcgtttgtgc ccatctgcat ggacaagagc cggtgggcag ttgtgtcgat tctcgcagtc  12780

ctgcaagccg gggccacctg cgtcctcctg gatccccaat atccgcgcca gcgcatgaag  12840

gacatcatta ccggtttatc tgttccggtg ttggtaaacg caccgtcgac ggcccggtg  12900

acaagaggtc tcagtgcgat ccagctgtgc gtatcagcaa agttcacgga gcagctgtgg  12960

accagcaatc cctctgggag tcacttccaa gcacacgtag acccggacga ccttgctttt  13020

gtgatcttta cctctggcag cacaggtgcc ccgaagggga ttgcgatgcc gcactctacc  13080

atcagttcga gtatccgcca taacagcgct gcgatgagat tcgacgctga tacccgtacc  13140

ctgcattttt cctcgtacgc ttttgacgtc agcatctacg agatcttcac cacgctggcc  13200

tccggcgggt gtgtctgcgt gccgtctgag ttccagcgga cgaatgagct ggccgatttc  13260

atccagcagt ggcgtgttaa ctgggccttt ctaactccct ccacggcgca gtccctccat  13320

ccgtcagagg tgcctggcct cgctacactt gtcttgggcg gcgaagcagt gacaccggac  13380

cacgttgaag tttgggcccc tggccggacc ctcattaatg gttacggccc cgcggaggca  13440

actatatgcg ccgtcggccc actgccagag catggatggg tccccgggaa gatcggccac  13500

gttgtcggcg gggtgggctg ggtcacggtt ccctctgatc ccaaccggtt ggctgcaatt  13560

ggagccatcg gtgagctatt gctggagggg ccgttccttg ctcgagggta tctgaaccag  13620

cacgaggcca ccgctgcctc ctttatcacc ccgccccccct ggcgccgcaa gctgctgccg  13680

ggctgtgatg ccgacacgac caggctctac cggacgggcg atctggtgcg gtaccaggaa  13740

gacggatccc tacgatacat tgggcgtcga gacacgcagg tcaaggtacg cggccagcgc  13800

atcgacctcg gggagataga gacacagcta caccggagct tccccggtgc gcacgacgtg  13860

gtggccgaga cagtccagct gccagtactc caggacagaa cagttctggt ggcgtttatc  13920

ggccgtcaag agggcctagt gatggagtcg gctctagggg aagaagtcgt agctgccgtc  13980

gatgcaggct ttcaacaagc cgtatcctcg gcgcaagccc gcctccagga tatcctacca  14040

tcatatatgc tgccatccgt cttcctgcct ctagcccact gcccgaagac cctcacaggc  14100

aaaacggacc gccgctatct acgtcaggtt gtgctgggtc tggagccgca cgaactacag  14160

cgttataggg tggccagtcg ccagaagacc aggatccctg tgtctcacgg ggctgagctg  14220

cgtctgcaga gcatttgggc agacctcctc cacatcccct gcgacgagat cggggcggaa  14280

gataccttc tcctccacgg tggcgattcc gtggcggcca tgcggatggt tgccctggca  14340

cgccgcgccg acttcacgtt cagggtcacc gacgtgctca ataactgcac cctatctgat  14400

ctagctcgct gtacgggtga agagcaatgt ttggctgccg agaccctgcc caccgtccac  14460

gatgtcgagt ctgacgatca agtggtagct agtcagactg acagtgacgc catcgcggtc  14520

tatcccacca cgcaggccca gtccttcctc atccagcggt atccatggac ccattggcgg  14580

tttgccttcc acggggaagt ttccatagac cgactgcgca cagcatgcgc acgcctcgtt  14640

gctgctcaca gcatcctgcg cacattgttc gtgggtggca aggggcaaag ggatcggcag  14700

gtcgtgatga aggcgctgga tatccccttg cacactgtca ccacgaacaa gagcctggag  14760
```

```
gaatactgtc aatcaatctg tgatgccgag caacagatgg atgtcgtcga gaccgtgctt  14820
cccactcgtt tgactctggt ctccgacgtc ctccacacgg cgcatatctt cgtcctgcgt  14880
ctttctcatg cccagtacga cggaatttgc gttcccaaga tcttcgccgg tctcgagtcc  14940
ttctacaaca ggacagagac agtcgcccca acgatatttg agcgatacct cgaccaacgc  15000
caacggttcg agggcgaggg tcctcatgag ttctggaggg cgtaccttgc cgggtcatcg  15060
cctccttgca cgatgcctgg gaaatcgaca cctcccacga ctgctgacag tgggcctgtg  15120
gctcctcctt ctgttatttc cgcgtcccag accgtgaaat tcactgccat tccatcccag  15180
gtcacactag cgacggtggt caaggccgcc gcgtgtctgg tcttagcccg tctcacaggg  15240
cgcagcgata tcaccgttgg ccagaccgtt aatggccgta gcctgcccct gccgtgggtg  15300
aacgaagtgg tagggccctg tgtgaattac atcccattcc gcgcaacgct gcagcagtcg  15360
atgtcgaccc aggactactt agttgacatg caaaggcagc ataaccgctg cgtccccttc  15420
gacggcgccg agctggacac aatagtcaag aactgcactg actgggagcc gacggcggaa  15480
tttgggttca ttctgcagca tcaaaacatc gacatggact tgagcctgac cctggacgga  15540
aaccggtgcg tctcctgtgc ttcttccggc cagctgcgtc cgtccaacga ggtctggatt  15600
tgctctacac cgtctccgtc tggtgtggac ttggatgtcg tcgcctctag tcatattcta  15660
actgcagatg ccgctaagaa tctggtggat gacatcgctg atatgattca aaccctacta  15720
tataatctag agacccccct gcgagatgct gtcgagttga actggtctga tgggagttga  15780
gccgtctgtc tctttctttg ctttttttata tcattgctct tttgacaaac agtacaagaa  15840
attgaagtta tattggaaac ctgtggcccg tagcttcaac ttcgccttac tagtcttttc  15900
cttcatacaa ctcctacaat cgggatcgct cagtccaaga taagtgactg ccactatgta  15960
aatagctgtc aacatgtgga cagatgacag ttaatccaag ctcaaccttc ctcccacaga  16020
taggtacttt gtgaatgaaa atacacgctc atgtagacgc cttttttggc agtgtaggaa  16080
tacgatatcc aagattgcaa acgggatgtc cgggaaacgt ccaggtccgg gctgtccaac  16140
ctgttagcag agacacttac cactgcgcaa ggcaaaggga aatcatgagg gagacatact  16200
acagctgttg caacatatcc ggataggcac aggcatgctc tgaccaaccc aaagaatccc  16260
aaaactgggc caacgaccga gccacgcgca gatcattctc gccatgcacg gggaggtaga  16320
acttgggcac ggggaagctg ctcccaggac tgatctcgta gttccatatg atgggcgatg  16380
ggatctggtc ggtggcactg gccttgccgt aatcaaaccc gcccttaaag gcccggctgc  16440
cttcgccaat ctgcaacaga gaccagatct gcttcaaccg ggccagcccc tccatgattt  16500
caggctcttc gatcagccgg ccgcctagag tccacatctc cgcaatcttc gcccaggtga  16560
cctccgtgtg agcgccgtag atcttgaccc gctgccgcga catttcaacc aggtcgcagg  16620
acagaaacgt gtactcgttg tagcccgtgc tttcctgcat gtagtcgttg atcagggaaa  16680
acgcgtgcat aaactgattc ctgtccgcgt cgatggcgcg caccgactcc gcgatgagtg  16740
tcgcaactgg cacgcccgcg gcctttgctt tcagatacgg gaacacgtag cccttgacga  16800
gaatggcgcc gtccgggtta aagtcaaagc caaacgcacc ctgcgacttg agcggctggt  16860
catccggcgg gagctggcgg acctcgtcca gcgacagttg gaaccgggtg agcagctgct  16920
ggaagcactg cgtgtcaaag ccacgcagtt gcaaccttgc gagctgggca agcagatcgg  16980
cgatggggat ccgattgaac ggatcctgcg acgagccaga caggaagttg acgggctcga  17040
acccgattcg tagcaggcgg tgcgagcctt tttggaagtt gagactgaat tcaatcggca  17100
gtccgctgcg cgagattgtg ctgcgccatt tctgcggata gggccccagg gcggggatga  17160
```

```
ggtggtgcat gaagaagaac ataaactggt actgttggtg cagtccgtac tgtccggcct  17220
cgaggaaccg gctgcacagc gagcctgtct cctggtacca gcgttcctgg tcgcttgtgg  17280
gaaagtggtg ataggaagat agggcttgtg cagggctcga ccgggcaggg ggctcctgag  17340
gatgcccagc aggtgcactg agctcggggg ccgtcatgtt gtgggaatat tccagtagac  17400
aagcaggaca ctggcaggca caacgctata gcaaagaaga tgaagcttca tcctcgtcgt  17460
cggaacaggc cttgaccttt gtgcaacaat cgtgccatgc aagggaactt gagcataaca  17520
cctcgccagg tctttttttt tttttttttt tttttttttt ttactctttc cctacacgcg  17580
ctcttccgat ctcacagact ctttccctac acgcgctctt ccgatctcac agttctacgg  17640
ccacatgtaa gggcacagtc tgggccttcg ttctcagatt acgcgaatgt aacaggggat  17700
gagtatgcca gaaggtctcg gattgatgca aattgactca gcttccagcc tgctctaact  17760
acgccccatt cctgatactc agcccttgtg aaaccatcag ggctgttgtg taacctccgt  17820
tgccggctcc tatccaacca cagaaggctt ggtatgcaag gacagacaac tatgcttatt  17880
ggtaagtggc cagaatgcta tcaaccacgc ctagtgagga cgacgggcat cctctcgatt  17940
cccatcgaga agtggtcctc tacattctcc attaagtggc tgccatcctc gcccgccggg  18000
aatcgaatct caaaggtcat aataagccgc gcgatggtcg tgcggatatt catcagggca  18060
agtggctttc caatgcagct atatgggcct gcggagagca cagcaacggt cagcccaatc  18120
acacgcacaa catccaagtc aatgagatac tgcctacctg tcaagaaggg ggcatacgcc  18180
gatcgatgct tgatcaagtc cgggtgcttg taccaccgct cggggttgaa ggaaagtggc  18240
gctatgaatg ctgcgtccgc tggatatacg caaacgtcag aacttggttt caagagggaa  18300
tccgcaaggg agagggttgc ctacagcgtc caatgaccca ctgggggcag aatacggcca  18360
tgccccccgg aatgtgcgtg cctttgacgt ggacaccctc cgcgggcgtt atgcgtggga  18420
tcaccgatgg aaccggcggg tgcagccgaa gcgtctcgtt gatgaagccg ttcaggtgag  18480
gcaggttgga gatttgctcg tgccggtact cgccattcgc atcggcgtcg attggcagca  18540
gctcagctcg gagcctctcc acgtcttctg gatgccgggc cagctcgtag acgacactcg  18600
tgagtgctgt tgccgtggta tcactgcttc ggtgttactg gcacagtgcg ccgactgcct  18660
ggatagaaat cacacacctt ccagccgtaa ctactaacat ggcgtcgccc atcaataagt  18720
tgaattcgtc gggagtaggg ctgcggccat tcaacggggc cagcaacgag gcgcaaatgt  18780
ccggtatctc caacttatcc tagacggcgt taatacacac tgcacggata atattaagga  18840
ttcttgtgcc atatcaacct acattcatcc ggtgcaccag cttctgtgtt gtaaattcaa  18900
caaacctatg ccagttcttg gagagagaag gcagcgtgac gaagcatcgg aacagccagg  18960
acggaacaaa gtatttatag aggacaattc catccaggag cacctggatg gcccaatggt  19020
tactatgcgt gtcaagcatg ttgaagctgc ggccaaatgc caaatcgccc atgacatcgt  19080
agctgtagaa gttgaaccag tcgctgatgt tcaccgtcag cccgacggcg tcattcagcc  19140
gggtaaacag cttctggcga tactcatgga cccgagtctc gtaccctcgg agagcccggt  19200
caccaaagcc agtgctccag gtgcgacgcc gttgatcgtg ggctgctcgg tcccgatacg  19260
agtgcagcga cttcatcggg tggccattgt catagaaggt gctcttataa cagcgcgact  19320
ggtgtccata gacgattccg actgcctctg gataggcgat agaaagctcc gagggtccaa  19380
cacgtacgat cgggccgtat tggttgtgga gctcctggag tttctgaaag gccggtcgat  19440
ctcgcaggcc catggacagc cacaggcccg agattcttgc gccgtatgga ccaggaaacc  19500
```

```
catgaagggg gtggaactgg acgcgataga gaagcaggga ggtgtagagg cccgcaaagt  19560
aggtcaaggc ccatcctccc gtggccttcg ctgcgtcgta gagggggaga ccccagacga  19620
tactcacaac caccgtgggc gcggtgatga taagtgtgta ccatcgcaaa taagcaaaag  19680
ggtacaggtg gtgttcgccc cgtcgaaagt aacactgatg agatataacg ccagcaatcc  19740
ctaccagcag atacagcagg ctcatggcgg agaagggcaa ttccatcgcg taaatgcgga  19800
agcctatgtc gttggcgagt gagtgcaagc agcgacaaga gaagggcgaa atagtaagct  19860
ggccggaact cttcaaccag gttattcagg gtcaggcata tggccaccga tgcgttccat  19920
cgaccacagg gcgtccggta gacagcgtcc catcccagtc cgcagagacg gcgacgatac  19980
gaggccactg gggatccga ggtgaggagt ataatgtcgt gtaacatcta ggggctccca  20040
cagccaaccc gatgaatcat ccattcttcc tcagtatgct ggactccttg catgtcaaag  20100
caaaacaacg acctcgaccc cccgcaggga gcatgccaac gccttacgac tactttgatc  20160
agtcggacat gcattgaatc tgggtataga cgtatcagac gactgtaaga tgcaggcata  20220
gaggttcaca tgcttgggcc acggaccaca ccgcatggtg tgcccagttc agcacccctt  20280
gtatgaagag gtatctacga acacacaggg atgaaatagc gtctgtgttc atccatgcat  20340
atatctggtc ggcaaagccc tcaccctcta tcgtacatta ttccttcggc ctcgtcaccc  20400
tggtaagcac aaataaagca gagattaccc gtctttcaat ggcgcaagac accgcactgc  20460
acttgcccct ggggctggag ccggcaggat gggctcttgc actcctgaca agcagcataa  20520
tctacctctt cctatcgcca aagtccaaga gcccccgatt cccagtggta aataaatatt  20580
ggtgggattt tttccaggcc aaggcaaagc gtgatttcga ggccggggcg gaggacttga  20640
tcaagctcgg gctttccaag gcaaggacca aaccacggag agaataccca gtcctcgcta  20700
acagctgcag tcgcctgttg catttgaaat ggtaacaagc attggcttta ggctggtcct  20760
gtcagatcaa ctggcggatg cagtcggaat ggataatcgg tttgaccagg acaaaggaat  20820
tgcacctgta taactcttgc atccccgggg gccctgctct gactccgcac agctgactag  20880
gtgccattat tcaggtcaat ttggttacgt tgaagggttt tgagtccatg tatgcagggg  20940
cactccacga ctcggttcca cgtcctgcta cgagcgcgac gtcgaaaaga ctcggtaggt  21000
agttggatcc ctcggtcaac ggagactcga cggctgatga tacgcgtgta aagtgcattt  21060
aactcggccc ttttccgagg aaacgacaga ttttctgcag agagagtgga cggaatcgcc  21120
cggtaaggaa aagccgcagc tggtcctgtt gattgttccc gactaacagg ggcctccaga  21180
ttggcatgat atcgaggtct acccagtgat atctaggcta accgcacagg ttctcagccg  21240
agcattcgtt gggccgaggc tctgccgtga tacgcgctgg ctggagattg ctacgacata  21300
catctcaaat agactcactg ccgtcgtggc cgtccagaaa tggggagccg tgctgcaccc  21360
cattgtccac tggtttcttc cttcctgccg caggcttcgt gcgcagaaca agagggcgcg  21420
agaactgctg cagccagagc tggaccggat caaggaaagt ccattggagg atgagacttt  21480
caccagcctg gcgtggatcc acggctatgg tcagggctat atatacgatc ccggcctagc  21540
ccagctgcgc ctctcggccg tggccaacca caccacttcc gatatgatga ccaagaccct  21600
gatccgaatt tgtgagaacc cggagttaat ccagcccctc cgcgaggagg caatcgaggc  21660
cgtccgaggg ggtggcttgc gtgttgctgc cctgcagaag atgttcctca tggaaagtgt  21720
gatgcaggaa agccagcgcc tcgagccatt tattctccgt acgagcaccc tggagcctac  21780
gtatctgagg ttgatattga catctgttgc tgctgtctag tgtccatgtt tcgctacgca  21840
acggaaacgg tcactcttcc agaaggcacg accatcccca agggaacgct tctcgctatt  21900
```

```
gcaaacccaa gcagacttga ccctgccatc tacccggatc ctcacaagtt cgatggctat  21960
cgctttgtcc ggatgcgcga ggaccccagg catgcgcacc tggccccttt taccaaaacc  22020
aactctacca acctgaattt cggccatgga aaacaggcat gtccgggacg atttatcgca  22080
gtgaaccaga tcaaaattgc cctctgccat atgttgctga agtatgatat tgagctggta  22140
gaagaatgcc cctcgcagct ggtacggtcc gggctcgtta cagtcaggaa ccctggcgca  22200
aagatccgag taagacgacg ccaggaagag gtctgtctct aatcacgccg tgtctagata  22260
caataatgtt gggacgacat ggtttagctc acactgaagg gtttgtctgt ctggtgatgt  22320
ggatttacgt ggatgtagtc ttcgtacaat gagaatctcc tctgtattcg gcagcaagga  22380
atcgccagca tcatattcca ttcccctccc ttgttttatg cggatgaaca atcctgtcct  22440
ccctcaccgg ctcccagttg ctgctgcttt ggtcctgttt ccccttgcat acttcgcaat  22500
ccttcggtac aagtatgctg cgtaacattc cttgtttttc tacccagtag agtactaccg  22560
acaccgtgcg gtcatcttcc acctcgcgtc tcccttgggt acattcatac gcctgccaaa  22620
tatatggtat aaggcggtcc catgcgcaca tggggtgcaa ttctgcagga cagctctttg  22680
ctagtcttgc accttcaaaa tcaaatccca aagccggacc ggccacactc cctggacatc  22740
tgtcctttat ctagacattt ggcaactcaa cttcgcatcc tcagcaaaca atggctatag  22800
acgcatctgg tgctgctgct cccaattcat cgggtatcac tgttatcata gtcggccttg  22860
gacccactgg gctagcagct gctattgaat gtcaccgacg gggccataag gtaatttgtt  22920
tcgagagaaa tcccaagagc taccgtttgg gtgagtgagc tgccgcaccc cggttagaac  22980
gttaagggct gatgggagca ttaaaggaga cttgatcaat gtgaccggga atgccgcgcg  23040
agtgttgcag ggctggggca atggctctgt gattaacgat ctacaggcat tccagtgcaa  23100
cctggacacc cttgaagtct atgacgagac tggcgacctc aagctttccg cgccgtataa  23160
tgcaaaccaa gcgaaagaca actacatgct gcggcggtcc aggctcctcg acatattcct  23220
gcagcatttg aagaaccttg acgtcgatat tcacttgggc accgaggtga ccgactactg  23280
ggagactgag agcagcgctg ggttactgt tggtggtaag agaattgctg ctgattgtgt  23340
cgtcgtggcg gacggcgtgc acagcaaagg caggccgcag gtttctgcag agccctttga  23400
cctcccgtcc accgatggaa ctgcattcag ggcattcttt cacgccagcg aaatagcaca  23460
ggatccagaa gcgtcgtgga tcctgcagga tgcaggcgaa ggggactgtt tcaagacctt  23520
ttacggaaaa ggccttgtca tgatgttggg gacggcggaa aaccacgaat acatcttctg  23580
gagctgtggc tccaaggaga atgtcctagc acagtcttct gccgtggccc aggttctcga  23640
tctcatcggg gactggcctg tatcgaagag gcttgctcct ctgatatcca aaaccccaag  23700
cgacaactgc ctggaccaaa cgttattcac acgatcgccg ttaaacaaat gggtatcgcg  23760
taagggaaga atgatcgttc tgggagatgc agctcatccg tttcttccac acgccggtca  23820
gggtgcaaac caagggattg aagatgccgc tgtcctggcc ctgtgccttc agattgccgg  23880
caaggacgac gtgcccctag cgctacgagt gacagagaag ctaaggttct atcctctttg  23940
tatctgtgtc ttctacgttc taacacatga tccaccaggt accaaagggt tgctgcaatc  24000
cagaaacggg gtgttgaggc cagggatcag tcattgagcg tggactggga gaatggcggc  24060
tttaccaaga agctcactct atatccggcc tggctgcatg accaggactg cattaaacaa  24120
gtctatgagg aattcgacaa ggctgttgct gctgttacaa aaggccatga atgtaccttc  24180
ggtggtatac cggtggatta attactatat ccacaaactg tttacgtgtc atatacccgg  24240
```

```
gtacttgatc taaagacatg aatctctaaa tatgcagatt ttggatacag agaacaccag  24300
gtcttcgaaa gtggtcacaa caatgcaggg tccacggtcc ttgctgagcc cttacagtgt  24360
ccctgtaaat tgactgacag acacaagccc ctccggcgtt ggggctgcgt cgctggtgct  24420
cgtccagttt gacaccataa gatacaattg attccgctcg ccggtcgacc acgggtggat  24480
gaatccaccg tacagcaacg actcgtcccc cgcctggttc acctgcacgg tttcctcgga  24540
ccaaggccca gtcgggcccc ttgcagtgcg tgagacgata tgcggcgttg aagtgctcgc  24600
attcagatag accatggccc aagtgccatc ctggagcctg cgcaccgacg gctctccaaa  24660
gtacccatcc agaataggcg agcagggtct ttgccagccc cagtcctctc cattccatcc  24720
ccatccctgg tactcggtct tatccgtcat cttgtcccat ggcacgcgct gcagcatcat  24780
tggcccgtac tgccgcgcac agcgcactgt aaatacgtac acccagtcgc catcgcgctg  24840
catcgtccac atctggaatg ggtcggtgtt gttgtcattg ttcagccact tggttgggag  24900
ccgcgagaag gaattgccgt ctgtcgagta tgccagcccc gcgtagttgg gggtccatga  24960
cgttgtgaag ttcattatgc tcgtatagga gatgatgtgt tcgccggtct cagggaagct  25020
tatgccgtcg ttcgggagca cagtgaactc ccatgtgccg gtgccatcat cgccgtggtc  25080
tccgttgtag aagagtctgg gcgcgagccc atcgccgtct accccggccg cactctcaaa  25140
gaaaatcccg ccatcttcgc cggggtggat gcctgagagc agcatgactg gcgagcgcag  25200
gtcttttgct tcttgcaccc acatcgtgct caccgtgtct ccaaaaaggt atccgacttg  25260
gccattgtgc atatcgtacg gaatgcctag atcagtggcc gcgacccccc agcgacgacc  25320
actctcacgg tcttcaccga tcagacggcg cttgggaact gcatttgcag tctgggtgga  25380
agcaggagag gtaagaagga tgagggtcag taagtgaagc attgtggcca tgtttctcat  25440
ttgggacgat aatttggagc attccacagc gacaatgcaa ggacatcact gttaagtaag  25500
agtcttttgt tttgtccagt ggatatggct gttcattccg caagcgctgg tccgggcatg  25560
taacagttgc ggttatgctg tccttgtgta accgcggttg gcccaaaata acaatgatgc  25620
tgcattcagt aagtaccgga ttgttaggcg ccacggcttt cgcaacagcg gagccagcat  25680
ctgaaaccag tccggggaat gcttatagct tcctatttgg caaacattcc aaacaggaca  25740
gccttgggta gttcagttag ttggttcgag gggtgagctg ggtaagctcg aagccgagga  25800
agtcccttta cttcgcgaag ggcacagtat tagaacttca gcgttgaccc cttgaaaatc  25860
cttcattctt gacgttctac tatccgtgat atatattcta tgttatcaca gcccctaaga  25920
ccatgtggtt tttggaaagg ccacgcgttc aaactgcagt gggattgtaa gacgttcgca  25980
tcatatcacc tacgatcttc aaacgcacca tcttcaatgc ctccgggagt ttcatcttct  26040
ttggcttgat gcgatcatga acgaatccag cttttgcagg attactgacc attgggcact  26100
tttgcgctca cgacctgtcg ggttgccgag ccaaagccat gagcagacct tgattgtacg  26160
gtgtaggtct aggggctgct ggcggccggc cccgccttgt gctaagattg tattaaagtt  26220
ggcatcggag acctcctgga aattgtatat actttctgg gattgtcagt atacatcaga  26280
ccgatcgcaa cggcggtggc catcccatat gacgcttgtc ggcgacccgc gaagatgata  26340
tttggtgatg cgcgcatgtg tccggcgtga tatctggttt gtatcgcgct acttgaagta  26400
tatcgcaaac aacaaacaag tcagatccag cagaatgggg ttgatgcaag ggatggacga  26460
cccgcacaga atccggggtg atggagggtg cgtgatcggt cacatcgatt cgctgtttca  26520
gctttgattg ttccgtatct gcagctgtaa gttcacgcta acaatgaatc tggcttggct  26580
cgtgagatat aacagggtgc tgataagact ggatttggaa gctgagaatt atgcgccggc  26640
```

```
atccgccgcc agcacggtcc tgcgatcggc ggttgaagcg accttcccct cttttatgaa  26700
aggtatctga cgtagagagt gtaggaagat gatgcttgtg gcgaaagtcc tcacgacctc  26760
gagcctgtca cggcgaacgt ctggggtcgt ggatcggcgg cagcggaaga atcggatcgc  26820
agagcaaccg tgggaataat tcgagaagaa cgcgaggaat ggagctgtgt aacagaagac  26880
gagataagtc ggtgagagag cctcggccgc gacaaaagac acaatttgcc aggcgtaagg  26940
cgatttgtcg ggctgataag cacgggctga tagctgacat cgaagtttcg aacattccaa  27000
cggtggccgg ggaggtccgc tgcatggtaa agtctgacat ctgactcgca ggaacaagac  27060
ttcgttccgt gggttagctc ggcaagtgct acggtgatag cctatcgcag acggtcccac  27120
tgagggtccg aaagataacg ggaatgaagt tttttacacg gttcgccttc cagaaataaa  27180
atctgctccg cgccgctcgt gtgagcttct tgtcggtcgc ttcgtgtagg cttcgtgttc  27240
tcatttcgcc gcaaacctgc gaacagcaat tctgcagtga tatcttttcc atatcccctg  27300
tccatcgcca gatataatgg gacacgctga gtggattggc cgcactaata cggccgtggc  27360
tcgaagcgcg gtcgggaagt ggtttcgcct ggaggggtct ggtcatgtat gtctctgagc  27420
gcatgttgaa gcttgccttg ctttagattg gcatgctcgt gtttctccca tgtgggaagg  27480
gatggccttt gctcactaat ttcgccatat cagccccgcg agcgaaaagg cgcgtatttc  27540
tttacggagc tgcgtgcagg ccttgcaaca ttctttgcaa tggcatacat catctcagtc  27600
aatgccaata tcacgaggta tgcggtagcg gacgtcccat acgtggtcgc aatggggttg  27660
atgacgggaa gggctaacaa gacacgctta tagtgacacg ggagcaacgt gtgtgtgtcc  27720
ggccgaagat ctcgaaaccc actgcaacaa caacaccgag tatcttctct gcaaacaaga  27780
agtcaaccgt gacatcgtga ccgcaacggc agcgatagct tctgtcgcca gcttcttcct  27840
cggtctcctt gccaacctac cggtagccct tgccccggc atgggtctca acgcatactt  27900
cgcttatacc gtcgtcggac accatggaag cggcttgatt ccgtacagcc tcgcagtgac  27960
tgcagtgttc gttgaaggct ggattttcct tgggttgact atgttgggta ttcgacaatg  28020
gcttgcccgt gctattccgg catccatcaa gctagcaact ggtgctggta tcggattgta  28080
tctgactcta attggtctga gttatagtgc tgggcttggt ctcgtccaag gtgcccagga  28140
cagtcccatt caattggcgg gttgtgcgtc cgatgaattc gactcggatg ggctgtgtcc  28200
ttcgtatgct aaaatgcgaa acccgacgat gtggattggc atcttttgcg gcggtttctt  28260
cacggttttc ttaatgatgt atcgagtcaa gggtgcagtc attgctggta ttcttctggt  28320
ctccatcatt tcttggccgc gcaccacgcc ggtcacctat ttccctcaca caacggaagg  28380
tgacagcatg ttcgacttct tcaagaaggt ggttactttc catccgatcc agcacacgtt  28440
agtggcccag gactggaaca tctcgagcaa cgggggccag tttggtcttg ccttgatcac  28500
attcctctat gttgacatcc tcgacgcaac gggtactttg tattcgatgg cgaagtttgc  28560
tggagcgatg gatgagcgca ctcaggattt cgagggcagt gccatggctt atgtaggttt  28620
tccacaaacc tttcgtttcc atcgcatatc actaaccgat attttagacg gttgacgcga  28680
tttgcatctc aatcgggtct ctgtttggct ccccgccagt gacggcattt gtcgagagtg  28740
gtgctggtat ctcggaaggt ggtaaaactg gactgacatc gtgtatgacg gggatctgct  28800
tcttcatcgc cgttttcttt gcgccgatct ttgcgtcgat ccctccgtgg gccactggca  28860
gtaccctagt cattgttggc tcaatgatga tgcacgctac cctcgagatc aactggcggt  28920
atatgggaga cgcgattccc gccttcctga cgatctcggt tatgcctttc acttacagta  28980
```

```
tcgcggacgg cctcattgcc ggtatcatca gctatatctt gatcaacggc ggagtgtggg  29040
ttatcgccaa gtgcacggga ggccggattg ttccaccaaa ccgcgatgac gagcatgagg  29100
cgtggacctg gaagattccc ggaggattct tcccgccatg gctcgtccgt gcagttcacg  29160
gaaagaagga cttttggcga gcagacgacg aggctagcca gttggacctt ggcgttatgc  29220
cgccaaatgg gtcgatgtca tcagggtctc cggagcaagt cgcggagaaa gcagtcggga  29280
agtattaagt ttaatatgga attcggtcac atttcagaga gtgacctaag catgtattta  29340
gtgagcgaga tttgcatatt tttgtttcca actagtcgta cgaatttcaa ccagcagtcc  29400
ttcggggcgc agtgtttatc aataatcacc agatcttcca ggcgcggtag aatgcggaat  29460
tattagcgcg gaatgcggca gggagcagat cgacgactat tgacgcaagg ctgacggtcg  29520
agcggtgaag aggccggttc tggcagtgtt cttagccggg gaggccaacc gagcaatgga  29580
tcagaaattg ggcgaaggat aaatgaggcg tgagctggtg atgggtggat ggaagaaaga  29640
agatggtgga gagagaatgg aaatcagttc cggcgggcag gccaatcgca gcgtggcagc  29700
ctcaggcacc ccggcagtca ggagaactgc gaccgaactg ggaccaaatt tctcacggcg  29760
gttgcagtgc aaggaaagac acgtcagacc ccccttgact cgcgacaagc tgaggacact  29820
gggcccgtcg caagtgcatc ctgacagcca gacgcttctt tcgattggtc acatcctgca  29880
gcgtgaccgg tcgcatccag gtttgagttg ggctccgggc attcttctgg aagacacttt  29940
ccaggcctcg gaaccttgca aggttgcgt tcgcctccgc gcccaattcc cggtttattt  30000
gtatcgccct ctcgcccgct tctgtccgag catggagtga accagaatgc cccccagctc  30060
caagtcccgt cgcctgccgc ccgcggcctc cgactccgcc gcaagtgacg cacagaaacg  30120
cagaaagaac gtgggcaccg catgttccgc ttgcaaagct cgcaagctca aggtagatga  30180
gctttgatct tccgtcgggc tgctcaggcc ttagactgtt gcgctaacac tgttgttgga  30240
tagtgtactg gagcgcctcc ctgcgcaaac tgcgtcaaaa gccgcatcga atgcaccctc  30300
gacgagaccg ccgatagacg ccgacggggc gtcttgaaac gcaagattga taagttggag  30360
gaccaggagg atttgctggg tcgtctgctc gagtttttca gagagggcaa taaccgttgc  30420
acgattcccc tcttaaatct catccgcagc catgcctcgc cacccgagat ccgtttctat  30480
atcgaacacc aactaccgct atcgaaacgt acgcagaccc ccgagctaat agaagtatgc  30540
cgggaaatcg aacagcgcca ctcttttgaa ccgctaccta agcgtcacat ccttgatacc  30600
actcctaatg gatcccacga tacgccacga ttatccgtcc ccgcgcagcc gtggacctcg  30660
atcattaccg acgatggcct ggtatcccga ttgatatttt tatggtttac ttgggttcac  30720
ccgttttgca acttcattga ccgcgatcgc ttcatccggg acatgaagtc tggttcgctc  30780
tcagcatcat actgctcccc gttgttggtg aacatcatac tttccgacgc atgtgtacgt  30840
tatattgaaa tattgtggtt tggcttggga actcactgtc ttggtaggcc tactcggagc  30900
actctgcgtc tgggctccca gacgacctaa cctccaaacg gatcgagttt tacgaggagg  30960
ctgaacgatt gcttgataag gaagagggcc gcatcagctt gccaactgcc cagggcctag  31020
gagtattatg gatgtggtaa gaaacatatc tccggtcaat atctcccaag ctgaccgctg  31080
tagcgcatct atcaccggcc gtgacagaca agcgtggatt aagggtacgc agcttgcata  31140
ttcactccgc gagctatccc aagtgtcttg taacctcccg tcagaggcca atcgggatgc  31200
aactgccctg gccacaattg ttaacagcac aaactggggt ttgttcaacg tcgccatgta  31260
agttcagacc cgtttcatga ttatcgttgg gcatcaactc atctgtcagg gttcacgctc  31320
tatttgcaag gaaacgccct atcatcgaac cgcccgccca acctccgtct gtcagcaacc  31380
```

```
aatgcgacca cggtatgtgg tattcatatc caaacaaatc gactggtgtc gagtcacaca  31440
catcctgcct attcacggca gcttgtaact taaaccgaat cgcttacaac ctcgggagat  31500
ttctgttctc ccaagagaaa aaatcttcgg ctcgtctcga tctaacggat ggggagcttg  31560
acgcactacg ggatttaaac gaatgggccg accagctacc ggtatgtcta aaagaaagca  31620
ttgccgatct ccctcatgtt ctctctttgc agtaagtcaa tatcttccga tgcgcccaga  31680
ataactagct aaccccctct agcatgtata accacgccat tttaactgta gtctacggat  31740
ttctaagaac tcggccctta tacctgccga atccttcagc ctcgaccccc actgtccgtg  31800
acgctctcat gtctcctgct cgtgcctggg ctgcaagtct ttcatcggct cgcaagattg  31860
cccatttgac acttgtccat cgcgcgaatt ggggatccga ccgcatgccg ggggccaccg  31920
tgcactgtat catggctgcc ctgttcgctc tacttgacag cgtggacgac ccggccaacc  31980
gtgacgcatt catttcactc acggcagcgg ccgccgcgtt ttcgcgtcgg tgggaaagtc  32040
ccatagccct cctgcgcaac atccagaaca tcgcgcggca gcgggacgtt accctccctc  32100
cggaaacagg cgctttcttc ttggatccag accagccctc ggggaacagc actcccataa  32160
aatccgaaac ccccgagggt acagcaattt catgataccc atgcggccac cgttatgatt  32220
tcagcagcat tttggagttt gggttggtat ccggtttata tacatggatt gacggccctg  32280
ggttgtaatt tattgattgc atagcgtcat tacgtgttca ttactcatat ataatcatca  32340
atatccattc acatcgtttc ccttcgaagc tggtgcattc tgcactcaca ccgtctcttt  32400
ccgctgtatc tcgttcaatc ttgtagctgt acgtatacgc tgtcgcaagt tgaaaggttc  32460
cggattccgg tcggccgtcg catccttttc gtccgacttg gtgcttttgg ccttcttgtc  32520
gcgcatcttc tgcacccagc caacatacgt atcccaccag tgccaaactc cccagacccc  32580
cagagtaagc agtgtcagag ggatcgtaac agcccagtac atccagaact catcggccgt  32640
gagccacgta ttaccggggt cggcctggaa gctgaagaag ttggttccaa acaggccctg  32700
tgttacgccg tcagtactga gcagatatcc gcacgtgatg ggcacactta cagacacaaa  32760
cgtcccaggc agatacacca tactcacaaa cgcgaccgtc gtcatcatgt tgctgtcgga  32820
tcgcgcgtct cgcccgaagt cttgcgatac caggttgaat gcctgtctct gttagttggt  32880
tcttaagtcc tctgcgatgg aactagttta cgcaccaagt taatctcgtt ctgatgccga  32940
tcgttcaaag acttcgatcg cgtcttgagt gagtgcgccc ttttctcctc gtgcaggatc  33000
cgtcggcgcg tctccagcca ggtccctatg ttctgctgga tgttgtttcc gtcttcgtgg  33060
cgccaattga gcagttcctt ggccatcact tgcagcgtgt gctcggcgac ttcgatcgtt  33120
tcttggtagt ggaagaggtg ccgtgcgata tcgtgcagaa gggggaatat cttcctttca  33180
tgttcttttt cggctttgct tttcttcctc ttcggctttt tctcctttga ccgcgcctat  33240
attgccccgc aggatgggtc agtaatgcac gaaacaacgg ctagcaagga gggatgaacg  33300
aatggatgag tggcttagtt aagacatacc ttttcgtggt gccgcaccag gtctctcaac  33360
aaccaaaacg catcgtcata ctgttggagg atgatccggg agaatgcagc gtgtaaggag  33420
aacgggttac acttgcgctc ggccgccgtc gggagtttat ccatgaagac gctctgttga  33480
tctggattga aaccaaatac gtggacgatt tggctgccgg tttctgcgtt ccactgtacg  33540
tggatggtgg gttgtttcca gctatagtct tctgctgttt tgacttcttt gattttgaag  33600
caggaccacg agactaatgc aatgttagat acgacgaaca tgacgggcga agaaaccgac  33660
tcgggcgaac cttctggcca tacgcgggat tgagaacatc cataatgaca gtcgaaagac  33720
```

```
ccgttaatat cggcgtctag caccggacgg aactcttctt ggaatcgaag cttgaaggac  33780
ttgtccgtgt cattgatatc gctcgttacg aaactattcg atggatgtta gcgccgtatc  33840
ctagattggt aggttgatag ccgtacatga taaagttggc gctctgatct ctctatacga  33900
tagacgcaaa aactggtcag catctgcatt atccccgtca ggcagtcgtc ggtaaatatg  33960
tacctcaact atattcatat cattgccaca atatctccac ccgtcggggt cacctagttg  34020
caagttagcc ggtagcccag agcgcggatg tgagcgtgga ggtcgcacca acgtccatgt  34080
atatctgaac cccaggcggt gctctttctg cggcgtaatc catcgcggtg tcgttaacta  34140
tactggaagc gtcggcttga atggcgttgt ccacgaggca gattctttga agaaattcgc  34200
gcgaccacaa tgggcttctg catgttatag cctcaatcca caccgccgcc tcaggggact  34260
gtctaacatt cgacgtcaga acgaggctgg gcccttgagc tggagccgca gcagctgggc  34320
gctaacatgg tgcgatctgc gacgcttggc cagattgatt ggcggagaac gacgaggcag  34380
gttgcacgcg agccacagcc atttctcagg ttgggaacaa gctgctgatc ggtcagaaaa  34440
acgaattgtt gattggcttc gagatgcttg ttcagtgagc gggtggagag atgccgcttt  34500
gcgatgtttg acagccaaag caagtctggg actggagatg gctcggaccg tgatgggctg  34560
gaccgcgagg ctgtcctgcc gccggtcgcc attcgccaac aggacacaac caggcataac  34620
tctgggcacg gctgcctatt caaagtagcg atttcctcca tgagcagcgt ggctgtgctg  34680
ggttatcggc gtctcagcgg cattgtggcg tcgtggctgt acgtgcgagc agcaagcaga  34740
ttcagaattg aatagctgcc agaatagctg cgagaatgac aatgacggtc ctactatcta  34800
aagtggttaa aaaggaaacc atcgtggaat aggagaaaag cgttcaaaaa attcaactgt  34860
tgtggaagat tcgggttgcg gcggcacaaa tatatattgg acaagtgcgc cccgtcggcc  34920
accagctata cttctgaaaa tctattgttt cgtacatcct ctttatcgct accttgatct  34980
ggacgaaata agatgtcctc ttgattagta tcgcaagaga tctggaacaa gatacaaaga  35040
tcaagtatat gcgcctgcaa attggctatg gtatatgtat ttaaagctgg ttggtcccga  35100
ttgttgaagt cctaagcgcc gacgctctcg gacccttcaa tgacagtcat ttcgatgact  35160
caaaagacct tgccttagtt tcgcttaact acttttcgaa agaaatgttc cagctccacc  35220
aatcgctgaa actgtgatag ggacctgagg ttgcaggtgc cgagagccgc actatggact  35280
aggtaggcga ggctaaccgc tatcatcaca agttcgcaag ctagcacagt cgaggccacg  35340
ctaccgcagg acggttggcg atacaaggct tgcaataggc tgggtttcaa tgcaaaatcg  35400
acttgtgaaa tcgaagccct tttgcctctg acccgtcgtt cgctaggtct cttcgttagg  35460
taccagtgga gataaatacc atcgaacccc cgccccattc ttcccagcaa aaaataattg  35520
caactctgtt ttcaatctgg atcaaagatt tgttccatac aatgcgcgct gcacttctga  35580
ctctggcctt cacggccctc gctgctgctg ccgacgacgc cacaacaaca gtcggcttct  35640
tcggcggtgg agaatgggaa aacagcaacg acgatgattc cctccctctg atcccatcct  35700
acacctccat tggcgcctcc gttgttgatg tcaacgcggt ggagaccgtc ctcgccatct  35760
cctgcctcga gggcgccgcc acggaatcct gctccatcaa cgacccctgg accatgaccc  35820
agggcatctc gtcttttagc tggtatgctg aatacacagc ctttgactgg aacccgcctg  35880
tcacggcgac gcttgactat aactgcgcct acgagaacta caccctcagc gcaacttgca  35940
catacagcat gagctactcg ggctcttcgg atggcgcgga gacttccact agcttcagta  36000
ccgagacatc atgggacagt gtggcgacgt atgctgcact tgaagttacc ggaggcctgg  36060
acaagtttaa ccagcctgaa gcgactgaga caccggaggg aggggctggg tttgcagggc  36120
```

```
ctattcaggc gatggtgacg gctgctccag ttctggcggc gggtcttctt ggtatgcttt  36180

gagggaagaa ctttcattag ttcgtaattt catggtacta gcttgttata tatgaagtga  36240

aacggattgc ctagttcgca gaattctgta ccagccaact gcttgtagtt accttttggt  36300

tgatgtttat caaatggtac ttgactgtag taagatcgag tctgtttagc ttctgactag  36360

aatagtctga gaattgaaga tgtagcctgt tcggaggcat ccgaatacga gatgcgacgg  36420

cataagcttg cttacttctg gctcccgtca acctggataa ggaccttgat tccctggccc  36480

cttcgagcag cctcccacgc atcaggggcc tggcgaaagg ggaagatatt actgataaag  36540

cctttcaagg ggatcttgcc tcgactggcg agactggagg ccagcgtgaa atcgccaaac  36600

ccataccgga acgagcctct cacagtaagc tccttctcgc tcatcaccac cataggaaag  36660

tcgacaatct tcttccccag cccaacctgg acatacgagc cccctcgtct ggccagtgca  36720

acgccagttt gtatacacga caccaccccg gttgcttcga cgacgacatc gactccctcg  36780

ggcaggttgt gttgagcagc caagtcctcg gcgttttctt caaccgactt tgccgtgtcg  36840

aatttgtatg tccagatgcc caattcgcct gccgcgaatg ccagccggtc ttcgttgaca  36900

tccactgcaa tgatgtgccc agcaccaaac tcccgtgctg ccgcggccga aagcaaacca  36960

accggccctg ccccaagaac aagcacatct tggcctggct tgagctttgc aaggcggagg  37020

ccatgcaccg cgacagcaag ggctcaagg ataacgcctt cgtcaagccc tatgtggtcg  37080

gggagcttgt agcagaagtc cccggcagg cggaaaaagg tcgccaacgt gccatggaca  37140

acatcgcccg gtccaggaac tgcggcaaag gtcatgtccg gacatagatt atacttgcct  37200

gccaggcaaa acgagcagtg gcgacaggga tatccaggtt cgatagccac gcggtccccc  37260

acgcgcacct ttgttaccgc cgatccaacg ctcgcgacga cgccagacgc ttcatggccc  37320

agcgtgaccg ggtgccccgg gcgtaccatc tcgtttatgc cccatgcgc ccagaaatgg  37380

acctaatccc agaagtgagc gaggtggtgc gcgagagcag ccagtatcgg gtcgtgcgaa  37440

ctcacatcgc tcccgcagac tccagtgtat gcgatccgaa ccaggacatc tcgggggttg  37500

ttttctagtg atgggatggg aatctcttca aagcgagcat cgcctgggcc atagagcaaa  37560

caggctttgt ttgtttcggt tgccattttc gtgtaaacgc gtagccccgc gactccctac  37620

ttaatagacc attcctcagc tacagacctg ggaacgtgca gggcttatag tcttactgcc  37680

aaagactggc tgctcgcaaa ccccgctatc tccaaatgca accaactgct gatcccgacg  37740

gtgtagacac ggcccgtgtg gccatttctg gcccacactg ggtccatagg gtctgcacca  37800

gttggagcac gctgcggggg ccgatccccg tgttcaagcc ctggggttga taccccagag  37860

gagatgtcat atataatgcg ccggagtggc acggtcgtgg aagctcatgc tcttcttcca  37920

tgtcgcgtgt tttccctgat ctcacagctt atccagaatg aacacaccaa ctcccactca  37980

acgaacctgg tatcgcacca cgattttcaa tgtctcggtt gtcgccgtat gcgccttcat  38040

cgcaccaggg ctatgggctg cgatgaatgg tctcggtggc gcaggatcag ccgatccata  38100

ctatgtgaac gctgccaacg cggtcatctt ctgtctgcag gtcgttgtct gcgtctttgg  38160

cagttctctg attgctaaaa tcggcctgaa gtgggccttt gcgttaggca tggtaggctt  38220

cccgatatat gcgtcgagtg tctactgcaa tgtgaagtat aataatagct ggtatatcat  38280

gctggcctgt gtgattgacg gcatctgctc cggcatcttt tggctaactg aaggcgccat  38340

cgtgcttgca tatcctgaaa agcatcggcg tgggaaatac ctggcttact ggcttgccag  38400

ccggattatg ggccagatga tcggtggcgc tgtcacgctg ggtgtcaatg ctggtaacca  38460
```

```
ggaggagggc catatcagtg tgcagacata cctggtgttt atttccatcc aggccatcgg  38520
ccctttcgtt gctgcgacac tgtctcctcc tgagaaggtg cagcgttcgg accagtccaa  38580
agtcaagatc aatctaccgg cgggtctcaa agcagagctg cacgccatgt ggaaactgct  38640
tggacgcact gaaatcctgc ttctcctgcc gatgatgttc cagagtgtct tttcagaggc  38700
cttcttctcg acatataacg ccacctattt taccgtgcgg tctcgcgccc tgtcatcgct  38760
ggtagccagc acttgtgtga ttatatctaa cttcctgctg ggattcttcc tcgactggcg  38820
caggctctca gtcaacacgc gcgccatggc tgcgtttatt ataatctacg cctttgagct  38880
atcactatat gtatacgcca tggttgtaaa caaggagtat gagcggcagg aaccacggcc  38940
gctctttgac tggacagatg acggctttgg ccgcgcggtc tgtgtctata tcctgatgct  39000
ggtgggcttt aatctcatgt acgactatct gtactggttg atcggcacgg ttaatcgcga  39060
tggtggtgat attatccgac tcagtgctgt tgtgcgtggc gtggaaagtg ccgggcaggc  39120
catatcctac ggcatcaact ctgttgactc cttcctgctg tccagtgctg ttgcagtgaa  39180
cctgtcattc tttgctgcat gtattgttcc atctgccttt gttatttatc gtgttggcgt  39240
tgtcaacggg gtcaaggtac atcatatcca gcaggacgag acgctacaga cgtctgggga  39300
gggctctcac gatattatgg acgccaacgg gaaatcggat gactgatagt cctgtctgtc  39360
accgattagt tacttaattc agacgatctg tcaaggtact tggagtctcg ggcgactgac  39420
ggcccgcctg cgtggacttg catttgtatt tcctgttctt tattttagtt gcataaatat  39480
aactaccgag gactgataga gtaaagacag aactttttct cattctcccg tcccgcacat  39540
cacaatgcct cagaccagcg acggcaacgt acacgcaccc cagtaccgcg aggcaaagcc  39600
ctcgcaggga gatccatctc tgtcggtctc acagctcttc cgtctcgaca atcgcacgat  39660
tatcagtgag tccatacctg cttaatgcct gctcaatgcg acacactgac taaagcaaca  39720
aaaagtcacc ggcgccacag gcttcctggg aagcacgctt gccatcgcaa ttctcgaaag  39780
cggtgcagat gttgtctgcc tcgacctccc tcctacgcca acagctgaaa actggagtca  39840
gtatcttctc tgtgtaaccc gctgtctaac tgtgtaactg cgctcacacg gacacagacg  39900
atgtcaagac caccgcttcc aggcacgaac agcagctttc gtactaccag ctagacgtca  39960
ccgacgaaga cgcggtcgca gacaccttcg caaagttcct gccgacctta cgctacccag  40020
tgaggggact ggtaacctgt gctggactat cgctcaacgg cccttcatct gaattcccgg  40080
catccgcgtt tcgtaaagtc ctcgacatca acgttacggg gacattcctc gttgcaaagg  40140
ccacagcccg cgcgatgatc agcgcgaaca ccacagggag catggtcttt gttgcgagca  40200
tgagtggcta tggcgctaac aaggtacgag ttcatccttc ctctatcata gaccgtgcct  40260
cattgcatgc agggtgttga tacagccggc tacaactctt ccaaggcagc cgtccaccag  40320
ctcacgcgct ctctggcggc agaatggggt tctagggttg gtcttccgct gatccgcgtg  40380
aactcgctat ccccagggta tattcgcacg gctgcgacgg ccgaggcgct gcagaagccc  40440
gggatggagg atcaatggac aggtgataac atgctttacc ggctcagcag ggtggatgag  40500
ttccgggcac cggtgctttt catgcttggt gatggcagca gttttatgac cggtgctgat  40560
ttacgggttg atggtgggca ttgcagctgg tagctaagaa accgtagcag ggagaccaat  40620
aaactattgt ttaatttact tgcataacac ttcatgtact ttctactagc taagaacctc  40680
aaacactgcg tagaacaggc gatgagtagc gatcgaccca gcgctggaga aggtggcaga  40740
tttcagcaac cgcataccgc aggtcgtaga actcaatggg caatgccgac tgcagggccg  40800
gggtgcggtg ttcagcgaca gctgtacgga tcaccgattc aaacatttta gccagaggcc  40860
```

```
agcgacgact acagatgtgc aagctatacg cgagtgagtg gaggctgacg gagacgtctg  40920
cgtgtaggca cttcgtatgc actggatagg acatcagaac gagccaaaca gacaactcaa  40980
ggagacagga cataccaata tagaaacggg cagcggcgaa gatgggaaga acgagacatg  41040
gactgcagct ctccagctcg gactcttcca ttcgccggat cttggctgcc atgttctcgc  41100
aagcgtacat gcagcgatgg ttggcatacg gccactggga taaagtagtc agtttgtatg  41160
ccatgtagaa cgagctgcat ttgccttact ggctccgttt cctgtccaac gccttccggc  41220
agcgaagtct gcgactgcag cagtgtaatc acggccctgc cttgaattag ttgccgcaat  41280
gctttgagtg aatggggcag ggcgagcaca tgttgagaac gcaatttgtg agaataatat  41340
acggcctcat ctcggcgcga gcatcatggg ggcactcggc gttaatgagc cggaaaacag  41400
ctgctacgaa ttcctcgcgc cagatggtga gtcgctcgtc gaggcgctgg gctgcactct  41460
gccactcggg acctccggcc atagcacccg tttgaatcac gctgtgctgg aactgatgca  41520
caggcgccag ctcaacggtg cacaggctga tgcacatgga gaagccggag gagtactgca  41580
ggtcatggaa gggaacacac tcaccgaagt ggtcctgcaa agcccatgca gtgtcactgc  41640
agggaagtat cgcacccagt ggtgctgccg tcgtcggtgg ataactcggc agacccaggg  41700
caaagatgct atccagcatt tcgatcatcc agaaggctcg gagtcgttcc tcgtggtcga  41760
ttttggtgtc ggagagaact gcatcaaggg agcacatctt ggacggctga gcggctgcca  41820
caccagcgac tgtaggaagg cccaattgct gagatagcct gagatcataa gtaagtggca  41880
gttattagca gtcctagtac agagggcaac gcaccgcttg cacattgctg ccagattgct  41940
atactggacc catttcccct cgccccagaa aaggattgac aaggtaagca aggcttggac  42000
agtgcgaagg tgcagtgacc ccattgcgtt cacgataacc tcctggcgaa gtctttccga  42060
taggaattgc ttgcgttccc atggaattcc agggctatcc cagatggcga cagccttgac  42120
tgccttttgc aacagaccag gaccattttc agcttctaca aatgcgtcac tcacagaggt  42180
gtggtgcata attgggaacc acggctgata cttctgcagc cataccagct ggagttcgta  42240
tgtcagggcc gtagtctcca caggcgcagt atcggcctgt gggctgttcg tggactccac  42300
attctggacg cacaacgggg gagccagccg acccgtagac ggggttgtag caagatcatc  42360
tcgttctgtt gcaggctgcg atggctgcga ctgcgatagt cgtcccagaa cgtcctccat  42420
ctgtctttcc agatcctctg gacggatcag cagtccggct gggataccag gacaggaggc  42480
cacacgcacc gacgcgtttc tccagctggg atacgtaacc ggcccttagt ccaggccgat  42540
gctcgcgtgt tttgtactcg caatcgaagc catttttgcg gcatagtccg cattgcgggc  42600
ggccccgatc acaggcgacc ttgcgatggc gacagaccag acacctagat cgcgcatatt  42660
gagtgagacg gcagaagcca caagcccagg catcacttac gccagctttc tctcagactc  42720
cggaggcatg tttgtcgggc agtggcggac cgaggggatg taacttgagc gccgtgtcga  42780
ggccgacggg tcaaagacgg ccggaaatta ccagctgatc atgattcagg atcaggagat  42840
ctagtgcaag ctgttggagt acagtctttg accgtcagct cgtgttggag aagcagagac  42900
cgggggattc tccgcgaaag gcccagtctc cactgccgat ctcgcagcaa cttgcagctg  42960
ccgacatctc gattatttaa tcactgcctc ttccttcgac tggtgaacgg tacaagccat  43020
tctatacctc cgacacgatg gtcgttgcag ggctggagac cccggaccat gtcgactacc  43080
tggcgcgcaa ggccataggt aaaaacatct tccagccccg gagaattccc aattgatgcc  43140
ctgccaggtc tcagtaaagg caaagaccag acctcgcgca ttctgatcgg cgtgtctggc  43200
```

```
atcccaggat caggcaagac aacactcgct acagcggtgg ctgaccgagt caaccagctg  43260

gccagcagca gccaggacct tgcagtgtgc atatcaatgg atggctacca tctgcccaga  43320

gcccagctgg ccgcgatgcc ggaccctgcc actgcgatct accgcagagg cgccgagttt  43380

acgtttgacg gagagggatt ctatcggctc gtgcagcgcc tgagagagcg cctgaccgcc  43440

gcttcaccca ctgtcttcgc accgagcttt gatcatgcaa tcaaagaccc ggtgccagac  43500

gatgttgcca tctcgccagg atctcgagtg atcattctcg agggtcttta tctgagcttg  43560

aaccgtgaac cctggagctc tgctgctgct cttatggacg agtcttggtt tgttggcgtt  43620

gaccgcgaga tcgctcgtgc taggctggtc aagcgtcatg tcacgtcggg cattgtgcct  43680

gatactgcag ctgctgagca tcgaatcttg agcacggact ttttgaacgc agatgacatt  43740

gttaagaatc gtttgcctgt ccaggaaatg gttccaggta actggcgaga gctgtctcaa  43800

gacagacttg actga                                                   43815
```

<210> SEQ ID NO 17
<211> LENGTH: 1074
<212> TYPE: DNA
<213> ORGANISM: Aspergillus versicolor NRRL35600

<400> SEQUENCE: 17

```
ctagagcagc ggtgccacat gcttttcaaa ccactcgaca agagttatga gtttacggtc    60

gctggggtct ttgccctggg cctcagcagc ctttgccttc aaagtggccg agatgtccgt   120

tgaaatgggc tcatcgccaa aatacttgcc attggtaaat ttgccaaact tgaagattgc   180

aaggctttct ttcccgtggt gagaatcgcc aaagtgagct tcccagtctg taactggtat   240

gtatcgtgcc ttttggccag tggctaatgc atggaccgat gttagacgac agaccaggaa   300

ccagaaaagg gatggcatac ctgattggaa agcatcgatc atctctggat aggtgcgaat   360

gtcactgaca gtcggaacga ctcgtccgtt atagtcctct ggcgtgagga agatgccatg   420

tacaatgtcg ccaaaatcgt cttcgagcga tatccaagga aggggcatat cggtatgggt   480

gccccatcgc ggaagacgga gtgtgcggaa tttatcctca tcctcgaaat aaggaaagcc   540

tccaagagcg tgcgcgtact cctgtcctcg aaagacatcc atgtaccaac cttggtatag   600

agggcagacg gtgtcaaagt gccccgaact cgcagcatac cgctcgattt tcgacttctc   660

atcagctgcc tcgataatcg cctggccatt ggtgaagctt gatgtgtcaa caaacgacga   720

gtagacgagg tgtttgacag tgccagcctg gataatccca tcgataatga tctttccaag   780

gtcgaattcg gttggatgat tggcatccca aaagcacgga tcgtccgagt tggtgttgac   840

aaaggccgcc cacgatccag aaaacgctgc caccatctgc tccttcttcc atccatcccc   900

ctggacaatc tcagcgccga ggtcggccag ggcctttgcc gcctcagatt caggcttccg   960

ggtaattgct cggactttga atgcattgtt cttcagcaag gaccggacca cggggccgcc  1020

ctgggcaccc gtcgcgccat acactgttat ggttctgcgg ttggtattgg tcat        1074
```

<210> SEQ ID NO 18
<211> LENGTH: 357
<212> TYPE: PRT
<213> ORGANISM: Aspergillus versicolor NRRL35600

<400> SEQUENCE: 18

```
Met Thr Asn Thr Asn Arg Arg Thr Ile Thr Val Tyr Gly Ala Thr Gly
1               5                   10                  15

Ala Gln Gly Gly Pro Val Val Arg Ser Leu Leu Lys Asn Asn Ala Phe
            20                  25                  30
```

```
Lys Val Arg Ala Ile Thr Arg Lys Pro Glu Ser Glu Ala Ala Lys Ala
        35                  40                  45

Leu Ala Asp Leu Gly Ala Glu Ile Val Gln Gly Asp Gly Trp Lys Lys
    50                  55                  60

Glu Gln Met Val Ala Ala Phe Ser Gly Ser Trp Ala Ala Phe Val Asn
65                  70                  75                  80

Thr Asn Ser Asp Asp Pro Cys Phe Trp Asp Ala Asn His Pro Thr Glu
                85                  90                  95

Phe Asp Leu Gly Lys Ile Ile Ile Asp Gly Ile Ile Gln Ala Gly Thr
            100                 105                 110

Val Lys His Leu Val Tyr Ser Ser Phe Val Asp Thr Ser Ser Phe Thr
        115                 120                 125

Asn Gly Gln Ala Ile Ile Glu Ala Ala Asp Glu Lys Ser Lys Ile Glu
    130                 135                 140

Arg Tyr Ala Ala Ser Ser Gly His Phe Asp Thr Val Cys Pro Leu Tyr
145                 150                 155                 160

Gln Gly Trp Tyr Met Asp Val Phe Arg Gly Gln Glu Tyr Ala His Ala
                165                 170                 175

Leu Gly Gly Phe Pro Tyr Phe Glu Asp Glu Asp Lys Phe Arg Thr Leu
            180                 185                 190

Arg Leu Pro Arg Trp Gly Thr His Thr Asp Met Pro Leu Pro Trp Ile
        195                 200                 205

Ser Leu Glu Asp Asp Phe Gly Asp Ile Val His Gly Ile Phe Leu Thr
    210                 215                 220

Pro Glu Asp Tyr Asn Gly Arg Val Val Pro Thr Val Ser Asp Ile Arg
225                 230                 235                 240

Thr Tyr Pro Glu Met Ile Asp Ala Phe Gln Ser Gly Met Pro Ser Leu
                245                 250                 255

Phe Trp Phe Leu Val Cys Arg Leu Thr Ser Val His Ala Leu Ala Thr
            260                 265                 270

Gly Gln Lys Ala Arg Tyr Ile Pro Val Thr Asp Trp Glu Ala His Phe
        275                 280                 285

Gly Asp Ser His His Gly Lys Glu Ser Leu Ala Ile Phe Lys Phe Gly
    290                 295                 300

Lys Phe Thr Asn Gly Lys Tyr Phe Gly Asp Glu Pro Ile Ser Thr Asp
305                 310                 315                 320

Ile Ser Ala Thr Leu Lys Ala Lys Ala Ala Glu Ala Gln Gly Lys Asp
                325                 330                 335

Pro Ser Asp Arg Lys Leu Ile Thr Leu Val Glu Trp Phe Glu Lys His
            340                 345                 350

Val Ala Pro Leu Leu
        355
```

<210> SEQ ID NO 19
<211> LENGTH: 1368
<212> TYPE: DNA
<213> ORGANISM: Aspergillus versicolor NRRL35600

<400> SEQUENCE: 19

```
atgacaaaaa gccagaccaa cccacgggga ccagccatat tgtccccggc agatctgact      60

gtgattattg tcggtctagg aatcgccggg ctcactgctg ccattgaatg tcaccgaaag     120

ggatacactg ttattggcct cgagaagaag ccagatgcca accaactagg tgatatcatc     180

gggctaagcg gcaatagcat gaggattctg gcagagtgga acaatggctc tctcgcgcat     240
```

```
ttgatagacg acgacatcac ctgcgatgtg accgcactgg agcttttcga cgccgagggg    300

catcgcaaac ttgcgatgcc gtacaatgct aataatccca tccagggata tctgttccgg    360

cgaacagggc ttcttaccag cttgtgccac tatgctagcc agctgggaat tgatctccgc    420

ttcggagtta ccgtggacga ctactgggaa acagacagca atgccggcgt atatgccaac    480

aacgagaaga tcacaggcga ctgcgtggtt gcagccgacg gattccacag caaggccagg    540

ggaatcatta ccggagaaaa ccctgagccg aaggacattg ggttgtcgc ctacaggtcc    600

attttcgatg ccaatgcgat tgcggacgtg ccagaggcgc agtggatatt gaagaacgca    660

caaacagcgg atattttcca ctcctattac ggtaaagaca ccatggtagc gattgggacg    720

gcagccaggg gccgctacgt gcactggggc tgcgcggttc gtggcgcttt ggaggagaag    780

tatgaagcct ggatgcaacc tgctcccccc gatcccatcc tgaaatgtct ggagagctgg    840

ccggtgggga gcaagcttgc agctggtatc gcgagaactc caccggggaa gtgtttccag    900

cagtccctcc gtgcaatgcc gccgttgaag agatgggtgt caactggagg gaggatgatt    960

gtcattggtg atgcagcaca ttcctttctc ccttacgccg gccagggggg caaccaagca   1020

attgaggatg cagcggtttt gggtatctgt ctggagcttg cgggcacatc aaatgtgcca   1080

ctagccctgc gtgttgtgga aaaactccga cacaagcgag tatcgctcat ccagaaaggt   1140

tctgcggagg caggagactc tttcctcaat gccgcctggg agagtgacaa cgcagcagaa   1200

aagccaacgg cattcacaca tcaggcctgg gtttacgcgc ataactgcgt ggaccacgcg   1260

tatgaacagt tcaatgctgc cgccgaagct gttatgaatg gctgggaata tactccaaca   1320

aatatcccag caaacggcaa attccgtcaa gaagagggaa acatatag                1368
```

```
<210> SEQ ID NO 20
<211> LENGTH: 455
<212> TYPE: PRT
<213> ORGANISM: Aspergillus versicolor NRRL35600

<400> SEQUENCE: 20

Met Thr Lys Ser Gln Thr Asn Pro Arg Gly Pro Ala Ile Leu Ser Pro
1               5                   10                  15

Ala Asp Leu Thr Val Ile Ile Val Gly Leu Gly Ile Ala Gly Leu Thr
            20                  25                  30

Ala Ala Ile Glu Cys His Arg Lys Gly Tyr Thr Val Ile Gly Leu Glu
        35                  40                  45

Lys Lys Pro Asp Ala Asn Gln Leu Gly Asp Ile Ile Gly Leu Ser Gly
    50                  55                  60

Asn Ser Met Arg Ile Leu Ala Glu Trp Asn Asn Gly Ser Leu Ala His
65                  70                  75                  80

Leu Ile Asp Asp Asp Ile Thr Cys Asp Val Thr Ala Leu Glu Leu Phe
                85                  90                  95

Asp Ala Glu Gly His Arg Lys Leu Ala Met Pro Tyr Asn Ala Asn Asn
            100                 105                 110

Pro Ile Gln Gly Tyr Leu Phe Arg Arg Thr Gly Leu Leu Thr Ser Leu
        115                 120                 125

Cys His Tyr Ala Ser Gln Leu Gly Ile Asp Leu Arg Phe Gly Val Thr
    130                 135                 140

Val Asp Asp Tyr Trp Glu Thr Asp Ser Asn Ala Gly Val Tyr Ala Asn
145                 150                 155                 160

Asn Glu Lys Ile Thr Gly Asp Cys Val Val Ala Ala Asp Gly Phe His
                165                 170                 175
```

```
Ser Lys Ala Arg Gly Ile Ile Thr Gly Glu Asn Pro Glu Pro Lys Asp
            180                 185                 190

Ile Gly Val Val Ala Tyr Arg Ser Ile Phe Asp Ala Asn Ala Ile Ala
        195                 200                 205

Asp Val Pro Glu Ala Gln Trp Ile Leu Lys Asn Ala Gln Thr Ala Asp
    210                 215                 220

Ile Phe His Ser Tyr Tyr Gly Lys Asp Thr Met Val Ala Ile Gly Thr
225                 230                 235                 240

Ala Ala Arg Gly Arg Tyr Val His Trp Gly Cys Ala Val Arg Gly Ala
                245                 250                 255

Leu Glu Glu Lys Tyr Glu Ala Trp Met Gln Pro Ala Pro Pro Asp Pro
            260                 265                 270

Ile Leu Lys Cys Leu Glu Ser Trp Pro Val Gly Ser Lys Leu Ala Ala
        275                 280                 285

Gly Ile Ala Arg Thr Pro Pro Gly Lys Cys Phe Gln Gln Ser Leu Arg
    290                 295                 300

Ala Met Pro Pro Leu Lys Arg Trp Val Ser Thr Gly Gly Arg Met Ile
305                 310                 315                 320

Val Ile Gly Asp Ala Ala His Ser Phe Leu Pro Tyr Ala Gly Gln Gly
                325                 330                 335

Gly Asn Gln Ala Ile Glu Asp Ala Ala Val Leu Gly Ile Cys Leu Glu
            340                 345                 350

Leu Ala Gly Thr Ser Asn Val Pro Leu Ala Leu Arg Val Val Glu Lys
        355                 360                 365

Leu Arg His Lys Arg Val Ser Leu Ile Gln Lys Gly Ser Ala Glu Ala
    370                 375                 380

Gly Asp Ser Phe Leu Asn Ala Ala Trp Glu Ser Asp Asn Ala Ala Glu
385                 390                 395                 400

Lys Pro Thr Ala Phe Thr His Gln Ala Trp Val Tyr Ala His Asn Cys
                405                 410                 415

Val Asp His Ala Tyr Glu Gln Phe Asn Ala Ala Ala Glu Ala Val Met
            420                 425                 430

Asn Gly Trp Glu Tyr Thr Pro Thr Asn Ile Pro Ala Asn Gly Lys Phe
        435                 440                 445

Arg Gln Glu Glu Gly Asn Ile
    450                 455
```

<210> SEQ ID NO 21
<211> LENGTH: 1281
<212> TYPE: DNA
<213> ORGANISM: Aspergillus versicolor NRRL35600

<400> SEQUENCE: 21

```
atggctattg aagaatctcc aacatacgct gagccgggac catacgaagc cctgagccgg      60

ttctcttcac ttactcgcga ggaccaccga aaatggtggg aacacacagg ccctgtactg     120

gagaaggtct tgaaagactc cggatatgag ctccaaagcc agtacacata tctatacttt     180

gtccagcaac atctcgttcc ataccttggg acattcccca ccaggggtga agacgagcat     240

cgctggcaga gcaatctgac cccctacaag gttccctacg agttgagctg gaatatttca     300

aacaaagtgg tcagaatctc atgggatccg gtctgcgatg catctgggac cgaggccgat     360

gctttcaata agaaggcaat ccacgactgc actcgtcaaa tcgcccagct aagcaacacc     420

attgtcctcg accggtacag aattcttcac caggagctgg tcatctcaga ccaagaagaa     480
```

```
caggaactcc ttcgccgcga tgacctacca aagtccggca gaggacaaca taacttggcc    540

gtggatttcc agaatggagg catagccctg aaagtctact tttatcctta catgaaattc    600

ctagcgactg gatctccggt tgagcaactc tttttcgctg ccattgaaaa gataggcacc    660

gcagatattc aagagcctgt gaagatgctg agatgcttcc tgagcccgag ctttgacgac    720

ggcaagccct ctgttgatca aaaggtgttt cctagcctcc tcgcctgcga cctgtgcgac    780

cccagcaaga gtcgcatcaa gtactatgtg atcgacaaat gggtgaagtg ggagcgaata    840

gcaagcctgt ggacgatcgg tggccggcgc ctcgaagacc cctcttgcgc caaaggtctg    900

gccctgctca aggaactgtg ggatcttttg gcaatcccag aaggcgaccg tggagatata    960

tggcctaacc tcgtccttgg acaacctccg acgcatctga tgacgacgat ggccaactat   1020

acgttgtcgc ccgcgagtcg tttccccgag cctcaagtgt acctgaccac gtttggaatg   1080

aacgacatgg caatcatgga tgccttgaca gccttttatg agcgtgctgg ccttaccgac   1140

atggccaagt cgtataaaaa gaacgtccag tcgtactatc ccaatctcga tctcagccaa   1200

acaaactggg tgcacgaggc catttcattt tcgtatcgga attcgaagcc atacctcagc   1260

gtgtactatt cccctttctg a                                             1281


<210> SEQ ID NO 22
<211> LENGTH: 426
<212> TYPE: PRT
<213> ORGANISM: Aspergillus versicolor NRRL35600

<400> SEQUENCE: 22

Met Ala Ile Glu Glu Ser Pro Thr Tyr Ala Glu Pro Gly Pro Tyr Glu
1               5                   10                  15

Ala Leu Ser Arg Phe Ser Ser Leu Thr Arg Glu Asp His Arg Lys Trp
            20                  25                  30

Trp Glu His Thr Gly Pro Val Leu Glu Lys Val Leu Lys Asp Ser Gly
        35                  40                  45

Tyr Glu Leu Gln Ser Gln Tyr Thr Tyr Leu Tyr Phe Val Gln Gln His
    50                  55                  60

Leu Val Pro Tyr Leu Gly Thr Phe Pro Thr Arg Gly Glu Asp Glu His
65                  70                  75                  80

Arg Trp Gln Ser Asn Leu Thr Pro Tyr Lys Val Pro Tyr Glu Leu Ser
                85                  90                  95

Trp Asn Ile Ser Asn Lys Val Val Arg Ile Ser Trp Asp Pro Val Cys
            100                 105                 110

Asp Ala Ser Gly Thr Glu Ala Asp Ala Phe Asn Lys Lys Ala Ile His
        115                 120                 125

Asp Cys Thr Arg Gln Ile Ala Gln Leu Ser Asn Thr Ile Val Leu Asp
    130                 135                 140

Arg Tyr Arg Ile Leu His Gln Glu Leu Val Ile Ser Asp Gln Glu Glu
145                 150                 155                 160

Gln Glu Leu Leu Arg Arg Asp Asp Leu Pro Lys Ser Gly Arg Gly Gln
                165                 170                 175

His Asn Leu Ala Val Asp Phe Gln Asn Gly Gly Ile Ala Leu Lys Val
            180                 185                 190

Tyr Phe Tyr Pro Tyr Met Lys Phe Leu Ala Thr Gly Ser Pro Val Glu
        195                 200                 205

Gln Leu Phe Phe Ala Ala Ile Glu Lys Ile Gly Thr Ala Asp Ile Gln
    210                 215                 220

Glu Pro Val Lys Met Leu Arg Cys Phe Leu Ser Pro Ser Phe Asp Asp
```

```
225                 230                 235                 240

Gly Lys Pro Ser Val Asp Gln Lys Val Phe Pro Ser Leu Leu Ala Cys
                245                 250                 255

Asp Leu Cys Asp Pro Ser Lys Ser Arg Ile Lys Tyr Tyr Val Ile Asp
            260                 265                 270

Lys Trp Val Lys Trp Glu Arg Ile Ala Ser Leu Trp Thr Ile Gly Gly
        275                 280                 285

Arg Arg Leu Glu Asp Pro Ser Cys Ala Lys Gly Leu Ala Leu Leu Lys
    290                 295                 300

Glu Leu Trp Asp Leu Leu Ala Ile Pro Glu Gly Asp Arg Gly Asp Ile
305                 310                 315                 320

Trp Pro Asn Leu Val Leu Gly Gln Pro Pro Thr His Leu Met Thr Thr
                325                 330                 335

Met Ala Asn Tyr Thr Leu Ser Pro Ala Ser Arg Phe Pro Glu Pro Gln
            340                 345                 350

Val Tyr Leu Thr Thr Phe Gly Met Asn Asp Met Ala Ile Met Asp Ala
        355                 360                 365

Leu Thr Ala Phe Tyr Glu Arg Ala Gly Leu Thr Asp Met Ala Lys Ser
    370                 375                 380

Tyr Lys Lys Asn Val Gln Ser Tyr Tyr Pro Asn Leu Asp Leu Ser Gln
385                 390                 395                 400

Thr Asn Trp Val His Glu Ala Ile Ser Phe Ser Tyr Arg Asn Ser Lys
                405                 410                 415

Pro Tyr Leu Ser Val Tyr Tyr Ser Pro Phe
            420                 425
```

<210> SEQ ID NO 23
<211> LENGTH: 1839
<212> TYPE: DNA
<213> ORGANISM: Aspergillus versicolor NRRL35600

<400> SEQUENCE: 23

```
atgcgtgata ttcgagagct tctgcttgtg cttttcacat cttgccttgc actgggctcc     60

gttccttcta gcttcgatgg cgatcggtat tgtcggtgtc aaccaggaga ggcttgttgg    120

ccgtctcttg cagattggca ggccctgaac atgtcaatac agggtaccct cgttgaggtc    180

aggccaattg gacacgtttg ccatgagcct acatataaca aggcggactg tgagcgggta    240

tccaagttgt cgtcaaatgg gacgtggaga gcaagccagc caggtgcaca acaggagcat    300

gcatgggagg tttccctgtc acgaaatgag agctgttatg ttggtcccgc caatcctgcc    360

gagccatgcg gccagggccg tatcccgcga tactcggcta tggtagagac caccgaacag    420

gcgcagaagg caatcaggtt cgccagggag agacggcttc gtcttgtcat caagaacacg    480

ggccatgatt ccggggggcg ctccagtgcg gtggattcgt ttcagatcct cacacagcgg    540

ctaaaagata ttagcttcat cgaggaattc acgccgactc tcgcggagac aagggggccc    600

agtgtcagga tcggagcggg agtcctgacg aaagagctct atgccgtcgc ggatgagcac    660

ggctatacgg ctatgggtgg cgagtgcgca acagtcgggg tggccggagg atacatccaa    720

gggggggcg tgtcgacggc gctgacaccc atgatgggcc tggccgcaga cctggtgcag    780

gagtttgagg tgatcagtgc ggagggcagc cttgtcatag caaacgaatt tcaaaaccag    840

gacctcttct gggctctccg cgggggcggc ggagggacag ttggactggt gacaagcatc    900

acaatgcctg tcttcggcgc gattccggca aatatatcag agttgtcgtt tgaaagccag    960

caacccgatg aagccttctg gaccgccgta aaggagatga tctatgtcac acgcgatata   1020
```

```
accactgggg ggaactcggg tcagtattgg gttggtcgcg gtcccacggg gagctatttc   1080

gtccgacaaa cactgttctt tctaggcgag acagacatag agccggcaga caagatggga   1140

agcctcctcc gtgtccttca ggatcaagag attgcctttc gtttcaatgt gacggcatac   1200

ccccggctga gttcttttct tgcgattccc caaggcgagt tcgtgggtgg gatcgcattc   1260

caccaggaaa acatcctaat tccccagggg ttttacgact cccctgaagg cccggcacag   1320

ctggtcgacc gcctcgcgga agttaaattg aatccaggtg atatgtgggt ggctaatacg   1380

ctgggcggac aggtgatggc caacaaggat gtggataacg ccatgcactc cggctggcgg   1440

acggcgtctg ttctgctggt gggaaatcgg atcttcgagc cagcgttaaa gtcacagctt   1500

gatgtgcagg agcgcttgac ggcggttgaa gggcctcttt tacactccat cggacagccg   1560

gctcctgagg ccatatactt gaatgaggcg gacgcagacc tcgagaactg gcaggactgg   1620

ttttggggcg agaagtacgc ccgtctccgc gatatcaaga gcaaatggga tcctgacgat   1680

ctgtttctcg tgaggcatgg ggtaggaagt gaggactggg atgaggacgg catgtgtcgc   1740

atgcagctgt caccgcaaga atgcccggtg agagaacact cacggtgcac ctgtaaattc   1800

ttcgaatgcg caatgttgca tgtgcccggg ttgctatag                          1839
```

<210> SEQ ID NO 24
<211> LENGTH: 612
<212> TYPE: PRT
<213> ORGANISM: Aspergillus versicolor NRRL35600

<400> SEQUENCE: 24

```
Met Arg Asp Ile Arg Glu Leu Leu Leu Val Leu Phe Thr Ser Cys Leu
1               5                   10                  15

Ala Leu Gly Ser Val Pro Ser Ser Phe Asp Gly Asp Arg Tyr Cys Arg
            20                  25                  30

Cys Gln Pro Gly Glu Ala Cys Trp Pro Ser Leu Ala Asp Trp Gln Ala
        35                  40                  45

Leu Asn Met Ser Ile Gln Gly Thr Leu Val Glu Val Arg Pro Ile Gly
    50                  55                  60

His Val Cys His Glu Pro Thr Tyr Asn Lys Ala Asp Cys Glu Arg Val
65                  70                  75                  80

Ser Lys Leu Ser Ser Asn Gly Thr Trp Arg Ala Ser Gln Pro Gly Ala
                85                  90                  95

Gln Gln Glu His Ala Trp Glu Val Ser Leu Ser Arg Asn Glu Ser Cys
            100                 105                 110

Tyr Val Gly Pro Ala Asn Pro Ala Glu Pro Cys Gly Gln Gly Arg Ile
        115                 120                 125

Pro Arg Tyr Ser Ala Met Val Glu Thr Thr Glu Gln Ala Gln Lys Ala
    130                 135                 140

Ile Arg Phe Ala Arg Glu Arg Arg Leu Arg Leu Val Ile Lys Asn Thr
145                 150                 155                 160

Gly His Asp Ser Gly Gly Arg Ser Ser Ala Val Asp Ser Phe Gln Ile
                165                 170                 175

Leu Thr Gln Arg Leu Lys Asp Ile Ser Phe Ile Glu Glu Phe Thr Pro
            180                 185                 190

Thr Leu Ala Glu Thr Arg Gly Pro Ser Val Arg Ile Gly Ala Gly Val
        195                 200                 205

Leu Thr Lys Glu Leu Tyr Ala Val Ala Asp Glu His Gly Tyr Thr Ala
    210                 215                 220
```

```
Met Gly Gly Glu Cys Ala Thr Val Gly Val Ala Gly Gly Tyr Ile Gln
225                 230                 235                 240

Gly Gly Gly Val Ser Thr Ala Leu Thr Pro Met Met Gly Leu Ala Ala
                245                 250                 255

Asp Leu Val Gln Glu Phe Glu Val Ile Ser Ala Glu Gly Ser Leu Val
            260                 265                 270

Ile Ala Asn Glu Phe Gln Asn Gln Asp Leu Phe Trp Ala Leu Arg Gly
        275                 280                 285

Gly Gly Gly Gly Thr Val Gly Leu Val Thr Ser Ile Thr Met Pro Val
    290                 295                 300

Phe Gly Ala Ile Pro Ala Asn Ile Ser Glu Leu Ser Phe Glu Ser Gln
305                 310                 315                 320

Gln Pro Asp Glu Ala Phe Trp Thr Ala Val Lys Glu Met Ile Tyr Val
                325                 330                 335

Thr Arg Asp Ile Thr Thr Gly Gly Asn Ser Gly Gln Tyr Trp Val Gly
            340                 345                 350

Arg Gly Pro Thr Gly Ser Tyr Phe Val Arg Gln Thr Leu Phe Phe Leu
        355                 360                 365

Gly Glu Thr Asp Ile Glu Pro Ala Asp Lys Met Gly Ser Leu Leu Arg
    370                 375                 380

Val Leu Gln Asp Gln Glu Ile Ala Phe Arg Phe Asn Val Thr Ala Tyr
385                 390                 395                 400

Pro Arg Leu Ser Ser Phe Leu Ala Ile Pro Gln Gly Glu Phe Val Gly
                405                 410                 415

Gly Ile Ala Phe His Gln Glu Asn Ile Leu Ile Pro Gln Gly Phe Tyr
            420                 425                 430

Asp Ser Pro Glu Gly Pro Ala Gln Leu Val Asp Arg Leu Ala Glu Val
        435                 440                 445

Lys Leu Asn Pro Gly Asp Met Trp Val Ala Asn Thr Leu Gly Gly Gln
    450                 455                 460

Val Met Ala Asn Lys Asp Val Asp Asn Ala Met His Ser Gly Trp Arg
465                 470                 475                 480

Thr Ala Ser Val Leu Leu Val Gly Asn Arg Ile Phe Glu Pro Ala Leu
                485                 490                 495

Lys Ser Gln Leu Asp Val Gln Glu Arg Leu Thr Ala Val Glu Gly Pro
            500                 505                 510

Leu Leu His Ser Ile Gly Gln Pro Ala Pro Glu Ala Ile Tyr Leu Asn
        515                 520                 525

Glu Ala Asp Ala Asp Leu Glu Asn Trp Gln Asp Trp Phe Trp Gly Glu
    530                 535                 540

Lys Tyr Ala Arg Leu Arg Asp Ile Lys Ser Lys Trp Asp Pro Asp Asp
545                 550                 555                 560

Leu Phe Leu Val Arg His Gly Val Gly Ser Glu Asp Trp Asp Glu Asp
                565                 570                 575

Gly Met Cys Arg Met Gln Leu Ser Pro Gln Glu Cys Pro Val Arg Glu
            580                 585                 590

His Ser Arg Cys Thr Cys Lys Phe Phe Glu Cys Ala Met Leu His Val
        595                 600                 605

Pro Gly Leu Leu
    610
```

<210> SEQ ID NO 25
<211> LENGTH: 6678
<212> TYPE: DNA

<213> ORGANISM: Aspergillus versicolor NRRL35600

<400> SEQUENCE: 25

```
atggattcaa cacaaattac agagtcaaat cgagagtgca gtgtgctcca gggcaagctg     60
gccactgaga cagtcagaga gtcactctct tcgtctccct cgccattgcc ttccctcgcc    120
tctcctgtct cctctggctc tgaacctcca gcatttggag agacgcagcc ccagagccgg    180
gattccaccc tgttatttaa cgcccaagtg cccgagttct gggagacatg tgtacacgac    240
gtaatccagg aaaggtgtaa ggaagcgccg caatcaacag cagtggcggc ttgggacggg    300
tcctttacgt acggtgaatt ggacgacctt tccaatcgcc tggcgtcagc cttgacctta    360
ctgggcgtca aggccgaaac gttcgtccca atatgcatgg agaaatcgcg gtgggcgaca    420
gtcgcggtgt tgggagtgat gaaggccggt ggcgcgttca ccctgctcga tgcatcatac    480
cctctgcccc ggctaaagac aatttgccag gagctgtcca gtctcgtggt tctctcctcc    540
actgcccagt ccgagcgctg cacgcagctg gcgaatatga ttgttgtaga gcacctgtgc    600
cgagcgtggc accctgttgc tcacaccacc cagtccccgg ccactgtctg cccttcgaac    660
gccctatatg tgtcctttac ctccggatcg accggccggc cgaagggggt cctgattgaa    720
catcgggcat acagctcagg cgcccgagag catctaaagg ccttccgaat cgaccagacc    780
tcccgggtcc tgcagttctc ctcgtacgcc tttgacgtca gcatcatgga gacgcttagc    840
acgctgatgg cgggtggctg cctctgcgtg ctgggggatg cccaacgctc ggacgtctgc    900
ttgtttgctg cggcggtcga cgagttccaa gttagccatg ctctactgac gccgtcgttt    960
gcacggacgg tgccgtggga gaacgtgagg cacctccaga cactggtcct cggcggggag   1020
gaaatgcgag tttcggacgc agcaatgtgc gtggagcgag gagtcagact gatcaatgcc   1080
tacggcacag ctgaatgctc ggtgaatgcc acggcacggc ccggggtcca gcctggggat   1140
aatctcagca ccatcgggca ccccacggga gcggtagcct ggctcatcga cccggacgac   1200
ccggagacgc cgatagggcc cgggatggaa ggggagctgc tcctggaagg gccgattgtg   1260
ggccgtgggt atttgaacaa cccggccgcg actgcagcgg cgtttatagg ccccccaaag   1320
tggctgcagc agctccggaa gacggactac cagcaccagc tgtatcggac gggggacctc   1380
gcggtgcagg acagcactgg ggccttgatg ctccttggcc gcagggacgg gcagctgaag   1440
atccgaggcc agcgggtgga ggtggccgaa atagaacagc atattgaccg cgtgctggcc   1500
gcagtgaagg aggtgattgt tgagaaggtg acccccgagt gcgagcagcg agaaatccta   1560
atggcgttcg tccagactgg ggcgacttca caggcttgga ctgagggctc gcccttgttt   1620
ctgcctccag ggccaacctc cgtacaagaa tttaggacag cccagagcca gctgcgcggg   1680
cagctcccca gctacatggt ccctaccatt ttcatcggtg ttgctgcagt cccacgaacc   1740
gcctctggca agatggatcg ccggctactg cgagtgaccg ctgggcgctt gtcgagagaa   1800
gagctgcagg cgttcaccgg ctcacccgtt gacagtcgct ctcctaccac tgcgactgag   1860
ctcatgttgc aacgactgta tgcagaggtg ctcgaactgc ctaccacgag catcagcatg   1920
gaggactcct tcgtgcgcct cggtggggac tccatcatgg ctgtccgact gctgggggcc   1980
gctcggcggg cagggcttgt gttagacatc ggcgatgtgc ttgggacggc acggctggag   2040
gagcaagcgc aacgagctac ccctatgaca gagggaacag catgtgagac ctacatcccc   2100
ttctcggcgc tgggaagccg gtatatgaac cgcgaggaag tgctgcgcct agcggcagag   2160
cagtgcggga cctccctatc tgagattgaa gatatatacc catgtacgcc gctgcaggaa   2220
ggaatgttgg cgttggcatc cagtcagacc tggatgtacg tcggccatat tgtctttgga   2280
```

```
ctaccggagg gcgtcgacgt ctcccgattc aaggccgcgt ggcagtccac ggcagatacg   2340
actcccatcc tgcgcacgcg catcatcgag acaccacagg gactcttgca ggtggtgctt   2400
cgaggcagcc tggtctggga aacctacaac gagccgccag acgcgtgcgt agccgatggg   2460
ggctcccaga tcgggtcccc cggtgcaccg ctgatgcgct ttgctctagg ggatggggat   2520
catcgtgatg aatttgtcct caccgtccac catgcagtat gggatgcctg gtcgatgcgc   2580
ctgatccacg atgcagtcga acggtccttc cagggcgagc aggtaaagaa acagccgttc   2640
cacccgttca tccagcacct gcagcaagtt gacggcggaa tggacgaatt ctggcgcacc   2700
gaactggcca acctggaggc ggtcccattc ccagctctgc catcgactca ctaccggcca   2760
tcacccacgg cgatgctgcg gcacaccgtg gagaagatcg agatttgtgc gccgcgcagc   2820
cacacaatgg ccagctacat ccacttggcc tggtcgctac tggtggcgca ctatacagat   2880
tcgacagagg ctgtgtacgg tgccaccatg agcggccgca atgcccctgt agaagctatt   2940
aatgagctgg cagggcccac cattgctacg gtgcctgtga gagtccacgt ccgaccggag   3000
gataccatct cggcggcgct ggagcagatc cagtcttgca tggtgcgcat ggtcccgcat   3060
gagcaagccg ggctccttcg tattgcaaag accagctcgg atgctgccag ggcgtgcgcc   3120
ttccagagcc acctgaacat ccaagtcgtc gagcccgagc ggcgcctgtt ccctgtcagg   3180
cggggaatcg ccagcaccgg catggacctg acacggttct ccagctacgc cctcaatctg   3240
atgctactgc taagccccga caatactagc gtcatcgtga atattgcgta cgacccccaa   3300
gtgttgagtg cgtgggaggt ctaccggatg atccaccagt gggagcatat cctgcgccaa   3360
gtttgccgag agccgactgg gtctctccag gagctcgact tggccagtcc actagatcag   3420
gatctgctga gggtatggaa tgcaaagaca ccggccgtgg accggcgctg cttgcacgat   3480
ctcgtgctgg cccaggcgat gcagcagcct tcacgacagg ctgtgtccgc gtgggacggt   3540
ggattcacgt acggcgagct ggcccatctg tcctcgaact ttgcccggct gctcagtcta   3600
tttgcagtgg ggcgcgggtc gtttgtgccc atctgcatgg acaagagccg gtgggcagtt   3660
gtgtcgattc tcgcagtcct gcaagccggg gccacctgcg tcctcctgga tccccaatat   3720
ccgcgccagc gcatgaagga catcattacc ggtttatctg ttccggtgtt ggtaaacgca   3780
ccgtcgacgg ccccggtgac aagaggtctc agtgcgatcc agctgtgcgt atcagcaaag   3840
ttcacggagc agctgtggac cagcaatccc tctgggagtc acttccaagc acacgtagac   3900
ccggacgacc ttgcttttgt gatctttacc tctggcagca caggtgcccc gaaggggatt   3960
gcgatgccgc actctaccat cagttcgagt atccgccata acagcgctgc gatgagattc   4020
gacgctgata cccgtaccct gcatttttcc tcgtacgctt ttgacgtcag catctacgag   4080
atcttcacca cgctggcctc cggcgggtgt gtctgcgtgc cgtctgagtt ccagcggacg   4140
aatgagctgg ccgatttcat ccagcagtgg cgtgttaact gggcctttct aactccctcc   4200
acggcgcagt ccctccatcc gtcagaggtg cctggcctcg ctacacttgt cttgggcggc   4260
gaagcagtga caccggacca cgttgaagtt tgggcccctg gccggaccct cattaatggt   4320
tacggccccg cggaggcaac tatatgcgcc gtcggcccac tgccagagca tggatgggtc   4380
cccgggaaga tcggccacgt tgtcggcggg gtgggctggg tcacggttcc ctctgatccc   4440
aaccggttgg ctgcaattgg agccatcggt gagctattgc tggaggggcc gttccttgct   4500
cgagggtatc tgaaccagca cgaggccacc gctgcctcct ttatcacccc gcccccctgg   4560
cgccgcaagc tgctgccggg ctgtgatgcc gacacgacca ggctctaccg gacgggcgat   4620
```

```
ctggtgcggt accaggaaga cggatcccta cgatacattg ggcgtcgaga cacgcaggtc   4680

aaggtacgcg gccagcgcat cgacctcggg gagatagaga cacagctaca ccggagcttc   4740

cccggtgcgc acgacgtggt ggccgagaca gtccagctgc cagtactcca ggacagaaca   4800

gttctggtgg cgtttatcgg ccgtcaagag ggcctagtga tggagtcggc tctaggggaa   4860

gaagtcgtag ctgccgtcga tgcaggcttt caacaagccg tatcctcggc gcaagcccgc   4920

ctccaggata tcctaccatc atatatgctg ccatccgtct tcctgcctct agcccactgc   4980

ccgaagaccc tcacaggcaa aacggaccgc cgctatctac gtcaggttgt gctgggtctg   5040

gagccgcacg aactacagcg ttatagggtg gccagtcgcc agaagaccag gatccctgtg   5100

tctcacgggg ctgagctgcg tctgcagagc atttgggcag acctcctcca catcccctgc   5160

gacgagatcg gggcggaaga tacctttctc ctccacggtg gcgattccgt ggcggccatg   5220

cggatggttg ccctggcacg ccgcgccgac ttcacgttca gggtcaccga cgtgctcaat   5280

aactgcaccc tatctgatct agctcgctgt acgggtgaag agcaatgttt ggctgccgag   5340

accctgccca ccgtccacga tgtcgagtct gacgatcaag tggtagctag tcagactgac   5400

agtgacgcca tcgcggtcta tcccaccacg caggcccagt ccttcctcat ccagcggtat   5460

ccatggaccc attggcggtt tgccttccac ggggaagttt ccatagaccg actgcgcaca   5520

gcatgcgcac gcctcgttgc tgctcacagc atcctgcgca cattgttcgt gggtggcaag   5580

gggcaaaggg atcggcaggt cgtgatgaag gcgctggata tccccttgca cactgtcacc   5640

acgaacaaga gcctggagga atactgtcaa tcaatctgtg atgccgagca acagatggat   5700

gtcgtcgaga ccgtgcttcc cactcgtttg actctggtct ccgacgtcct ccacacggcg   5760

catatcttcg tcctgcgtct ttctcatgcc cagtacgacg gaatttgcgt tcccaagatc   5820

ttcgccggtc tcgagtcctt ctacaacagg acagagacag tcgccccaac gatatttgag   5880

cgatacctcg accaacgcca acggttcgag ggcgagggtc ctcatgagtt ctggagggcg   5940

taccttgccg ggtcatcgcc tccttgcacg atgcctggga aatcgacacc tcccacgact   6000

gctgacagtg ggcctgtggc tcctccttct gttatttccg cgtcccagac cgtgaaattc   6060

actgccattc catcccaggt cacactagcg acggtggtca aggccgccgc gtgtctggtc   6120

ttagcccgtc tcacagggcg cagcgatatc accgttggcc agaccgttaa tggccgtagc   6180

ctgcccctgc cgtgggtgaa cgaagtggta gggccctgtg tgaattacat cccattccgc   6240

gcaacgctgc agcagtcgat gtcgacccag gactacttag ttgacatgca aaggcagcat   6300

aaccgctgcg tcccctcga cggcgccgag ctggacacaa tagtcaagaa ctgcactgac   6360

tgggagccga cggcggaatt tgggttcatt ctgcagcatc aaaacatcga catggacttg   6420

agcctgaccc tggacggaaa ccggtgcgtc tcctgtgctt cttccggcca gctgcgtccg   6480

tccaacgagg tctggatttg ctctacaccg tctccgtctg gtgtggactt ggatgtcgtc   6540

gcctctagtc atattctaac tgcagatgcc gctaagaatc tggtggatga catcgctgat   6600

atgattcaaa ccctactata taatctagag acccccctgc gagatgctgt cgagttgaac   6660

tggtctgatg ggagttga                                                 6678
```

<210> SEQ ID NO 26
<211> LENGTH: 2225
<212> TYPE: PRT
<213> ORGANISM: Aspergillus versicolor NRRL35600

<400> SEQUENCE: 26

Met Asp Ser Thr Gln Ile Thr Glu Ser Asn Arg Glu Cys Ser Val Leu

```
1               5                   10                  15

Gln Gly Lys Leu Ala Thr Glu Thr Val Arg Glu Ser Leu Ser Ser Ser
            20                  25                  30

Pro Ser Pro Leu Pro Ser Leu Ala Ser Pro Val Ser Ser Gly Ser Glu
        35                  40                  45

Pro Pro Ala Phe Gly Glu Thr Gln Pro Gln Ser Arg Asp Ser Thr Leu
    50                  55                  60

Leu Phe Asn Ala Gln Val Pro Glu Phe Trp Glu Thr Cys Val His Asp
65                  70                  75                  80

Val Ile Gln Glu Arg Cys Lys Glu Ala Pro Gln Ser Thr Ala Val Ala
                85                  90                  95

Ala Trp Asp Gly Ser Phe Thr Tyr Gly Glu Leu Asp Asp Leu Ser Asn
            100                 105                 110

Arg Leu Ala Ser Ala Leu Thr Leu Leu Gly Val Lys Ala Glu Thr Phe
        115                 120                 125

Val Pro Ile Cys Met Glu Lys Ser Arg Trp Ala Thr Val Ala Val Leu
    130                 135                 140

Gly Val Met Lys Ala Gly Gly Ala Phe Thr Leu Leu Asp Ala Ser Tyr
145                 150                 155                 160

Pro Leu Pro Arg Leu Lys Thr Ile Cys Gln Glu Leu Ser Ser Leu Val
                165                 170                 175

Val Leu Ser Ser Thr Ala Gln Ser Glu Arg Cys Thr Gln Leu Ala Asn
            180                 185                 190

Met Ile Val Val Glu His Leu Cys Arg Ala Trp His Pro Val Ala His
        195                 200                 205

Thr Thr Gln Ser Pro Ala Thr Val Cys Pro Ser Asn Ala Leu Tyr Val
    210                 215                 220

Ser Phe Thr Ser Gly Ser Thr Gly Arg Pro Lys Gly Val Leu Ile Glu
225                 230                 235                 240

His Arg Ala Tyr Ser Ser Gly Ala Arg Glu His Leu Lys Ala Phe Arg
                245                 250                 255

Ile Asp Gln Thr Ser Arg Val Leu Gln Phe Ser Ser Tyr Ala Phe Asp
            260                 265                 270

Val Ser Ile Met Glu Thr Leu Ser Thr Leu Met Ala Gly Gly Cys Leu
        275                 280                 285

Cys Val Leu Gly Asp Ala Gln Arg Ser Asp Val Cys Leu Phe Ala Ala
    290                 295                 300

Ala Val Asp Glu Phe Gln Val Ser His Ala Leu Leu Thr Pro Ser Phe
305                 310                 315                 320

Ala Arg Thr Val Pro Trp Glu Asn Val Arg His Leu Gln Thr Leu Val
                325                 330                 335

Leu Gly Gly Glu Glu Met Arg Val Ser Asp Ala Ala Met Cys Val Glu
            340                 345                 350

Arg Gly Val Arg Leu Ile Asn Ala Tyr Gly Thr Ala Glu Cys Ser Val
        355                 360                 365

Asn Ala Thr Ala Arg Pro Gly Val Gln Pro Gly Asp Asn Leu Ser Thr
    370                 375                 380

Ile Gly His Pro Thr Gly Ala Val Ala Trp Leu Ile Asp Pro Asp Asp
385                 390                 395                 400

Pro Glu Thr Pro Ile Gly Pro Gly Met Glu Gly Glu Leu Leu Leu Glu
                405                 410                 415

Gly Pro Ile Val Gly Arg Gly Tyr Leu Asn Asn Pro Ala Ala Thr Ala
            420                 425                 430
```

```
Ala Ala Phe Ile Gly Pro Pro Lys Trp Leu Gln Gln Leu Arg Lys Thr
        435                 440                 445

Asp Tyr Gln His Gln Leu Tyr Arg Thr Gly Asp Leu Ala Val Gln Asp
    450                 455                 460

Ser Thr Gly Ala Leu Met Leu Leu Gly Arg Arg Asp Gly Gln Leu Lys
465                 470                 475                 480

Ile Arg Gly Gln Arg Val Glu Val Ala Glu Ile Glu Gln His Ile Asp
                485                 490                 495

Arg Val Leu Ala Ala Val Lys Glu Val Ile Val Glu Lys Val Thr Pro
            500                 505                 510

Glu Cys Glu Gln Arg Glu Ile Leu Met Ala Phe Val Gln Thr Gly Ala
        515                 520                 525

Thr Ser Gln Ala Trp Thr Glu Gly Ser Pro Leu Phe Leu Pro Pro Gly
    530                 535                 540

Pro Thr Ser Val Gln Glu Phe Arg Thr Ala Gln Ser Gln Leu Arg Gly
545                 550                 555                 560

Gln Leu Pro Ser Tyr Met Val Pro Thr Ile Phe Ile Gly Val Ala Ala
                565                 570                 575

Val Pro Arg Thr Ala Ser Gly Lys Met Asp Arg Arg Leu Leu Arg Val
            580                 585                 590

Thr Ala Gly Arg Leu Ser Arg Glu Glu Leu Gln Ala Phe Thr Gly Ser
        595                 600                 605

Pro Val Asp Ser Arg Ser Pro Thr Thr Ala Thr Glu Leu Met Leu Gln
    610                 615                 620

Arg Leu Tyr Ala Glu Val Leu Glu Leu Pro Thr Thr Ser Ile Ser Met
625                 630                 635                 640

Glu Asp Ser Phe Val Arg Leu Gly Gly Asp Ser Ile Met Ala Val Arg
                645                 650                 655

Leu Leu Gly Ala Ala Arg Arg Ala Gly Leu Val Leu Asp Ile Gly Asp
            660                 665                 670

Val Leu Gly Thr Ala Arg Leu Glu Glu Gln Ala Gln Arg Ala Thr Pro
        675                 680                 685

Met Thr Glu Gly Thr Ala Cys Glu Thr Tyr Ile Pro Phe Ser Ala Leu
    690                 695                 700

Gly Ser Arg Tyr Met Asn Arg Glu Glu Val Leu Arg Leu Ala Ala Glu
705                 710                 715                 720

Gln Cys Gly Thr Ser Leu Ser Glu Ile Glu Asp Ile Tyr Pro Cys Thr
                725                 730                 735

Pro Leu Gln Glu Gly Met Leu Ala Leu Ala Ser Ser Gln Thr Trp Met
            740                 745                 750

Tyr Val Gly His Ile Val Phe Gly Leu Pro Glu Gly Val Asp Val Ser
        755                 760                 765

Arg Phe Lys Ala Ala Trp Gln Ser Thr Ala Asp Thr Thr Pro Ile Leu
    770                 775                 780

Arg Thr Arg Ile Ile Glu Thr Pro Gln Gly Leu Leu Gln Val Val Leu
785                 790                 795                 800

Arg Gly Ser Leu Val Trp Glu Thr Tyr Asn Glu Pro Pro Asp Ala Cys
                805                 810                 815

Val Ala Asp Gly Gly Ser Gln Ile Gly Ser Pro Gly Ala Pro Leu Met
            820                 825                 830

Arg Phe Ala Leu Gly Asp Gly Asp His Arg Asp Glu Phe Val Leu Thr
        835                 840                 845
```

```
Val His His Ala Val Trp Asp Ala Trp Ser Met Arg Leu Ile His Asp
    850                 855                 860

Ala Val Glu Arg Ser Phe Gln Gly Glu Gln Val Lys Lys Gln Pro Phe
865                 870                 875                 880

His Pro Phe Ile Gln His Leu Gln Gln Val Asp Gly Gly Met Asp Glu
                885                 890                 895

Phe Trp Arg Thr Glu Leu Ala Asn Leu Glu Ala Val Pro Phe Pro Ala
            900                 905                 910

Leu Pro Ser Thr His Tyr Arg Pro Ser Pro Thr Ala Met Leu Arg His
        915                 920                 925

Thr Val Glu Lys Ile Glu Ile Cys Ala Pro Arg Ser His Thr Met Ala
    930                 935                 940

Ser Tyr Ile His Leu Ala Trp Ser Leu Leu Val Ala His Tyr Thr Asp
945                 950                 955                 960

Ser Thr Glu Ala Val Tyr Gly Ala Thr Met Ser Gly Arg Asn Ala Pro
                965                 970                 975

Val Glu Ala Ile Asn Glu Leu Ala Gly Pro Thr Ile Ala Thr Val Pro
            980                 985                 990

Val Arg Val His Val Arg Pro Glu  Asp Thr Ile Ser Ala  Ala Leu Glu
        995                 1000                1005

Gln Ile  Gln Ser Cys Met Val  Arg Met Val Pro His  Glu Gln Ala
    1010                 1015                 1020

Gly Leu  Leu Arg Ile Ala Lys  Thr Ser Ser Asp Ala  Ala Arg Ala
    1025                 1030                 1035

Cys Ala  Phe Gln Ser His Leu  Asn Ile Gln Val Val  Glu Pro Glu
    1040                 1045                 1050

Arg Arg  Leu Phe Pro Val Arg  Arg Gly Ile Ala Ser  Thr Gly Met
    1055                 1060                 1065

Asp Leu  Thr Arg Phe Ser Ser  Tyr Ala Leu Asn Leu  Met Leu Leu
    1070                 1075                 1080

Leu Ser  Pro Asp Asn Thr Ser  Val Ile Val Asn Ile  Ala Tyr Asp
    1085                 1090                 1095

Pro Gln  Val Leu Ser Ala Trp  Glu Val Tyr Arg Met  Ile His Gln
    1100                 1105                 1110

Trp Glu  His Ile Leu Arg Gln  Val Cys Arg Glu Pro  Thr Gly Ser
    1115                 1120                 1125

Leu Gln  Glu Leu Asp Leu Ala  Ser Pro Leu Asp Gln  Asp Leu Leu
    1130                 1135                 1140

Arg Val  Trp Asn Ala Lys Thr  Pro Ala Val Asp Arg  Arg Cys Leu
    1145                 1150                 1155

His Asp  Leu Val Leu Ala Gln  Ala Met Gln Gln Pro  Ser Arg Gln
    1160                 1165                 1170

Ala Val  Ser Ala Trp Asp Gly  Gly Phe Thr Tyr Gly  Glu Leu Ala
    1175                 1180                 1185

His Leu  Ser Ser Asn Phe Ala  Arg Leu Leu Ser Leu  Phe Ala Val
    1190                 1195                 1200

Gly Arg  Gly Ser Phe Val Pro  Ile Cys Met Asp Lys  Ser Arg Trp
    1205                 1210                 1215

Ala Val  Val Ser Ile Leu Ala  Val Leu Gln Ala Gly  Ala Thr Cys
    1220                 1225                 1230

Val Leu  Leu Asp Pro Gln Tyr  Pro Arg Gln Arg Met  Lys Asp Ile
    1235                 1240                 1245

Ile Thr  Gly Leu Ser Val Pro  Val Leu Val Asn Ala  Pro Ser Thr
```

```
    1250                1255                1260

Ala Pro  Val Thr Arg Gly Leu  Ser Ala Ile Gln Leu  Cys Val Ser
    1265                1270                1275

Ala Lys  Phe Thr Glu Gln Leu  Trp Thr Ser Asn Pro  Ser Gly Ser
    1280                1285                1290

His Phe  Gln Ala His Val Asp  Pro Asp Asp Leu Ala  Phe Val Ile
    1295                1300                1305

Phe Thr  Ser Gly Ser Thr Gly  Ala Pro Lys Gly Ile  Ala Met Pro
    1310                1315                1320

His Ser  Thr Ile Ser Ser Ser  Ile Arg His Asn Ser  Ala Ala Met
    1325                1330                1335

Arg Phe  Asp Ala Asp Thr Arg  Thr Leu His Phe Ser  Ser Tyr Ala
    1340                1345                1350

Phe Asp  Val Ser Ile Tyr Glu  Ile Phe Thr Thr Leu  Ala Ser Gly
    1355                1360                1365

Gly Cys  Val Cys Val Pro Ser  Glu Phe Gln Arg Thr  Asn Glu Leu
    1370                1375                1380

Ala Asp  Phe Ile Gln Gln Trp  Arg Val Asn Trp Ala  Phe Leu Thr
    1385                1390                1395

Pro Ser  Thr Ala Gln Ser Leu  His Pro Ser Glu Val  Pro Gly Leu
    1400                1405                1410

Ala Thr  Leu Val Leu Gly Gly  Glu Ala Val Thr Pro  Asp His Val
    1415                1420                1425

Glu Val  Trp Ala Pro Gly Arg  Thr Leu Ile Asn Gly  Tyr Gly Pro
    1430                1435                1440

Ala Glu  Ala Thr Ile Cys Ala  Val Gly Pro Leu Pro  Glu His Gly
    1445                1450                1455

Trp Val  Pro Gly Lys Ile Gly  His Val Val Gly Gly  Val Gly Trp
    1460                1465                1470

Val Thr  Val Pro Ser Asp Pro  Asn Arg Leu Ala Ala  Ile Gly Ala
    1475                1480                1485

Ile Gly  Glu Leu Leu Leu Glu  Gly Pro Phe Leu Ala  Arg Gly Tyr
    1490                1495                1500

Leu Asn  Gln His Glu Ala Thr  Ala Ala Ser Phe Ile  Thr Pro Pro
    1505                1510                1515

Pro Trp  Arg Arg Lys Leu Leu  Pro Gly Cys Asp Ala  Asp Thr Thr
    1520                1525                1530

Arg Leu  Tyr Arg Thr Gly Asp  Leu Val Arg Tyr Gln  Glu Asp Gly
    1535                1540                1545

Ser Leu  Arg Tyr Ile Gly Arg  Arg Asp Thr Gln Val  Lys Val Arg
    1550                1555                1560

Gly Gln  Arg Ile Asp Leu Gly  Glu Ile Glu Thr Gln  Leu His Arg
    1565                1570                1575

Ser Phe  Pro Gly Ala His Asp  Val Val Ala Glu Thr  Val Gln Leu
    1580                1585                1590

Pro Val  Leu Gln Asp Arg Thr  Val Leu Val Ala Phe  Ile Gly Arg
    1595                1600                1605

Gln Glu  Gly Leu Val Met Glu  Ser Ala Leu Gly Glu  Glu Val Val
    1610                1615                1620

Ala Ala  Val Asp Ala Gly Phe  Gln Gln Ala Val Ser  Ser Ala Gln
    1625                1630                1635

Ala Arg  Leu Gln Asp Ile Leu  Pro Ser Tyr Met Leu  Pro Ser Val
    1640                1645                1650
```

```
Phe Leu  Pro Leu Ala His Cys  Pro Lys Thr Leu Thr  Gly Lys Thr
    1655                 1660                 1665

Asp Arg  Arg Tyr Leu Arg Gln  Val Val Leu Gly Leu  Glu Pro His
    1670                 1675                 1680

Glu Leu  Gln Arg Tyr Arg Val  Ala Ser Arg Gln Lys  Thr Arg Ile
    1685                 1690                 1695

Pro Val  Ser His Gly Ala Glu  Leu Arg Leu Gln Ser  Ile Trp Ala
    1700                 1705                 1710

Asp Leu  Leu His Ile Pro Cys  Asp Glu Ile Gly Ala  Glu Asp Thr
    1715                 1720                 1725

Phe Leu  Leu His Gly Gly Asp  Ser Val Ala Ala Met  Arg Met Val
    1730                 1735                 1740

Ala Leu  Ala Arg Arg Ala Asp  Phe Thr Phe Arg Val  Thr Asp Val
    1745                 1750                 1755

Leu Asn  Asn Cys Thr Leu Ser  Asp Leu Ala Arg Cys  Thr Gly Glu
    1760                 1765                 1770

Glu Gln  Cys Leu Ala Ala Glu  Thr Leu Pro Thr Val  His Asp Val
    1775                 1780                 1785

Glu Ser  Asp Asp Gln Val Val  Ala Ser Gln Thr Asp  Ser Asp Ala
    1790                 1795                 1800

Ile Ala  Val Tyr Pro Thr Thr  Gln Ala Gln Ser Phe  Leu Ile Gln
    1805                 1810                 1815

Arg Tyr  Pro Trp Thr His Trp  Arg Phe Ala Phe His  Gly Glu Val
    1820                 1825                 1830

Ser Ile  Asp Arg Leu Arg Thr  Ala Cys Ala Arg Leu  Val Ala Ala
    1835                 1840                 1845

His Ser  Ile Leu Arg Thr Leu  Phe Val Gly Gly Lys  Gly Gln Arg
    1850                 1855                 1860

Asp Arg  Gln Val Val Met Lys  Ala Leu Asp Ile Pro  Leu His Thr
    1865                 1870                 1875

Val Thr  Thr Asn Lys Ser Leu  Glu Glu Tyr Cys Gln  Ser Ile Cys
    1880                 1885                 1890

Asp Ala  Glu Gln Gln Met Asp  Val Val Glu Thr Val  Leu Pro Thr
    1895                 1900                 1905

Arg Leu  Thr Leu Val Ser Asp  Val Leu His Thr Ala  His Ile Phe
    1910                 1915                 1920

Val Leu  Arg Leu Ser His Ala  Gln Tyr Asp Gly Ile  Cys Val Pro
    1925                 1930                 1935

Lys Ile  Phe Ala Gly Leu Glu  Ser Phe Tyr Asn Arg  Thr Glu Thr
    1940                 1945                 1950

Val Ala  Pro Thr Ile Phe Glu  Arg Tyr Leu Asp Gln  Arg Gln Arg
    1955                 1960                 1965

Phe Glu  Gly Glu Gly Pro His  Glu Phe Trp Arg Ala  Tyr Leu Ala
    1970                 1975                 1980

Gly Ser  Ser Pro Pro Cys Thr  Met Pro Gly Lys Ser  Thr Pro Pro
    1985                 1990                 1995

Thr Thr  Ala Asp Ser Gly Pro  Val Ala Pro Pro Ser  Val Ile Ser
    2000                 2005                 2010

Ala Ser  Gln Thr Val Lys Phe  Thr Ala Ile Pro Ser  Gln Val Thr
    2015                 2020                 2025

Leu Ala  Thr Val Val Lys Ala  Ala Ala Cys Leu Val  Leu Ala Arg
    2030                 2035                 2040
```

```
Leu Thr  Gly Arg Ser Asp Ile  Thr Val Gly Gln Thr  Val Asn Gly
    2045                 2050                 2055

Arg Ser  Leu Pro Leu Pro Trp  Val Asn Glu Val Val  Gly Pro Cys
    2060                 2065                 2070

Val Asn  Tyr Ile Pro Phe Arg  Ala Thr Leu Gln Gln  Ser Met Ser
    2075                 2080                 2085

Thr Gln  Asp Tyr Leu Val Asp  Met Gln Arg Gln His  Asn Arg Cys
    2090                 2095                 2100

Val Pro  Phe Asp Gly Ala Glu  Leu Asp Thr Ile Val  Lys Asn Cys
    2105                 2110                 2115

Thr Asp  Trp Glu Pro Thr Ala  Glu Phe Gly Phe Ile  Leu Gln His
    2120                 2125                 2130

Gln Asn  Ile Asp Met Asp Leu  Ser Leu Thr Leu Asp  Gly Asn Arg
    2135                 2140                 2145

Cys Val  Ser Cys Ala Ser Ser  Gly Gln Leu Arg Pro  Ser Asn Glu
    2150                 2155                 2160

Val Trp  Ile Cys Ser Thr Pro  Ser Pro Ser Gly Val  Asp Leu Asp
    2165                 2170                 2175

Val Val  Ala Ser Ser His Ile  Leu Thr Ala Asp Ala  Ala Lys Asn
    2180                 2185                 2190

Leu Val  Asp Asp Ile Ala Asp  Met Ile Gln Thr Leu  Leu Tyr Asn
    2195                 2200                 2205

Leu Glu  Thr Pro Leu Arg Asp  Ala Val Glu Leu Asn  Trp Ser Asp
    2210                 2215                 2220

Gly Ser
    2225
```

<210> SEQ ID NO 27
<211> LENGTH: 1308
<212> TYPE: DNA
<213> ORGANISM: Aspergillus versicolor NRRL35600

<400> SEQUENCE: 27

```
tcaaccttcc tcccacagat aggtactttg tgaatgaaaa tacacgctca tgtagacgcc     60

ttttttggca gtgtaggaat acgatatcca agattgcaaa cgggatgtcc gggaaacgtc    120

caggtccggg tacagctgtt gcaacatatc cggataggca caggcatgct ctgaccaacc    180

caaagaatcc caaaactggg ccaacgaccg agccacgcgc agatcattct cgccatgcac    240

ggggaggtag aacttgggca cggggaagct gctcccagga ctgatctcgt agttccatat    300

gatgggcgat gggatctggt cggtggcact ggccttgccg taatcaaacc cgcccttaaa    360

ggcccggctg ccttcgccaa tctgcaacag agaccagatc tgcttcaacc gggccagccc    420

ctccatgatt tcaggctctt cgatcagccg gccgcctaga gtccacatct ccgcaatctt    480

cgcccaggtg acctccgtgt gagcgccgta gatcttgacc cgctgccgcg acatttcaac    540

caggtcgcag gacagaaacg tgtactcgtt gtagcccgtg ctttcctgca tgtagtcgtt    600

gatcagggaa aacgcgtgca taaactgatt cctgtccgcg tcgatggcgc gcaccgactc    660

cgcgatgagt gtcgcaactg gcacgcccgc ggcctttgct ttcagatacg ggaacacgta    720

gcccttgacg agaatggcgc cgtccgggtt aaagtcaaag ccaaacgcac cctgcgactt    780

gagcggctgg tcatccggcg ggagctggcg gacctcgtcc agcgacagtt ggaaccgggt    840

gagcagctgc tggaagcact gcgtgtcaaa gccacgcagt tgcaaccttg cgagctgggc    900

aagcagatcg gcgatgggga tccgattgaa cggatcctgc gacgagccag acaggaagtt    960
```

```
gacgggctcg aacccgattc gtagcaggcg gtgcgagcct ttttggaagt tgagactgaa   1020

ttcaatcggc agtccgctgc gcgagattgt gctgcgccat ttctgcggat agggccccag   1080

ggcggggatg aggtggtgca tgaagaagaa cataaactgg tactgttggt gcagtccgta   1140

ctgtccggcc tcgaggaacc ggctgcacag cgagcctgtc tcctggtacc agcgttcctg   1200

gtcgcttgtg ggaaagtggt gataggaaga tagggcttgt gcagggctcg accgggcagg   1260

gggctcctga ggatgcccag caggtgcact gagctcgggg gccgtcat                 1308


<210> SEQ ID NO 28
<211> LENGTH: 435
<212> TYPE: PRT
<213> ORGANISM: Aspergillus versicolor NRRL35600

<400> SEQUENCE: 28

Met Thr Ala Pro Glu Leu Ser Ala Pro Ala Gly His Pro Gln Glu Pro
1               5                   10                  15

Pro Ala Arg Ser Ser Pro Ala Gln Ala Leu Ser Ser Tyr His His Phe
            20                  25                  30

Pro Thr Ser Asp Gln Glu Arg Trp Tyr Gln Glu Thr Gly Ser Leu Cys
        35                  40                  45

Ser Arg Phe Leu Glu Ala Gly Gln Tyr Gly Leu His Gln Gln Tyr Gln
    50                  55                  60

Phe Met Phe Phe Phe Met His His Leu Ile Pro Ala Leu Gly Pro Tyr
65                  70                  75                  80

Pro Gln Lys Trp Arg Ser Thr Ile Ser Arg Ser Gly Leu Pro Ile Glu
                85                  90                  95

Phe Ser Leu Asn Phe Gln Lys Gly Ser His Arg Leu Leu Arg Ile Gly
            100                 105                 110

Phe Glu Pro Val Asn Phe Leu Ser Gly Ser Ser Gln Asp Pro Phe Asn
        115                 120                 125

Arg Ile Pro Ile Ala Asp Leu Leu Ala Gln Leu Ala Arg Leu Gln Leu
    130                 135                 140

Arg Gly Phe Asp Thr Gln Cys Phe Gln Gln Leu Leu Thr Arg Phe Gln
145                 150                 155                 160

Leu Ser Leu Asp Glu Val Arg Gln Leu Pro Pro Asp Asp Gln Pro Leu
                165                 170                 175

Lys Ser Gln Gly Ala Phe Gly Phe Asp Phe Asn Pro Asp Gly Ala Ile
            180                 185                 190

Leu Val Lys Gly Tyr Val Phe Pro Tyr Leu Lys Ala Lys Ala Ala Gly
        195                 200                 205

Val Pro Val Ala Thr Leu Ile Ala Glu Ser Val Arg Ala Ile Asp Ala
    210                 215                 220

Asp Arg Asn Gln Phe Met His Ala Phe Ser Leu Ile Asn Asp Tyr Met
225                 230                 235                 240

Gln Glu Ser Thr Gly Tyr Asn Glu Tyr Thr Phe Leu Ser Cys Asp Leu
                245                 250                 255

Val Glu Met Ser Arg Gln Arg Val Lys Ile Tyr Gly Ala His Thr Glu
            260                 265                 270

Val Thr Trp Ala Lys Ile Ala Glu Met Trp Thr Leu Gly Gly Arg Leu
        275                 280                 285

Ile Glu Glu Pro Glu Ile Met Glu Gly Leu Ala Arg Leu Lys Gln Ile
    290                 295                 300

Trp Ser Leu Leu Gln Ile Gly Glu Gly Ser Arg Ala Phe Lys Gly Gly
305                 310                 315                 320
```

```
Phe Asp Tyr Gly Lys Ala Ser Ala Thr Asp Gln Ile Pro Ser Pro Ile
                325                 330                 335

Ile Trp Asn Tyr Glu Ile Ser Pro Gly Ser Ser Phe Pro Val Pro Lys
            340                 345                 350

Phe Tyr Leu Pro Val His Gly Glu Asn Asp Leu Arg Val Ala Arg Ser
        355                 360                 365

Leu Ala Gln Phe Trp Asp Ser Leu Gly Trp Ser Glu His Ala Cys Ala
    370                 375                 380

Tyr Pro Asp Met Leu Gln Gln Leu Tyr Pro Asp Leu Asp Val Ser Arg
385                 390                 395                 400

Thr Ser Arg Leu Gln Ser Trp Ile Ser Tyr Ser Tyr Thr Ala Lys Lys
                405                 410                 415

Gly Val Tyr Met Ser Val Tyr Phe His Ser Gln Ser Thr Tyr Leu Trp
            420                 425                 430

Glu Glu Gly
        435


<210> SEQ ID NO 29
<211> LENGTH: 1635
<212> TYPE: DNA
<213> ORGANISM: Aspergillus versicolor NRRL35600

<400> SEQUENCE: 29

tcaaccacgc ctagtgagga cgacgggcat cctctcgatt cccatcgaga agtggtcctc     60

tacattctcc attaagtggc tgccatcctc gcccgccggg aatcgaatct caaaggtcat    120

aataagccgc gcgatggtcg tgcggatatt catcagggca agtggctttc caatgcagct    180

atatgggcct gtcaagaagg gggcatacgc cgatcgatgc ttgatcaagt ccgggtgctt    240

gtaccaccgc tcggggttga aggaaagtgg cgctatgaat gctgcgtccg agcgtccaat    300

gacccactgg gggcagaata cggccatgcc ccccggaatg tgcgtgcctt tgacgtggac    360

accctccgcg ggcgttatgc gtgggatcac cgatggaacc ggcgggtgca gccgaagcgt    420

ctcgttgatg aagccgttca ggtgaggcag gttggagatt tgctcgtgcc ggtactcgcc    480

attcgcatcg gcgtcgattg gcagcagctc agctcggagc ctctccacgt cttctggatg    540

ccgggccagc tcgtagacga cactcgtgag tgctgttgcc gtggtatcac ttccagccgt    600

aactactaac atggcgtcgc ccatcaataa gttgaattcg tcgggagtag ggctgcggcc    660

attcaacggg gccagcaacg aggcgcaaat gtccggtatc tccaacttat cattcatccg    720

gtgcaccagc ttctgtgttg taaattcaac aaacctatgc cagttcttgg agagagaagg    780

cagcgtgacg aagcatcgga acagccagga cggaacaaag tatttataga ggacaattcc    840

atccaggagc acctggatgg cccaatggtt actatgcgtg tcaagcatgt tgaagctgcg    900

gccaaatgcc aaatcgccca tgacatcgta gctgtagaag ttgaaccagt cgctgatgtt    960

caccgtcagc ccgacggcgt cattcagccg ggtaaacagc ttctggcgat actcatggac   1020

ccgagtctcg taccctcgga gagcccggtc accaaagcca gtgctccagg tgcgacgccg   1080

ttgatcgtgg gctgctcggt cccgatacga gtgcagcgac ttcatcgggt ggccattgtc   1140

atagaaggtg ctcttataac agcgcgactg gtgtccatag acgattccga ctgcctctgg   1200

ataggcgata gaaagctccg agggtccaac acgtacgatc gggccgtatt ggttgtggag   1260

ctcctggagt ttctgaaagg ccggtcgatc tcgcaggccc atggacagcc acaggcccga   1320

gattcttgcg ccgtatggac caggaaaccc atgaaggggg tggaactgga cgcgatagag   1380
```

```
aagcagggag gtgtagaggc ccgcaaagta ggtcaaggcc catcctcccg tggccttcgc   1440

tgcgtcgtag agggggagac cccagacgat actcacaacc accgtgggcg cggtgatgat   1500

aagtgtgtac catcgcaaat aagcaaaagg gtacaggtgg tgttcgcccc gtcgaaagta   1560

acactgatga gatataacgc cagcaatccc taccagcaga tacagcaggc tcatggcgga   1620

gaagggcaat tccat                                                    1635


<210> SEQ ID NO 30
<211> LENGTH: 544
<212> TYPE: PRT
<213> ORGANISM: Aspergillus versicolor NRRL35600

<400> SEQUENCE: 30

Met Glu Leu Pro Phe Ser Ala Met Ser Leu Leu Tyr Leu Leu Val Gly
1               5                   10                  15

Ile Ala Gly Val Ile Ser His Gln Cys Tyr Phe Arg Arg Gly Glu His
            20                  25                  30

His Leu Tyr Pro Phe Ala Tyr Leu Arg Trp Tyr Thr Leu Ile Ile Thr
        35                  40                  45

Ala Pro Thr Val Val Val Ser Ile Val Trp Gly Leu Pro Leu Tyr Asp
    50                  55                  60

Ala Ala Lys Ala Thr Gly Gly Trp Ala Leu Thr Tyr Phe Ala Gly Leu
65                  70                  75                  80

Tyr Thr Ser Leu Leu Leu Tyr Arg Val Gln Phe His Pro Leu His Gly
                85                  90                  95

Phe Pro Gly Pro Tyr Gly Ala Arg Ile Ser Gly Leu Trp Leu Ser Met
            100                 105                 110

Gly Leu Arg Asp Arg Pro Ala Phe Gln Lys Leu Gln Glu Leu His Asn
        115                 120                 125

Gln Tyr Gly Pro Ile Val Arg Val Gly Pro Ser Glu Leu Ser Ile Ala
    130                 135                 140

Tyr Pro Glu Ala Val Gly Ile Val Tyr Gly His Gln Ser Arg Cys Tyr
145                 150                 155                 160

Lys Ser Thr Phe Tyr Asp Asn Gly His Pro Met Lys Ser Leu His Ser
                165                 170                 175

Tyr Arg Asp Arg Ala Ala His Asp Gln Arg Arg Arg Thr Trp Ser Thr
            180                 185                 190

Gly Phe Gly Asp Arg Ala Leu Arg Gly Tyr Glu Thr Arg Val His Glu
        195                 200                 205

Tyr Arg Gln Lys Leu Phe Thr Arg Leu Asn Asp Ala Val Gly Leu Thr
    210                 215                 220

Val Asn Ile Ser Asp Trp Phe Asn Phe Tyr Ser Tyr Asp Val Met Gly
225                 230                 235                 240

Asp Leu Ala Phe Gly Arg Ser Phe Asn Met Leu Asp Thr His Ser Asn
                245                 250                 255

His Trp Ala Ile Gln Val Leu Leu Asp Gly Ile Val Leu Tyr Lys Tyr
            260                 265                 270

Phe Val Pro Ser Trp Leu Phe Arg Cys Phe Val Thr Leu Pro Ser Leu
        275                 280                 285

Ser Lys Asn Trp His Arg Phe Val Glu Phe Thr Thr Gln Lys Leu Val
    290                 295                 300

His Arg Met Asn Asp Lys Leu Glu Ile Pro Asp Ile Cys Ala Ser Leu
305                 310                 315                 320

Leu Ala Pro Leu Asn Gly Arg Ser Pro Thr Pro Asp Glu Phe Asn Leu
```

```
                325                 330                 335

Leu Met Gly Asp Ala Met Leu Val Val Thr Ala Gly Ser Asp Thr Thr
            340                 345                 350

Ala Thr Ala Leu Thr Ser Val Val Tyr Glu Leu Ala Arg His Pro Glu
        355                 360                 365

Asp Val Glu Arg Leu Arg Ala Glu Leu Leu Pro Ile Asp Ala Asp Ala
    370                 375                 380

Asn Gly Glu Tyr Arg His Glu Gln Ile Ser Asn Leu Pro His Leu Asn
385                 390                 395                 400

Gly Phe Ile Asn Glu Thr Leu Arg Leu His Pro Pro Val Pro Ser Val
                405                 410                 415

Ile Pro Arg Ile Thr Pro Ala Glu Gly Val His Val Lys Gly Thr His
            420                 425                 430

Ile Pro Gly Gly Met Ala Val Phe Cys Pro Gln Trp Val Ile Gly Arg
        435                 440                 445

Ser Asp Ala Ala Phe Ile Ala Pro Leu Ser Phe Asn Pro Glu Arg Trp
    450                 455                 460

Tyr Lys His Pro Asp Leu Ile Lys His Arg Ser Ala Tyr Ala Pro Phe
465                 470                 475                 480

Leu Thr Gly Pro Tyr Ser Cys Ile Gly Lys Pro Leu Ala Leu Met Asn
                485                 490                 495

Ile Arg Thr Thr Ile Ala Arg Leu Ile Met Thr Phe Glu Ile Arg Phe
            500                 505                 510

Pro Ala Gly Glu Asp Gly Ser His Leu Met Glu Asn Val Glu Asp His
        515                 520                 525

Phe Ser Met Gly Ile Glu Arg Met Pro Val Val Leu Thr Arg Arg Gly
    530                 535                 540
```

<210> SEQ ID NO 31
<211> LENGTH: 1500
<212> TYPE: DNA
<213> ORGANISM: Aspergillus versicolor NRRL35600

<400> SEQUENCE: 31

```
atggcgcaag acaccgcact gcacttgccc ctggggctgg agccggcagg atgggctctt      60

gcactcctga caagcagcat aatctacctc ttcctatcgc caaagtccaa gagcccccga     120

ttcccagtgg taaataaata ttggtgggat tttttccagg ccaaggcaaa gcgtgatttc     180

gaggccgggg cggaggactt gatcaagctc gggctttcca aggcaaggac caaaccacgg     240

agagaatacc caaggctggt cctgtcagat caactggcgg atgcagtcgg aatggataat     300

cggtttgacc aggacaaagg aattgcacct gtcaatttgg ttacgttgaa gggttttgag     360

tccatgtatg caggggcact ccacgactcg gttccacgtc ctgctacgag cgcgacgtcg     420

aaaagactcg tgcatttaac tcggcccttt tccgaggaaa cgacagattt tctgcagaga     480

gagtggacgg aatcgcccga ttggcatgat atcgaggtct acccagtgat atctaggcta     540

accgcacagg ttctcagccg agcattcgtt gggccgaggc tctgccgtga tacgcgctgg     600

ctggagattg ctacgacata catctcaaat agactcactg ccgtcgtggc cgtccagaaa     660

tggggagccg tgctgcaccc cattgtccac tggtttcttc cttcctgccg caggcttcgt     720

gcgcagaaca agagggcgcg agaactgctg cagccagagc tggaccggat caaggaaagt     780

ccattggagg atgagacttt caccagcctg gcgtggatcc acggctatgg tcagggctat     840

atatacgatc ccggcctagc ccagctgcgc ctctcggccg tggccaacca caccacttcc     900
```

```
gatatgatga ccaagaccct gatccgaatt tgtgagaacc cggagttaat ccagcccctc    960
cgcgaggagg caatcgaggc cgtccgaggg ggtggcttgc gtgttgctgc cctgcagaag   1020
atgttcctca tggaaagtgt gatgcaggaa agccagcgcc tcgagccatt tattctcctg   1080
tccatgtttc gctacgcaac ggaaacggtc actcttccag aaggcacgac catccccaag   1140
ggaacgcttc tcgctattgc aaacccaagc agacttgacc ctgccatcta cccggatcct   1200
cacaagttcg atggctatcg ctttgtccgg atgcgcgagg accccaggca tgcgcacctg   1260
gcccctttta ccaaaaccaa ctctaccaac ctgaatttcg gccatggaaa acaggcatgt   1320
ccgggacgat ttatcgcagt gaaccagatc aaaattgccc tctgccatat gttgctgaag   1380
tatgatattg agctggtaga agaatgcccc tcgcagctgg tacggtccgg gctcgttaca   1440
gtcaggaacc ctggcgcaaa gatccgagta agacgacgcc aggaagaggt ctgtctctaa   1500
```

<210> SEQ ID NO 32
<211> LENGTH: 499
<212> TYPE: PRT
<213> ORGANISM: Aspergillus versicolor NRRL35600

<400> SEQUENCE: 32

```
Met Ala Gln Asp Thr Ala Leu His Leu Pro Leu Gly Leu Glu Pro Ala
1               5                   10                  15

Gly Trp Ala Leu Ala Leu Leu Thr Ser Ser Ile Ile Tyr Leu Phe Leu
            20                  25                  30

Ser Pro Lys Ser Lys Ser Pro Arg Phe Pro Val Val Asn Lys Tyr Trp
        35                  40                  45

Trp Asp Phe Phe Gln Ala Lys Ala Lys Arg Asp Phe Glu Ala Gly Ala
    50                  55                  60

Glu Asp Leu Ile Lys Leu Gly Leu Ser Lys Ala Arg Thr Lys Pro Arg
65                  70                  75                  80

Arg Glu Tyr Pro Arg Leu Val Leu Ser Asp Gln Leu Ala Asp Ala Val
                85                  90                  95

Gly Met Asp Asn Arg Phe Asp Gln Asp Lys Gly Ile Ala Pro Val Asn
            100                 105                 110

Leu Val Thr Leu Lys Gly Phe Glu Ser Met Tyr Ala Gly Ala Leu His
        115                 120                 125

Asp Ser Val Pro Arg Pro Ala Thr Ser Ala Thr Ser Lys Arg Leu Val
    130                 135                 140

His Leu Thr Arg Pro Phe Ser Glu Glu Thr Thr Asp Phe Leu Gln Arg
145                 150                 155                 160

Glu Trp Thr Glu Ser Pro Asp Trp His Asp Ile Glu Val Tyr Pro Val
                165                 170                 175

Ile Ser Arg Leu Thr Ala Gln Val Leu Ser Arg Ala Phe Val Gly Pro
            180                 185                 190

Arg Leu Cys Arg Asp Thr Arg Trp Leu Glu Ile Ala Thr Thr Tyr Ile
        195                 200                 205

Ser Asn Arg Leu Thr Ala Val Val Ala Val Gln Lys Trp Gly Ala Val
    210                 215                 220

Leu His Pro Ile Val His Trp Phe Leu Pro Ser Cys Arg Arg Leu Arg
225                 230                 235                 240

Ala Gln Asn Lys Arg Ala Arg Glu Leu Leu Gln Pro Glu Leu Asp Arg
                245                 250                 255

Ile Lys Glu Ser Pro Leu Glu Asp Glu Thr Phe Thr Ser Leu Ala Trp
            260                 265                 270
```

```
Ile His Gly Tyr Gly Gln Gly Tyr Ile Tyr Asp Pro Gly Leu Ala Gln
        275                 280                 285

Leu Arg Leu Ser Ala Val Ala Asn His Thr Thr Ser Asp Met Met Thr
    290                 295                 300

Lys Thr Leu Ile Arg Ile Cys Glu Asn Pro Glu Leu Ile Gln Pro Leu
305                 310                 315                 320

Arg Glu Glu Ala Ile Glu Ala Val Arg Gly Gly Gly Leu Arg Val Ala
                325                 330                 335

Ala Leu Gln Lys Met Phe Leu Met Glu Ser Val Met Gln Glu Ser Gln
            340                 345                 350

Arg Leu Glu Pro Phe Ile Leu Leu Ser Met Phe Arg Tyr Ala Thr Glu
        355                 360                 365

Thr Val Thr Leu Pro Glu Gly Thr Thr Ile Pro Lys Gly Thr Leu Leu
    370                 375                 380

Ala Ile Ala Asn Pro Ser Arg Leu Asp Pro Ala Ile Tyr Pro Asp Pro
385                 390                 395                 400

His Lys Phe Asp Gly Tyr Arg Phe Val Arg Met Arg Glu Asp Pro Arg
                405                 410                 415

His Ala His Leu Ala Pro Phe Thr Lys Thr Asn Ser Thr Asn Leu Asn
            420                 425                 430

Phe Gly His Gly Lys Gln Ala Cys Pro Gly Arg Phe Ile Ala Val Asn
        435                 440                 445

Gln Ile Lys Ile Ala Leu Cys His Met Leu Leu Lys Tyr Asp Ile Glu
    450                 455                 460

Leu Val Glu Glu Cys Pro Ser Gln Leu Val Arg Ser Gly Leu Val Thr
465                 470                 475                 480

Val Arg Asn Pro Gly Ala Lys Ile Arg Val Arg Arg Arg Gln Glu Glu
                485                 490                 495

Val Cys Leu
```

```
<210> SEQ ID NO 33
<211> LENGTH: 1302
<212> TYPE: DNA
<213> ORGANISM: Aspergillus versicolor NRRL35600

<400> SEQUENCE: 33

atggctatag acgcatctgg tgctgctgct cccaattcat cgggtatcac tgttatcata      60

gtcggccttg gacccactgg gctagcagct gctattgaat gtcaccgacg gggccataag     120

gtaatttgtt tcgagagaaa tcccaagagc taccgtttgg gagacttgat caatgtgacc     180

gggaatgccg cgcgagtgtt gcagggctgg ggcaatggct ctgtgattaa cgatctacag     240

gcattccagt gcaacctgga cacccttgaa gtctatgacg agactggcga cctcaagctt     300

tccgcgccgt ataatgcaaa ccaagcgaaa gacaactaca tgctgcggcg gtccaggctc     360

ctcgacatat tcctgcagca tttgaagaac cttgacgtcg atattcactt gggcaccgag     420

gtgaccgact actgggagac tgagagcagc gctggggtta ctgttggtgg taagagaatt     480

gctgctgatt gtgtcgtcgt ggcggacggc gtgcacagca aaggcaggcc gcaggtttct     540

gcagagccct ttgacctccc gtccaccgat ggaactgcat tcagggcatt ctttcacgcc     600

agcgaaatag cacaggatcc agaagcgtcg tggatcctgc aggatgcagg cgaaggggac     660

tgtttcaaga ccttttacgg aaaaggcctt gtcatgatgt tggggacggc ggaaaaccac     720

gaatacatct tctggagctg tggctccaag gagaatgtcc tagcacagtc ttctgccgtg     780

gcccaggttc tcgatctcat cggggactgg cctgtatcga agaggcttgc tcctctgata     840
```

```
tccaaaaccc caagcgacaa ctgcctggac caaacgttat tcacacgatc gccgttaaac    900

aaatgggtat cgcgtaaggg aagaatgatc gttctgggag atgcagctca tccgtttctt    960

ccacacgccg gtcagggtgc aaaccaaggg attgaagatg ccgctgtcct ggccctgtgc   1020

cttcagattg ccggcaagga cgacgtgccc ctagcgctac gagtgacaga gaagctaagg   1080

taccaaaggg ttgctgcaat ccagaaacgg ggtgttgagg ccagggatca gtcattgagc   1140

gtggactggg agaatggcgg ctttaccaag aagctcactc tatatccggc ctggctgcat   1200

gaccaggact gcattaaaca agtctatgag gaattcgaca aggctgttgc tgctgttaca   1260

aaaggccatg aatgtacctt cggtggtata ccggtggatt aa                      1302


<210> SEQ ID NO 34
<211> LENGTH: 433
<212> TYPE: PRT
<213> ORGANISM: Aspergillus versicolor NRRL35600

<400> SEQUENCE: 34

Met Ala Ile Asp Ala Ser Gly Ala Ala Ala Pro Asn Ser Ser Gly Ile
1               5                   10                  15

Thr Val Ile Ile Val Gly Leu Gly Pro Thr Gly Leu Ala Ala Ala Ile
            20                  25                  30

Glu Cys His Arg Arg Gly His Lys Val Ile Cys Phe Glu Arg Asn Pro
        35                  40                  45

Lys Ser Tyr Arg Leu Gly Asp Leu Ile Asn Val Thr Gly Asn Ala Ala
    50                  55                  60

Arg Val Leu Gln Gly Trp Gly Asn Gly Ser Val Ile Asn Asp Leu Gln
65                  70                  75                  80

Ala Phe Gln Cys Asn Leu Asp Thr Leu Glu Val Tyr Asp Glu Thr Gly
                85                  90                  95

Asp Leu Lys Leu Ser Ala Pro Tyr Asn Ala Asn Gln Ala Lys Asp Asn
            100                 105                 110

Tyr Met Leu Arg Arg Ser Arg Leu Leu Asp Ile Phe Leu Gln His Leu
        115                 120                 125

Lys Asn Leu Asp Val Asp Ile His Leu Gly Thr Glu Val Thr Asp Tyr
    130                 135                 140

Trp Glu Thr Glu Ser Ser Ala Gly Val Thr Val Gly Gly Lys Arg Ile
145                 150                 155                 160

Ala Ala Asp Cys Val Val Val Ala Asp Gly Val His Ser Lys Gly Arg
                165                 170                 175

Pro Gln Val Ser Ala Glu Pro Phe Asp Leu Pro Ser Thr Asp Gly Thr
            180                 185                 190

Ala Phe Arg Ala Phe Phe His Ala Ser Glu Ile Ala Gln Asp Pro Glu
        195                 200                 205

Ala Ser Trp Ile Leu Gln Asp Ala Gly Glu Gly Asp Cys Phe Lys Thr
    210                 215                 220

Phe Tyr Gly Lys Gly Leu Val Met Met Leu Gly Thr Ala Glu Asn His
225                 230                 235                 240

Glu Tyr Ile Phe Trp Ser Cys Gly Ser Lys Glu Asn Val Leu Ala Gln
                245                 250                 255

Ser Ser Ala Val Ala Gln Val Leu Asp Leu Ile Gly Asp Trp Pro Val
            260                 265                 270

Ser Lys Arg Leu Ala Pro Leu Ile Ser Lys Thr Pro Ser Asp Asn Cys
        275                 280                 285
```

```
Leu Asp Gln Thr Leu Phe Thr Arg Ser Pro Leu Asn Lys Trp Val Ser
    290                 295                 300

Arg Lys Gly Arg Met Ile Val Leu Gly Asp Ala Ala His Pro Phe Leu
305                 310                 315                 320

Pro His Ala Gly Gln Gly Ala Asn Gln Gly Ile Glu Asp Ala Ala Val
                325                 330                 335

Leu Ala Leu Cys Leu Gln Ile Ala Gly Lys Asp Asp Val Pro Leu Ala
            340                 345                 350

Leu Arg Val Thr Glu Lys Leu Arg Tyr Gln Arg Val Ala Ala Ile Gln
        355                 360                 365

Lys Arg Gly Val Glu Ala Arg Asp Gln Ser Leu Ser Val Asp Trp Glu
    370                 375                 380

Asn Gly Gly Phe Thr Lys Lys Leu Thr Leu Tyr Pro Ala Trp Leu His
385                 390                 395                 400

Asp Gln Asp Cys Ile Lys Gln Val Tyr Glu Glu Phe Asp Lys Ala Val
                405                 410                 415

Ala Ala Val Thr Lys Gly His Glu Cys Thr Phe Gly Gly Ile Pro Val
            420                 425                 430

Asp
```

<210> SEQ ID NO 35
<211> LENGTH: 1089
<212> TYPE: DNA
<213> ORGANISM: Aspergillus versicolor NRRL35600

<400> SEQUENCE: 35

```
ttacagtgtc cctgtaaatt gactgacaga cacaagcccc tccggcgttg ggctgcgtc      60

gctggtgctc gtccagtttg acaccataag atacaattga ttccgctcgc cggtcgacca    120

cgggtggatg aatccaccgt acagcaacga ctcgtccccc gcctggttca cctgcacggt    180

ttcctcggac caaggcccag tcgggcccct tgcagtgcgt gagacgatat gcggcgttga    240

agtgctcgca ttcagataga ccatggccca agtgccatcc tggagcctgc gcaccgacgg    300

ctctccaaag tacccatcca gaataggcga gcagggtctt tgccagcccc agtcctctcc    360

attccatccc catccctggt actcggtctt atccgtcatc ttgtcccatg gcacgcgctg    420

cagcatcatt ggcccgtact gccgcgcaca gcgcactgta aatacgtaca cccagtcgcc    480

atcgcgctgc atcgtccaca tctggaatgg gtcggtgttg ttgtcattgt tcagccactt    540

ggttgggagc cgcgagaagg aattgccgtc tgtcgagtat gccagccccg cgtagttggg    600

ggtccatgac gttgtgaagt tcattatgct cgtataggag atgatgtgtt cgccggtctc    660

agggaagctt atgccgtcgt tcgggagcac agtgaactcc catgtgccgg tgccatcatc    720

gccgtggtct ccgttgtaga agagtctggg cgcgagccca tcgccgtcta ccccggccgc    780

actctcaaag aaaatcccgc catcttcgcc ggggtggatg cctgagagca gcatgactgg    840

cgagcgcagg tcttttgctt cttgcaccca catcgtgctc accgtgtctc caaaaaggta    900

tccgacttgg ccattgtgca tatcgtacgg aatgcctaga tcagtggccg cgacccccca    960

gcgacgacca ctctcacggt cttcaccgat cagacggcgc ttgggaactg catttgcagt   1020

ctgggtggaa gcaggagagg taagaaggat gagggtcagt aagtgaagca ttgtggccat   1080

gtttctcat                                                           1089
```

<210> SEQ ID NO 36
<211> LENGTH: 362
<212> TYPE: PRT

<213> ORGANISM: Aspergillus versicolor NRRL35600

<400> SEQUENCE: 36

```
Met Arg Asn Met Ala Thr Met Leu His Leu Leu Thr Leu Ile Leu Leu
1               5                   10                  15

Thr Ser Pro Ala Ser Thr Gln Thr Ala Asn Ala Val Pro Lys Arg Arg
            20                  25                  30

Leu Ile Gly Glu Asp Arg Glu Ser Gly Arg Arg Trp Gly Val Ala Ala
        35                  40                  45

Thr Asp Leu Gly Ile Pro Tyr Asp Met His Asn Gly Gln Val Gly Tyr
    50                  55                  60

Leu Phe Gly Asp Thr Val Ser Thr Met Trp Val Gln Glu Ala Lys Asp
65                  70                  75                  80

Leu Arg Ser Pro Val Met Leu Leu Ser Gly Ile His Pro Gly Glu Asp
                85                  90                  95

Gly Gly Ile Phe Phe Glu Ser Ala Ala Gly Val Asp Gly Asp Gly Leu
            100                 105                 110

Ala Pro Arg Leu Phe Tyr Asn Gly Asp His Gly Asp Asp Gly Thr Gly
        115                 120                 125

Thr Trp Glu Phe Thr Val Leu Pro Asn Asp Gly Ile Ser Phe Pro Glu
    130                 135                 140

Thr Gly Glu His Ile Ile Ser Tyr Thr Ser Ile Met Asn Phe Thr Thr
145                 150                 155                 160

Ser Trp Thr Pro Asn Tyr Ala Gly Leu Ala Tyr Ser Thr Asp Gly Asn
                165                 170                 175

Ser Phe Ser Arg Leu Pro Thr Lys Trp Leu Asn Asn Asp Asn Asn Thr
            180                 185                 190

Asp Pro Phe Gln Met Trp Thr Met Gln Arg Asp Gly Asp Trp Val Tyr
        195                 200                 205

Val Phe Thr Val Arg Cys Ala Arg Gln Tyr Gly Pro Met Met Leu Gln
    210                 215                 220

Arg Val Pro Trp Asp Lys Met Thr Asp Lys Thr Glu Tyr Gln Gly Trp
225                 230                 235                 240

Gly Trp Asn Gly Glu Asp Trp Gly Trp Gln Arg Pro Cys Ser Pro Ile
                245                 250                 255

Leu Asp Gly Tyr Phe Gly Glu Pro Ser Val Arg Arg Leu Gln Asp Gly
            260                 265                 270

Thr Trp Ala Met Val Tyr Leu Asn Ala Ser Thr Ser Thr Pro His Ile
        275                 280                 285

Val Ser Arg Thr Ala Arg Gly Pro Thr Gly Pro Trp Ser Glu Glu Thr
    290                 295                 300

Val Gln Val Asn Gln Ala Gly Asp Glu Ser Leu Leu Tyr Gly Gly Phe
305                 310                 315                 320

Ile His Pro Trp Ser Thr Gly Glu Arg Asn Gln Leu Tyr Leu Met Val
                325                 330                 335

Ser Asn Trp Thr Ser Thr Ser Asp Ala Ala Pro Thr Pro Glu Gly Leu
            340                 345                 350

Val Ser Val Ser Gln Phe Thr Gly Thr Leu
        355                 360
```

<210> SEQ ID NO 37
<211> LENGTH: 1734
<212> TYPE: DNA
<213> ORGANISM: Aspergillus versicolor NRRL35600

<400> SEQUENCE: 37

```
atgggacacg ctgagtggat tggccgcact aatacggccg tggctcgaag cgcggtcggg      60
aagtggtttc gcctggaggg gtctggtcat ccccgcgagc gaaaaggcgc gtatttcttt     120
acggagctgc gtgcaggcct tgcaacattc tttgcaatgg catacatcat ctcagtcaat     180
gccaatatca cgagtgacac gggagcaacg tgtgtgtgtc cggccgaaga tctcgaaacc     240
cactgcaaca acaacaccga gtatcttctc tgcaaacaag aagtcaaccg tgacatcgtg     300
accgcaacgg cagcgatagc ttctgtcgcc agcttcttcc tcggtctcct tgccaaccta     360
ccggtagccc ttgcccccgg catgggtctc aacgcatact tcgcttatac cgtcgtcgga     420
caccatggaa gcggcttgat tccgtacagc ctcgcagtga ctgcagtgtt cgttgaaggc     480
tggattttcc ttgggttgac tatgttgggt attcgacaat ggcttgcccg tgctattccg     540
gcatccatca agctagcaac tggtgctggt atcggattgt atctgactct aattggtctg     600
agttatagtg ctgggcttgg tctcgtccaa ggtgcccagg acagtcccat tcaattggcg     660
ggttgtgcgt ccgatgaatt cgactcggat gggctgtgtc cttcgtatgc taaaatgcga     720
aacccgacga tgtggattgg catcttttgc ggcggtttct tcacggtttt cttaatgatg     780
tatcgagtca agggtgcagt cattgctggt attcttctgg tctccatcat ttcttggccg     840
cgcaccacgc cggtcaccta tttccctcac acaacggaag gtgacagcat gttcgacttc     900
ttcaagaagg tggttacttt ccatccgatc cagcacacgt tagtggccca ggactggaac     960
atctcgagca acgggggcca gtttggtctt gccttgatca cattcctcta tgttgacatc    1020
ctcgacgcaa cgggtacttt gtattcgatg gcgaagtttg ctggagcgat ggatgagcgc    1080
actcaggatt tcgagggcag tgccatggct tatacggttg acgcgatttg catctcaatc    1140
gggtctctgt ttggctcccc gccagtgacg gcatttgtcg agagtggtgc tggtatctcg    1200
gaaggtggta aaactggact gacatcgtgt atgacgggga tctgcttctt catcgccgtt    1260
ttctttgcgc cgatctttgc gtcgatccct ccgtgggcca ctggcagtac cctagtcatt    1320
gttggctcaa tgatgatgca cgctaccctc gagatcaact ggcggtatat gggagacgcg    1380
attcccgcct tcctgacgat ctcggttatg cctttcactt acagtatcgc ggacggcctc    1440
attgccggta tcatcagcta tatcttgatc aacggcggag tgtgggttat cgccaagtgc    1500
acgggaggcc ggattgttcc accaaaccgc gatgacgagc atgaggcgtg gacctggaag    1560
attcccggag gattcttccc gccatggctc gtccgtgcag ttcacggaaa gaaggacttt    1620
tggcgagcag acgacgaggc tagccagttg gaccttggcg ttatgccgcc aaatgggtcg    1680
atgtcatcag ggtctccgga gcaagtcgcg gagaaagcag tcgggaagta ttaa          1734
```

<210> SEQ ID NO 38
<211> LENGTH: 577
<212> TYPE: PRT
<213> ORGANISM: Aspergillus versicolor NRRL35600

<400> SEQUENCE: 38

```
Met Gly His Ala Glu Trp Ile Gly Arg Thr Asn Thr Ala Val Ala Arg
1               5                   10                  15

Ser Ala Val Gly Lys Trp Phe Arg Leu Glu Gly Ser Gly His Pro Arg
            20                  25                  30

Glu Arg Lys Gly Ala Tyr Phe Phe Thr Glu Leu Arg Ala Gly Leu Ala
        35                  40                  45

Thr Phe Phe Ala Met Ala Tyr Ile Ile Ser Val Asn Ala Asn Ile Thr
    50                  55                  60
```

```
Ser Asp Thr Gly Ala Thr Cys Val Cys Pro Ala Glu Asp Leu Glu Thr
65                  70                  75                  80

His Cys Asn Asn Asn Thr Glu Tyr Leu Leu Cys Lys Gln Glu Val Asn
                85                  90                  95

Arg Asp Ile Val Thr Ala Thr Ala Ala Ile Ala Ser Val Ala Ser Phe
            100                 105                 110

Phe Leu Gly Leu Leu Ala Asn Leu Pro Val Ala Leu Ala Pro Gly Met
        115                 120                 125

Gly Leu Asn Ala Tyr Phe Ala Tyr Thr Val Val Gly His His Gly Ser
    130                 135                 140

Gly Leu Ile Pro Tyr Ser Leu Ala Val Thr Ala Val Phe Val Glu Gly
145                 150                 155                 160

Trp Ile Phe Leu Gly Leu Thr Met Leu Gly Ile Arg Gln Trp Leu Ala
                165                 170                 175

Arg Ala Ile Pro Ala Ser Ile Lys Leu Ala Thr Gly Ala Gly Ile Gly
            180                 185                 190

Leu Tyr Leu Thr Leu Ile Gly Leu Ser Tyr Ser Ala Gly Leu Gly Leu
        195                 200                 205

Val Gln Gly Ala Gln Asp Ser Pro Ile Gln Leu Ala Gly Cys Ala Ser
    210                 215                 220

Asp Glu Phe Asp Ser Asp Gly Leu Cys Pro Ser Tyr Ala Lys Met Arg
225                 230                 235                 240

Asn Pro Thr Met Trp Ile Gly Ile Phe Cys Gly Gly Phe Phe Thr Val
                245                 250                 255

Phe Leu Met Met Tyr Arg Val Lys Gly Ala Val Ile Ala Gly Ile Leu
            260                 265                 270

Leu Val Ser Ile Ile Ser Trp Pro Arg Thr Thr Pro Val Thr Tyr Phe
        275                 280                 285

Pro His Thr Thr Glu Gly Asp Ser Met Phe Asp Phe Phe Lys Lys Val
    290                 295                 300

Val Thr Phe His Pro Ile Gln His Thr Leu Val Ala Gln Asp Trp Asn
305                 310                 315                 320

Ile Ser Ser Asn Gly Gly Gln Phe Gly Leu Ala Leu Ile Thr Phe Leu
                325                 330                 335

Tyr Val Asp Ile Leu Asp Ala Thr Gly Thr Leu Tyr Ser Met Ala Lys
            340                 345                 350

Phe Ala Gly Ala Met Asp Glu Arg Thr Gln Asp Phe Glu Gly Ser Ala
        355                 360                 365

Met Ala Tyr Thr Val Asp Ala Ile Cys Ile Ser Ile Gly Ser Leu Phe
    370                 375                 380

Gly Ser Pro Pro Val Thr Ala Phe Val Glu Ser Gly Ala Gly Ile Ser
385                 390                 395                 400

Glu Gly Gly Lys Thr Gly Leu Thr Ser Cys Met Thr Gly Ile Cys Phe
                405                 410                 415

Phe Ile Ala Val Phe Phe Ala Pro Ile Phe Ala Ser Ile Pro Pro Trp
            420                 425                 430

Ala Thr Gly Ser Thr Leu Val Ile Val Gly Ser Met Met Met His Ala
        435                 440                 445

Thr Leu Glu Ile Asn Trp Arg Tyr Met Gly Asp Ala Ile Pro Ala Phe
    450                 455                 460

Leu Thr Ile Ser Val Met Pro Phe Thr Tyr Ser Ile Ala Asp Gly Leu
465                 470                 475                 480
```

```
Ile Ala Gly Ile Ile Ser Tyr Ile Leu Ile Asn Gly Gly Val Trp Val
                485                 490                 495

Ile Ala Lys Cys Thr Gly Gly Arg Ile Val Pro Pro Asn Arg Asp Asp
            500                 505                 510

Glu His Glu Ala Trp Thr Trp Lys Ile Pro Gly Gly Phe Phe Pro Pro
        515                 520                 525

Trp Leu Val Arg Ala Val His Gly Lys Lys Asp Phe Trp Arg Ala Asp
    530                 535                 540

Asp Glu Ala Ser Gln Leu Asp Leu Gly Val Met Pro Pro Asn Gly Ser
545                 550                 555                 560

Met Ser Ser Gly Ser Pro Glu Gln Val Ala Glu Lys Ala Val Gly Lys
                565                 570                 575

Tyr


<210> SEQ ID NO 39
<211> LENGTH: 1863
<212> TYPE: DNA
<213> ORGANISM: Aspergillus versicolor NRRL35600

<400> SEQUENCE: 39

atgcccccca gctccaagtc ccgtcgcctg ccgcccgcgg cctccgactc cgccgcaagt      60

gacgcacaga aacgcagaaa gaacgtgggc accgcatgtt ccgcttgcaa agctcgcaag     120

ctcaagtgta ctggagcgcc tccctgcgca aactgcgtca aaagccgcat cgaatgcacc     180

ctcgacgaga ccgccgatag acgccgacgg ggcgtcttga aacgcaagat tgataagttg     240

gaggaccagg aggatttgct gggtcgtctg ctcgagtttt tcagagaggg caataaccgt     300

tgcacgattc ccctcttaaa tctcatccgc agccatgcct cgccacccga gatccgtttc     360

tatatcgaac accaactacc gctatcgaaa cgtacgcaga cccccgagct aatagaagta     420

tgccgggaaa tcgaacagcg ccactctttt gaaccgctac ctaagcgtca catccttgat     480

accactccta atggatccca cgatacgcca cgattatccg tccccgcgca gccgtggacc     540

tcgatcatta ccgacgatgg cctggtatcc cgattgatat ttttatggtt tacttgggtt     600

cacccgtttt gcaacttcat tgaccgcgat cgcttcatcc gggacatgaa gtctggttcg     660

ctctcagcat catactgctc cccgttgttg gtgaacatca tactttccga cgcatgtcac     720

tctgcgtctg ggctcccaga cgacctaacc tccaaacgga tcgagtttta cgaggaggct     780

gaacgattgc ttgataagga agagggccgc atcagcttgc caactgccca gggcctagga     840

gtattatgga tgtgcgcatc tatcaccggc cgtgacagac aagcgtggat taagggtacg     900

cagcttgcat attcactccg cgagctatcc caagtgtctt gtaacctccc gtcagaggcc     960

aatcgggatg caactgccct ggccacaatt gttaacagca caaactgggg tttgttcaac    1020

gtcgccatgg ttcacgctct atttgcaagg aaacgcccta tcatcgaacc gcccgcccaa    1080

cctccgtctg tcagcaacca atgcgaccac ggtatgtggt attcatatcc aaacaaatcg    1140

actggtgtcg agtcacacac atcctgccta ttcacggcag cttgtaactt aaaccgaatc    1200

gcttacaacc tcgggagatt tctgttctcc caagagaaaa aatcttcggc tcgtctcgat    1260

ctaacggatg gggagcttga cgcactacgg gatttaaacg aatgggccga ccagctaccg    1320

gtatgtctaa aagaaagcat tgccgatctc cctcatgttc tctctttgca catgtataac    1380

cacgccattt taactgtagt ctacggattt ctaagaactc ggcccttata cctgccgaat    1440

ccttcagcct cgaccccccac tgtccgtgac gctctcatgt ctcctgctcg tgcctgggct    1500

gcaagtcttt catcggctcg caagattgcc catttgacac ttgtccatcg cgcgaattgg    1560
```

```
ggatccgacc gcatgccggg ggccaccgtg cactgtatca tggctgccct gttcgctcta   1620

cttgacagcg tggacgaccc ggccaaccgt gacgcattca tttcactcac ggcagcggcc   1680

gccgcgtttt cgcgtcggtg ggaaagtccc atagccctcc tgcgcaacat ccagaacatc   1740

gcgcggcagc gggacgttac cctccctccg gaaacaggcg ctttcttctt ggatccagac   1800

cagccctcgg ggaacagcac tcccataaaa tccgaaaccc ccgagggtac agcaatttca   1860

tga                                                                 1863
```

<210> SEQ ID NO 40
<211> LENGTH: 620
<212> TYPE: PRT
<213> ORGANISM: Aspergillus versicolor NRRL35600

<400> SEQUENCE: 40

```
Met Pro Pro Ser Ser Lys Ser Arg Arg Leu Pro Pro Ala Ala Ser Asp
1               5                   10                  15

Ser Ala Ala Ser Asp Ala Gln Lys Arg Arg Lys Asn Val Gly Thr Ala
            20                  25                  30

Cys Ser Ala Cys Lys Ala Arg Lys Leu Lys Cys Thr Gly Ala Pro Pro
        35                  40                  45

Cys Ala Asn Cys Val Lys Ser Arg Ile Glu Cys Thr Leu Asp Glu Thr
    50                  55                  60

Ala Asp Arg Arg Arg Arg Gly Val Leu Lys Arg Lys Ile Asp Lys Leu
65                  70                  75                  80

Glu Asp Gln Glu Asp Leu Leu Gly Arg Leu Leu Glu Phe Phe Arg Glu
                85                  90                  95

Gly Asn Asn Arg Cys Thr Ile Pro Leu Leu Asn Leu Ile Arg Ser His
            100                 105                 110

Ala Ser Pro Pro Glu Ile Arg Phe Tyr Ile Glu His Gln Leu Pro Leu
        115                 120                 125

Ser Lys Arg Thr Gln Thr Pro Glu Leu Ile Glu Val Cys Arg Glu Ile
    130                 135                 140

Glu Gln Arg His Ser Phe Glu Pro Leu Pro Lys Arg His Ile Leu Asp
145                 150                 155                 160

Thr Thr Pro Asn Gly Ser His Asp Thr Pro Arg Leu Ser Val Pro Ala
                165                 170                 175

Gln Pro Trp Thr Ser Ile Ile Thr Asp Asp Gly Leu Val Ser Arg Leu
            180                 185                 190

Ile Phe Leu Trp Phe Thr Trp Val His Pro Phe Cys Asn Phe Ile Asp
        195                 200                 205

Arg Asp Arg Phe Ile Arg Asp Met Lys Ser Gly Ser Leu Ser Ala Ser
    210                 215                 220

Tyr Cys Ser Pro Leu Leu Val Asn Ile Ile Leu Ser Asp Ala Cys His
225                 230                 235                 240

Ser Ala Ser Gly Leu Pro Asp Asp Leu Thr Ser Lys Arg Ile Glu Phe
                245                 250                 255

Tyr Glu Glu Ala Glu Arg Leu Leu Asp Lys Glu Glu Gly Arg Ile Ser
            260                 265                 270

Leu Pro Thr Ala Gln Gly Leu Gly Val Leu Trp Met Cys Ala Ser Ile
        275                 280                 285

Thr Gly Arg Asp Arg Gln Ala Trp Ile Lys Gly Thr Gln Leu Ala Tyr
    290                 295                 300

Ser Leu Arg Glu Leu Ser Gln Val Ser Cys Asn Leu Pro Ser Glu Ala
```

```
305                 310                 315                 320

Asn Arg Asp Ala Thr Ala Leu Ala Thr Ile Val Asn Ser Thr Asn Trp
                325                 330                 335

Gly Leu Phe Asn Val Ala Met Val His Ala Leu Phe Ala Arg Lys Arg
            340                 345                 350

Pro Ile Ile Glu Pro Pro Ala Gln Pro Pro Ser Val Ser Asn Gln Cys
        355                 360                 365

Asp His Gly Met Trp Tyr Ser Tyr Pro Asn Lys Ser Thr Gly Val Glu
    370                 375                 380

Ser His Thr Ser Cys Leu Phe Thr Ala Ala Cys Asn Leu Asn Arg Ile
385                 390                 395                 400

Ala Tyr Asn Leu Gly Arg Phe Leu Phe Ser Gln Glu Lys Lys Ser Ser
                405                 410                 415

Ala Arg Leu Asp Leu Thr Asp Gly Glu Leu Asp Ala Leu Arg Asp Leu
            420                 425                 430

Asn Glu Trp Ala Asp Gln Leu Pro Val Cys Leu Lys Glu Ser Ile Ala
        435                 440                 445

Asp Leu Pro His Val Leu Ser Leu His Met Tyr Asn His Ala Ile Leu
    450                 455                 460

Thr Val Val Tyr Gly Phe Leu Arg Thr Arg Pro Leu Tyr Leu Pro Asn
465                 470                 475                 480

Pro Ser Ala Ser Thr Pro Thr Val Arg Asp Ala Leu Met Ser Pro Ala
                485                 490                 495

Arg Ala Trp Ala Ala Ser Leu Ser Ser Ala Arg Lys Ile Ala His Leu
            500                 505                 510

Thr Leu Val His Arg Ala Asn Trp Gly Ser Asp Arg Met Pro Gly Ala
        515                 520                 525

Thr Val His Cys Ile Met Ala Ala Leu Phe Ala Leu Leu Asp Ser Val
    530                 535                 540

Asp Asp Pro Ala Asn Arg Asp Ala Phe Ile Ser Leu Thr Ala Ala Ala
545                 550                 555                 560

Ala Ala Phe Ser Arg Arg Trp Glu Ser Pro Ile Ala Leu Leu Arg Asn
                565                 570                 575

Ile Gln Asn Ile Ala Arg Gln Arg Asp Val Thr Leu Pro Pro Glu Thr
            580                 585                 590

Gly Ala Phe Phe Leu Asp Pro Asp Gln Pro Ser Gly Asn Ser Thr Pro
        595                 600                 605

Ile Lys Ser Glu Thr Pro Glu Gly Thr Ala Ile Ser
    610                 615                 620
```

<210> SEQ ID NO 41
<211> LENGTH: 1365
<212> TYPE: DNA
<213> ORGANISM: Aspergillus versicolor NRRL35600

<400> SEQUENCE: 41

```
tcacaccgtc tctttccgct gtatctcgtt caatcttgta gctgtacgta tacgctgtcg     60

caagttgaaa ggttccggat tccggtcggc cgtcgcatcc ttttcgtccg acttggtgct    120

tttggccttc ttgtcgcgca tcttctgcac ccagccaaca tacgtatccc accagtgcca    180

aactccccag acccccagag taagcagtgt cagagggatc gtaacagccc agtacatcca    240

gaactcatcg gccgtgagcc acgtattacc ggggtcggcc tggaagctga agaagttggt    300

tccaaacagg ccagacacaa acgtcccagg cagatacacc atactcacaa acgcgaccgt    360
```

```
cgtcatcatg ttgctgtcgg atcgcgcgtc tcgcccgaag tcttgcgata ccaggttgaa    420

tgcctgtctc aagttaatct cgttctgatg ccgatcgttc aaagacttcg atcgcgtctt    480

gagtgagtgc gccctttttct cctcgtgcag gatccgtcgg cgcgtctcca gccaggtccc    540

tatgttctgc tggatgttgt ttccgtcttc gtggcgccaa ttgagcagtt ccttggccat    600

cacttgcagc gtgtgctcgg cgacttcgat cgtttcttgg tagtggaaga ggtgccgtgc    660

gatatcgtgc agaaggggga atatcttcct ttcatgttct ttttcggctt tgcttttctt    720

cctcttcggc tttttctcct ttgaccgcgc cttttcgtgg tgccgcacca ggtctctcaa    780

caaccaaaac gcatcgtcat actgttggag gatgatccgg gagaatgcag cgtgtaagga    840

gaacgggtta cacttgcgct cggccgccgt cgggagttta tccatgaaga cgctctgttg    900

atctggattg aaaccaaata cgtggacgat ttggctgccg gtttctgcgt tccactgtac    960

gtggatggtg ggttgtttcc agctatagtc ttctgctgtt ttgacttctt tgattttgaa   1020

gcaggaccac gagactaatg caatgttaga tacgacgaac atgacgggcg aagaaaccga   1080

ctcgggcgaa ccttctggcc atacgcggga ttgagaacat ccataatgac agtcgaaaga   1140

cccgttaata tcggcgtcta gcaccggacg gaactcttct tggaatcgaa gcttgaagga   1200

cttgtccgtg tcattgatat cgctcgttac gaaaatgata aagttggcgc tctgatctct   1260

ctcaactata ttcatatcat tgccacaata tctccacccg tcggggtcac caacgtccat   1320

gtatatctga accccaggcg gtgctctttc tgcggcgtaa tccat                   1365
```

<210> SEQ ID NO 42
<211> LENGTH: 454
<212> TYPE: PRT
<213> ORGANISM: Aspergillus versicolor NRRL35600

<400> SEQUENCE: 42

```
Met Asp Tyr Ala Ala Glu Arg Ala Pro Pro Gly Val Gln Ile Tyr Met
1               5                   10                  15

Asp Val Gly Asp Pro Asp Gly Trp Arg Tyr Cys Gly Asn Asp Met Asn
            20                  25                  30

Ile Val Glu Arg Asp Gln Ser Ala Asn Phe Ile Ile Phe Val Thr Ser
        35                  40                  45

Asp Ile Asn Asp Thr Asp Lys Ser Phe Lys Leu Arg Phe Gln Glu Glu
    50                  55                  60

Phe Arg Pro Val Leu Asp Ala Asp Ile Asn Gly Ser Phe Asp Cys His
65                  70                  75                  80

Tyr Gly Cys Ser Gln Ser Arg Val Trp Pro Glu Gly Ser Pro Glu Ser
                85                  90                  95

Val Ser Ser Pro Val Met Phe Val Val Ser Asn Ile Ala Leu Val Ser
            100                 105                 110

Trp Ser Cys Phe Lys Ile Lys Glu Val Lys Thr Ala Glu Asp Tyr Ser
        115                 120                 125

Trp Lys Gln Pro Thr Ile His Val Gln Trp Asn Ala Glu Thr Gly Ser
    130                 135                 140

Gln Ile Val His Val Phe Gly Phe Asn Pro Asp Gln Gln Ser Val Phe
145                 150                 155                 160

Met Asp Lys Leu Pro Thr Ala Ala Glu Arg Lys Cys Asn Pro Phe Ser
                165                 170                 175

Leu His Ala Ala Phe Ser Arg Ile Ile Leu Gln Gln Tyr Asp Asp Ala
            180                 185                 190

Phe Trp Leu Leu Arg Asp Leu Val Arg His His Glu Lys Ala Arg Ser
```

```
        195                 200                 205

Lys Glu Lys Lys Pro Lys Arg Lys Lys Ser Lys Ala Glu Lys Glu His
    210                 215                 220

Glu Arg Lys Ile Phe Pro Leu Leu His Asp Ile Ala Arg His Leu Phe
225                 230                 235                 240

His Tyr Gln Glu Thr Ile Glu Val Ala Glu His Thr Leu Gln Val Met
                245                 250                 255

Ala Lys Glu Leu Leu Asn Trp Arg His Glu Asp Gly Asn Asn Ile Gln
            260                 265                 270

Gln Asn Ile Gly Thr Trp Leu Glu Thr Arg Arg Arg Ile Leu His Glu
        275                 280                 285

Glu Lys Arg Ala His Ser Leu Lys Thr Arg Ser Lys Ser Leu Asn Asp
    290                 295                 300

Arg His Gln Asn Glu Ile Asn Leu Arg Gln Ala Phe Asn Leu Val Ser
305                 310                 315                 320

Gln Asp Phe Gly Arg Asp Ala Arg Ser Asp Ser Asn Met Met Thr Thr
                325                 330                 335

Val Ala Phe Val Ser Met Val Tyr Leu Pro Gly Thr Phe Val Ser Gly
            340                 345                 350

Leu Phe Gly Thr Asn Phe Phe Ser Phe Gln Ala Asp Pro Gly Asn Thr
        355                 360                 365

Trp Leu Thr Ala Asp Glu Phe Trp Met Tyr Trp Ala Val Thr Ile Pro
    370                 375                 380

Leu Thr Leu Leu Thr Leu Gly Val Trp Gly Val Trp His Trp Trp Asp
385                 390                 395                 400

Thr Tyr Val Gly Trp Val Gln Lys Met Arg Asp Lys Lys Ala Lys Ser
                405                 410                 415

Thr Lys Ser Asp Glu Lys Asp Ala Thr Ala Asp Arg Asn Pro Glu Pro
            420                 425                 430

Phe Asn Leu Arg Gln Arg Ile Arg Thr Ala Thr Arg Leu Asn Glu Ile
        435                 440                 445

Gln Arg Lys Glu Thr Val
    450
```

<210> SEQ ID NO 43
<211> LENGTH: 1251
<212> TYPE: DNA
<213> ORGANISM: Aspergillus versicolor NRRL35600

<400> SEQUENCE: 43

```
atgcgcgctg cacttctgac tctggccttc acggccctcg ctgctgctgc cgacgacgcc      60

acaacaacag tcggcttctt cggcggtgga gaatgggaaa acagcaacga cgatgattcc     120

ctccctctga tcccatccta cacctccatt ggcgcctccg ttgttgatgt caacgcggtg     180

gagaccgtcc tcgccatctc ctgcctcgag ggcgccgcca cggaatcctg ctccatcaac     240

gacccctgga ccatgaccca gggcatctcg tcttttagct ggtatgctga atacacagcc     300

tttgactgga acccgcctgt cacggcgacg cttgactata actgcgccta cgagaactac     360

accctcagcg caacttgcac atacagcatg agctactcgg gctcttcgga tggcgcggag     420

acttccacta gcttcagtac cgagacatca tgggacagtg tggcgacgta tgctgcactt     480

gaagttaccg gaggcctgga caagtttaac cagcctgaag cgactgagac accggaggga     540

ggggctgggt ttgcagggcc tattcaggcg atggtgacgg ctgctccagt tctggcggcg     600

ggtcttcttg cctcccacgc atcaggggcc tggcgaaagg ggaagatatt actgataaag     660
```

```
cctttcaagg ggatcttgcc tcgactggcg agactggagg ccagcgtgaa atcgccaaac    720

ccataccgga acgagcctct cacacccaac ctggacatac gagccccctc gtctggccag    780

tgcaacgcca gtttgtatac acgacaccac cccggttgct tcgacgacga catcgactcc    840

ctcgggcagg ttgtgttgag cagccaagtc ctcggcgttt tcttcaaccg actttgccgt    900

gtcgaatttg tatgtccaga tgcccaattc gcctgccgcg aatgccagcc ggtcttcgtt    960

gacatccact gcaatgatgt gcccagcacc aaactcccgt gctgccgcgg ccgaaagcaa   1020

accaaccggc cctgccccaa gaacaagcac atcttggcct ggcttgagct ttgcaaggcg   1080

gaggccatgc accgcgacag caaggggctc aaggataacg ccttcgtcaa gccctatgtg   1140

gtcggggagc ttgtagcaga agtcccccgg caggcggaaa aaggtcgcca acgtgccatg   1200

gacaacatcg cccggtccag gaactgcggc aaaggtcatg tccggacata g            1251


<210> SEQ ID NO 44
<211> LENGTH: 416
<212> TYPE: PRT
<213> ORGANISM: Aspergillus versicolor NRRL35600

<400> SEQUENCE: 44

Met Arg Ala Ala Leu Leu Thr Leu Ala Phe Thr Ala Leu Ala Ala Ala
1               5                   10                  15

Ala Asp Asp Ala Thr Thr Thr Val Gly Phe Phe Gly Gly Gly Glu Trp
            20                  25                  30

Glu Asn Ser Asn Asp Asp Asp Ser Leu Pro Leu Ile Pro Ser Tyr Thr
        35                  40                  45

Ser Ile Gly Ala Ser Val Val Asp Val Asn Ala Val Glu Thr Val Leu
    50                  55                  60

Ala Ile Ser Cys Leu Glu Gly Ala Ala Thr Glu Ser Cys Ser Ile Asn
65                  70                  75                  80

Asp Pro Trp Thr Met Thr Gln Gly Ile Ser Ser Phe Ser Trp Tyr Ala
                85                  90                  95

Glu Tyr Thr Ala Phe Asp Trp Asn Pro Pro Val Thr Ala Thr Leu Asp
            100                 105                 110

Tyr Asn Cys Ala Tyr Glu Asn Tyr Thr Leu Ser Ala Thr Cys Thr Tyr
        115                 120                 125

Ser Met Ser Tyr Ser Gly Ser Ser Asp Gly Ala Glu Thr Ser Thr Ser
    130                 135                 140

Phe Ser Thr Glu Thr Ser Trp Asp Ser Val Ala Thr Tyr Ala Ala Leu
145                 150                 155                 160

Glu Val Thr Gly Gly Leu Asp Lys Phe Asn Gln Pro Glu Ala Thr Glu
                165                 170                 175

Thr Pro Glu Gly Gly Ala Gly Phe Ala Gly Pro Ile Gln Ala Met Val
            180                 185                 190

Thr Ala Ala Pro Val Leu Ala Ala Gly Leu Leu Ala Ser His Ala Ser
        195                 200                 205

Gly Ala Trp Arg Lys Gly Lys Ile Leu Leu Ile Lys Pro Phe Lys Gly
    210                 215                 220

Ile Leu Pro Arg Leu Ala Arg Leu Glu Ala Ser Val Lys Ser Pro Asn
225                 230                 235                 240

Pro Tyr Arg Asn Glu Pro Leu Thr Pro Asn Leu Asp Ile Arg Ala Pro
                245                 250                 255

Ser Ser Gly Gln Cys Asn Ala Ser Leu Tyr Thr Arg His His Pro Gly
            260                 265                 270
```

```
Cys Phe Asp Asp Asp Ile Asp Ser Leu Gly Gln Val Val Leu Ser Ser
        275                 280                 285

Gln Val Leu Gly Val Phe Phe Asn Arg Leu Cys Arg Val Glu Phe Val
    290                 295                 300

Cys Pro Asp Ala Gln Phe Ala Cys Arg Glu Cys Gln Pro Val Phe Val
305                 310                 315                 320

Asp Ile His Cys Asn Asp Val Pro Ser Thr Lys Leu Pro Cys Cys Arg
                325                 330                 335

Gly Arg Lys Gln Thr Asn Arg Pro Cys Pro Lys Asn Lys His Ile Leu
            340                 345                 350

Ala Trp Leu Glu Leu Cys Lys Ala Glu Ala Met His Arg Asp Ser Lys
        355                 360                 365

Gly Leu Lys Asp Asn Ala Phe Val Lys Pro Tyr Val Val Gly Glu Leu
    370                 375                 380

Val Ala Glu Val Pro Arg Gln Ala Glu Lys Gly Arg Gln Arg Ala Met
385                 390                 395                 400

Asp Asn Ile Ala Arg Ser Arg Asn Cys Gly Lys Gly His Val Arg Thr
                405                 410                 415
```

<210> SEQ ID NO 45
<211> LENGTH: 1389
<212> TYPE: DNA
<213> ORGANISM: Aspergillus versicolor NRRL35600

<400> SEQUENCE: 45

```
atgaacacac caactcccac tcaacgaacc tggtatcgca ccacgatttt caatgtctcg      60

gttgtcgccg tatgcgcctt catcgcacca gggctatggg ctgcgatgaa tggtctcggt     120

ggcgcaggat cagccgatcc atactatgtg aacgctgcca acgcggtcat cttctgtctg     180

caggtcgttg tctgcgtctt tggcagttct ctgattgcta aaatcggcct gaagtgggcc     240

tttgcgttag gcatggtagg cttcccgata tatgcgtcga gtgtctactg caatgtgaag     300

tataataata gctggtatat catgctggcc tgtgtgattg acggcatctg ctccggcatc     360

ttttggctaa ctgaaggcgc catcgtgctt gcatatcctg aaaagcatcg gcgtgggaaa     420

tacctggctt actggcttgc cagccggatt atgggccaga tgatcggtgg cgctgtcacg     480

ctgggtgtca atgctggtaa ccaggaggag ggccatatca gtgtgcagac atacctggtg     540

tttatttcca tccaggccat cggccctttc gttgctgcga cactgtctcc tcctgagaag     600

gtgcagcgtt cggaccagtc caaagtcaag atcaatctac cggcgggtct caaagcagag     660

ctgcacgcca tgtggaaact gcttggacgc actgaaatcc tgcttctcct gccgatgatg     720

ttccagagtg tcttttcaga ggccttcttc tcgacatata acgccaccta ttttaccgtg     780

cggtctcgcg ccctgtcatc gctggtagcc agcacttgtg tgattatatc taacttcctg     840

ctgggattct tcctcgactg gcgcaggctc tcagtcaaca cgcgcgccat ggctgcgttt     900

attataatct acgcctttga gctatcacta tatgtatacg ccatggttgt aaacaaggag     960

tatgagcggc aggaaccacg gccgctcttt gactggacag atgacggctt tggccgcgcg    1020

gtctgtgtct atatcctgat gctggtgggc tttaatctca tgtacgacta tctgtactgg    1080

ttgatcggca cggttaatcg cgatggtggt gatattatcc gactcagtgc tgttgtgcgt    1140

ggcgtggaaa gtgccgggca ggccatatcc tacggcatca actctgttga ctccttcctg    1200

ctgtccagtg ctgttgcagt gaacctgtca ttctttgctg catgtattgt tccatctgcc    1260

tttgttattt atcgtgttgg cgttgtcaac ggggtcaagg tacatcatat ccagcaggac    1320
```

```
gagacgctac agacgtctgg ggagggctct cacgatatta tggacgccaa cgggaaatcg   1380

gatgactga                                                           1389


<210> SEQ ID NO 46
<211> LENGTH: 462
<212> TYPE: PRT
<213> ORGANISM: Aspergillus versicolor NRRL35600

<400> SEQUENCE: 46

Met Asn Thr Pro Thr Pro Thr Gln Arg Thr Trp Tyr Arg Thr Thr Ile
1               5                   10                  15

Phe Asn Val Ser Val Val Ala Val Cys Ala Phe Ile Ala Pro Gly Leu
            20                  25                  30

Trp Ala Ala Met Asn Gly Leu Gly Gly Ala Gly Ser Ala Asp Pro Tyr
        35                  40                  45

Tyr Val Asn Ala Ala Asn Ala Val Ile Phe Cys Leu Gln Val Val Val
    50                  55                  60

Cys Val Phe Gly Ser Ser Leu Ile Ala Lys Ile Gly Leu Lys Trp Ala
65                  70                  75                  80

Phe Ala Leu Gly Met Val Gly Phe Pro Ile Tyr Ala Ser Ser Val Tyr
                85                  90                  95

Cys Asn Val Lys Tyr Asn Asn Ser Trp Tyr Ile Met Leu Ala Cys Val
            100                 105                 110

Ile Asp Gly Ile Cys Ser Gly Ile Phe Trp Leu Thr Glu Gly Ala Ile
        115                 120                 125

Val Leu Ala Tyr Pro Glu Lys His Arg Arg Gly Lys Tyr Leu Ala Tyr
    130                 135                 140

Trp Leu Ala Ser Arg Ile Met Gly Gln Met Ile Gly Gly Ala Val Thr
145                 150                 155                 160

Leu Gly Val Asn Ala Gly Asn Gln Glu Glu Gly His Ile Ser Val Gln
                165                 170                 175

Thr Tyr Leu Val Phe Ile Ser Ile Gln Ala Ile Gly Pro Phe Val Ala
            180                 185                 190

Ala Thr Leu Ser Pro Pro Glu Lys Val Gln Arg Ser Asp Gln Ser Lys
        195                 200                 205

Val Lys Ile Asn Leu Pro Ala Gly Leu Lys Ala Glu Leu His Ala Met
    210                 215                 220

Trp Lys Leu Leu Gly Arg Thr Glu Ile Leu Leu Leu Leu Pro Met Met
225                 230                 235                 240

Phe Gln Ser Val Phe Ser Glu Ala Phe Phe Ser Thr Tyr Asn Ala Thr
                245                 250                 255

Tyr Phe Thr Val Arg Ser Arg Ala Leu Ser Ser Leu Val Ala Ser Thr
            260                 265                 270

Cys Val Ile Ile Ser Asn Phe Leu Leu Gly Phe Phe Leu Asp Trp Arg
        275                 280                 285

Arg Leu Ser Val Asn Thr Arg Ala Met Ala Ala Phe Ile Ile Ile Tyr
    290                 295                 300

Ala Phe Glu Leu Ser Leu Tyr Val Tyr Ala Met Val Val Asn Lys Glu
305                 310                 315                 320

Tyr Glu Arg Gln Glu Pro Arg Pro Leu Phe Asp Trp Thr Asp Asp Gly
                325                 330                 335

Phe Gly Arg Ala Val Cys Val Tyr Ile Leu Met Leu Val Gly Phe Asn
            340                 345                 350
```

```
Leu Met Tyr Asp Tyr Leu Tyr Trp Leu Ile Gly Thr Val Asn Arg Asp
        355                 360                 365

Gly Gly Asp Ile Ile Arg Leu Ser Ala Val Val Arg Gly Val Glu Ser
    370                 375                 380

Ala Gly Gln Ala Ile Ser Tyr Gly Ile Asn Ser Val Asp Ser Phe Leu
385                 390                 395                 400

Leu Ser Ser Ala Val Ala Val Asn Leu Ser Phe Phe Ala Ala Cys Ile
                405                 410                 415

Val Pro Ser Ala Phe Val Ile Tyr Arg Val Gly Val Val Asn Gly Val
            420                 425                 430

Lys Val His His Ile Gln Gln Asp Glu Thr Leu Gln Thr Ser Gly Glu
        435                 440                 445

Gly Ser His Asp Ile Met Asp Ala Asn Gly Lys Ser Asp Asp
    450                 455                 460


<210> SEQ ID NO 47
<211> LENGTH: 779
<212> TYPE: DNA
<213> ORGANISM: Aspergillus versicolor NRRL35600

<400> SEQUENCE: 47

atgcctcaga ccagcgacgg caacgtacac gcaccccagt accgcgaggc aaagccctcg      60

cagggagatc catctctgtc ggtctcacag ctcttccgtc tcgacaatcg cacgattatc     120

atcaccggcg ccacgatgtc aagaccaccg cttccaggca cgaacagcag ctttcgtact     180

accagctaga cgtcaccgac gaagacgcgg tcgcagacac cttcgcaaag ttcctgccga     240

ccttacgcta cccagtgagg ggactggtaa cctgtgctgg actatcgctc aacggccctt     300

catctgaatt cccggcatcc gcgtttcgta aagtcctcga catcaacgtt acggggacat     360

tcctcgttgc aaaggccaca gcccgcgcga tgatcagcgc gaacaccaca gggagcatgg     420

tctttgttgc gagcatgagt ggctatggcg ctaacaaggg tgttgataca gccggctaca     480

actcttccaa ggcagccgtc caccagctca cgcgctctct ggcggcagaa tggggttcta     540

gggttggtct tccgctgatc cgcgtgaact cgctatcccc agggtatatt cgcacggctg     600

cgacggccga ggcgctgcag aagcccggga tggaggatca atggacaggt gataacatgc     660

tttaccggct cagcagggtg gatgagttcc gggcaccggt gcttttcatg cttggtgatg     720

gcagcagttt tatgaccggt gctgatttac gggttgatgg tgggcattgc agctggtag      779


<210> SEQ ID NO 48
<211> LENGTH: 292
<212> TYPE: PRT
<213> ORGANISM: Aspergillus versicolor NRRL35600

<400> SEQUENCE: 48

Met Pro Gln Thr Ser Asp Gly Asn Val His Ala Pro Gln Tyr Arg Glu
1               5                   10                  15

Ala Lys Pro Ser Gln Gly Asp Pro Ser Leu Ser Val Ser Gln Leu Phe
            20                  25                  30

Arg Leu Asp Asn Arg Thr Ile Ile Ile Thr Gly Ala Thr Gly Phe Leu
        35                  40                  45

Gly Ser Thr Leu Ala Ile Ala Ile Leu Glu Ser Gly Ala Asp Val Val
    50                  55                  60

Cys Leu Asp Leu Pro Pro Thr Pro Thr Ala Glu Asn Trp Asn Asp Val
65                  70                  75                  80

Lys Thr Thr Ala Ser Arg His Glu Gln Gln Leu Ser Tyr Tyr Gln Leu
```

```
                85                  90                  95

Asp Val Thr Asp Glu Asp Ala Val Ala Asp Thr Phe Ala Lys Phe Leu
            100                 105                 110

Pro Thr Leu Arg Tyr Pro Val Arg Gly Leu Val Thr Cys Ala Gly Leu
        115                 120                 125

Ser Leu Asn Gly Pro Ser Ser Glu Phe Pro Ala Ser Ala Phe Arg Lys
    130                 135                 140

Val Leu Asp Ile Asn Val Thr Gly Thr Phe Leu Val Ala Lys Ala Thr
145                 150                 155                 160

Ala Arg Ala Met Ile Ser Ala Asn Thr Thr Gly Ser Met Val Phe Val
                165                 170                 175

Ala Ser Met Ser Gly Tyr Gly Ala Asn Lys Gly Val Asp Thr Ala Gly
            180                 185                 190

Tyr Asn Ser Ser Lys Ala Ala Val His Gln Leu Thr Arg Ser Leu Ala
        195                 200                 205

Ala Glu Trp Gly Ser Arg Val Gly Leu Pro Leu Ile Arg Val Asn Ser
    210                 215                 220

Leu Ser Pro Gly Tyr Ile Arg Thr Ala Ala Thr Ala Glu Ala Leu Gln
225                 230                 235                 240

Lys Pro Gly Met Glu Asp Gln Trp Thr Gly Asp Asn Met Leu Tyr Arg
                245                 250                 255

Leu Ser Arg Val Asp Glu Phe Arg Ala Pro Val Leu Phe Met Leu Gly
            260                 265                 270

Asp Gly Ser Ser Phe Met Thr Gly Ala Asp Leu Arg Val Asp Gly Gly
        275                 280                 285

His Cys Ser Trp
    290
```

<210> SEQ ID NO 49
<211> LENGTH: 1511
<212> TYPE: DNA
<213> ORGANISM: Aspergillus versicolor NRRL35600

<400> SEQUENCE: 49

```
tcaaacactg cgtagaacag gcgatgagta gcgatcgacc cagcgctgga gaaggtggca      60

gatttcagca accgcatacc gcaggtcgta gaactcaatg ggcaatgccg actgcagggc     120

cggggtgcgg tgttcagcga cagacgggca gcggcgaaga tgggaagaac gagacatgga     180

ctgcagctct ccagctcgga ctcttccatt cgccggatct tggctgccat gttctcgcaa     240

gcgtacatgc agcgatggtt ggcatacggc catggctccg tttcctgtcc aacgccttcc     300

ggcagcgaag tctgcgactg cagcagtgta atcacggccg gcctcatctc ggcgcgagca     360

tcatgggggc actcggcgtt aatgagccgg aaaacagctg ctacgaattc ctcgcgccag     420

atggtgagtc gctcgtcgag gcgctgggct gcactctgcc actcgggacc tccggccata     480

gcacccgttt gaatcacgct gtgctggaac tgatgcacag gcgccagctc aacggtgcac     540

aggctgatgc acatggagaa gccggaggag tactgcaggt catggaaggg aacacactca     600

ccgaagtggt cctgcaaagc ccatgcagtg tcactgcagg gaagtatcgc acccagtggt     660

gctgccgtcg tcggtggata actcggcaga cccagggcaa agatgctatc cagcatttcg     720

atcatccaga aggctcggag tcgttcctcg tggtcgattt tggtgtcgga gagaactgca     780

tcaagggagc acatcttgga cggctgagcg gctgccacac cagcgactgt aggaaggccc     840

aattgctgag atagccgctt gcacattgct gccagattgc tatactggac ccatttcccc     900
```

```
tcgccccaga aaaggattga caaggtaagc aaggcttgga cagtgcgaag gtgcagtgac    960

cccattgcgt tcacgataac ctcctggcga agtctttccg ataggaattg cttgcgttcc   1020

catggaattc cagggctatc ccagatggcg acagccttga ctgcagaggt gtggtgcata   1080

attgggaacc acggctgata cttctgcagc cataccagct ggagttcgta tgtcagggcc   1140

gtagtctcca caggcgcagt atcggcctgt gggctgttcg tggactccac attctggacg   1200

cacaacgggg gagccagccg acccgtagac ggggttgtag caagatcatc tcgttctgtt   1260

gcaggctgcg atggctgcga ctgcgatagt cgtcccagaa cgtcctccat ctgtctttcc   1320

agatcctcga cgcgtttctc cagctgggat acgtaaccgg cccttagtcc aggccgatgc   1380

tcgcgtgttt tgtactcgca atcgaagcca tttttgcggc atagtccgca ttgcgggcgg   1440

ccccgatcac aggcgacctt gcgatggcga cagaccagac acgccagctt tctctcagac   1500

tccggaggca t                                                        1511
```

<210> SEQ ID NO 50
<211> LENGTH: 506
<212> TYPE: PRT
<213> ORGANISM: Aspergillus versicolor NRRL35600

<400> SEQUENCE: 50

```
Met Pro Pro Glu Ser Glu Arg Lys Leu Ala Cys Leu Val Cys Arg His
1               5                   10                  15

Arg Lys Val Ala Cys Asp Arg Gly Arg Pro Gln Cys Gly Leu Cys Arg
            20                  25                  30

Lys Asn Gly Phe Asp Cys Glu Tyr Lys Thr Arg Glu His Arg Pro Gly
        35                  40                  45

Leu Arg Ala Gly Tyr Val Ser Gln Leu Glu Lys Arg Val Glu Asp Leu
    50                  55                  60

Glu Arg Gln Met Glu Asp Val Leu Gly Arg Leu Ser Gln Ser Gln Pro
65                  70                  75                  80

Ser Gln Pro Ala Thr Glu Arg Asp Asp Leu Ala Thr Thr Pro Ser Thr
                85                  90                  95

Gly Arg Leu Ala Pro Pro Leu Cys Val Gln Asn Val Glu Ser Thr Asn
            100                 105                 110

Ser Pro Gln Ala Asp Thr Ala Pro Val Glu Thr Thr Ala Leu Thr Tyr
        115                 120                 125

Glu Leu Gln Leu Val Trp Leu Gln Lys Tyr Gln Pro Trp Phe Pro Ile
    130                 135                 140

Met His His Thr Ser Ala Val Lys Ala Val Ala Ile Trp Asp Ser Pro
145                 150                 155                 160

Gly Ile Pro Trp Glu Arg Lys Gln Phe Leu Ser Glu Arg Leu Arg Gln
                165                 170                 175

Glu Val Ile Val Asn Ala Met Gly Ser Leu His Leu Arg Thr Val Gln
            180                 185                 190

Ala Leu Leu Thr Leu Ser Ile Leu Phe Trp Gly Glu Gly Lys Trp Val
        195                 200                 205

Gln Tyr Ser Asn Leu Ala Ala Met Cys Lys Arg Leu Ser Gln Gln Leu
    210                 215                 220

Gly Leu Pro Thr Val Ala Gly Val Ala Ala Ala Gln Pro Ser Lys Met
225                 230                 235                 240

Cys Ser Leu Asp Ala Val Leu Ser Asp Thr Lys Ile Asp His Glu Glu
                245                 250                 255

Arg Leu Arg Ala Phe Trp Met Ile Glu Met Leu Asp Ser Ile Phe Ala
```

```
            260                 265                 270

Leu Gly Leu Pro Ser Tyr Pro Pro Thr Thr Ala Ala Pro Leu Gly Ala
        275                 280                 285

Ile Leu Pro Cys Ser Asp Thr Ala Trp Ala Leu Gln Asp His Phe Gly
    290                 295                 300

Glu Cys Val Pro Phe His Asp Leu Gln Tyr Ser Ser Gly Phe Ser Met
305                 310                 315                 320

Cys Ile Ser Leu Cys Thr Val Glu Leu Ala Pro Val His Gln Phe Gln
                325                 330                 335

His Ser Val Ile Gln Thr Gly Ala Met Ala Gly Gly Pro Glu Trp Gln
            340                 345                 350

Ser Ala Ala Gln Arg Leu Asp Glu Arg Leu Thr Ile Trp Arg Glu Glu
        355                 360                 365

Phe Val Ala Ala Val Phe Arg Leu Ile Asn Ala Glu Cys Pro His Asp
    370                 375                 380

Ala Arg Ala Glu Met Arg Pro Ala Val Ile Thr Leu Leu Gln Ser Gln
385                 390                 395                 400

Thr Ser Leu Pro Glu Gly Val Gly Gln Glu Thr Glu Pro Trp Pro Tyr
                405                 410                 415

Ala Asn His Arg Cys Met Tyr Ala Cys Glu Asn Met Ala Ala Lys Ile
            420                 425                 430

Arg Arg Met Glu Glu Ser Glu Leu Glu Ser Cys Ser Pro Cys Leu Val
        435                 440                 445

Leu Pro Ile Phe Ala Ala Ala Arg Phe Tyr Ile Ala Val Ala Glu His
    450                 455                 460

Arg Thr Pro Ala Leu Gln Ser Ala Leu Pro Ile Glu Phe Tyr Asp Leu
465                 470                 475                 480

Arg Tyr Ala Val Ala Glu Ile Cys His Leu Leu Gln Arg Trp Val Asp
                485                 490                 495

Arg Tyr Ser Ser Pro Val Leu Arg Ser Val
            500                 505
```

<210> SEQ ID NO 51
<211> LENGTH: 519
<212> TYPE: DNA
<213> ORGANISM: Aspergillus versicolor NRRL35600

<400> SEQUENCE: 51

```
atggatggct accatctgcc cagagcccag ctggccgcga tgccggaccc tgccactgcg     60

atctaccgca gaggcgccga gtttacgttt gacggagagg gattctatcg gctcgtgcag    120

cgcctgagag agcgcctgac cgccgcttca cccactgtct tcgcaccgag ctttgatcat    180

gcaatcaaag acccggtgcc agacgatgtt gccatctcgc caggatctcg agtgatcatt    240

ctcgagggtc tttatctgag cttgaaccgt gaaccctgga gctctgctgc tgctcttatg    300

gacgagtctt ggtttgttgg cgttgaccgc gagatcgctc gtgctaggct ggtcaagcgt    360

catgtcacgt cgggcattgt gcctgatact gcagctgctg agcatcgaat cttgagcacg    420

gactttttga acgcagatga cattgttaag aatcgtttgc ctgtccagga aatggttcca    480

ggtaactggc gagagctgtc tcaagacaga cttgactga                           519
```

<210> SEQ ID NO 52
<211> LENGTH: 172
<212> TYPE: PRT
<213> ORGANISM: Aspergillus versicolor NRRL35600

<400> SEQUENCE: 52

```
Met Asp Gly Tyr His Leu Pro Arg Ala Gln Leu Ala Ala Met Pro Asp
1               5                   10                  15

Pro Ala Thr Ala Ile Tyr Arg Arg Gly Ala Glu Phe Thr Phe Asp Gly
            20                  25                  30

Glu Gly Phe Tyr Arg Leu Val Gln Arg Leu Arg Glu Arg Leu Thr Ala
        35                  40                  45

Ala Ser Pro Thr Val Phe Ala Pro Ser Phe Asp His Ala Ile Lys Asp
    50                  55                  60

Pro Val Pro Asp Asp Val Ala Ile Ser Pro Gly Ser Arg Val Ile Ile
65                  70                  75                  80

Leu Glu Gly Leu Tyr Leu Ser Leu Asn Arg Glu Pro Trp Ser Ser Ala
                85                  90                  95

Ala Ala Leu Met Asp Glu Ser Trp Phe Val Gly Val Asp Arg Glu Ile
            100                 105                 110

Ala Arg Ala Arg Leu Val Lys Arg His Val Thr Ser Gly Ile Val Pro
        115                 120                 125

Asp Thr Ala Ala Ala Glu His Arg Ile Leu Ser Thr Asp Phe Leu Asn
    130                 135                 140

Ala Asp Asp Ile Val Lys Asn Arg Leu Pro Val Gln Glu Met Val Pro
145                 150                 155                 160

Gly Asn Trp Arg Glu Leu Ser Gln Asp Arg Leu Asp
                165                 170
```

<210> SEQ ID NO 53
<211> LENGTH: 47884
<212> TYPE: DNA
<213> ORGANISM: Penicillium fellutanum ATCC20841

<400> SEQUENCE: 53

```
atgggttcta ttaatattgt taccccctat atgaagatag ggcaatatct gtcttttcga     60

aatcgtgacc acttcagctg gtggcaccag aaaggtccag tcctttctca aatgcttcaa    120

gcctgtcact acggggtcca tgagcaatat caatatttga cactcttcta tgctcatctg    180

attccggcat taggagccta tactgagcca tcggtcggcc agaaaggaaa cacccttcta    240

tccggcgcag ggagacttga attgagccgc actttcacgg tcgatgattc ttccttgcgc    300

attgcatttg agcctaccag cttcctggcg tccgaaaaag ggacagatcc actcaatcgg    360

gtcccgctta gtcgtctcct gagcgtcctg ggccagctca gtggtgtgtc tctgggaact    420

gatcggtacc gtacccttgc agaccagctc actacttctg atgatgacga agaaaagttg    480

ctgaacgaac caacgcttgc ggagcagctt caaagcctgc cctctcgcac tcaaaatatc    540

ctggcccttg agctagtgaa cggattcgtc aaaccagaac tgtacttcca tccccagatg    600

aaggcactgg cctccggtgc gctagtggaa gatctcctgt ttgatgcact tcgttccgtc    660

gactcggccg ggcgtcttgg gaaagccatt gacctagcca aggaatttgt gcaagcagct    720

ccgacaacga cgcgtccgca atttatctct tatcagattg agagatccca tagcggcgca    780

gcgaagctct tcctcacgga aagcgcgatt aattgggatc agatttccgg tctctggaga    840

tatgctcagc cagagaccat ccaaacagaa cagaatcggg ccttgcgtgt cctctgggag    900

agtctcaatg tggttgaggg taaccgtggc cccaaccaat tccctatcat gatggttctg    960

ggtttgttcg ctgaagagcc gttcgtgagg cctcaggtag ccttccccgt ggttggaatg   1020

actgaaggtg ccattgcaag aagcattggg cgtttctttg acaatatggg atggaaagaa   1080
```

-continued

```
agctcccaat cctacgttga tggtttacgc tcatacttgt aagtctctct gagctgttcc   1140
ctatcctaag gcaaggggtg gaaaggctaa tatgaaaata gtccaaatga ggatctagat   1200
cagccattgg gcaaacaggc gtgggttgca ctctccctgt ttgacagcga gaacccagct   1260
ctcaccgtct tttactattg atgtgtgcct tggatgctac cagtgcattt gaaagccttc   1320
acatgttatg attgtttgga aatactcagc gaagttggct ggttggacat gaattttgga   1380
taatttgtga acacagtggg gcaatgtgtc ctagactagg tcaataaatg cttcgcgggt   1440
acttactttt tagggaaaag tctggaatat atatctgttt attttgcgca attcgttggg   1500
taggcagtga gtgtagaatt tcaattggat aaattacgta tagagaaaca gaacagataa   1560
agagaaggtt tgccatagaa aataacttgt agaagggaaa gggcattaag agttgataag   1620
accattcccc aaggcgacct tgttgcgccg tttgaacagc attgtagagg cagccaggtc   1680
ctcaagtgac gccaggtatt cggcattgcg caccacagcc tggcgaatca tatttgtcaa   1740
cgagggcggt tgatatatag gcacaggcaa gggatctgta ggcgcaacac ccaggcagcc   1800
tccagaagcg cgaaggaaac ccatcagcgg ccacaaggga tgcgatgtgc caacctcgtt   1860
gacttgctgt tcaactgtgt ccatccacct ttgtgaagag gaaggaatca gatctcgtcc   1920
gagccccagc atgatcgctt tccagaaatc cgacatattt agcccgtcac ctatgctgac   1980
agctttggca gagggtgcca ggggatttgc attgtcattg acactgtgag atgacggccg   2040
agcgtgaagc gtttcatgga tgatcaggct tgcgacccag tcgacagcgg ccacaaagag   2100
ccaattgtca gactcgtccg agttgtaact gcaagtggtc attgcagtcg tcaccacacg   2160
ccagaggagg tcgtccccgt tggccactgc gttgctgaca ggtccgatca taaaaccagg   2220
ccgcacaatg gtcagggaat gcgccttgtg tcgcgctgaa aaagctccga ttagctgttc   2280
cgaggcaaac tttgtttgtg tataaccatc ggtaagttca atcggaggaa agactgcgtg   2340
accatttgac atgcttgggt gattatctgt gtccgttgtt gcgagcgcgg catcgcctgg   2400
tatcagcgca gagatgtaag tcaaggcaat aggtgttgga gagcgattga ggcattgcaa   2460
tatatcgaat gtactgcgaa cattcgcagc ctctagagtg tcataatcgt agccccagtg   2520
gatgaccgct ccgcagtgaa tgatcgcgtc aactgcacca atcgaagaat tcagactgct   2580
ttcggtgcca gaaagtgttt cccagtgttc atcagccaga cctagatgcg gctgggagag   2640
atcgccaggc caaacttgaa tgaggcgtcg gtagtcgttc cgccaccatc gagcgagtcg   2700
tgctgcctga ataatgcgcg ctagcccctt tcgtggacaa ggcgcccgtg ccaacacgta   2760
gacaatgcta acgtcgttgt cgaccaggag ctggtgaaga atatgtgtcc ccaagaaccc   2820
tgtagcccca gtgaggaaaa gacgtttccc tgatggccga gaatgtatcg tccgtcgaga   2880
agattggcag acaggtaggt cgttgatttg acgtatcata cattgcaccc tctcccacca   2940
gccaggggat aacagagctt tctctgggac tgagttgggt gtgcgatcga tcatctctgc   3000
caccattctg acggtcaaag tactgtcaaa gagattcgtc atggagatgg agcaatcgta   3060
gtgccgggag atgaactggg acaaggctat gatatcaatt gagtccagac cgacgcgaga   3120
caagccaaca tttcggccaa caatctcagc tgccattttt tcatgaccgg ttttgcgttg   3180
gagaagttga ccaatgtgct tggacaacgc ccaagcaact ggctcatctg tgtgatccaa   3240
gagccctgtg ctcctgctct catttcggct cagtcctcct agatcatgta gatcgactgg   3300
gctcagttcc gtggcctcat caaggagaga acgacggttg actttgcccg agatcgtcaa   3360
gggaatgctt ggcagctgca ggtatagctc aggaaccatc actggaggga aactttgtcg   3420
caatttttgt tgcacccgag atgctcgaag agcgaagtca tgactatggg attggaacgc   3480
```

```
tatattcgaa aatccattca tgtcggagat atccggtact ttggcggcca gcgatggaat   3540
gtggaccatg gccaccaagc aggggggcat gtccgattta gtgggttgta gaatagcagc   3600
aatcccgcta gcatcagtgc caaagaatcg caggacatgg cgttcaattt ccgctagatc   3660
tatacgttgc ccatgaagct tcgtgtgttg attcgtgcga cccaggaaag tgaaggttcc   3720
atccaagttg cgacggacca tatcgcccgt gcgatacata cgcgaggctt gccggtcctt   3780
gaactgtggt gcccacgaag gcggctgcag gaagcactcg gtcgactttt tgggattgtt   3840
caggtaccca cgaccgacga tggggccctg aaggatcagc tcgccaactg tattgactgg   3900
catacgcctg gtcacatctt ctttgtcaac tacccatagg actgcgccca tgccttttcc   3960
gatcagtcga gcgtctgcgt cggtggacgt gacccgatga acggcagccc ctgtacagca   4020
ttcggtcgga ccgtagccac agtagagatg tacacgactg caccacagtt tgatttggcc   4080
tgggagcatc gactcaccta cggcaacaac agtacggagg cttggcacat cgtcgggagt   4140
caacaaccgc agcacagaag gcgtgatgca aagccagttg ctccgatatt tctcaacgac   4200
gtggcccagg tcctctgcga tttcggactc cgaaggaatg cagacacaac caccgctagc   4260
gagcactgtc aggatttcca ctgcaaacga gtcaaaagcg taagaggaaa gctgcagaac   4320
tcgagaactg gaagttattt ccaatttgtt ttgctgtgct ataacggccg aggcgtagga   4380
ggcgtgctcg atcagcactg ccttgggctc accagttgaa ccagaggtga aggcagcgta   4440
caagaggtcg cgaggactag ggttcggcat gggtggcatt gtcgttgttg tccctgatgg   4500
cacagcctgg gcgtgggaga tcagcgcttc ggtagacagc gaaatccagg gtccgtcgca   4560
tacggtcgac gccaaattct gcatttgtgc tgatgtgatc cccagggttc ctgaaatggc   4620
acggcatatt tttacgttgc gctcgtgagg ttgattgggg tccagcagga cgaaggcgac   4680
acccagcttg gccaccgcga gcattgagat tgggacccag taggaccgct caaggaaaat   4740
gggaatgaat tgaatgcctt gaccgacaat gagcggcagc aacaactgtg ccagttggcg   4800
cgcactggat tgtaattctg cataagagag gtccccatca caggcagaaa ccgcacattt   4860
cgatggattg cgagttacct gagcctccac aagatctaca attgtagaat ccaagcaggt   4920
cggtatgctc ttgagacagg tagaaagcaa ttcagaatcc cgatccgata tgagatccag   4980
ttgcgcaata gtcagatttt gggtgtggca gtcatcgatt tgcttgagta agtggctcaa   5040
ttgagacagc atgagctctg cctgctcacg gggcacgacg gcttcgtcga ccagcatttc   5100
aaatttccac gaggtctctg atggtgccac ttgaaggatg agcgcatatc cggggaagct   5160
attgatggaa ccaacggata cttcaactgg gccaaaaata ggggagtcag ggatcatgtc   5220
gtcggcctgt atgacgagta agttctggaa cttgcaggct gtggcgggac cgtggcccat   5280
attccgaatc cgttgcaagc ccgtgtgctc gaaagggatc atcctcttca tgttctcttg   5340
gacttgcgcc agggactctt ctactgtgga ctcgcgctgg atggttgtcc gaacagggag   5400
tgtggcgatg gtaggaccca gcacggaccc aaggatgacg ccgagtccac ggcgaccatc   5460
gacgaccgtg ccgtaaacaa tatctggcga gtctgtgtac aagctgatca agagcgccca   5520
ggcgagacga actttggcgg atggactact gatttgcttc gaagaggttg cattggcccg   5580
acaaccctca tatacgaccg aggtgcttgt gtgcgggaga tactgcggcg atggaagggc   5640
agggaagaca ttgctctgca attcgaccat ctcctttagc cagaattgac gggttctctc   5700
cccgtcggct agtttttgct ggttcaaatg gttaatgaag ccggtgaacg ttgatggaaa   5760
taaagtttcc gatgtatatg ccttctctgc ttgcttgata catgcgtgaa gcgtgaaagc   5820
```

-continued

```
gtcgtagaca gagtggtgaa atgtcacagc cagcttcgca ggctgttctc tggcttccga   5880
gtcttggatg agggtcagcc ggactagcgg cgaacccaag cccatggatc gagctcggtc   5940
tttctcgtaa aactgggact ccgagctcgc cgtctgccac tgaatcttcc gttcagggcg   6000
caccacaatc tgatacgtac gaccgtcatc cgcctggatg atacgagttc ggagaatgct   6060
ggtcgcttgc accacattct gccaggcctg ttgagccaat tccacgctgc agtccgccgg   6120
gagcgagaag agaacccgat caacatatgc gtcgccgctg tgaatctccg tgactgccag   6180
aagaccctct tgtagtggag tcgtcggata gatgtcctgg atatcctcct cctggatctt   6240
gcattcctgg ctggctacac ggcgcaaaca ggtgatggca ttcgcatcgt tgacaccgat   6300
caatgagaat ggcggggggc catctgccaa cgtcactgca tcagtgggtc tcgcctcctt   6360
tgcgacggtt cggaggctgc attcaatatc tagtaggcgc tcggtatgaa ggagcaggtt   6420
gtacgccaag aggaccctgg tgagacggat cgcagtcgtc gaatcgccac ccagttgagg   6480
gaaactagcc ttcaagtcaa tcgaagacgt tgagatctta cacacactcg cgataacctt   6540
cactagaacg tcttcattag gcgtcattgg taaggagtct gcttttgcca gacaacgtga   6600
ccgattccct cctaaccagt ccatcaactg cgaagaggaa aattgctgga agcactgaca   6660
aaggcggcga cggtccacct tgtcggtagc cgttcgcggc aaagacttca cgggtatgat   6720
aagggaaggc accatgtatt gaggcagata tgggcgcaaa agggactggt agtgatggct   6780
cagagcccac gatccggact cgagcgccgt catgctctct ccaggccgct gtgaactcca   6840
gtcaatttcg aatccagtgc ggtcgacgag aaactgcacg agcgtcattg cacctgcggc   6900
atcgtaaaac ttgaccgcac tgacgacgga gtcgacatgt ggatccaatt gtcgtagttg   6960
gagttcgacg gcatcgacat caacgcgttg gccccggatc ttgacgacag tatccctgcg   7020
accgacatag cgcagggtgc cgtccgggtt ataatggcac aaatcgcccg tcctaaaaaa   7080
gcgacattgg acgggaatct ctgtgaaacg ctcgcgccag cgaggagcct cgatgaaaac   7140
ctgttgcgtg cgtgtagggt cgttgaggta gccatctgcg accacagcgc cctcgatgat   7200
catctcaccc actgttccaa tgggtgccag ggagtcactg tcatcgggca tcgtaatcca   7260
agagatgcag ccggccgccg tgccaaaggt cccaggaatc cacccgctcg tcggtgaaat   7320
tgggccagca ccagcgggtc caacttcggc cggtccccag aggttgaaaa tactcacacg   7380
gctctcccaa tgacgagcca ggtccacagg gattgtctcg ccaccaagag taagggtctc   7440
tagggtcggg aaatcgctag gttcaaagtt cctgagcgtg gtcggtgtga aaaatgccca   7500
ggtcacacgg tgctgctgga taaattcggg catactgttc aagcgttgag tctcggacgg   7560
aatgcaaagg caggccccgc gtgtcaaggc ctgccatgtt tcaatgatgc tcatatcaaa   7620
agcatacgac gagaattgta gcacacgtgc ttctgatgta acttggagcc tgtcgcccac   7680
gtagtgaccc gccgtggcta tcgctcgatg actgaggacg ataccettgg gcacgccagt   7740
actgcctgac gagaagacga tgaaagccac atcgtccgaa ctagcgctgg gaaaagcagt   7800
ggacactggc tgttccgccg tcgctgaacg aggggaactg tataaatcct ccgggatgat   7860
gaggaccggg tactcgccga tttgacgaat gagtggttcc tgtgctctgg acaacaaaat   7920
gatcgcagga ttggactgat acagaatgcg tttcatgaga tccatcgggt ggctgataca   7980
gatgcatact gcagtggcgc gaactttggc cacagcgagc atcgcaacgg ccatccattt   8040
ggatttttca aataacaagg gaacaaccat tccaggacgg acattttgtt caagtagacg   8100
ttgtgcagac tgattggcaa gctcatcaag ttgaccgtat gtgagctcgc cgtcccatgc   8160
cgatacagcc aaccgtccag ggcctgagtg aacctgaatt gcgaacaggt cttgaaagca   8220
```

```
cgcatcgatg atggccggag gatcatggtt ccactcgatc agttgatgct catctgccgt   8280
atttagcaaa gagagatcgt tgatgcttgc ctgcaggcct ctggagtgac tcccaagttg   8340
cttgtaaatg tgtgcgaact gttcagcgat gcgttgcgcg gcatctctgt ccaccagatt   8400
ctcgtcatgg accacctcac aaaaccaaga gatgtcgggc tcgctgggct ggcagatgat   8460
gcgtaagtgc aaaccttccc cgtcgtgaat cgggggaaag gactcttctg tcgcagaatg   8520
actggatggt acgctttgca tcagaagact ggctgtccgc tccccgaaat ccaaaacgac   8580
attggggttg tcattggccg cgtcactttc cgccgggata tgcttgatct gctgaagaaa   8640
gtctgccatt tgacgttcta acgattgtat ttcagaatct ggtgccatgt ccactatggc   8700
atccgcacac ggctcacaag gactcccgag ttcacttggc aggacgccat ttaacaggac   8760
agttgctgat ccatgataca agctggccag gagtgcccag ctgatcagac aatactcctc   8820
agacaaagat gatcccaacg ggagtcgtgt agttcgtcct tgatgcgacg cacgtaggtt   8880
ggtcgaatca gacgtggtcg gggcatatac taatggaaag ggcactgaaa ctcgaataca   8940
gccttgtttc gccatttaga gggctttaga caggtgatag ggcgattaat tcaatgcgtt   9000
ggatagaaga ctccttgatg aacgtatgcc tcggaagccc tgacaccttc tcctagctag   9060
cacactatat cgtttgtgac ttatcccaat agataaaagg aagtatagta cggtgaacga   9120
tctaaggtgc agtacgagta ttgcaggcac tgcatcaggt gccaattgta tctcgagctg   9180
caagggacac ataatcgcca tactgtatac agtagagtca gctagccacg gccttttttt   9240
tttttttttt tttttttttt tttttcattc ctcgcagaac ccttgcagca cttgcagagg   9300
ttgaattcta gaattccaac tggaggcctt gcgtgatttg aatgcgccat ctgcttggct   9360
gaaggcagag aatgcaggcc tgcatctgga gtaacctgac gagtcattta aaatacaatt   9420
gagcatggta atggaggtat taagacgaaa acactgacta taacagacgc catacctcag   9480
ttaaagttct cccatcatac atttatattc ccaatcgggc acaatcacca tgtctaaaac   9540
cactgaggtg aaggtagtgg aagtccaact ggaggacccg ttgcccggta ttgtcgacgc   9600
ctcccggttt atttccggct ctcccactga gcagcgggct ttcgctgtcg aactggtaga   9660
ttccgttcgc cgctgcggtt tcgtgaaggt catcaaccat ggtctgtccg acgaactcat   9720
cgacgagctc tttgcgtggg taagtgacac tcagctgcct gtccaagaga gaattacatt   9780
gccggattgt cgcagtgcca aagctcacat gttgtccaga acgagcgctt ttttgcaatc   9840
gaccccgagc aaaagctggc cgtcgtcaac cccccgggac catcgccgca gcgagggtgg   9900
agttgtgtcg gcgccgagaa agcctcgcgc ctgttcagca gaggccagac ctctcttgat   9960
ctgaccgatg cgcgtgtatg tgcagcgacc acaagctagt tagaatcttc atttttgcta  10020
atagagaaac caggagcatt ttgacgccgg ttctcccagt gacaccaaat ggccctcgcg  10080
ttggcctgat gaggcggtga tcccaggctt caaggccttt ctggaagact tctatgtccg  10140
atctcatcaa gctgcgctgc tcatactgga agctcttgag atggggctga acctgcccgc  10200
gggagtattg aaatctcgtt gcggtggatg tgcgagtgaa cttcgcctga acaactaccc  10260
tgagatcgat atcgaggagc tgcgccgtgg caagatcagt cgcatccatc cgcatgctga  10320
tctgggtgtc attacgtgcc tcttccaaga tggacttgga ggtctggagc tcgaacatcg  10380
atctcatgcc ggctcgttct tgcctgtgcc gcccggcgct cgttcggaaa tggtggtcaa  10440
cataagcgaa acttttcagc tgtggacaaa caatgtcatt accgccggaa tccatcaggt  10500
caccgttccg ccggagatga aaacccgcac cgaaggccgt atctctgctc ggcgttcttg  10560
```

```
cgcattcttt ctcaaggcga atggtgatgc ttctgtcgcg ccactgcctc aattcgtaac  10620
gcaagagcga ccagctgcct actcagagat gaccgcattg gactatcatc agaagcgttt  10680
agccacggcg tattagacgc cctcgtagct ccatgccaac gaaattaaca ggcgttcgac  10740
aggtactagg actacggatt gaatcaatct acaagagcac atagattgac atgggtatct  10800
aggtcttgtt gcaatactag agtgatggtt aggggctcat caaatttttg tttaattcaa  10860
ctatttgttc ctataaggct ccaggccgca atacaattct catctcgaag agtcaagctc  10920
gggacgtctt gctgtctgtc gtattgtctt caccatggga accggcactt tgtgagagtg  10980
cagctgtggc ttctgcggtg attgcagcgc aagtccgaag tgtttgaacc aacttttcct  11040
tttccaaaac cctcaatcca gcggcagtcg cgccaccctt agtggctact tgcgcgacca  11100
agtcagccgg agaggttgac tgctggagaa gggcggccgt tccccgagcc gcctgtgctg  11160
taattgctag tgccgtctct aatggcagtt gttgcgcatt gttggcgcca ttactatgtt  11220
gttctgcaac gccctgggcc agaccctcga tcatctgagc aaagaaggcc agagacgatg  11280
cgcctaccgc agaagcgaca tgcatttggc attctgggag ccactgcacc actcctaccg  11340
atgcgaaaag ctcggtcact gcgcgccggc tctctgcgtc gtttgtgtga tcgtcgctgg  11400
tggatagaag tgtgatggat tcgccgaccg ccactgcaac actgcagacg gcacgcacga  11460
cgggccccgt ccagaagtgc aatgcttcta cgatgagacc tggcgatacg ccccccatca  11520
ggctgatcag gatccgacga tggtcatgac gcatgccctg caaatcatgt actagctcac  11580
cgaggctgga atgtttgcac ccaagcagga cgatatctgc ttgctcggcg acattgcaat  11640
tctgatcttg ttggaggatc cagaccggag ggaccgcccg atctctcagt aagggggaga  11700
ttcgctcgcg gactagttgc gcggtccgag ccgatcggac cgtaaccttc agctcccgaa  11760
tctttaccct tcctgggtgg cccgatgccg accggagcag gccaaccagc aaggcttgcc  11820
ccagttttcc tgaatgtcat gatcagcaac gcatccgatg taagactcat tgccatggtt  11880
ccatgtcaga taagctgaat gaatgccgca cggtgagacc ttaccgcatc ccagaatcgc  11940
tacattcggg tattcgacag cagacatgag cgccattctc gtattgaagg gtgaaaaaaa  12000
aaaaaaaaaa aaaaaaaaaa aaaaaaagaa aagggagagg gaacgaaaaa caaagaaaga  12060
gagagaaaag gaacaaaaat acacagcaga aagtaccgca cggttgtgtc tatatattat  12120
cggcaatctt tctgggatcg tcatccaaca ggtgctaggg ccccttcctc cacgtgagac  12180
tgggcaccaa ctcggccagt ggacaggccg accgagcggg tatctgaagc ctttgatgga  12240
agctggattc tcaccccttg tgcgtttttt ccgatttcat agaaccctaa gccaaagccc  12300
taagccgtaa tcatgactgt cagttcggtg atctcaacta ggcattgtgg tctactacta  12360
ctgtacaccg gtctatacgt gtctgctaca tgctaatgca tggtgtacaa tattttgtaa  12420
aaatcttgct aaggtacagt aacgtgccgg ggcgcgcaag aggctgttac gttcgcggct  12480
ctaccggtga gtccccccctg agaaaatatg tgaaaaaaaa agaaaagata aaaaagaaaa  12540
gataaactaa ttactgcctg agacgtcgcc tgcagaagca ccggaagagc ggtccacata  12600
tccttcaccg catgaatgac cgcgagaatg agagcaaggc aaggggtcga agaagcaact  12660
cgtcgccagc agagtcagtc ttaacgcacg atgctcaaag ccctgctatc tgatatttct  12720
tgactactag atttcaatca ccacaagttt ggccattcac agttcaacaa atatcgccag  12780
ctcatccgcc aggtcaattc gcaatgacac ccgctccgac accacgtact gatcagctcc  12840
atggctcccg agtacttgtt attgggggaa cctctggaat cggttttgcc gtgtgcgcag  12900
ccgcacttgg tcatggagca atcgttacca tcgtgggatc gaatgcccaa aaactcaagg  12960
```

```
attccgtcgc ccggctgaaa tcctcgttcc catccacgga ccccgatgac attgtcgcag  13020
tccggtgtga tctcagcaac tccgacaccg tcgagcagga tattgagaag gctctccagc  13080
tggcggctgg aaactccaag atcaatcaca ttgtgatcac cgcagcggat atgaccgctc  13140
cacctcccct ggaggatctc accgttgact ctgtgcagcg cccggggatt atccgactag  13200
tcgccccact gatggtagca aagcaccttc caaaatacat gaacaaatgc cctcagagct  13260
cgctcaccct aacgagcggt gcacactgtt tgagaccaga ccctggctgg accgttatct  13320
cgggatattg tggtgcggtt gaagctatgt cgagaggatt ggccatcgat ttgaagccac  13380
tgcgggtgaa cgttgtcgct ccaggagcag ttctcacaga agctgtaaag gatatcctcg  13440
gcgatgcata tgatgctgcg gtggaaatgg cggaggcaaa atcgacggtc ggacaaactg  13500
ggtccccgga aagcgtagcc caagcatata tttatctgat gaaggatcac tatgcctcgg  13560
gatctgttgt ctcgacaaac ggtggcatgc ttcttgtcta agtcgttgcg taatggcttg  13620
atgggcacga tctgaatatc cgaagccatt cctccacttc ctatcacctt acgcattgat  13680
atatatcaaa tgccgagtca agaaataaga atctgtttta aaaataagaa aaaaaaaagt  13740
gtgtgaatag tgaccttatt cccctccgtt aattcattgc ctcgcatttt cgcagcatca  13800
gtcgtcctcg ccgcattcta ggtagggatc aacatcaaca ccgccttcgt ttttgtaacg  13860
tgcttctggc cggagtcgtt gcagagaagg tagatcaatg tctgaatgta gttttggcga  13920
gacttagtac attccttagg ccccccttgtt tgtctgatgg ctcacatttg gtgagatacg  13980
tacaattatt cagcatatta agtggattta ttgatatatg atgtctcctt acacgatatt  14040
ctgcggcgga agtggatctt attgatctga aggtattctt ggcgagacct acatttgttt  14100
acaccccttt gtttgtttga tggtcctacg taggaagtgt ctaattattc agcatacaaa  14160
aggtttattg atatataagt gttctcttgg acgtcattaa ctgggtttga tgactgccac  14220
tcacggtaga tgcaatctta accagaattg aatcaggcga tcatcacaac aaaagtaaac  14280
ccgaaaacat gcacaacacg caaagcgaca caaaatgtga aaatgcgtca gataccccgg  14340
aaagtcccac aggagaagaa gagagcgtcg gacttgctcg ttggaagtta gggctattaa  14400
tgttcggaaa tacgcttgcg gtgttctgtg tcgcactggt acgtaagttt ccatgaacta  14460
atatcggatt ctaaagcgtt agcaggataa tacgattatg tcaaatgcca tccccagagt  14520
cacgcagacc tttgactcgc tagaggatat cggatggtac tcaagcatct attttttcac  14580
taattgctcg gttgttctac tctttggaaa actctatacg cattactcaa tgaaatgggt  14640
tttcctggtg gcacttctat tattcgaggt tggctccttg atctgcggtg tcgcgccgtc  14700
ttccgtcgcc ctcattgtgg gcagagccat tgctggactt ggtgcagggg gagtcctgcc  14760
aggcgccatt ttgatcgtca gcgagagcgt accacttcac caaagaccgc tgtatacggc  14820
tgttttgggg ggtatgtcag gcgtcgcagc agttgttggg cctttgttcg tcaatcactc  14880
tattgcgttc tttcataaac gcaccgctaa ttatgtcttt tcctaggatc ggtggtgctt  14940
tcgctgaaaa tagtacttgg cgttggtgtt tctatattaa tttgccactg ggcgccgtca  15000
ccacggttct tattttgtgt ttcttttttg actcgcggac tggcacctct gatgtatcca  15060
tgagcagctg gaaccgattt aggggcctcg acatccctgg cctgctccta tttctgccga  15120
cggtcttttg cttactgctg gcacttcagt ggggtggagc gaaatacccc tggaacaatg  15180
tgcgtgtcat agttctattc gtcattttta tcctagcggg aggctgttgg atatttatcc  15240
aacattccat gaaagaccaa gcatcggttc ctccgcgcct gatacgcaac cgtaacgttt  15300
```

```
ggagctcagc ggtgtacatg gggtgcattg ttggctcatt tattatcatt ctctactacg  15360
taagtctatc actacgatgt tcaaaaatat taactaatgg ctcagttccc tatttggttc  15420
caagccgtca agggcggttc cccaatacag tcaggcacca tgatcttgcc gatcatcatt  15480
gggctcattg tatgtatgtc attgggcgcg gtatttgtca ctgtcgtggg atactatcat  15540
cccataatgg caatcggcac tatcatttca actatcggcg ctggcctctg cagtaccctc  15600
gaagtggact ctagcgcgag caaatggatc ggataccaag ctatgtgtgg tatagggcta  15660
ggatttgggt tccagttacc attcatcgcc gtgcagactg cgctacctag atcagacatt  15720
cctgtcgcta cagccattgt cacctttgcc cagaacctga gcgaggctgt tttagtggct  15780
ttggcgcaaa caatctttca aaaccggcta tttgctcatg tcaagcaatt atcaacatta  15840
gttgatccga acgctctcgt tcatgccggt gcggccaatt tggatcaaca tttctcagct  15900
gatgtgctac cggagattgt gcgtgcatac agtgctgctg ttaccgaaac cttctatgcg  15960
gcaacaggga tcgcagcact ttccttcatt gggctgatca ggctgcaatg gttatcggta  16020
aagaaaacta aaaccaacgg gaatgcggcc cagacgcatc tctaacaacg caagagatgt  16080
agggcctcta taaaatacta ccggtccaat cggcttgtcg agtgtgatgc tgaatacgag  16140
agcaggcatt aattgttcag gtttcaacag tctgtaatac cgctgagctt ttcctggggt  16200
tgacatgttg atatgtacaa ctaagctaca cagtactggc ataaaagcaa gcgaattaca  16260
cttgaaatct taatcgttgg atcacgttct tcgcctactt agataaggta cattagacga  16320
gggcttcgtg gagtccaaaa ctgttaatat tgacgaaatg cccacctctg ccatacgtgg  16380
cccttgcgga tgaatcctgg aatgtgatac cttgatcatt aaatcttgat atatcaaaat  16440
tatgcccatc atgtgactga gagctcctgt ttctcttcgt cttccgggac gagcagatct  16500
tcaaacgccc caatgagctc agtccagagc gctggtcaaa ccgtcggggc cttattgatt  16560
atctagaggg gtttgctcct tttttcatgg gagtatgcaa tcgaattttt gcctattgta  16620
accatttagg gcaaatcaac cgatgttgca tgcattcagg caattgggca cctcccgaac  16680
tccgcactac attaccaaag accgggtgca gtaaataccg aacccottga tgagaattcc  16740
tccatgtgat tcatacgttt cgcaaagtag tatgttgtat caaaagctat gtcggaaaag  16800
ccaatagaaa tggatagata cctggctctc tcattacgac aacaacaaca acaacaacaa  16860
caacaaagcc gcacagatta cctcgataac atgtgccgtt caggaatatc gatgttggtc  16920
tttttgtcag ggcccctatc tgaactttca cactcgcggg tcgaatacca tgttgtcaga  16980
aaccgtggac tgaatggctt gcgtgtaaag actttctacc ctattccttc gcaaattcac  17040
ataggcctct gctatttgat atgcttcgca tgcttttcga tttagataac agcggtcata  17100
agtaaactgg caacatttta tgagatcatt tcagaataat taataattct ctcaggactc  17160
gttaataatt aaattagcct ctggatctgt cacgaatcgg tggcattagc ccatatttcc  17220
gcaccgacgg ctgccttgct gctagatcta ctctaaagcc tcttcagatc gagctcaggt  17280
actactgtac ttgttaactg catgaggcga ggtaactccc gggccatgag agcagtattg  17340
ggaaaatcga gccacagacc cacaattatt gacggttata ggactcattg caggaagcaa  17400
gtatgtagca tgcaagggaa accctttcat ggcccacagc attgtgcatg cataagccag  17460
ctcatatctt ttcttttgcc cgtcatgaaa taaaacggag ctatcatata gcgctcgcag  17520
ataaatcgtg gcgttgtaca gtagtcaagg gcacgctttg tgcgtcagac ggcacaatga  17580
catgaaagtc ggtgagcaaa tagccaattc aatgctcatg catgcatgtt catttgcggt  17640
gtgagtgaaa acgattatcc agtatccgac atgatatata aaggtgccga tgcattcaat  17700
```

```
ccagaccgag atgtaacagt cagaattaag ttaatatcga cctagaacat caaccctgcg  17760
cccattttca gctgttaatc atgactatcc aagtgaagag agttgtgacg gtatttggag  17820
ggactggtat gaagcttttt atactcgaga aaatctacca ggaattagct gaccgataca  17880
ggaaaccagg gcagcagtgt ggcacgttct ttgctggcac acaaagccaa gatctttcac  17940
gttcgtgtaa tcacgagaga ccctcaatca gacaaagcga aagctattgc gtcgctaggg  18000
gcggagttag ttcaggcaga tggattcaac ctcggtgaaa tgaccaatgc ctttgctggc  18060
agttgggggg tatttatcaa cacgaattcc gatgatgagg taaagtcaca atgggaagtc  18120
acatgcttag tagccagtaa gctcactcac tcacttaatc tgtccgacaa caggctttga  18180
agtcattgga tggtcctagt gactatgacc ttggcgtctc agtaatcgat tctgctaaga  18240
aagcaggcgt ccagcatgtg gtctatagct ctggaccatc catcacaaac gctacaaaag  18300
gcagaatgca tctggaaggc tttgagagta ggtagattct atcgccgcca ttgttacatt  18360
tgcttattaa caaattgaag ccaaatacca cgttgagcaa tatgggcgta ggaaagggtt  18420
tacgagcttt actcccatcc tatgcgcctc gtttatggag tgctttttct acgatccgtt  18480
tgtggatgcc ttcggtgggt ttccttggat tcctgagcca gaaacaggcg aagtggtctt  18540
ccgcactccg gactacgggg gtaaaggcga tatgccctgg gtcagttgtg aggaagacct  18600
cggggacatt gtgcatggta tctttttgaa cccgtgcaaa tacgatcagg tattggttca  18660
ggcaacgagc caacagataa cgatgtttga tgtagcagct tcatatacac aaggtacgcc  18720
gccactcctc ttctcttttt ttcgatcctg tccattggcg gtgatgtctt tgatgtaact  18780
gatagttgct acttgaagcg accggaattc ctgcccgata cgaggaattg ccgtcctggt  18840
ctagcatcaa gctcaatggg acaaggtgcc gagccgaaac tcgccaaatg ttctggtaca  18900
tgaagcattg cggtggccgt tggtttgcag aacacgagag tgatatgtct actgcggtcg  18960
ctttgaagga atcagcaatg ttgtctcagg atcgggtggg aggtcttgtt acatttcagg  19020
cctggtttaa aaaggcgaaa gtcctgaaag accaaaatgt gtgattcctc cgagatcaag  19080
cgacaatatg taccctagcc tcaatgtcta gtatcaggcg tgtagaaatt gaattatctt  19140
gaacctgaga cgtaggaatc acttcattgc ttcatttatg gtcgataaaa gtacgacgat  19200
gcccacattt tctcggttgg gctaaacagt accgagcggt caactcaagg agtccgtatc  19260
gtaacttcaa gaaatagaag cagtggttgt ttcacgaact aggaaaatca gcaacacact  19320
cttgatttca atctttctcc gtatggactc aaccattcat caggatgtat acgaggcctg  19380
ccttttgaac gaataagaga caactaggta acgtattcgg caaacgaatg ttccagctag  19440
aacaacacct taagttcgag attaaattat tatatatctt gacagtcaac ctttcagtga  19500
cccaatatta accctcatat cagagtatag catatatagg tagttactcc aatcctatca  19560
caatgatata tgacgatgtc aacataaaat acgacatact gttgccgaaa atatataact  19620
tcatacctaa gttttaaaac aaaccaatgc tccttaaata ttgccaaacg cttgattaga  19680
ctatgtggtt agattcaacc atgctataag accttatgtt gtgtaagcgc cttgacggcc  19740
gacctcgtca atctggtatg gtcctgtatc ccatatctga cgtcgaggtg tcagagctgc  19800
tacccaggcc ttccggtctg tgcccatcta tcgtgggcag actttctgtg ggcgttgcat  19860
ggttcacaca caatatccag tcactctaga gagatttggt acatttcgct acatagaaac  19920
tgagaggaat gtttaaaaag ctcgacagct tcatttaagt accagattga tgcataacag  19980
tgcaaggttt tgattcattc caaagaaata ctgctgagag ctgccgatcc tcattatacc  20040
```

```
agatcattat agcttgatag ttcaactgga caggtaaggc tcaccaaaaa gcttgatcaa  20100
ctactatata ggaacacaaa gttaactaag agtgtgttag ataagatatc aacataaagc  20160
atctcgcgtt ttacggtggt ggtcgtactg cacagccttt catgtaagtt acaccgtgtg  20220
gctctaaaaa aaagactttt ccaccaaata tttcatatct acatcgaact tgctcatggg  20280
ataacggtgg gtgttgcata ctgcatgtac gtgagcatgt acaataggtt cagagtcctt  20340
gttgtccctg agcgaggtat ccactgattt gaaaatgcaa ggcgcatgcc gcgctacagc  20400
catattgatt gttcttcttt ggattctagt ttataacgag aataggtggt agatcaaagt  20460
cgacatgtca taatctgcac gtttgtcagt gattaaatac actgagatgc cgtgaaactt  20520
gaatcctgca tgcatagttt ggagcaaatg tcaacactag ggcccatgtg ggacgattag  20580
gtacttaagc ggctggaggc cgagaatcac ctatgacatg cgcggaatgg tttgcaaacg  20640
tcattctata gtacacatcc agtgacagat cataagtttt aacagcaacc atggacccac  20700
tacgaattac ataattttct gcctgtttta aaacctcatg ccatttaact aatactgtgt  20760
atactatccc cggctctcga ttattgcctg cacacgacgg gatactatct tgagtaaaat  20820
ataagattaa taaaaggggc gaaatacgtt gaagaagtga gaaatgcgag agatacgaag  20880
tttactagcg tgtttaaact aggcggtgta gtattattga gaaggcggta aatgggtggg  20940
tccatgggtg ttgtcaaaac ttatgaaccg tcactgtagc agtttagcag ccgccacacg  21000
gccccccctac ttcttcctct acagactgaa ttattaccct atgcttggcc aacgtacttt  21060
cttcggctaa agtaactgaa acaaactcta tactttgttg cagatttgcc tgggacacag  21120
ccatttggaa gtagtcgggt tgaatattgt gaagggctgg tacacgacgg cccgatccgc  21180
atgacccgga cctaattaaa tagtgtgctg taagctactt acgattcttt ccaaatttat  21240
attacattta ctctgctttt cgggtccaaa aattcgatgc accaatgatt gtcgctttgc  21300
tggctttgca gcaagttttc ggctttatgg tcgaagagac ccattttgga ctactgcatt  21360
tcatggtcgc gatcacagaa tggggaatga aaccagtttc ctgcatgaat ggattgcccc  21420
ttacatacgt atactgccag gcagggcgat ggtactctct gaggacccac tgcgaacccc  21480
acctccctta caggtctacc aaatcatcac caacccaatc ctatcatggg agagattggt  21540
gggagtgcca ggccggtgat gctatctcga cagtaaatag ttttcgaact tcactaccat  21600
cgcctcgtca ttcatagtaa tcttaacact caaggtccga ctgcgggtca acttcagccc  21660
ataggcctga atcattccac gatggcgttc cagctagctg gctttttcct gatcctcgcc  21720
ctcggcttgg gacattactt ctccaacgac caggagtccc gatgtcggtg tggcccggat  21780
gatgattgct ggccctcgcc gacggcgtgg aaacatctca atgagacaat caatggctat  21840
ctgatgcagt tacagccagt tggagctgta tgccacgaaa agtattattc ccacaactcc  21900
tgcaatgagc tcattcaaca ctatcgcaac accacatggc gcgttaacaa tcccggtaaa  21960
ttggctatac cccgaagtcc caaaagtgac ttctgctcat actaactgcc tcttcatcgc  22020
agctgcattg caggtagaca cctgggaaca ttcgcgacca ctgaagcaga gttgccacgc  22080
ccaagacctg ccggagcacg gtcaatgcca ccagggtcgc gtggcacact actcggccta  22140
tgtcaattcc gtatcggcgg tgcagcaggt gatccaattt gccgcctccc atcgcctgcg  22200
actggccatt cgcaacaccg gtcacgatct ggcaggacgt tcatcagccc ccaactcact  22260
gcagcttcat actgctggtc ttaagggcat tgattatgtg gaatcgttca ctcctcaggc  22320
tccagcgggt caatcagtgc cctcagacgg tcccgcggtg acagtagggg caggggttct  22380
cacaggagag ctttactcgg cggccgcaga ggcaggatat accgtggtag gaggaagctg  22440
```

```
cagtacggtt ggaatcgcgg gtggctggat gcaaggtggt ggctatggga ttctgacccc  22500
atcacgagga ctgggagtgg acaatgtgtt ggaaattggg gttgtaacgg cgcaggtaag  22560
tggccaaccg gtctatatgg ccgatctggt tagcttgcaa gtttggctca caagttgttt  22620
ctcctagggt gtctatgtca ctgcaaacca gtaccaaaac caggatctct tttgggccat  22680
tcgtggaggc ggcggaggca catttggggc cgtcgtgcac gtcacattcc gcacctaccc  22740
agattctccc gccaccgtgt ccaaactgaa tgtggttagt ccccatgggc tgaattctgc  22800
cttctgggaa gccataacgg atttgctccg cgcaattccc gtcctggtgg atcgcggcga  22860
cgctgtccaa gcattcgtga tgccggtcat gcctggcaac accacatttc tcaccatcga  22920
gtcctatctc atcaatgaaa cccatgtcag cggtctcgat gttatccggg agctaaaaaa  22980
aagcatggaa gcgcgcggtt tatcagtgga gtcctccgag gaatccttcg attggttgtc  23040
tgcgtatctt gcgattccca aaggtttgga ccaggccggc atggggatga tgaccgcgtc  23100
aagacttgtg tcgcgagagc taatgacatc agctcaggga ccttcgctga ttagtcagac  23160
cctcgcccag cttagttatg accctggaaa tgtgctgagc ctagagggaa tggtcggggg  23220
gcccgcggtg cgaggtagag agacagcgga ccgcgcaacc catccatcgt ggcaatctgc  23280
tgtcatgtcc ctaactttgg gccacagcct accctcagct ccagattgga ccgcctacag  23340
ccgtgcccag cgggaactgg caatgacgca gctaccggct cttcaggccc tcgaacaggg  23400
gacgatggga gggtacctgg gcataccatt cccgtacgaa agccatcctt cccgtgtatt  23460
ctgggggtcc cattacgata ggcttttgac tctcaaaggg cgttgggacc ccgatgattt  23520
attcttaact cgattggggg tcggttcgga gcggtgggat gaggaaggca tgtgtcgagt  23580
tggtcgggcg caggcttttc tgtggtggta ttccagcatt gtagatcgcg tcaaatcatg  23640
gacagcgtaa ataatatgta gtcatttgcc gaaacggatt attgtatgga agaagtggga  23700
cgctcttgtc actgggatag gttggccttc gatccagcaa tctcatgagc tgcttacaat  23760
tcgtcatttc tactcttgct aacattggga ttgtcaatgg atctgtcagt gtaaagttct  23820
aaatatgtta tgttcaaaaa gtaccttccc tttgactttc tacaaaatca tgttcaaatt  23880
ctcaataatt ttcaatgaaa accctgcctc agcatgctac tgtattcgga ctctctctcc  23940
actcgctaaa cctcattaag cctgctgcag tgattgtatt tcaaatgcat tgattcttgg  24000
cagtacagat acgtcgagca ttggaggttt gcctaagacc tagtctgcct cttgagtacc  24060
tacattcact atgtagatca ctaacttagt aaaaagaagt cacttcgttg tacttataat  24120
ttcttcttaa tttccaagtc agcggagcat taagtttgtt tctagcaaga tatttgaatg  24180
ctcccatctg ttaatggggt atatacggag tagaaatagc ttaaagtcgt tcggttaatg  24240
tcccggtgag aatcattcaa agcgacttta ttttactaag cgggactagg gcggggggtg  24300
gcgggggtgc atactaaaca aaagtacctc agcgccataa gctctcccac aatgcaggct  24360
gaccaaataa tgcattggaa atacaattac tgcatgacgt ctaatgaggt ttagcgagtg  24420
gagagggggt gcgaatagca tcgtgagggt gtcctttcca gattgcccta aagtaaaatg  24480
actttgcgct tgttaaccac cgacaaaaaa acagtctcaa gaccagacgc gctggatagg  24540
ctggggatta ttacctggat tacggagtac acgtagatta attcttgagt tctactgtaa  24600
tcttctgtat tcagggggaa tagccgagta taccgcaaag gggagagaaa ctgaaagaag  24660
atgatcggac ccattatgcc agttgcctta ttccataggg agaaacacag aagcgatgta  24720
gcaatgaata cctactgtat gtacattgtt gatagttcca cgaaagaaat tactgcattg  24780
```

```
catttggata acgtggtttg atacttgaca agactgtact gtgcatcggg cgacacgctc  24840
aaggtgcggt atcctttgca gactggcttt ccttaccttt cttcgtacgt tcatgtgtgc  24900
tgtgcaagaa ttagatgaat cttatgcgct gttcaaatat ctgatcggac gtcgtcgact  24960
tcctggtacc cgtgatggtt taattaaaaa ttcgaaggat cttttttgca cagcgtcatg  25020
ttggcaaatt ctaaatcatg aatttacctt tcgatacctt aacgtggata tgtcgcttgg  25080
agtcaaagca aatgaggtga aacgtgcacc aagcctttcg atttatacgc aaatcagtca  25140
tattttgaca gcctctactt taatctgata ggtatggaaa ccatatatga gagttacgtg  25200
tcgttgtgac taaaggtagg atgaaatttt ttgcagggtt ctattttgat tgcggaactc  25260
gggtaaaccg gggacagtgg tctgcgagac aaatgaatgt agtccataat gatcgagagt  25320
ttcacctcgc cttggaatgg agtagcaact tcgattgagc tgcctaataa ttgcgtgaaa  25380
ggccgcttga atctatcaat taatctcctc taattccaac catggatact catcagagga  25440
atggtagtat acactcaggt aaacccccgt cttttccgtg tacgcaaaag aaatccacga  25500
tgtcagacga gcagttttgc ttaggtctct ctcggggctg tcaaagttag caattgaatc  25560
atttttacag gggacaggag aagtagagaa gtcatacaaa tagtgccgta ccgtcgcctc  25620
gtaattgtca ccatacttag acaagccgat acgggacaag aattgagcta ggccaccaat  25680
gacgttttga tcactctcgc catggattgg aaaatagaac ttcgtgagtg ggaaggcctc  25740
gccaatttc atctcgtaat tccataccat cggggttgcg gtggcatctt tgccgtcgtc  25800
gaagccgcca ttgaattcac ggtgcccttc ggatagctta gttaactccc acagctcctt  25860
tagatacact agaccctctt ggacaacagg cgacttggcc cgccctccaa gtgtccaaat  25920
ctcctctacc ttggaccaga ccacgctgtt gtgagagcta tagagcttga ggcgtgattg  25980
ggcagggtca acacagtcaa acgaccaaaa ggcaaactgg ctatatccat tcgttccttc  26040
cagataagag tggaccatat caaacgaggg gatggggccc atttgcgccg caagaggctg  26100
aattgattca gaaatgaagt tcccaaatcc tttctcgttg agggtgcatt tgatagcggg  26160
gaatgtgtag cccttgactg agatagcttt ttccttcaga tcaaacccaa aagcactctg  26220
ggaggttaac tcgctgcctt caatcttctt ctccttcagc agccctttct cgtggccatt  26280
gacggtatga gcgtccagga aatatcggaa cagtgatggg tcgaatgccg gtatattgag  26340
cacttcaagc tggttcaaga gatcaacaac tgggatttgg ttgtagggat caatttctgt  26400
cccagacgct gcagcaactg gttcaaatcc gatgcgaacc accgggtcga tatctccccg  26460
ttgctggtag ttgacgctga actccagcgg cagcccactt cgggtaattg cgctgcggaa  26520
ttgatgcggg tgcgggccca gaaatggaat cagcacctga atgtaaaacg tgagagcctc  26580
caagcgacgg gcagggttat agcctgctga agctaggatt ttgtcgagca gctggccggt  26640
cctctcccac cagaccttct ggtggctatc aacgaagaca tggtctcggc tcagtacgtc  26700
gaaaattgtg ggaatgggag aagtggaatc ccccttagcc agcatgcctt tggatacatg  26760
gccctcggtc gcttcaatcg tcatggtgat tggagagtgt caagcgacat gggaataatc  26820
aacaaagtag tgaggttgcc tttgcctggt gtggaagcgg cttccagggc acatatatat  26880
aattgaacgg gtcaggatca tggaaggttt cttgtacgtg tatcgggata catcgcacca  26940
aagaagcgag cagaaccacg tcacgaacat aaccacttga ccggcatttt ctcccaagac  27000
tatttagttt ctgcattggt ttgctgcaca atatttgctg tttcgcctgg ctggagattg  27060
tgcatcgtat tgcaagttgc atggccatct catgtaagga gtaatggcgc acgtatttta  27120
atgcttagct ggtcatttcc cccattggga gctaggcaca gtatttcctt tttttgctcc  27180
```

```
caatttgaat cccaagtctc cgtactgtat ctttacagta cagtaagata aggcgccaat  27240
atgcgaatat atcttaaatt gtactgccca gcatgtacta tggtgctagc ctgcatatcg  27300
gcgtctgttt atcggactta aacatgcact tcactctctg cccaaaaaaa atagtaaact  27360
ttcgggacga ctagagcata gtcatcgtaa ggaaaccagg acgcctgtat gaagtacgaa  27420
gtatgcacgt cgttgtgcag ttagacagac ctacgaaagt ctagacccct acaaaagttc  27480
gtgtatacgc ttggtcatat atcttacctg cactgtccgc atgtaatcac ggtgtcctta  27540
gaatgtgcat gaagctacag cgctactaac aagcgatggc atatcaacac gggtacgccg  27600
ggtacgcgca attccatcag taggagattt ctcctttggg gctcactccg tggcattccg  27660
gttaaatgag cgtggcggta aggggggcag cctgagcatt cgtctcgagg gccttccgca  27720
aagggagctg gtgggtatca ttgctagatt tgttgtcctc accaccacgg tcacttttta  27780
gaccctgggc cagcacagag atcatcttgg tgagaagcgc aattgaagag gcaccagaaa  27840
ggaaccgagc gcagacgcag catacatgtg tacctccggt agccccttca caagttggac  27900
cagggcaaag agagcggtga cgagatcata gcattcggtg tacccggaat aacacggtaa  27960
atgattcgtg gatagcggct acgatactgg ataatgcttc tgcaccaagc ccaccctgct  28020
caatgctatt gtttccattt acctgactcc caatgttgtc gctcgagacg ccccgattgg  28080
acttaccagc attctgggtc tggaactgtg agacttgtaa ggaatacctc tcataccttg  28140
cagatcagac agtatgtcgg atagaccggt atgcttgctt aaggcggagt agaactatgt  28200
cgacgtccca agcgatggcg actctgctca tgtttgcaga tcttaacatg aggaacgttc  28260
agccggggct gaaagggctc ggtgactcgt gtcgggcgct ccactgcggc ccatgaacgg  28320
acagttacct taatgttatc gatgtggaca ggtgagtcat tggcggtggt cacttctgtg  28380
gcggaaagga ggccctgcag ggctgctcgc ccgattttgc ctgccgggct ctgctcggtc  28440
agctcttgtg caatgaggct gtagctggcg tgtattacat accacgccca agtctcgcaa  28500
tcataaatcc cgtgcttaca ttggctgact atgggatagt atgcatgatg tgttggcttg  28560
cgctacgggg tggtccactg gtgctgccac ggaacgatac atagagagcc tgatcactgt  28620
gcagagaccg tgattgaaaa tatcgatgtc gatggattcg tgcccgactc agagagtatt  28680
tagcagttgc tgcaggcggc ctgcaagcac atgtagtacc agtgcaacta cttatgaccg  28740
acgaattgaa aactatgcgg tgtggcaagt ccttacgccg aaccacatta tctctagaga  28800
tctttaaaga atttctcttt tggagcggtc atagtggttt ctctgtgtaa tatgcaagta  28860
gatcgatcgc catttccttg caaaaagtac atgtgctggg tcttgcaccc cttgcatgca  28920
aaggcaaatg aatgtcgagt tgattccaga cgatctgttg gcagaccgat aaccattggt  28980
gtattaaaat ggtcttgccg agtcccattc cttctcatgt ccaaatacct cttgtgaaac  29040
tgcttagcct tcctgtgtat acttcattcg gtctcagcgg aataccatca atattttcta  29100
tcaaaatgac cgtctcaact gaatcaaatt tcccacatgg ggcgagcact cagaaacctc  29160
agagcgcgga accagagata tactcctccc taacaaaatc tttggacttc agcaacgatg  29220
cagaagagaa atggtggacg cgaacagctc ctctcctttc cagaatcctc gattcagccg  29280
gctacacgct tccccagcaa tgccagttcc tcaccctctt caacacgctt atgatcccga  29340
actttgggcc ccatcctcac atatggcact cctctattac gcactccggg cttcccgtgg  29400
aatttagcgt caattaccaa cccggaaagc aaccgaccgt gcgcattggt tttgaaccgg  29460
cttcgtccat atcgggcact gcgcgggatc catacaatat ggtcaccgtg ttaaacgtcc  29520
```

-continued

```
tgaacaaaat gtccaggctg aacttcaagg gcttcgaccc atctctgttc cacactttga  29580
ttagttcact cgccctctcg aagaacgaaa gtgacctgct ccaaggagcg aagcttgaag  29640
gctccaagtt caagacacag gcggcctttg ggctggatct gaagggagat gctgtgacgg  29700
tcaaaactta tctctatcct gcattgaaat gcaaggtgtc tggacttgca tttagcgagc  29760
ttctggaggc cgcacttgct aagcaccaga acgctcacga cttttctcgg gtgctcccat  29820
tggtccaaag ttatatggag gaagggcagt gctacaatca gtactctttt gttggatttg  29880
actgtgttga ctcttcaaag tcccggttga agatctacgg agctctgttg gatatatctt  29940
ggaagaaggt ggaggaggta tggacgcttg gtgctcggtt ggtaaatagt gagaccaaca  30000
aggagggcct taggtatatg cgggccctgt gggagtacct gacacccgga aaggtgagat  30060
caataccccg taacctcctt tcaagaggct taccaagaca ataggaacga cgacctgtgg  30120
gaatctggaa ctacgagcta ttacccggga gtgaagagcc gatgcctaag ttctatgtgg  30180
acatgaatgg cgagaacgat tttcaaaatg cgctgggcat aaccaagttc ttgcatcata  30240
tcggattgac gacaacggct gaaggcttga tcagcaaaat ccaggagtac ttgtacggag  30300
tcccccacta ccctttgtcg caaacacatg tgctctttgc taaccaaggt cccatgcagc  30360
cccggtgtga accttgagga aacgactgaa gtgattcagt acgtgtcttt tgcttggagt  30420
aagaatggac cttatttcag tgtttattac ctatcgtcct actaagacga taggttatat  30480
aatcggctaa gagacgttgt tacgtagctc ttacgttgct catactcgta gtcaaaacac  30540
ccagtgtgct ggcacaaatt tcggtccgtg cacgatgcat ctggaatttc ttgctctggg  30600
agtgatttct agaaagtctg gctagtctag tggtggaaat agtcacaaac aaagctttct  30660
atgcctgagg tgtctttcgt atctcctgtt atccgtatct tatcttgtct gtaggaagat  30720
tagacaagat aactactatt gattgaccta tacttttcgg ctttcttcgc tttagaattt  30780
tgatattgat ctttattcac tatatatcct tcatcactct tacaacgaca gtttgtatat  30840
gtgttggctt atgctacgtg gtcagagagc caacgagcga tctatctttc tgcaaggtcc  30900
cagtgcattg gtcatttgcc tcttttgctt gacggcagta aagcatttaa tatgaaaaat  30960
acaccgccat gcttcattcc agattgacac tgctgtgtct gagctgaacc ctgagcgcta  31020
catgactcgc atcgccacct tgtaccagtg gcaggtccta ctcgtggaca tgagaataaa  31080
ttattgggac aatttatcac tatgactaag atatgtctta ggtaacttga ttgtgatctc  31140
tgtaactctt agtttagcgt ccgtcttagt ctagctgtgc tgcggaggta ctcccataat  31200
cagtctactt ccaagcgcaa cataaatcaa cgaccttcct ttgcgttcac atttcccagc  31260
tcagacatca tgtcagtcta gcaagctgat ttaatcgcgg aaatatgagt tatattactt  31320
cttctgacag tgaatcacag tatttgattt ggacattgta tagtagtctc ctcccttact  31380
acgaagtgta aagtttgtgg ttgtaacgca gtgcaccact aagcttcgca ccactaagct  31440
ttctagggtg acttgttctg caatggctcc ttaacgtcaa cattccgaat ccccagttgt  31500
acccgtaact tgtcaggcag gttcgttgcg tgatattcct ctccttcctg gactgccctc  31560
accaccatct caaactcctg ctcagtataa gcctggctgt catgaccata gatccaggtc  31620
tcaagtggga gagaggcaat attctgctca tttggctcat aagcatccca gtcctgattc  31680
cgccagcctt cgttcacgcg atggcttatc agctgtacag ctgaggctcg agcatagcgt  31740
atccgttcag cgacgtgaag agccagggag actcgttgtc gtccggccag agacagacta  31800
gtagctagga catttgcgtc ttcaattccc tgggatgcac cttgccctgc ggcaggggag  31860
agtgggtggg ccgcgtcccc tataagaatc aatcgaccat ggctggatac ccaatggtct  31920
```

```
aagggcttgt ggttcaataa cgggtagttg atgaactttt gaggctgggt atgtcggatt  31980
acggaccaga ggcgctgccc aatgggccag actttgatca gatccagcat ttcgttgggg  32040
tcggcagggg acgtccagac gtctaggaga tttcttgtat cctacacgct tcgttagctc  32100
agatcatttg tactggatgg aattcaacat acctgatgaa tgcagaacca cgaaaagact  32160
ttccctttat tacaagactg cagggcgatc tgagcaccag aaaggaagaa gacatcaaac  32220
cgatcgtttt cttccactcc ctcaaacacc cagctcgctt ccgggtcacc tttaagtgtc  32280
tccgtatcta ccagtgcccg aaaggccgcg tatccagacg gacgaggctc aacaggttgc  32340
ggcatgatcg ccttccgcat tttgctgtgc accccgtcgc tgcagataat aaagtcacct  32400
cgtactatct gtcgttcgcc atctcgggta agggcaacaa cactggcgcc ctcctcgtcc  32460
tcggaaggct cacaaacttc cacaccgagg cttatctcca ccccgatctt gagcgcatgc  32520
tcatacatca ctcggataag ctctgaccgt gggaggaggt agtttggctg ctcgcacacc  32580
tccgagaggt cctgtcggat tatcagacgg ccggatgagt tgtgtatacg gatttccttg  32640
gatgagacta tccagggtcg gagggcttcg tgaacagcac catcgcccca tcgtttgatg  32700
atgcgcgtgg cgttgctttg aagaccaata cagtctccta cacgaagggc agtcgcacta  32760
ttagcttcta ccaccaaagt tgcggggcac agtcttaccg atggacttca gtatattgct  32820
tttctcaaaa gcgtggacac tatgtccctt ctcgcgacac tcgatcgctg cggcaagtcc  32880
gacgatgccc aggccgacaa ttattacttg aacttcttca cctaaagagc ccatatttag  32940
tcacttttgg gtatgtgcaa ttctttgctg acaattccaa tcacagatga tgcggcattt  33000
gacaatgata gggaagagct ctattcaatc ctgtctagaa cgttgatggc cactactgca  33060
ggtgaccagg gtttttaaaa gcaatgaatg ccaatagggt tacgccccaa aattattgta  33120
tttattactg ttagttacat aatattaact agtagttaga ctgcttttat gccggtatat  33180
gcatgacggc tgcatgttaa tgcatactcg caataatttg taagaaagaa aaggaagaaa  33240
aaaaagaaaa aaaagaaaaa gaaaaaaaag gaagaaaaaa ggacaaaaag aattggtcac  33300
ctacagtaca tgcgtccgaa tacaaacaac cagtctctgc acggaagatc ccgcgaagac  33360
cattcattac ttccttcctt atcccaccct tcgcctgtaa tgggcctaca ttccgcggtc  33420
cgctgagccg ctcatccgtg cgatatacgg aacagagaac ggattcacag tacggtgaag  33480
agcaaagcgg tccaaacgaa gtaagggatc tactattgag gagatcccac cgctggtttt  33540
cttcactgct ttttctgttc ttcgaagaac gttactacgt tgcacaacac ggggtacagt  33600
agttctgcag tacgcaatcg taacccttgc tgacagccac aacgttacac ttatatagcc  33660
ctatcttggg gaaacatgag gatgttgacg atgaggctgg tggggcttta cagagctaca  33720
gcgacccaaa aagagagatt tgatatgact gctgcaggga aatcccccgt gtcactagta  33780
ctcacatctt tgacctcctc cggaacccgc caaacagcac cagtcttgct atatttcgtt  33840
tacgccatcg ttctccttcc gttggacccc agtataacct agtaattacg cggtaaactg  33900
tgcaacttcc gggtcctaat tgttgcggca catttatcaa atttgccgtc gtagaggcag  33960
ccctcaagca cgaagccatt gtaactaccg ccagctctaa ccctggaaag ctaggaatgg  34020
gcattgcctc gtcttagatt ctgcaatcta tacgccagca cgaacatgtt caggagatgt  34080
agtctagcct tacggaggtt gtgaagagca ttctaggagg tgcagctgac ctattgtgga  34140
ccacatcgaa cttgggtatg gatgacatgc ctgccccagc taggctcttc gttgcccacc  34200
aggtcaagac ttttctctgc caaatgaggt tgaattacga tattaggctc ccgggtaaac  34260
```

```
agccacatga gaggatcctg tcgggcctct tttgtgctac gagccctggc aattggttgt  34320
taattaagag gcgcgagccg aaggttggac tctagtagat cactgcagcg taaaaatctc  34380
caacaagata atatatatat acgtatgtct ttgtctgctc agatatagtg attatcgcgc  34440
acggtcaagt aggcctgaca gaagactctg ggacggctag tattgatgtc tgcaacttgg  34500
cgaagtccta tgcaaggttt tcttgaactg aaagttgctt gttggacttg accgcctgag  34560
cgaagctcct agtcaaaacc cactcagttg cctgattacc gcggtagcct ttgtgttcaa  34620
ttgttggctg ttccccgttg gggtaagtct atctgacctt catttctttc gccctggccc  34680
tgtttgtgtt acgtacaagt tgttttggtc agtgccgcag atttgttttc gccatttgtt  34740
aagttggact cacagagcca ccggaccagc tggtacccat tactttggaa gttgctcgag  34800
ttgcctttta tcatatttgt ggtgtttcac tgatgtgtat agcaaagaac ataaaaaggg  34860
tggcattcac ccaataagtc tccggttcaa acccgacgct acatgtcata acaatcaaag  34920
aatgcaacac ttccaccttg aatcagagta gtaaaaccac taaggtacaa ctacctgcct  34980
agaacccagc catttccctc tccgtaaacg ccaagtccaa cggggccaac cccatcacaa  35040
acccatccgt cctctccctc caatacttct ccggatctgc accgggcgca agcacaattt  35100
catagcgccg aatcaactcc acaagcacat gtctcacctg cataagcgcc aaacttttgc  35160
cgagacaatt gtacgggccc agtaaaaacg gcgcgaaggc ctcgggattc ttcaccaact  35220
cctttcttgt tgtccagcgc tcggggatga acttttctgg ctctgcaaag ttacgctcgt  35280
ctaggaagag tgtgtagaag gggatcttga tgttggtgtt tcctgggatg taccgtccag  35340
cgatgtggag acccccctggg ggtgtttggc gttggaagcc ggagagggca gggtagtgga  35400
ggcggagggt ttcgttgatg acggcgttga gcgtttggac tttagaaagg gtatgcgagt  35460
tgatttcgtc tagtgtgtcg agctcttgtc tgatttgggt gaggtagtct ggggaggtgg  35520
aggtgaggaa gtagaggcag ccaatgattg tgacggcgac cgttccactg gagaagagcg  35580
tcagggtcta ttgtctggta ggggatggat gagaaaggat tgtactaacc tgcctgcgaa  35640
gatgacgagg gatgcatcag ccaccagatc aagtttcgac tgcggcgtct ccatcccctg  35700
ctccttaaaa tcctcccaca gccacgaaaa gacatcccgt tgcccggatg tctgcatctt  35760
ctgtctgttc tgaacctgtt cctcggaaaa cccaataagg gccttcatat tcgcattcaa  35820
gcctggcgtc gctttgatga aggagatgag ccaaacaacg tggctgacga caccggtgac  35880
taggttggac gagtcgttga tctccataat gggatgtctt ttgttgtgtt tcacgcattc  35940
gtattcttgg ctgaatgcga ctcggccggt caactaccag tttgattagt ttggtgacgt  36000
ggctggtgta gtagaggcgg atgcatacat caaatgtaaa tagattgatc cagtaagtca  36060
tatccataga cttccccttg cgcctctcga cctgttccaa gagctcattg gtacccttct  36120
ccagcgcagg caggtactcg agaaccgcta tctaccatta gcgcggccat tcgagggaaa  36180
agtttatcga gatcatctac cattcggtcg aaatgcaagc tcccaaggct tccggcgtcg  36240
gctatgttcc gccttgtctc taatcgcaaa gagagagatg aacgggtgga gcatactata  36300
ccatggcccc ttcgtacact ccgaccggcc ggagtggaca gcttgcaggg catcaggatg  36360
gttcaccgaa agctccgtcg gtcctgtgcg cacgaaatcg ccgtactgct gatgcagccc  36420
acgcacggta ttgaaggcat ccgggttctg cgcgtatagg ctggtcacat accacattga  36480
gaggcgagcg ggaaaggggc cagggaagct gttgagtcgg tggaagaatg ctcggtagga  36540
gagaatgctg acggtggttc cggctatgaa gccaagggtg atttggccta ccaaccatag  36600
cgcagtgtag attgaagttg gagggccggg gacgaagagg tagtagctga ataggcagct  36660
```

```
ttggaggata aacagaccga ctgggatcct ggcagcagcg atatcccatt ctccccgcct  36720
gaatatgatg atatgtgccg ctattccggc cacgaaggcg gtcgttagac gtgagaagtt  36780
ctcgttcgag gcaagcatgg gtagcacttt caggatgtgc ccgtcatgat gaggctccat  36840
attctagact ttagattaaa caatgctcac agatgaggtt cactaggcag tttggttcgc  36900
accagaggca aatttaaagt cctgctgttg ggataggaag gcagataagg ggaaggcaaa  36960
gatgagaaaa acatccgacc aggtcgggag gccattgccc actatttaga ttaccaagct  37020
tctctggact atggaagaga acggcacggc acggcagatc cgctgcgagg gtcgtataca  37080
ttccgtcgtt ttacaccgca acaagcagtc agcacataaa cggaagggat cggctgcggg  37140
ttatattgaa acgcctgtgg atattcagta ttggtgagac ctggcaagta cggctcacct  37200
aaagtatcga cactagcgat tgatctccca agccttgtcc taggggttga cgatcaactg  37260
gaaagtgtgt ggagtgctag caggtacatt acatactctg ggcctagatg tatgcctctg  37320
ttccaatttg aatatactgt agtccgattg ttccatctac tcctccttaa gcaaagtacc  37380
accggctatg gaatgcgcct ccttctccca ccgatcagac aatatcctga cctggacatc  37440
cttcctattc cgtgcactaa tccgatctac ccactgcatg ctgctctcat ccgtctcaaa  37500
caacgacatt tcaaaccgtg aaaatacgta tgctgtaaca caaaatagtt ctaggtatgc  37560
aaggctgcga tatcattagt gctcgcgctg catggcataa aattcgcctc gtggcctagg  37620
atataggggt atactaacct gctcccaatg catcgccgag ggccccggct gaacccgaca  37680
tgccatctct caagatcctt gccctcttca cccagccaac gctctggttt aaacttgtag  37740
gggtcgtgga agatggtgtc gtttgtgata attgacagat ggctggagga tacaatagtc  37800
tgctgagggt aagtcttgat aatacaataa cgataagcaa atagggcagg acatacgcct  37860
tcaggaagat agacagatcc caccgtgacg cctccggggg gaaccagtcg gggaaggttg  37920
ccgggcaccg ctgttgatag tcgcatggtc tccttgagca cggctccctg tcgagtagtg  37980
ttacggtcag cagagaaccg aaaacaaaaa cggaaacctg gggtccctat aggaaaacgt  38040
accagatacg gtagagcctg aatctgcttc gcattgaagt cattccgtat gaagtcgacc  38100
gaagcatcca gctcctcgtg cagctttttg aaaacctgcg gattattcaa gatatggaat  38160
gccgtagaag agagagtata ggccgttgac tcggtacctg ctgtcaggaa attgaaagca  38220
tcctcgacag gctgagccac gccgctcaca gcggtctcag ggccagcgcc cagctccgcg  38280
tagtagtcaa agagattctt ttgccctacc tgcacgcccg actcacgttt gagttgggct  38340
tttgcctccc aggtttcaca ttgctcgtgc cagtcagcaa gtggaagagc ttagtacagg  38400
ggcagtactc actcgtttga aatcgttaaa ttccggggcc agcttgtcgc caagaccaaa  38460
gggtaggtgg aattggattg acttgaccca aggaaaatag accactgtca gcaacattag  38520
taaccttcct ggcattagcc tcagatatct cataccgagc caggaaaacg cagtaaaccg  38580
atccagtgcc gcaacaaatg gatgatatcc attgccgtcg ccaatgaagt ccggactttc  38640
gccaaaaagt agctcgcata ccatatctga ctatgctcac gaagtatacc gtcagcacta  38700
ccatctgcag aaccacccaa tttggcaagg aaatacatac cgtgaaggag cgatacagtg  38760
cctgtatatt caacggatga taatccttcc ggtgcatatc aaagatgcgt gttgctttct  38820
cgagctcaag tttcaaacga ggtaccactc catcaacggc acggctggcg aagagtggtc  38880
gcaggtggtt ccggtacatg cggtggtgtt tagggtctag gattgaggcc attgcccctt  38940
ctgctccgag cgctttgtag aactcgggct ccttatagta cttcgttgtc atggaaaaca  39000
```

-continued

```
tcctgtgagt acgttagctg cgtgcttaca tctgctcaat gtatttgagg ctcactcctg  39060
gtagaaactc gggtcatcga catggacagc attggggccg attcggatga ctggggagtc  39120
tataaaacga acactcattt agacccaagc gatactgacg aaaccaatgt tcaacgtacc  39180
gtatttcttg tgaagtgaag aaaaagatag actgtattgg ccatcccgaa taacattgtg  39240
gtaaaagccg taccacttgg tcaatgcagc tagcttcggg cccggcactt tgctgagagg  39300
ctggaagaat attctgttga cggcaatgaa gaacccataa gagataattg ccagaagaaa  39360
tgatcccagc actgtattta tgcttggcgg tttactcccc aactgtatgc aacccgtctg  39420
gtggcagtcc atcgctcgca gatgtgataa tttagcaatt gatggatgag actgaggtcg  39480
tcaagcttcc ctcttacgag attatgccct cttgttctac aaacgcggac agtgggcggc  39540
ttggcgtagc ccgggggccg tagacaaggg gagtgggcat ccttggcgtt cgtgcagggg  39600
cctacttcac agtacatgcc agttgtccct tgcttcattt tgcagagtga tatcacatgc  39660
cttgaactta tccgtgcata attggggttt aaattgtccc tgcctcatgc gattgcgaaa  39720
attggattga tacaatttac atggacctca gccagcctca atttgtccca tgaccatgaa  39780
tcgcgtgttt tccgtcaatg gtacaatcca ttgttatttt acctgtcgag tatctgcaag  39840
gagtagagaa ctgcattagc tctttttac attacggtac tgtatagaca aaaaaatgca  39900
acacaataat tctcaggagg ctttgctcaa cgtttcatag ctctaaatgg ttccacgggc  39960
tacttgtgac cttcatggca tactgtatac cgactcaagg acacctatat aatattgcag  40020
agatcaatgg tacttttagc aagaaccctt tagcgtaacg cgcttgcttg agaatccata  40080
atttcttggg tatcgccaat ctggaatgaa tcaatattgc agaataattc ttttccgcgt  40140
cgaaagcgtt ctgattagaa tttcggctcc ctcttctgaa tccagtcatg gtacaattac  40200
taatttctct acagttcatc tgataacaca tctgggtgat attagtatct atcttgacga  40260
gaccaccaaa ctaaaatagg aagcctgaat ggaggcctgc aaatcctgtt ttagtgcgtc  40320
cactaacatc tgtgtccgaa acagtggtcg ttcattatta ctggttccat tcattttttc  40380
taagtcagtc ttctatagtc tctacatata ctcataacta tgtctggtat tcggtcggaa  40440
cacccggcca cgcatcagcc ccatccaaca acgccaacgc cacgccacca gactgatgtt  40500
cctgcgcatt acagtgaaga aaaaacgccc cggtttaata atttgttacc tatttgccaa  40560
ccagctacag cgaagtgata atcccggcgt cccaaacata tccctatctg cggagcttcg  40620
acaagtatag tttggttgat tgttcgttaa tgaggtgcga ggggctgcgc ggtgtataga  40680
acagagataa taatgtcgac ccaggagccg ttcctcgtgc gcaatgcggt gttgggagga  40740
agacagtcag gtgggatagt aaaggaaaga aattctactt tatctggagg aagatagctt  40800
tacccatgaa ccagccgtag gcggagtcac ggcccatcat gaaatggtat gtcgcgtcga  40860
cttgtagaag gcctttgtat ggggctgtgt tgaatggcac caagctattc acaaggagcc  40920
tcctatgctt gccttgttta aggtggaata ttggagccag aaattggtcg tttgtaataa  40980
tcaactttcg tctaatgccg gctactaccc ttttcttcta tgtaattgat agggaaacgc  41040
cttagagaca gacggtacct tcagacggcg gcgacggttt atatagtaag aactagacaa  41100
ttatgccttc ttctttttat tgcctctcgt actattgatt taggaaaggc tacttccgta  41160
cgggtgtcgc cttagaaata tatatacgct aactagtgta gtagatatat tcctctctat  41220
aagggcatac ataatagcac acttagggct acttagggct acttagggta acttaaaagt  41280
ctaaattccg taataagcgg taagggttag taagaaaaat ataacaatta gtagagcacg  41340
acttagctaa agctatagta gatagttaag ttaataccta gctacgagta ggaataactt  41400
```

```
aggcaataaa aagacataga ttaagcacga gtagaagcta ttttatatag tatatatact  41460
atatagtgac gaagcatagc cgataaatta atagcaaaag ataaccctct attcttatat  41520
cggtctatat tctaagaaga ataagaaaac tagttatcta ataccgttct gcctttaaat  41580
tcgtcccgga tatagggacc tatactacgg agaataatta caatttttag ttcctaattt  41640
agtttctagc cgttaagggg ggttcagcta taaagttagg gcgttataaa tgatcaaatt  41700
attaccgcga tagccttgtt ctcctttatc gctagcttcg ccgtcatcct ctccgtcggc  41760
tacggaatat acacaaccgt aacgtccact tccggatgtt acggacctac caggcaccaa  41820
tcgattatgg ggcagcaact tactgatggg ccaccgagag ccaaccgatc tatctgtcat  41880
cagatcacgt gcagtacctt atactctgga caccccaggt attcaaggga aagagaaacg  41940
tgatcatgct cagtgagcaa gagcatgatc taccctgggc ggacccaccc ggcagacttt  42000
atcctgtaca tatgtagcta tacatgatag acaaagtctg cgcgctaaga ggccactttc  42060
ggccttccac tcgccatatc attgtatacc gcaataacca ataagacgac caccacgtga  42120
tcatgcaagc agtagaaatg tcgacagtcg aaagatagat tttgccaagc caaatctact  42180
gttctacttt ctactattct accacggaag gactcacgat atatatataa ggacactcat  42240
tcatgtatca agtttagttc ttcgtgttca atcatctatt gttacttatg tctactgttc  42300
agaaccttta gtgactcggt acaacttgat tataacttga caacactacg aatagacccg  42360
tactccggta taggttagtt cggcgctcta cctggcatcg ctcctcgata ccccccaaag  42420
gacttagccc gtataaggcc tgttaggcga cggtacggtt gagagacaga ttgttgacgt  42480
tggaagcgag gaagcattca ggcaagtata acctaggaat cttctaacat agcgacgacc  42540
cgttagtcgt gcgtaacacc ggacacactt aatggatcgg ctgtcaagct ctcgtaggca  42600
tcggagctgc tctcggttat aatttccccc tcatcgccgt gcagggccct ctcccgcaag  42660
acaatatcgc agccgcaacg caatcgttct attcgcccag aagcttatcg gcgcgttaat  42720
cactgctatt tagcagacct tgtttcagaa tcatctttta gtcagtgtta tccattatgc  42780
accttccatg gcacccaaga acgtgaccgg gcctggggct gcagagttgc ccagctcgtt  42840
tcccccggcg atgctggcgt tactcaaagt gccttataac gctgctacgg gacaaacgct  42900
atgtgttcct atggcgagga gcgccctttc tctttttggg gcggttttct tgagtggttg  42960
aagaaacaga aaagttccaa aatccccgcg actacacatt gattttggcc atggggtttt  43020
cttcgagcaa gcccttgacc tccgtcatat tcatctagga ggcattcacc acttccgtag  43080
atttccttta ctcaacaaac tggcacaggt agtacgttgc tagatagaaa ttcaatgacc  43140
aatagagaag gacgcttttg ggaggaccat tattctactt ctaatgtgtc tccaccaatc  43200
tcccccctatt ctatttgtgc ggctctcatt cagacattat aatctgaaga aaaatctgag  43260
ttggttcttt atcaaaccca actcccgtga ctacgttgat cgcaattatg ggacgacctc  43320
aggcatgata gaggaatggt tgcaacaagt tcactgtccg gatttctcct cgggtttctg  43380
catagttcaa cgcagatgga tcgagatctc atatcagcaa ctctaaaata caaccgtatc  43440
ccaatgtcaa tacgtctccc tagccatcaa ctatgcctcc ggctttctag cgactatcaa  43500
aaacattggc gaaaaaattc ccaattcacc accacggtac attccatcca gaatcgtcac  43560
cacaagatcg acaaccttct gcgaacccgc agggaaaacc gtcatctgct ccagcttccc  43620
aacaacggcc tgcaagcccc ggttaataag cggcatggcc ctcgccgcaa agaaaacact  43680
cagcagcgca aatgacaata gcccctgctt ctccaaaaac gggtcagaca gctgcgtctc  43740
```

```
ccaggggatc tggtcgggtc gagcaccgag gtcgtcaatc gccagtacct cgaagccgac  43800
agctttcatt gcggcaatgg cctcagccga ggtgtgaatc ctagccaggc cgccgccgcg  43860
ctcgatgttg gtcttcacct cccggtgcat ggggttgttg tcgtcgtact tgtctgttag  43920
aactgcttcg tacactccga atcttgcgcc cggttttagc acgcggaaga tctcgctgta  43980
gacctcgaca aggtctgggg cgtaacaagt cgactcaatg gcgtacgccc cgtcaaatgt  44040
atcatctgca aattctatct ttaggaagtt ctgctcaaca aagttgacct ggtagctaag  44100
gccggcttcc tgagtcaact gacgcgcctg ccggagttgc tgcgcgttga tgttcaagcc  44160
tgtgatgttt gctccggtga atcgcgcgat tgaccgggct gggttcccga tgccgcatcc  44220
caggtcgata attcgttggc cctcttggat attgacgcgg tgggcaaggt agtgttcatg  44280
gcggacgagg gactgggcca tgggttcgtt cggggagagg cggcagaggt gtccgcacat  44340
acgaccggac ttttgaaaga tcgaagtcac taaattgtag tacctacaca gagtgtggta  44400
gagttagcgg tcgtcttctt ctgcggggcc gaggaggga accgactgga ctgagagggc  44460
atcctgggca gctttccgtc gcttgagaaa agtcaatgga tatgatcaag ttatcaccaa  44520
gtttcaatcc cagttactta catcgagttc ttcgggactt tcctggtgac ctgggctcgc  44580
ttcctcgggc ttccacacgc ggaagtaccc ttccgcatct tgattcattt gactcatggt  44640
catgatatcg ctaagcggcg ataccttggt tacagactag gaggaataga gaaatgaatg  44700
ggcgcaaatg tcacgaatgt tccgtttatg atcagttgga agggacacta agcatcttgc  44760
gttttatacc aaatccgcac ccaattagga caaatccaaa agccccgtc aaccaagcag  44820
tctcggagcc ccttgcctat ttcctctctt ctggcgcctc ttgtcccctg ttacacagaa  44880
agccatagat catagcctga agtacccagt aatctgcgcc accagctcga acgagttcct  44940
aataaggacc agtgagtgca acatgaatac aataggccaa tgccatgtcg atcgacacta  45000
cggtagagca gataccgctc accgactttt aatgcgttac gaaccatcga cgcatcgtta  45060
tagtatccat gatttcagtg tggcttgcgt cgagttgctg ccatcaaagg agctgaaccc  45120
ccctcactgt cccatttct gagaggaatt ctgcagtatc accttgcttt tgcatagggg  45180
agtggagaat atcaagaggg tagtagaaat ggaatgcaaa gatgtggagc tgacattgtt  45240
tcctccttgc tgcctcgacg cactgtatct ggccaatttt tctttttcaa aatattggac  45300
accatgcatt atcatgcagc cgtaacatat ataccagtct ctagcagtag aatgtagaat  45360
gcaatgacta gtcaatatcg cgcaatttac aataataatt acagttgttt cggtggagta  45420
agcctacggt attggcattt atcacggtaa aattatttgg ccaagctacc agtatagcgc  45480
tgggtttgcg aaaaccgagc tggcttggac cgcatgatca ctatcgtacg tagtgcccag  45540
gggcttctga ttgtgcaaat ttggcacctg cgcggacaag aaaaataggg cgcgtatcgc  45600
tcgacaataa ggatggatga tgaagcattg atggtcctcc tcttgagtga agaaaggccg  45660
catgctttct ggggcattta tgacacctcg ggccgctaat tcactactgt cacgggactc  45720
accactacaa tagtcaattg aacatgaaaa ggaaacggta tttcccttct agtggctcat  45780
tcctttgaga agtcgcagca tcagtggcca tcgccgactt cttgggatga acactgcatt  45840
gtacatttat tgcattccgc tgggcagggt aaccccact tcactcgtca tcttctgaac  45900
ccgtaatctt ctcatcccat actctccgta gcggcacttt cttacctgat tccaattttc  45960
cggcttttgt ttatttcacg agagagaggt gttgctttcg tgccccttat actcaaccta  46020
ttgtctcata cattttcgtg gattatcatg tcaaagtact tgttaatgtc gttcaccgaa  46080
ggatccatgt caacatggca ttatctagcc atgctcacca caatatggct agtctatcaa  46140
```

```
tatctgaagc ctgtaccaat agtccccggg cttccggtaa tcaatcgggc agagcgctgg  46200
gacttcttct cgatcaaaat gaagcgacgt ttcctaaata acgccgctgc actcatgaaa  46260
gaaggcttcg aacaggtgag ttgcattgga acacctctcc ccatcacttg agatgcagtt  46320
tctcagagct tgaagtcacc gaggggtttc acgatcatgt ctgtaaatgg acctaaattg  46380
gtcttgtcac cggactatgc agacgaactc aagaatgatg cacgtttttc tttggaggat  46440
gctggactga gggtaagcac tctgaatgag tttccgatga tggttcagat tcaaatgctc  46500
atgtctcata ataggactat ccacgcagta ttgactgctt gaagcctata agtggtggaa  46560
atttacaggt actacgggga tgcatcgcaa agattacaag aaacctcggt atcgcctgga  46620
ctgtgtaaat cgattgatgg acaatgtgtg ctaatattgt gggatttata gcctctttga  46680
cagcgccact atcggatgaa accagcaagt cttttcaaga tcattggaca gacgaccccg  46740
gttagtagca gttcactggg ctaattgaag gcgctcttat tctcggtcgc tggctaattt  46800
gcgagatact agactggcat cctgtcccac taggtagcgg cttgcaaagg atggtattgc  46860
agatatctgg tcgcgccttt ctggggccgg aggtttgcgg cgacatcaga tggattgagg  46920
caactatggg atatctggaa atgggggtca gaactgcttt ccttctccag gtctttcctc  46980
gcttcctgtt tccactccag aggtggttcc ctttgtgtcg caaagtccgg aagcatattg  47040
acatggctgg aaccattctg cgtcccgtaa ttgatagccg tcgggcagac ggaaggccag  47100
cacaggatgc gatcagttgg tttgatgaag cagccgctgg ggaaacgtac aaccctgttt  47160
attctcagct ctccctctcc ttcgcatcaa ctcacaccac tgccgataca atgaccaaag  47220
tcataattca cctggccgaa aacccagctg tggttacgga ccttcgaaag gaagttgtcg  47280
aggcaattgc caaacatggt gaattgacga agaccgctct atctcaaatg aatctattgg  47340
acagcacctt gaaggaatcc cagcgactag agcccttagc atcaggtatc tccaagccat  47400
ctgtctcctt tcgaattatg tgctctggca tcttgctgac aatacctttc ttccatgagc  47460
agcaacgatg aaccgggtga cgagggaaga agtgaccctc tcgaacggcc tatggattcc  47520
acggaacatg tatgtattgg tgtcgggtca tcgcatgaga gatccaaccc tatatccaga  47580
cccggaaaag ttcgacgcat accgattcgt caagatgcgc gagattgaga agaagaaaag  47640
cgattgtgca tacacagcag ccacggtgga ccacatggga tttggctacg ggaagcactc  47700
ttgccctggc cgattctttg ccgctcatga ggtaaagatt atcctgtgcc acttgatctt  47760
gaagtatgag ttcaaattac cagaagatca agcacgtacg tatttgcttg ccggattctt  47820
cacatccgct gggcccgaaa acgagcttct tgttcgcagg cgcgtcgagg aaattgcact  47880
ctga                                                                47884
```

<210> SEQ ID NO 54
<211> LENGTH: 1281
<212> TYPE: DNA
<213> ORGANISM: Penicillium fellutanum ATCC20841

<400> SEQUENCE: 54

```
atgggttcta ttaatattgt taccccctat atgaagatag ggcaatatct gtcttttcga     60
aatcgtgacc acttcagctg gtggcaccag aaaggtccag tcctttctca aatgcttcaa    120
gcctgtcact acggggtcca tgagcaatat caatatttga cactcttcta tgctcatctg    180
attccggcat taggagccta tactgagcca tcggtcggcc agaaaggaaa caccccttcta    240
tccggcgcag ggagacttga attgagccgc actttcacgg tcgatgattc ttccttgcgc    300
```

```
attgcatttg agcctaccag cttcctggcg tccgaaaaag ggacagatcc actcaatcgg    360

gtcccgctta gtcgtctcct gagcgtcctg ggccagctca gtggtgtgtc tctgggaact    420

gatcggtacc gtacccttgc agaccagctc actacttctg atgatgacga agaaaagttg    480

ctgaacgaac caacgcttgc ggagcagctt caaagcctgc cctctcgcac tcaaaatatc    540

ctggcccttg agctagtgaa cggattcgtc aaaccagaac tgtacttcca tccccagatg    600

aaggcactgg cctccggtgc gctagtggaa gatctcctgt ttgatgcact tcgttccgtc    660

gactcggccg ggcgtcttgg gaaagccatt gacctagcca aggaatttgt gcaagcagct    720

ccgacaacga cgcgtccgca atttatctct tatcagattg agagatccca tagcggcgca    780

gcgaagctct tcctcacgga aagcgcgatt aattgggatc agatttccgg tctctggaga    840

tatgctcagc cagagaccat ccaaacagaa cagaatcggg ccttgcgtgt cctctgggag    900

agtctcaatg tggttgaggg taaccgtggc cccaaccaat tccctatcat gatggttctg    960

ggtttgttcg ctgaagagcc gttcgtgagg cctcaggtag ccttccccgt ggttggaatg   1020

actgaaggtg ccattgcaag aagcattggg cgtttctttg acaatatggg atggaaagaa   1080

agctcccaat cctacgttga tggtttacgc tcatacttgt aagtctctct gagctgttcc   1140

ctatcctaag gcaaggggtg gaaaggctaa tatgaaaata gtccaaatga ggatctagat   1200

cagccattgg gcaaacaggc gtgggttgca ctctccctgt ttgacagcga gaacccagct   1260

ctcaccgtct tttactattg a                                              1281
```

```
<210> SEQ ID NO 55
<211> LENGTH: 405
<212> TYPE: PRT
<213> ORGANISM: Penicillium fellutanum ATCC20841

<400> SEQUENCE: 55

Met Gly Ser Ile Asn Ile Val Thr Pro Tyr Met Lys Ile Gly Gln Tyr
1               5                   10                  15

Leu Ser Phe Arg Asn Arg Asp His Phe Ser Trp Trp His Gln Lys Gly
            20                  25                  30

Pro Val Leu Ser Gln Met Leu Gln Ala Cys His Tyr Gly Val His Glu
        35                  40                  45

Gln Tyr Gln Tyr Leu Thr Leu Phe Tyr Ala His Leu Ile Pro Ala Leu
    50                  55                  60

Gly Ala Tyr Thr Glu Pro Ser Val Gly Gln Lys Gly Asn Thr Leu Leu
65                  70                  75                  80

Ser Gly Ala Gly Arg Leu Glu Leu Ser Arg Thr Phe Thr Val Asp Asp
                85                  90                  95

Ser Ser Leu Arg Ile Ala Phe Glu Pro Thr Ser Phe Leu Ala Ser Glu
            100                 105                 110

Lys Gly Thr Asp Pro Leu Asn Arg Val Pro Leu Ser Arg Leu Leu Ser
        115                 120                 125

Val Leu Gly Gln Leu Ser Gly Val Ser Leu Gly Thr Asp Arg Tyr Arg
    130                 135                 140

Thr Leu Ala Asp Gln Leu Thr Thr Ser Asp Asp Asp Glu Glu Lys Leu
145                 150                 155                 160

Leu Asn Glu Pro Thr Leu Ala Glu Gln Leu Gln Ser Leu Pro Ser Arg
                165                 170                 175

Thr Gln Asn Ile Leu Ala Leu Glu Leu Val Asn Gly Phe Val Lys Pro
            180                 185                 190

Glu Leu Tyr Phe His Pro Gln Met Lys Ala Leu Ala Ser Gly Ala Leu
```

```
        195                 200                 205

Val Glu Asp Leu Leu Phe Asp Ala Leu Arg Ser Val Asp Ser Ala Gly
    210                 215                 220

Arg Leu Gly Lys Ala Ile Asp Leu Ala Lys Glu Phe Val Gln Ala Ala
225                 230                 235                 240

Pro Thr Thr Thr Arg Pro Gln Phe Ile Ser Tyr Gln Ile Glu Arg Ser
                245                 250                 255

His Ser Gly Ala Ala Lys Leu Phe Leu Thr Glu Ser Ala Ile Asn Trp
            260                 265                 270

Asp Gln Ile Ser Gly Leu Trp Arg Tyr Ala Gln Pro Glu Thr Ile Gln
        275                 280                 285

Thr Glu Gln Asn Arg Ala Leu Arg Val Leu Trp Glu Ser Leu Asn Val
    290                 295                 300

Val Glu Gly Asn Arg Gly Pro Asn Gln Phe Pro Ile Met Met Val Leu
305                 310                 315                 320

Gly Leu Phe Ala Glu Glu Pro Phe Val Arg Pro Gln Val Ala Phe Pro
                325                 330                 335

Val Val Gly Met Thr Glu Gly Ala Ile Ala Arg Ser Ile Gly Arg Phe
            340                 345                 350

Phe Asp Asn Met Gly Trp Lys Glu Ser Ser Gln Ser Tyr Val Asp Gly
        355                 360                 365

Leu Arg Ser Tyr Phe Pro Asn Glu Asp Leu Asp Gln Pro Leu Gly Lys
    370                 375                 380

Gln Ala Trp Val Ala Leu Ser Leu Phe Asp Ser Glu Asn Pro Ala Leu
385                 390                 395                 400

Thr Val Phe Tyr Tyr
                405
```

<210> SEQ ID NO 56
<211> LENGTH: 7350
<212> TYPE: DNA
<213> ORGANISM: Penicillium fellutanum ATCC20841

<400> SEQUENCE: 56

```
ttaagagttg ataagaccat tccccaaggc gaccttgttg cgccgtttga acagcattgt     60

agaggcagcc aggtcctcaa gtgacgccag gtattcggca ttgcgcacca cagcctggcg    120

aatcatattt gtcaacgagg gcggttgata tataggcaca ggcaagggat ctgtaggcgc    180

aacacccagg cagcctccag aagcgcgaag gaaacccatc agcggccaca agggatgcga    240

tgtgccaacc tcgttgactt gctgttcaac tgtgtccatc cacctttgtg aagaggaagg    300

aatcagatct cgtccgagcc ccagcatgat cgctttccag aaatccgaca tatttagccc    360

gtcacctatg ctgacagctt tggcagaggg tgccagggga tttgcattgt cattgacact    420

gtgagatgac ggccgagcgt gaagcgtttc atggatgatc aggcttgcga cccagtcgac    480

agcggccaca aagagccaat tgtcagactc gtccgagttg taactgcaag tggtcattgc    540

agtcgtcacc acacgccaga ggaggtcgtc cccgttggcc actgcgttgc tgacaggtcc    600

gatcataaaa ccaggccgca caatggtcag ggaatgcgcc ttgtgtcgcg ctgaaaaagc    660

tccgattagc tgttccgagg caaactttgt ttgtgtataa ccatcggtaa gttcaatcgg    720

aggaaagact gcgtgaccat ttgacatgct tgggtgatta tctgtgtccg ttgttgcgag    780

cgcggcatcg cctggtatca gcgcagagat gtaagtcaag gcaataggtg ttggagagcg    840

attgaggcat tgcaatatat cgaatgtact gcgaacattc gcagcctcta gagtgtcata    900
```

```
atcgtagccc cagtggatga ccgctccgca gtgaatgatc gcgtcaactg caccaatcga    960
agaattcaga ctgctttcgg tgccagaaag tgtttcccag tgttcatcag ccagacctag   1020
atgcggctgg gagagatcgc caggccaaac ttgaatgagg cgtcggtagt cgttccgcca   1080
ccatcgagcg agtcgtgctg cctgaataat gcgcgctagc ccctttcgtg gacaaggcgc   1140
ccgtgccaac acgtagacaa tgctaacgtc gttgtcgacc aggagctggt gaagaatatg   1200
tgtccccaag aaccctgtag ccccagtgag gaaaagacgt ttccctgatg gccgagaatg   1260
tatcgtccgt cgagaagatt ggcagacagg taggtcgttg atttgacgta tcatacattg   1320
caccctctcc caccagccag gggataacag agctttctct gggactgagt tgggtgtgcg   1380
atcgatcatc tctgccacca ttctgacggt caaagtactg tcaaagagat tcgtcatgga   1440
gatggagcaa tcgtagtgcc gggagatgaa ctgggacaag gctatgatat caattgagtc   1500
cagaccgacg cgagacaagc caacatttcg gccaacaatc tcagctgcca ttttttcatg   1560
accggttttg cgttggagaa gttgaccaat gtgcttggac aacgcccaag caactggctc   1620
atctgtgtga tccaagagcc ctgtgctcct gctctcattt cggctcagtc ctcctagatc   1680
atgtagatcg actgggctca gttccgtggc ctcatcaagg agagaacgac ggttgacttt   1740
gcccgagatc gtcaagggaa tgcttggcag ctgcaggtat agctcaggaa ccatcactgg   1800
agggaaactt tgtcgcaatt tttgttgcac ccgagatgct cgaagagcga agtcatgact   1860
atgggattgg aacgctatat tcgaaaatcc attcatgtcg gagatatccg gtactttggc   1920
ggccagcgat ggaatgtgga ccatggccac caagcagggg ggcatgtccg atttagtggg   1980
ttgtagaata gcagcaatcc cgctagcatc agtgccaaag aatcgcagga catggcgttc   2040
aatttccgct agatctatac gttgcccatg aagcttcgtg tgttgattcg tgcgacccag   2100
gaaagtgaag gttccatcca agttgcgacg gaccatatcg cccgtgcgat acatacgcga   2160
ggcttgccgg tccttgaact gtggtgccca cgaaggcggc tgcaggaagc actcggtcga   2220
ctttttggga ttgttcaggt acccacgacc gacgatgggg ccctgaagga tcagctcgcc   2280
aactgtattg actggcatac gcctggtcac atcttctttg tcaactaccc ataggactgc   2340
gcccatgcct tttccgatca gtcgagcgtc tgcgtcggtg gacgtgaccc gatgaacggc   2400
agcccctgta cagcattcgg tcggaccgta gccacagtag agatgtacac gactgcacca   2460
cagtttgatt tggcctggga gcatcgactc acctacggca acaacagtac ggaggcttgg   2520
cacatcgtcg ggagtcaaca accgcagcac agaaggcgtg atgcaaagcc agttgctccg   2580
atatttctca acgacgtggc ccaggtcctc tgcgatttcg gactccgaag gaatgcagac   2640
acaaccaccg ctagcgagca ctgtcaggat ttccactgca aacgagtcaa aagcgtaaga   2700
ggaaagctgc agaactcgag aactggaagt tatttccaat ttgttttgct gtgctataac   2760
ggccgaggcg taggaggcgt gctcgatcag cactgccttg ggctcaccag ttgaaccaga   2820
ggtgaaggca gcgtacaaga ggtcgcgagg actagggttc ggcatgggtg gcattgtcgt   2880
tgttgtccct gatggcacag cctgggcgtg ggagatcagc gcttcggtag acagcgaaat   2940
ccagggtccg tcgcatacgg tcgacgccaa attctgcatt tgtgctgatg tgatccccag   3000
ggttcctgaa atggcacggc atattttac gttgcgctcg tgaggttgat tggggtccag     3060
caggacgaag gcgacaccca gcttggccac cgcgagcatt gagattggga cccagtagga   3120
ccgctcaagg aaaatgggaa tgaattgaat gccttgaccg acaatgagcg gcagcaacaa   3180
ctgtgccagt tggcgcgcac tggattgtaa ttctgcataa gagaggtccc catcacaggc   3240
agaaaccgca catttcgatg gattgcgagt tacctgagcc tccacaagat ctacaattgt   3300
```

```
agaatccaag caggtcggta tgctcttgag acaggtagaa agcaattcag aatcccgatc   3360
cgatatgaga tccagttgcg caatagtcag attttgggtg tggcagtcat cgatttgctt   3420
gagtaagtgg ctcaattgag acagcatgag ctctgcctgc tcacggggca cgacggcttc   3480
gtcgaccagc atttcaaatt tccacgaggt ctctgatggt gccacttgaa ggatgagcgc   3540
atatccgggg aagctattga tggaaccaac ggatacttca actgggccaa aaatagggga   3600
gtcagggatc atgtcgtcgg cctgtatgac gagtaagttc tggaacttgc aggctgtggc   3660
gggaccgtgg cccatattcc gaatccgttg caagcccgtg tgctcgaaag ggatcatcct   3720
cttcatgttc tcttggactt gcgccaggga ctcttctact gtggactcgc gctggatggt   3780
tgtccgaaca gggagtgtgg cgatggtagg acccagcacg gacccaagga tgacgccgag   3840
tccacggcga ccatcgacga ccgtgccgta aacaatatct ggcgagtctg tgtacaagct   3900
gatcaagagc gcccaggcga gacgaacttt ggcggatgga ctactgattt gcttcgaaga   3960
ggttgcattg gcccgacaac cctcatatac gaccgaggtg cttgtgtgcg ggagatactg   4020
cggcgatgga agggcaggga agacattgct ctgcaattcg accatctcct ttagccagaa   4080
ttgacgggtt ctctccccgt cggctagttt ttgctggttc aaatggttaa tgaagccggt   4140
gaacgttgat ggaaataaag tttccgatgt atatgccttc tctgcttgct tgatacatgc   4200
gtgaagcgtg aaagcgtcgt agacagagtg gtgaaatgtc acagccagct tcgcaggctg   4260
ttctctggct tccgagtctt ggatgagggt cagccggact agcggcgaac ccaagcccat   4320
ggatcgagct cggtctttct cgtaaaactg ggactccgag ctcgccgtct gccactgaat   4380
cttccgttca gggcgcacca caatctgata cgtacgaccg tcatccgcct ggatgatacg   4440
agttcggaga atgctggtcg cttgcaccac attctgccag gcctgttgag ccaattccac   4500
gctgcagtcc gccgggagcg agaagagaac ccgatcaaca tatgcgtcgc cgctgtgaat   4560
ctccgtgact gccagaagac cctcttgtag tggagtcgtc ggatagatgt cctggatatc   4620
ctcctcctgg atcttgcatt cctggctggc tacacggcgc aaacaggtga tggcattcgc   4680
atcgttgaca ccgatcaatg agaatggcgg ggggccatct gccaacgtca ctgcatcagt   4740
gggtctcgcc tcctttgcga cggttcggag gctgcattca atatctagta ggcgctcggt   4800
atgaaggagc aggttgtacg ccaagaggac cctggtgaga cggatcgcag tcgtcgaatc   4860
gccacccagt tgagggaaac tagccttcaa gtcaatcgaa gacgttgaga tcttacacac   4920
actcgcgata accttcacta gaacgtcttc attaggcgtc attggtaagg agtctgcttt   4980
tgccagacaa cgtgaccgat tccctcctaa ccagtccatc aactgcgaag aggaaaattg   5040
ctggaagcac tgacaaaggc ggcgacggtc caccttgtcg gtagccgttc gcggcaaaga   5100
cttcacgggt atgataaggg aaggcaccat gtattgaggc agatatgggc gcaaaaggga   5160
ctggtagtga tggctcagag cccacgatcc ggactcgagc gccgtcatgc tctctccagg   5220
ccgctgtgaa ctccagtcaa tttcgaatcc agtgcggtcg acgagaaact gcacgagcgt   5280
cattgcacct gcggcatcgt aaaacttgac cgcactgacg acggagtcga catgtggatc   5340
caattgtcgt agttggagtt cgacggcatc gacatcaacg cgttggcccc ggatcttgac   5400
gacagtatcc ctgcgaccga catagcgcag ggtgccgtcc gggttataat ggcacaaatc   5460
gcccgtccta aaaaagcgac attggacggg aatctctgtg aaacgctcgc gccagcgagg   5520
agcctcgatg aaaacctgtt gcgtgcgtgt agggtcgttg aggtagccat ctgcgaccac   5580
agcgccctcg atgatcatct cacccactgt tccaatgggt gccagggagt cactgtcatc   5640
```

```
gggcatcgta atccaagaga tgcagccggc cgccgtgcca aaggtcccag gaatccaccc   5700
gctcgtcggt gaaattgggc cagcaccagc gggtccaact tcggccggtc cccagaggtt   5760
gaaaatactc acacggctct cccaatgacg agccaggtcc acagggattg tctcgccacc   5820
aagagtaagg gtctctaggg tcgggaaatc gctaggttca aagttcctga gcgtggtcgg   5880
tgtgaaaaat gcccaggtca cacggtgctg ctggataaat tcgggcatac tgttcaagcg   5940
ttgagtctcg gacggaatgc aaaggcaggc cccgcgtgtc aaggcctgcc atgtttcaat   6000
gatgctcata tcaaaagcat acgacgagaa ttgtagcaca cgtgcttctg atgtaacttg   6060
gagcctgtcg cccacgtagt gacccgccgt ggctatcgct cgatgactga ggacgatacc   6120
cttgggcacg ccagtactgc ctgacgagaa gacgatgaaa gccacatcgt ccgaactagc   6180
gctgggaaaa gcagtggaca ctggctgttc cgccgtcgct gaacgagggg aactgtataa   6240
atcctccggg atgatgagga ccgggtactc gccgatttga cgaatgagtg gttcctgtgc   6300
tctggacaac aaaatgatcg caggattgga ctgatacaga atgcgtttca tgagatccat   6360
cgggtggctg atacagatgc atactgcagt ggcgcgaact ttggccacag cgagcatcgc   6420
aacggccatc catttggatt tttcaaataa caagggaaca accattccag gacggacatt   6480
ttgttcaagt agacgttgtg cagactgatt ggcaagctca tcaagttgac cgtatgtgag   6540
ctcgccgtcc catgccgata cagccaaccg tccagggcct gagtgaacct gaattgcgaa   6600
caggtcttga aagcacgcat cgatgatggc cggaggatca tggttccact cgatcagttg   6660
atgctcatct gccgtattta gcaaagagag atcgttgatg cttgcctgca ggcctctgga   6720
gtgactccca agttgcttgt aaatgtgtgc gaactgttca gcgatgcgtt gcgcggcatc   6780
tctgtccacc agattctcgt catggaccac ctcacaaaac caagagatgt cgggctcgct   6840
gggctggcag atgatgcgta agtgcaaacc ttccccgtcg tgaatcgggg gaaaggactc   6900
ttctgtcgca gaatgactgg atggtacgct ttgcatcaga agactggctg tccgctcccc   6960
gaaatccaaa acgacattgg ggttgtcatt ggccgcgtca ctttccgccg ggatatgctt   7020
gatctgctga agaaagtctg ccatttgacg ttctaacgat tgtatttcag aatctggtgc   7080
catgtccact atggcatccg cacacggctc acaaggactc ccgagttcac ttggcaggac   7140
gccatttaac aggacagttg ctgatccatg atacaagctg gccaggagtg cccagctgat   7200
cagacaatac tcctcagaca aagatgatcc caacgggagt cgtgtagttc gtccttgatg   7260
cgacgcacgt aggttggtcg aatcagacgt ggtcggggca tatactaatg gaaagggcac   7320
tgaaactcga atacagcctt gtttcgccat                                    7350
```

<210> SEQ ID NO 57
<211> LENGTH: 2449
<212> TYPE: PRT
<213> ORGANISM: Penicillium fellutanum ATCC20841

<400> SEQUENCE: 57

```
Met Ala Lys Gln Gly Cys Ile Arg Val Ser Val Pro Phe Pro Leu Val
1               5                   10                  15

Tyr Ala Pro Thr Thr Ser Asp Ser Thr Asn Leu Arg Ala Ser His Gln
            20                  25                  30

Gly Arg Thr Thr Arg Leu Pro Leu Gly Ser Ser Leu Ser Glu Glu Tyr
        35                  40                  45

Cys Leu Ile Ser Trp Ala Leu Leu Ala Ser Leu Tyr His Gly Ser Ala
    50                  55                  60

Thr Val Leu Leu Asn Gly Val Leu Pro Ser Glu Leu Gly Ser Pro Cys
```

```
65                  70                  75                  80

Glu Pro Cys Ala Asp Ala Ile Val Asp Met Ala Pro Asp Ser Glu Ile
                85                  90                  95

Gln Ser Leu Glu Arg Gln Met Ala Asp Phe Leu Gln Gln Ile Lys His
            100                 105                 110

Ile Pro Ala Glu Ser Asp Ala Ala Asn Asp Asn Pro Asn Val Val Leu
        115                 120                 125

Asp Phe Gly Glu Arg Thr Ala Ser Leu Leu Met Gln Ser Val Pro Ser
    130                 135                 140

Ser His Ser Ala Thr Glu Glu Ser Phe Pro Pro Ile His Asp Gly Glu
145                 150                 155                 160

Gly Leu His Leu Arg Ile Ile Cys Gln Pro Ser Glu Pro Asp Ile Ser
                165                 170                 175

Trp Phe Cys Glu Val Val His Asp Glu Asn Leu Val Asp Arg Asp Ala
            180                 185                 190

Ala Gln Arg Ile Ala Glu Gln Phe Ala His Ile Tyr Lys Gln Leu Gly
        195                 200                 205

Ser His Ser Arg Gly Leu Gln Ala Ser Ile Asn Asp Leu Ser Leu Leu
    210                 215                 220

Asn Thr Ala Asp Glu His Gln Leu Ile Glu Trp Asn His Asp Pro Pro
225                 230                 235                 240

Ala Ile Ile Asp Ala Cys Phe Gln Asp Leu Phe Ala Ile Gln Val His
                245                 250                 255

Ser Gly Pro Gly Arg Leu Ala Val Ser Ala Trp Asp Gly Glu Leu Thr
            260                 265                 270

Tyr Gly Gln Leu Asp Glu Leu Ala Asn Gln Ser Ala Gln Arg Leu Leu
        275                 280                 285

Glu Gln Asn Val Arg Pro Gly Met Val Val Pro Leu Leu Phe Glu Lys
    290                 295                 300

Ser Lys Trp Met Ala Val Ala Met Leu Ala Val Ala Lys Val Arg Ala
305                 310                 315                 320

Thr Ala Val Cys Ile Cys Ile Ser His Pro Met Asp Leu Met Lys Arg
                325                 330                 335

Ile Leu Tyr Gln Ser Asn Pro Ala Ile Ile Leu Leu Ser Arg Ala Gln
            340                 345                 350

Glu Pro Leu Ile Arg Gln Ile Gly Glu Tyr Pro Val Leu Ile Ile Pro
        355                 360                 365

Glu Asp Leu Tyr Ser Ser Pro Arg Ser Ala Thr Ala Glu Gln Pro Val
    370                 375                 380

Ser Thr Ala Phe Pro Ser Ala Ser Ser Asp Asp Val Ala Phe Ile Val
385                 390                 395                 400

Phe Ser Ser Gly Ser Thr Gly Val Pro Lys Gly Ile Val Leu Ser His
                405                 410                 415

Arg Ala Ile Ala Thr Ala Gly His Tyr Val Gly Asp Arg Leu Gln Val
            420                 425                 430

Thr Ser Glu Ala Arg Val Leu Gln Phe Ser Ser Tyr Ala Phe Asp Met
        435                 440                 445

Ser Ile Ile Glu Thr Trp Gln Ala Leu Thr Arg Gly Ala Cys Leu Cys
    450                 455                 460

Ile Pro Ser Glu Thr Gln Arg Leu Asn Ser Met Pro Glu Phe Ile Gln
465                 470                 475                 480

Gln His Arg Val Thr Trp Ala Phe Phe Thr Pro Thr Thr Leu Arg Asn
                485                 490                 495
```

```
Phe Glu Pro Ser Asp Phe Pro Thr Leu Glu Thr Leu Thr Leu Gly Gly
            500                 505                 510

Glu Thr Ile Pro Val Asp Leu Ala Arg His Trp Glu Ser Arg Val Ser
        515                 520                 525

Ile Phe Asn Leu Trp Gly Pro Ala Glu Val Gly Pro Ala Gly Ala Gly
    530                 535                 540

Pro Ile Ser Pro Thr Ser Gly Trp Ile Pro Gly Thr Phe Gly Thr Ala
545                 550                 555                 560

Ala Gly Cys Ile Ser Trp Ile Thr Met Pro Asp Asp Ser Asp Ser Leu
                565                 570                 575

Ala Pro Ile Gly Thr Val Gly Glu Met Ile Ile Glu Gly Ala Val Val
            580                 585                 590

Ala Asp Gly Tyr Leu Asn Asp Pro Thr Arg Thr Gln Gln Val Phe Ile
        595                 600                 605

Glu Ala Pro Arg Trp Arg Glu Arg Phe Thr Glu Ile Pro Val Gln Cys
    610                 615                 620

Arg Phe Phe Arg Thr Gly Asp Leu Cys His Tyr Asn Pro Asp Gly Thr
625                 630                 635                 640

Leu Arg Tyr Val Gly Arg Arg Asp Thr Val Val Lys Ile Arg Gly Gln
                645                 650                 655

Arg Val Asp Val Asp Ala Val Glu Leu Gln Leu Arg Gln Leu Asp Pro
            660                 665                 670

His Val Asp Ser Val Val Ser Ala Val Lys Phe Tyr Asp Ala Ala Gly
        675                 680                 685

Ala Met Thr Leu Val Gln Phe Leu Val Asp Arg Thr Gly Phe Glu Ile
    690                 695                 700

Asp Trp Ser Ser Gln Arg Pro Gly Glu Ser Met Thr Ala Leu Glu Ser
705                 710                 715                 720

Gly Ser Trp Ala Leu Ser His His Tyr Gln Ser Leu Leu Arg Pro Tyr
                725                 730                 735

Leu Pro Gln Tyr Met Val Pro Ser Leu Ile Ile Pro Val Lys Ser Leu
            740                 745                 750

Pro Arg Thr Ala Thr Asp Lys Val Asp Arg Arg Arg Leu Cys Gln Cys
        755                 760                 765

Phe Gln Gln Phe Ser Ser Ser Gln Leu Met Asp Trp Leu Gly Gly Asn
    770                 775                 780

Arg Ser Arg Cys Leu Ala Lys Ala Asp Ser Leu Pro Met Thr Pro Asn
785                 790                 795                 800

Glu Asp Val Leu Val Lys Val Ile Ala Ser Val Cys Lys Ile Ser Thr
                805                 810                 815

Ser Ser Ile Asp Leu Lys Ala Ser Phe Pro Gln Leu Gly Gly Asp Ser
            820                 825                 830

Thr Thr Ala Ile Arg Leu Thr Arg Val Leu Leu Ala Tyr Asn Leu Leu
        835                 840                 845

Leu His Thr Glu Arg Leu Leu Asp Ile Glu Cys Ser Leu Arg Thr Val
    850                 855                 860

Ala Lys Glu Ala Arg Pro Thr Asp Ala Val Thr Leu Ala Asp Gly Pro
865                 870                 875                 880

Pro Pro Phe Ser Leu Ile Gly Val Asn Asp Ala Asn Ala Ile Thr Cys
                885                 890                 895

Leu Arg Arg Val Ala Ser Gln Glu Cys Lys Ile Gln Glu Glu Asp Ile
            900                 905                 910
```

```
Gln Asp Ile Tyr Pro Thr Thr Pro Leu Gln Glu Gly Leu Leu Ala Val
        915                 920                 925

Thr Glu Ile His Ser Gly Asp Ala Tyr Val Asp Arg Val Leu Phe Ser
    930                 935                 940

Leu Pro Ala Asp Cys Ser Val Glu Leu Ala Gln Gln Ala Trp Gln Asn
945                 950                 955                 960

Val Val Gln Ala Thr Ser Ile Leu Arg Thr Arg Ile Ile Gln Ala Asp
                965                 970                 975

Asp Gly Arg Thr Tyr Gln Ile Val Val Arg Pro Glu Arg Lys Ile Gln
            980                 985                 990

Trp Gln Thr Ala Ser Ser Glu Ser  Gln Phe Tyr Glu Lys  Asp Arg Ala
        995                 1000                1005

Arg Ser  Met Gly Leu Gly Ser  Pro Leu Val Arg Leu  Thr Leu Ile
    1010                1015                1020

Gln Asp  Ser Glu Ala Arg Glu  Gln Pro Ala Lys Leu  Ala Val Thr
    1025                1030                1035

Phe His  His Ser Val Tyr Asp  Ala Phe Thr Leu His  Ala Cys Ile
    1040                1045                1050

Lys Gln  Ala Glu Lys Ala Tyr  Thr Ser Glu Thr Leu  Phe Pro Ser
    1055                1060                1065

Thr Phe  Thr Gly Phe Ile Asn  His Leu Asn Gln Gln  Lys Leu Ala
    1070                1075                1080

Asp Gly  Glu Arg Thr Arg Gln  Phe Trp Leu Lys Glu  Met Val Glu
    1085                1090                1095

Leu Gln  Ser Asn Val Phe Pro  Ala Leu Pro Ser Pro  Gln Tyr Leu
    1100                1105                1110

Pro His  Thr Ser Thr Ser Val  Val Tyr Glu Gly Cys  Arg Ala Asn
    1115                1120                1125

Ala Thr  Ser Ser Lys Gln Ile  Ser Ser Pro Ser Ala  Lys Val Arg
    1130                1135                1140

Leu Ala  Trp Ala Leu Leu Ile  Ser Leu Tyr Thr Asp  Ser Pro Asp
    1145                1150                1155

Ile Val  Tyr Gly Thr Val Val  Asp Gly Arg Arg Gly  Leu Gly Val
    1160                1165                1170

Ile Leu  Gly Ser Val Leu Gly  Pro Thr Ile Ala Thr  Leu Pro Val
    1175                1180                1185

Arg Thr  Thr Ile Gln Arg Glu  Ser Thr Val Glu Glu  Ser Leu Ala
    1190                1195                1200

Gln Val  Gln Glu Asn Met Lys  Arg Met Ile Pro Phe  Glu His Thr
    1205                1210                1215

Gly Leu  Gln Arg Ile Arg Asn  Met Gly His Gly Pro  Ala Thr Ala
    1220                1225                1230

Cys Lys  Phe Gln Asn Leu Leu  Val Ile Gln Ala Asp  Asp Met Ile
    1235                1240                1245

Pro Asp  Ser Pro Ile Phe Gly  Pro Val Glu Val Ser  Val Gly Ser
    1250                1255                1260

Ile Asn  Ser Phe Pro Gly Tyr  Ala Leu Ile Leu Gln  Val Ala Pro
    1265                1270                1275

Ser Glu  Thr Ser Trp Lys Phe  Glu Met Leu Val Asp  Glu Ala Val
    1280                1285                1290

Val Pro  Arg Glu Gln Ala Glu  Leu Met Leu Ser Gln  Leu Ser His
    1295                1300                1305

Leu Leu  Lys Gln Ile Asp Asp  Cys His Thr Gln Asn  Leu Thr Ile
```

```
    1310                1315                1320

Ala Gln  Leu Asp Leu Ile Ser  Asp Arg Asp Ser Glu  Leu Leu Ser
    1325                1330                1335

Thr Cys  Leu Lys Ser Ile Pro  Thr Cys Leu Asp Ser  Thr Ile Val
    1340                1345                1350

Asp Leu  Val Glu Ala Gln Val  Thr Arg Asn Pro Ser  Lys Cys Ala
    1355                1360                1365

Val Ser  Ala Cys Asp Gly Asp  Leu Ser Tyr Ala Glu  Leu Gln Ser
    1370                1375                1380

Ser Ala  Arg Gln Leu Ala Gln  Leu Leu Leu Pro Leu  Ile Val Gly
    1385                1390                1395

Gln Gly  Ile Gln Phe Ile Pro  Ile Phe Leu Glu Arg  Ser Tyr Trp
    1400                1405                1410

Val Pro  Ile Ser Met Leu Ala  Val Ala Lys Leu Gly  Val Ala Phe
    1415                1420                1425

Val Leu  Leu Asp Pro Asn Gln  Pro His Glu Arg Asn  Val Lys Ile
    1430                1435                1440

Cys Arg  Ala Ile Ser Gly Thr  Leu Gly Ile Thr Ser  Ala Gln Met
    1445                1450                1455

Gln Asn  Leu Ala Ser Thr Val  Cys Asp Gly Pro Trp  Ile Ser Leu
    1460                1465                1470

Ser Thr  Glu Ala Leu Ile Ser  His Ala Gln Ala Val  Pro Ser Gly
    1475                1480                1485

Thr Thr  Thr Thr Met Pro Pro  Met Pro Asn Pro Ser  Pro Arg Asp
    1490                1495                1500

Leu Leu  Tyr Ala Ala Phe Thr  Ser Gly Ser Thr Gly  Glu Pro Lys
    1505                1510                1515

Ala Val  Leu Ile Glu His Ala  Ser Tyr Ala Ser Ala  Val Ile Ala
    1520                1525                1530

Gln Gln  Asn Lys Leu Glu Ile  Thr Ser Ser Ser Arg  Val Leu Gln
    1535                1540                1545

Leu Ser  Ser Tyr Ala Phe Asp  Ser Phe Ala Val Glu  Ile Leu Thr
    1550                1555                1560

Val Leu  Ala Ser Gly Gly Cys  Val Cys Ile Pro Ser  Glu Ser Glu
    1565                1570                1575

Ile Ala  Glu Asp Leu Gly His  Val Val Glu Lys Tyr  Arg Ser Asn
    1580                1585                1590

Trp Leu  Cys Ile Thr Pro Ser  Val Leu Arg Leu Leu  Thr Pro Asp
    1595                1600                1605

Asp Val  Pro Ser Leu Arg Thr  Val Val Ala Val Gly  Glu Ser Met
    1610                1615                1620

Leu Pro  Gly Gln Ile Lys Leu  Trp Cys Ser Arg Val  His Leu Tyr
    1625                1630                1635

Cys Gly  Tyr Gly Pro Thr Glu  Cys Cys Thr Gly Ala  Ala Val His
    1640                1645                1650

Arg Val  Thr Ser Thr Asp Ala  Asp Ala Arg Leu Ile  Gly Lys Gly
    1655                1660                1665

Met Gly  Ala Val Leu Trp Val  Val Asp Lys Glu Asp  Val Thr Arg
    1670                1675                1680

Arg Met  Pro Val Asn Thr Val  Gly Glu Leu Ile Leu  Gln Gly Pro
    1685                1690                1695

Ile Val  Gly Arg Gly Tyr Leu  Asn Asn Pro Lys Lys  Ser Thr Glu
    1700                1705                1710
```

```
Cys Phe Leu Gln Pro Pro Ser Trp Ala Pro Gln Phe Lys Asp Arg
    1715                1720                1725

Gln Ala Ser Arg Met Tyr Arg Thr Gly Asp Met Val Arg Arg Asn
    1730                1735                1740

Leu Asp Gly Thr Phe Thr Phe Leu Gly Arg Thr Asn Gln His Thr
    1745                1750                1755

Lys Leu His Gly Gln Arg Ile Asp Leu Ala Glu Ile Glu Arg His
    1760                1765                1770

Val Leu Arg Phe Phe Gly Thr Asp Ala Ser Gly Ile Ala Ala Ile
    1775                1780                1785

Leu Gln Pro Thr Lys Ser Asp Met Pro Pro Cys Leu Val Ala Met
    1790                1795                1800

Val His Ile Pro Ser Leu Ala Ala Lys Val Pro Asp Ile Ser Asp
    1805                1810                1815

Met Asn Gly Phe Ser Asn Ile Ala Phe Gln Ser His Ser His Asp
    1820                1825                1830

Phe Ala Leu Arg Ala Ser Arg Val Gln Gln Lys Leu Arg Gln Ser
    1835                1840                1845

Phe Pro Pro Val Met Val Pro Glu Leu Tyr Leu Gln Leu Pro Ser
    1850                1855                1860

Ile Pro Leu Thr Ile Ser Gly Lys Val Asn Arg Arg Ser Leu Leu
    1865                1870                1875

Asp Glu Ala Thr Glu Leu Ser Pro Val Asp Leu His Asp Leu Gly
    1880                1885                1890

Gly Leu Ser Arg Asn Glu Ser Arg Ser Thr Gly Leu Leu Asp His
    1895                1900                1905

Thr Asp Glu Pro Val Ala Trp Ala Leu Ser Lys His Ile Gly Gln
    1910                1915                1920

Leu Leu Gln Arg Lys Thr Gly His Glu Lys Met Ala Ala Glu Ile
    1925                1930                1935

Val Gly Arg Asn Val Gly Leu Ser Arg Val Gly Leu Asp Ser Ile
    1940                1945                1950

Asp Ile Ile Ala Leu Ser Gln Phe Ile Ser Arg His Tyr Asp Cys
    1955                1960                1965

Ser Ile Ser Met Thr Asn Leu Phe Asp Ser Thr Leu Thr Val Arg
    1970                1975                1980

Met Val Ala Glu Met Ile Asp Arg Thr Pro Asn Ser Val Pro Glu
    1985                1990                1995

Lys Ala Leu Leu Ser Pro Gly Trp Trp Glu Arg Val Gln Cys Met
    2000                2005                2010

Ile Arg Gln Ile Asn Asp Leu Pro Val Cys Gln Ser Ser Arg Arg
    2015                2020                2025

Thr Ile His Ser Arg Pro Ser Gly Lys Arg Leu Phe Leu Thr Gly
    2030                2035                2040

Ala Thr Gly Phe Leu Gly Thr His Ile Leu His Gln Leu Leu Val
    2045                2050                2055

Asp Asn Asp Val Ser Ile Val Tyr Val Leu Ala Arg Ala Pro Cys
    2060                2065                2070

Pro Arg Lys Gly Leu Ala Arg Ile Ile Gln Ala Ala Arg Leu Ala
    2075                2080                2085

Arg Trp Trp Arg Asn Asp Tyr Arg Arg Leu Ile Gln Val Trp Pro
    2090                2095                2100
```

```
Gly Asp  Leu Ser Gln Pro His  Leu Gly Leu Ala Asp  Glu His Trp
    2105                 2110                 2115

Glu Thr  Leu Ser Gly Thr Glu  Ser Ser Leu Asn Ser  Ser Ile Gly
    2120                 2125                 2130

Ala Val  Asp Ala Ile Ile His  Cys Gly Ala Val Ile  His Trp Gly
    2135                 2140                 2145

Tyr Asp  Tyr Asp Thr Leu Glu  Ala Ala Asn Val Arg  Ser Thr Phe
    2150                 2155                 2160

Asp Ile  Leu Gln Cys Leu Asn  Arg Ser Pro Thr Pro  Ile Ala Leu
    2165                 2170                 2175

Thr Tyr  Ile Ser Ala Leu Ile  Pro Gly Asp Ala Ala  Leu Ala Thr
    2180                 2185                 2190

Thr Asp  Thr Asp Asn His Pro  Ser Met Ser Asn Gly  His Ala Val
    2195                 2200                 2205

Phe Pro  Pro Ile Glu Leu Thr  Asp Gly Tyr Thr Gln  Thr Lys Phe
    2210                 2215                 2220

Ala Ser  Glu Gln Leu Ile Gly  Ala Phe Ser Ala Arg  His Lys Ala
    2225                 2230                 2235

His Ser  Leu Thr Ile Val Arg  Pro Gly Phe Met Ile  Gly Pro Val
    2240                 2245                 2250

Ser Asn  Ala Val Ala Asn Gly  Asp Asp Leu Leu Trp  Arg Val Val
    2255                 2260                 2265

Thr Thr  Ala Met Thr Thr Cys  Ser Tyr Asn Ser Asp  Glu Ser Asp
    2270                 2275                 2280

Asn Trp  Leu Phe Val Ala Ala  Val Asp Trp Val Ala  Ser Leu Ile
    2285                 2290                 2295

Ile His  Glu Thr Leu His Ala  Arg Pro Ser Ser His  Ser Val Asn
    2300                 2305                 2310

Asp Asn  Ala Asn Pro Leu Ala  Pro Ser Ala Lys Ala  Val Ser Ile
    2315                 2320                 2325

Gly Asp  Gly Leu Asn Met Ser  Asp Phe Trp Lys Ala  Ile Met Leu
    2330                 2335                 2340

Gly Leu  Gly Arg Asp Leu Ile  Pro Ser Ser Ser Gln  Arg Trp Met
    2345                 2350                 2355

Asp Thr  Val Glu Gln Gln Val  Asn Glu Val Gly Thr  Ser His Pro
    2360                 2365                 2370

Leu Trp  Pro Leu Met Gly Phe  Leu Arg Ala Ser Gly  Gly Cys Leu
    2375                 2380                 2385

Gly Val  Ala Pro Thr Asp Pro  Leu Pro Val Pro Ile  Tyr Gln Pro
    2390                 2395                 2400

Pro Ser  Leu Thr Asn Met Ile  Arg Gln Ala Val Val  Arg Asn Ala
    2405                 2410                 2415

Glu Tyr  Leu Ala Ser Leu Glu  Asp Leu Ala Ala Ser  Thr Met Leu
    2420                 2425                 2430

Phe Lys  Arg Arg Asn Lys Val  Ala Leu Gly Asn Gly  Leu Ile Asn
    2435                 2440                 2445

Ser
```

<210> SEQ ID NO 58
<211> LENGTH: 1167
<212> TYPE: DNA
<213> ORGANISM: Penicillium fellutanum ATCC20841

<400> SEQUENCE: 58

```
atgtctaaaa ccactgaggt gaaggtagtg gaagtccaac tggaggaccc gttgcccggt      60
attgtcgacg cctcccggtt tatttccggc tctcccactg agcagcgggc tttcgctgtc     120
gaactggtag attccgttcg ccgctgcggt ttcgtgaagg tcatcaacca tggtctgtcc     180
gacgaactca tcgacgagct ctttgcgtgg gtaagtgaca ctcagctgcc tgtccaagag     240
agaattacat tgccggattg tcgcagtgcc aaagctcaca tgttgtccag aacgagcgct     300
tttttgcaat cgaccccgag caaaagctgg ccgtcgtcaa ccccccggga ccatcgccgc     360
agcgagggtg gagttgtgtc ggcgccgaga aagcctcgcg cctgttcagc agaggccaga     420
cctctcttga tctgaccgat gcgcgtgtat gtgcagcgac cacaagctag ttagaatctt     480
catttttgct aatagagaaa ccaggagcat tttgacgccg gttctcccag tgacaccaaa     540
tggccctcgc gttggcctga tgaggcggtg atcccaggct tcaaggcctt tctggaagac     600
ttctatgtcc gatctcatca agctgcgctg ctcatactgg aagctcttga gatggggctg     660
aacctgcccg cgggagtatt gaaatctcgt tgcggtggat gtgcgagtga acttcgcctg     720
aacaactacc ctgagatcga tatcgaggag ctgcgccgtg gcaagatcag tcgcatccat     780
ccgcatgctg atctgggtgt cattacgtgc ctcttccaag atggacttgg aggtctggag     840
ctcgaacatc gatctcatgc cggctcgttc ttgcctgtgc cgcccggcgc tcgttcggaa     900
atggtggtca acataagcga aacttttcag ctgtggacaa acaatgtcat taccgccgga     960
atccatcagg tcaccgttcc gccggagatg aaaacccgca ccgaaggccg tatctctgct    1020
cggcgttctt gcgcattctt tctcaaggcg aatggtgatg cttctgtcgc gccactgcct    1080
caattcgtaa cgcaagagcg accagctgcc tactcagaga tgaccgcatt ggactatcat    1140
cagaagcgtt tagccacggc gtattag                                        1167
```

<210> SEQ ID NO 59
<211> LENGTH: 353
<212> TYPE: PRT
<213> ORGANISM: Penicillium fellutanum ATCC20841

<400> SEQUENCE: 59

```
Met Ser Lys Thr Thr Glu Val Lys Val Val Glu Val Gln Leu Glu Asp
1               5                   10                  15

Pro Leu Pro Gly Ile Val Asp Ala Ser Arg Phe Ile Ser Gly Ser Pro
            20                  25                  30

Thr Glu Gln Arg Ala Phe Ala Val Glu Leu Val Asp Ser Val Arg Arg
        35                  40                  45

Cys Gly Phe Val Lys Val Ile Asn His Gly Leu Ser Asp Glu Leu Ile
    50                  55                  60

Asp Glu Leu Phe Ala Trp Cys Gln Ser Ser His Val Val Gln Asn Glu
65                  70                  75                  80

Arg Phe Phe Ala Ile Asp Pro Glu Gln Lys Leu Ala Val Val Asn Pro
                85                  90                  95

Pro Gly Pro Ser Pro Gln Arg Gly Trp Ser Cys Val Gly Ala Glu Lys
            100                 105                 110

Ala Ser Arg Leu Phe Ser Arg Gly Gln Thr Ser Leu Asp Leu Thr Asp
        115                 120                 125

Ala Arg Arg Asn Gln Glu His Phe Asp Ala Gly Ser Pro Ser Asp Thr
    130                 135                 140

Lys Trp Pro Ser Arg Trp Pro Asp Glu Ala Val Ile Pro Gly Phe Lys
145                 150                 155                 160

Ala Phe Leu Glu Asp Phe Tyr Val Arg Ser His Gln Ala Ala Leu Leu
```

```
                165                 170                 175

Ile Leu Glu Ala Leu Glu Met Gly Leu Asn Leu Pro Ala Gly Val Leu
            180                 185                 190

Lys Ser Arg Cys Gly Gly Cys Ala Ser Glu Leu Arg Leu Asn Asn Tyr
        195                 200                 205

Pro Glu Ile Asp Ile Glu Glu Leu Arg Arg Gly Lys Ile Ser Arg Ile
    210                 215                 220

His Pro His Ala Asp Leu Gly Val Ile Thr Cys Leu Phe Gln Asp Gly
225                 230                 235                 240

Leu Gly Gly Leu Glu Leu Glu His Arg Ser His Ala Gly Ser Phe Leu
                245                 250                 255

Pro Val Pro Pro Gly Ala Arg Ser Glu Met Val Val Asn Ile Ser Glu
            260                 265                 270

Thr Phe Gln Leu Trp Thr Asn Asn Val Ile Thr Ala Gly Ile His Gln
        275                 280                 285

Val Thr Val Pro Pro Glu Met Lys Thr Arg Thr Glu Gly Arg Ile Ser
    290                 295                 300

Ala Arg Arg Ser Cys Ala Phe Phe Leu Lys Ala Asn Gly Asp Ala Ser
305                 310                 315                 320

Val Ala Pro Leu Pro Gln Phe Val Thr Gln Glu Arg Pro Ala Ala Tyr
                325                 330                 335

Ser Glu Met Thr Ala Leu Asp Tyr His Gln Lys Arg Leu Ala Thr Ala
            340                 345                 350

Tyr
```

<210> SEQ ID NO 60
<211> LENGTH: 1064
<212> TYPE: DNA
<213> ORGANISM: Penicillium fellutanum ATCC20841

<400> SEQUENCE: 60

```
tcaagctcgg gacgtcttgc tgtctgtcgt attgtcttca ccatgggaac cggcactttg      60

tgagagtgca gctgtggctt ctgcggtgat tgcagcgcaa gtccgaagtg tttgaaccaa     120

cttttccttt tccaaaaccc tcaatccagc ggcagtcgcg ccacccttag tggctacttg     180

cgcgaccaag tcagccggag aggttgactg ctggagaagg gcggccgttc cccgagccgc     240

ctgtgctgta attgctagtg ccgtctctaa tggcagttgt tgcgcattgt tggcgccatt     300

actatgttgt tctgcaacgc cctgggccag accctcgatc atctgagcaa agaaggccag     360

agacgatgcg cctaccgcag aagcgacatg catttggcat tctgggagcc actgcaccac     420

tcctaccgat gcgaaaagct cggtcactgc gcgccggctc tctgcgtcgt ttgtgtgatc     480

gtcgctggtg gatagaagtg tgatggattc gccgaccgcc actgcaacac tgcagacggc     540

acgcacgacg ggccccgtcc agaagtgcaa tgcttctacg atgagacctg gcgatacgcc     600

ccccatcagg ctgatcagga tccgacgatg gtcatgacgc atgccctgca aatcatgtac     660

tagctcaccg aggctggaat gtttgcaccc aagcaggacg atatctgctt gctcggcgac     720

attgcaattc tgatcttgtt ggaggatcca gaccggaggg accgcccgat ctctcagtaa     780

gggggagatt cgctcgcgga ctagttgcgc ggtccgagcc gatcggaccg taaccttcag     840

ctcccgaatc tttacccttc ctgggtggcc cgatgccgac cggagcaggc caaccagcaa     900

ggcttgcccc agttttcctg aatgtcatga tcagcaacgc atccgatgta agactcattg     960

ccatggttcc atgtcagata agctgaatga atgccgcacg gtgagacctt accgcatccc    1020
```

```
agaatcgcta cattcgggta ttcgacagca gacatgagcg ccat                   1064


<210> SEQ ID NO 61
<211> LENGTH: 322
<212> TYPE: PRT
<213> ORGANISM: Penicillium fellutanum ATCC20841

<400> SEQUENCE: 61

Met Ala Leu Met Ser Ala Val Glu Tyr Pro Asn Val Ala Ile Leu Gly
1               5                   10                  15

Cys Gly Lys Leu Gly Gln Ala Leu Leu Val Gly Leu Leu Arg Ser Ala
            20                  25                  30

Ser Gly His Pro Gly Arg Val Lys Ile Arg Glu Leu Lys Val Thr Val
        35                  40                  45

Arg Ser Ala Arg Thr Ala Gln Leu Val Arg Glu Arg Ile Ser Pro Leu
    50                  55                  60

Leu Arg Asp Arg Ala Val Pro Pro Val Trp Ile Leu Gln Gln Asp Gln
65                  70                  75                  80

Asn Cys Asn Val Ala Glu Gln Ala Asp Ile Val Leu Leu Gly Cys Lys
                85                  90                  95

His Ser Ser Leu Gly Glu Leu Val His Asp Leu Gln Gly Met Arg His
            100                 105                 110

Asp His Arg Arg Ile Leu Ile Ser Leu Met Gly Gly Val Ser Pro Gly
        115                 120                 125

Leu Ile Val Glu Ala Leu His Phe Trp Thr Gly Pro Val Val Arg Ala
    130                 135                 140

Val Cys Ser Val Ala Val Ala Val Gly Glu Ser Ile Thr Leu Leu Ser
145                 150                 155                 160

Thr Ser Asp Asp His Thr Asn Asp Ala Glu Ser Arg Arg Ala Val Thr
                165                 170                 175

Glu Leu Phe Ala Ser Val Gly Val Val Gln Trp Leu Pro Glu Cys Gln
            180                 185                 190

Met His Val Ala Ser Ala Val Gly Ala Ser Ser Leu Ala Phe Phe Ala
        195                 200                 205

Gln Met Ile Glu Gly Leu Ala Gln Gly Val Ala Glu Gln His Ser Asn
    210                 215                 220

Gly Ala Asn Asn Ala Gln Gln Leu Pro Leu Glu Thr Ala Leu Ala Ile
225                 230                 235                 240

Thr Ala Gln Ala Ala Arg Gly Thr Ala Ala Leu Leu Gln Gln Ser Thr
                245                 250                 255

Ser Pro Ala Asp Leu Val Ala Gln Val Ala Thr Lys Gly Gly Ala Thr
            260                 265                 270

Ala Ala Gly Leu Arg Val Leu Glu Lys Glu Lys Leu Val Gln Thr Leu
        275                 280                 285

Arg Thr Cys Ala Ala Ile Thr Ala Glu Ala Thr Ala Ala Leu Ser Gln
    290                 295                 300

Ser Ala Gly Ser His Gly Glu Asp Asn Thr Thr Asp Ser Lys Thr Ser
305                 310                 315                 320

Arg Ala


<210> SEQ ID NO 62
<211> LENGTH: 798
<212> TYPE: DNA
<213> ORGANISM: Penicillium fellutanum ATCC20841

<400> SEQUENCE: 62
```

```
atgacacccg ctccgacacc acgtactgat cagctccatg gctcccgagt acttgttatt     60

gggggaacct ctggaatcgg ttttgccgtg tgcgcagccg cacttggtca tggagcaatc    120

gttaccatcg tgggatcgaa tgcccaaaaa ctcaaggatt ccgtcgcccg gctgaaatcc    180

tcgttcccat ccacggaccc cgatgacatt gtcgcagtcc ggtgtgatct cagcaactcc    240

gacaccgtcg agcaggatat tgagaaggct ctccagctgg cggctggaaa ctccaagatc    300

aatcacattg tgatcaccgc agcggatatg accgctccac ctcccctgga ggatctcacc    360

gttgactctg tgcagcgccc ggggattatc cgactagtcg ccccactgat ggtagcaaag    420

caccttccaa aatacatgaa caaatgccct cagagctcgc tcaccctaac gagcggtgca    480

cactgtttga gaccagaccc tggctggacc gttatctcgg gatattgtgg tgcggttgaa    540

gctatgtcga gaggattggc catcgatttg aagccactgc gggtgaacgt tgtcgctcca    600

ggagcagttc tcacagaagc tgtaaaggat atcctcggcg atgcatatga tgctgcggtg    660

gaaatggcgg aggcaaaatc gacggtcgga caaactgggt ccccggaaag cgtagcccaa    720

gcatatattt atctgatgaa ggatcactat gcctcgggat ctgttgtctc gacaaacggt    780

ggcatgcttc ttgtctaa                                                  798
```

<210> SEQ ID NO 63
<211> LENGTH: 265
<212> TYPE: PRT
<213> ORGANISM: Penicillium fellutanum ATCC20841

<400> SEQUENCE: 63

```
Met Thr Pro Ala Pro Thr Pro Arg Thr Asp Gln Leu His Gly Ser Arg
1               5                   10                  15

Val Leu Val Ile Gly Gly Thr Ser Gly Ile Gly Phe Ala Val Cys Ala
            20                  25                  30

Ala Ala Leu Gly His Gly Ala Ile Val Thr Ile Val Gly Ser Asn Ala
        35                  40                  45

Gln Lys Leu Lys Asp Ser Val Ala Arg Leu Lys Ser Ser Phe Pro Ser
    50                  55                  60

Thr Asp Pro Asp Asp Ile Val Ala Val Arg Cys Asp Leu Ser Asn Ser
65                  70                  75                  80

Asp Thr Val Glu Gln Asp Ile Glu Lys Ala Leu Gln Leu Ala Ala Gly
                85                  90                  95

Asn Ser Lys Ile Asn His Ile Val Ile Thr Ala Ala Asp Met Thr Ala
            100                 105                 110

Pro Pro Pro Leu Glu Asp Leu Thr Val Asp Ser Val Gln Arg Pro Gly
        115                 120                 125

Ile Ile Arg Leu Val Ala Pro Leu Met Val Ala Lys His Leu Pro Lys
    130                 135                 140

Tyr Met Asn Lys Cys Pro Gln Ser Ser Leu Thr Leu Thr Ser Gly Ala
145                 150                 155                 160

His Cys Leu Arg Pro Asp Pro Gly Trp Thr Val Ile Ser Gly Tyr Cys
                165                 170                 175

Gly Ala Val Glu Ala Met Ser Arg Gly Leu Ala Ile Asp Leu Lys Pro
            180                 185                 190

Leu Arg Val Asn Val Val Ala Pro Gly Ala Val Leu Thr Glu Ala Val
        195                 200                 205

Lys Asp Ile Leu Gly Asp Ala Tyr Asp Ala Ala Val Glu Met Ala Glu
    210                 215                 220
```

```
Ala Lys Ser Thr Val Gly Gln Thr Gly Ser Pro Glu Ser Val Ala Gln
225                 230                 235                 240

Ala Tyr Ile Tyr Leu Met Lys Asp His Tyr Ala Ser Gly Ser Val Val
                245                 250                 255

Ser Thr Asn Gly Gly Met Leu Leu Val
            260                 265
```

<210> SEQ ID NO 64
<211> LENGTH: 1777
<212> TYPE: DNA
<213> ORGANISM: Penicillium fellutanum ATCC20841

<400> SEQUENCE: 64

```
atgcacaaca cgcaaagcga cacaaaatgt gaaaatgcgt cagatacccc ggaaagtccc     60

acaggagaag aagagagcgt cggacttgct cgttggaagt tagggctatt aatgttcgga    120

aatacgcttg cggtgttctg tgtcgcactg gtacgtaagt ttccatgaac taatatcgga    180

ttctaaagcg ttagcaggat aatacgatta tgtcaaatgc catccccaga gtcacgcaga    240

cctttgactc gctagaggat atcggatggt actcaagcat ctattttttc actaattgct    300

cggttgttct actctttgga aaactctata cgcattactc aatgaaatgg gttttcctgg    360

tggcacttct attattcgag gttggctcct tgatctgcgg tgtcgcgccg tcttccgtcg    420

ccctcattgt gggcagagcc attgctggac ttggtgcagg gggagtcctg ccaggcgcca    480

ttttgatcgt cagcgagagc gtaccacttc accaaagacc gctgtatacg gctgttttgg    540

ggggtatgtc aggcgtcgca gcagttgttg ggcctttgtt cgtcaatcac tctattgcgt    600

tctttcataa acgcaccgct aattatgtct tttcctagga tcggtggtgc tttcgctgaa    660

aatagtactt ggcgttggtg tttctatatt aatttgccac tgggcgccgt caccacggtt    720

cttattttgt gtttcttttt tgactcgcgg actggcacct ctgatgtatc catgagcagc    780

tggaaccgat ttaggggcct cgacatccct ggcctgctcc tatttctgcc gacggtcttt    840

tgcttactgc tggcacttca gtggggtgga gcgaaatacc cctggaacaa tgtgcgtgtc    900

atagttctat tcgtcatttt tatcctagcg ggaggctgtt ggatatttat ccaacattcc    960

atgaaagacc aagcatcggt tcctccgcgc ctgatacgca accgtaacgt ttggagctca   1020

gcggtgtaca tggggtgcat tgttggctca tttattatca ttctctacta cgtaagtcta   1080

tcactacgat gttcaaaaat attaactaat ggctcagttc cctatttggt tccaagccgt   1140

caagggcggt tccccaatac agtcaggcac catgatcttg ccgatcatca ttgggctcat   1200

tgtatgtatg tcattgggcg cggtatttgt cactgtcgtg ggatactatc atcccataat   1260

ggcaatcggc actatcattt caactatcgg cgctggcctc tgcagtaccc tcgaagtgga   1320

ctctagcgcg agcaaatgga tcggatacca agctatgtgt ggtatagggc taggatttgg   1380

gttccagtta ccattcatcg ccgtgcagac tgcgctacct agatcagaca ttcctgtcgc   1440

tacagccatt gtcacctttg cccagaacct gagcgaggct gttttagtgg ctttggcgca   1500

aacaatcttt caaaaccggc tatttgctca tgtcaagcaa ttatcaacat tagttgatcc   1560

gaacgctctc gttcatgccg gtgcggccaa tttggatcaa catttctcag ctgatgtgct   1620

accggagatt gtgcgtgcat acagtgctgc tgttaccgaa accttctatg cggcaacagg   1680

gatcgcagca ctttccttca ttgggctgat caggctgcaa tggttatcgg taaagaaaac   1740

taaaaccaac gggaatgcgg cccagacgca tctctaa                           1777
```

<210> SEQ ID NO 65

```
<211> LENGTH: 411
<212> TYPE: PRT
<213> ORGANISM: Penicillium fellutanum ATCC20841

<400> SEQUENCE: 65

Met His Asn Thr Gln Ser Asp Thr Lys Cys Glu Asn Ala Ser Asp Thr
1               5                   10                  15

Pro Glu Ser Pro Thr Gly Glu Glu Glu Ser Val Gly Leu Ala Arg Trp
            20                  25                  30

Lys Leu Gly Leu Leu Met Phe Gly Asn Thr Leu Ala Val Phe Cys Val
        35                  40                  45

Ala Leu Asp Asn Thr Ile Met Ser Asn Ala Ile Pro Arg Val Thr Gln
    50                  55                  60

Thr Phe Asp Ser Leu Glu Asp Ile Gly Trp Gly Ser Pro Ala Arg Arg
65                  70                  75                  80

His Phe Asp Arg Gln Arg Glu Arg Thr Thr Ser Pro Lys Thr Ala Val
                85                  90                  95

Tyr Gly Cys Phe Gly Gly Ile Gly Gly Ala Phe Ala Glu Asn Ser Thr
            100                 105                 110

Trp Arg Trp Cys Phe Tyr Ile Asn Leu Pro Leu Gly Ala Val Thr Thr
        115                 120                 125

Val Leu Ile Leu Cys Phe Phe Phe Asp Ser Arg Thr Gly Thr Ser Asp
    130                 135                 140

Val Ser Met Ser Ser Trp Asn Arg Phe Arg Gly Leu Asp Ile Pro Gly
145                 150                 155                 160

Leu Leu Leu Phe Leu Pro Thr Val Phe Cys Leu Leu Leu Ala Leu Gln
                165                 170                 175

Trp Gly Gly Ala Lys Tyr Pro Trp Asn Asn Val Arg Val Ile Val Leu
            180                 185                 190

Phe Val Ile Phe Ile Leu Ala Gly Gly Cys Trp Ile Phe Ile Gln His
        195                 200                 205

Ser Met Lys Asp Gln Ala Ser Val Pro Pro Arg Leu Ile Arg Asn Arg
    210                 215                 220

Asn Val Trp Ser Ser Ala Val Tyr Met Gly Cys Ile Val Gly Ser Phe
225                 230                 235                 240

Ile Ile Ile Leu Tyr Tyr Phe Pro Ile Trp Phe Gln Ala Val Lys Gly
                245                 250                 255

Gly Ser Pro Ile Gln Ser Gly Thr Met Ile Leu Pro Ile Ile Ile Gly
            260                 265                 270

Leu Ile Val Trp Leu Gly Phe Gly Phe Gln Leu Pro Phe Ile Ala Val
        275                 280                 285

Gln Thr Ala Leu Pro Arg Ser Asp Ile Pro Val Ala Thr Ala Ile Val
    290                 295                 300

Thr Phe Ala Gln Asn Leu Ser Glu Ala Val Leu Val Ala Leu Ala Gln
305                 310                 315                 320

Thr Ile Phe Gln Asn Arg Leu Phe Ala His Val Lys Gln Leu Ser Thr
                325                 330                 335

Leu Val Asp Pro Asn Ala Leu Val His Ala Gly Ala Ala Asn Leu Asp
            340                 345                 350

Gln His Phe Ser Ala Asp Val Leu Pro Glu Ile Val Arg Ala Tyr Ser
        355                 360                 365

Ala Ala Val Thr Glu Thr Phe Tyr Ala Ala Thr Gly Ile Ala Ala Leu
    370                 375                 380

Ser Phe Ile Gly Leu Ile Arg Leu Gln Trp Leu Ser Val Lys Lys Thr
```

```
385                 390                 395                 400

Lys Thr Asn Gly Asn Ala Ala Gln Thr His Leu
                405                 410


<210> SEQ ID NO 66
<211> LENGTH: 1284
<212> TYPE: DNA
<213> ORGANISM: Penicillium fellutanum ATCC20841

<400> SEQUENCE: 66

atgactatcc aagtgaagag agttgtgacg gtatttggag ggactggtat gaagcttttt     60

atactcgaga aaatctacca ggaattagct gaccgataca ggaaaccagg gcagcagtgt    120

ggcacgttct ttgctggcac acaaagccaa gatctttcac gttcgtgtaa tcacgagaga    180

ccctcaatca gacaaagcga aagctattgc gtcgctaggg gcggagttag ttcaggcaga    240

tggattcaac ctcggtgaaa tgaccaatgc ctttgctggc agttgggggg tatttatcaa    300

cacgaattcc gatgatgagg taaagtcaca atgggaagtc acatgcttag tagccagtaa    360

gctcactcac tcacttaatc tgtccgacaa caggctttga agtcattgga tggtcctagt    420

gactatgacc ttggcgtctc agtaatcgat tctgctaaga aagcaggcgt ccagcatgtg    480

gtctatagct ctggaccatc catcacaaac gctacaaaag gcagaatgca tctggaaggc    540

tttgagagta ggtagattct atcgccgcca ttgttacatt tgcttattaa caaattgaag    600

ccaaatacca cgttgagcaa tatgggcgta ggaaagggtt tacgagcttt actcccatcc    660

tatgcgcctc gtttatggag tgctttttct acgatccgtt tgtggatgcc ttcggtgggt    720

ttccttggat tcctgagcca gaaacaggcg aagtggtctt ccgcactccg gactacgggg    780

gtaaaggcga tatgccctgg gtcagttgtg aggaagacct cggggacatt gtgcatggta    840

tctttttgaa cccgtgcaaa tacgatcagg tattggttca ggcaacgagc caacagataa    900

cgatgtttga tgtagcagct tcatatacac aaggtacgcc gccactcctc ttctcttttt    960

ttcgatcctg tccattggcg gtgatgtctt tgatgtaact gatagttgct acttgaagcg   1020

accggaattc ctgcccgata cgaggaattg ccgtcctggt ctagcatcaa gctcaatggg   1080

acaaggtgcc gagccgaaac tcgccaaatg ttctggtaca tgaagcattg cggtggccgt   1140

tggtttgcag aacacgagag tgatatgtct actgcggtcg ctttgaagga atcagcaatg   1200

ttgtctcagg atcgggtggg aggtcttgtt acatttcagg cctggtttaa aaaggcgaaa   1260

gtcctgaaag accaaaatgt gtga                                          1284


<210> SEQ ID NO 67
<211> LENGTH: 338
<212> TYPE: PRT
<213> ORGANISM: Penicillium fellutanum ATCC20841

<400> SEQUENCE: 67

Met Thr Ile Gln Val Lys Arg Val Val Thr Val Phe Gly Gly Thr Gly
1               5                   10                  15

Asn Gln Gly Ser Ser Val Ala Arg Ser Leu Leu Ala His Lys Ala Lys
            20                  25                  30

Ile Phe His Val Arg Val Ile Thr Arg Asp Pro Gln Ser Asp Lys Ala
        35                  40                  45

Lys Ala Ile Ala Ser Leu Gly Ala Glu Leu Val Gln Ala Asp Gly Phe
    50                  55                  60

Asn Leu Gly Glu Met Thr Asn Ala Phe Ala Gly Ser Trp Gly Val Phe
65                  70                  75                  80
```

```
Ile Asn Thr Asn Ser Asp Asp Glu Ala Leu Lys Ser Leu Asp Gly Pro
                85                  90                  95

Ser Asp Tyr Asp Leu Gly Val Ser Val Ile Asp Ser Ala Lys Lys Ala
            100                 105                 110

Gly Val Gln His Val Val Tyr Ser Ser Gly Pro Ser Ile Thr Asn Ala
        115                 120                 125

Thr Lys Gly Arg Met His Leu Glu Gly Phe Glu Thr Lys Tyr His Val
    130                 135                 140

Glu Gln Tyr Gly Arg Arg Lys Gly Phe Thr Ser Phe Thr Pro Ile Leu
145                 150                 155                 160

Cys Ala Ser Phe Met Glu Cys Phe Phe Tyr Asp Pro Phe Val Asp Ala
                165                 170                 175

Phe Gly Gly Phe Pro Trp Ile Pro Glu Pro Glu Thr Gly Glu Val Val
            180                 185                 190

Phe Arg Thr Pro Asp Tyr Gly Gly Lys Gly Asp Met Pro Trp Val Ser
        195                 200                 205

Cys Glu Glu Asp Leu Gly Asp Ile Val His Gly Ile Phe Leu Asn Pro
    210                 215                 220

Cys Lys Tyr Asp Gln Val Leu Val Gln Ala Thr Ser Gln Gln Ile Thr
225                 230                 235                 240

Met Phe Asp Val Ala Ala Ser Tyr Thr Gln Ala Thr Gly Ile Pro Ala
                245                 250                 255

Arg Tyr Glu Glu Leu Pro Ser Trp Ser Ser Ile Lys Leu Asn Gly Thr
            260                 265                 270

Arg Cys Arg Ala Glu Thr Arg Gln Met Phe Trp Tyr Met Lys His Cys
        275                 280                 285

Gly Gly Arg Trp Phe Ala Glu His Glu Ser Asp Met Ser Thr Ala Val
    290                 295                 300

Ala Leu Lys Glu Ser Ala Met Leu Ser Gln Asp Arg Val Gly Gly Leu
305                 310                 315                 320

Val Thr Phe Gln Ala Trp Phe Lys Lys Ala Lys Val Leu Lys Asp Gln
                325                 330                 335

Asn Val
```

<210> SEQ ID NO 68
<211> LENGTH: 1969
<212> TYPE: DNA
<213> ORGANISM: Penicillium fellutanum ATCC20841

<400> SEQUENCE: 68

```
atggcgttcc agctagctgg ctttttcctg atcctcgccc tcggcttggg acattacttc      60

tccaacgacc aggagtcccg atgtcggtgt ggcccggatg atgattgctg gccctcgccg     120

acggcgtgga aacatctcaa tgagacaatc aatggctatc tgatgcagtt acagccagtt     180

ggagctgtat gccacgaaaa gtattattcc cacaactcct gcaatgagct cattcaacac     240

tatcgcaaca ccacatggcg cgttaacaat cccggtaaat tggctatacc ccgaagtccc     300

aaaagtgact tctgctcata ctaactgcct cttcatcgca gctgcattgc aggtagacac     360

ctgggaacat tcgcgaccac tgaagcagag ttgccacgcc caagacctgc cggagcacgg     420

tcaatgccac cagggtcgcg tggcacacta ctcggcctat gtcaattccg tatcggcggt     480

gcagcaggtg atccaatttg ccgcctccca tcgcctgcga ctggccattc gcaacaccgg     540

tcacgatctg gcaggacgtt catcagcccc caactcactg cagcttcata ctgctggtct     600
```

```
taagggcatt gattatgtgg aatcgttcac tcctcaggct ccagcgggtc aatcagtgcc    660

ctcagacggt cccgcggtga cagtaggggc aggggttctc acaggagagc tttactcggc    720

ggccgcagag gcaggatata ccgtggtagg aggaagctgc agtacggttg gaatcgcggg    780

tggctggatg caaggtggtg gctatgggat tctgacccca tcacgaggac tgggagtgga    840

caatgtgttg gaaattgggg ttgtaacggc gcaggtaagt ggccaaccgg tctatatggc    900

cgatctggtt agcttgcaag tttggctcac aagttgtttc tcctagggtg tctatgtcac    960

tgcaaaccag taccaaaacc aggatctctt ttgggccatt cgtggaggcg gcggaggcac   1020

atttggggcc gtcgtgcacg tcacattccg cacctaccca gattctcccg ccaccgtgtc   1080

caaactgaat gtggttagtc cccatgggct gaattctgcc ttctgggaag ccataacgga   1140

tttgctccgc gcaattcccg tcctggtgga tcgcggcgac gctgtccaag cattcgtgat   1200

gccggtcatg cctggcaaca ccacatttct caccatcgag tcctatctca tcaatgaaac   1260

ccatgtcagc ggtctcgatg ttatccggga gctaaaaaaa agcatggaag cgcgcggttt   1320

atcagtggag tcctccgagg aatccttcga ttggttgtct gcgtatcttg cgattcccaa   1380

aggtttggac caggccggca tggggatgat gaccgcgtca agacttgtgt cgcgagagct   1440

aatgacatca gctcagggac cttcgctgat tagtcagacc ctcgcccagc ttagttatga   1500

ccctggaaat gtgctgagcc tagagggaat ggtcgggggg cccgcggtgc gaggtagaga   1560

gacagcggac cgcgcaaccc atccatcgtg gcaatctgct gtcatgtccc taactttggg   1620

ccacagccta ccctcagctc cagattggac cgcctacagc cgtgcccagc gggaactggc   1680

aatgacgcag ctaccggctc ttcaggccct cgaacagggg acgatgggag ggtacctggg   1740

cataccattc ccgtacgaaa gccatccttc ccgtgtattc tgggggtccc attacgatag   1800

gcttttgact ctcaaagggc gttgggaccc cgatgattta ttcttaactc gattgggggt   1860

cggttcggag cggtgggatg aggaaggcat gtgtcgagtt ggtcgggcgc aggcttttct   1920

gtggtggtat tccagcattg tagatcgcgt caaatcatgg acagcgtaa               1969


<210> SEQ ID NO 69
<211> LENGTH: 602
<212> TYPE: PRT
<213> ORGANISM: Penicillium fellutanum ATCC20841

<400> SEQUENCE: 69

Met Ala Phe Gln Leu Ala Gly Phe Phe Leu Ile Leu Ala Leu Gly Leu
1               5                   10                  15

Gly His Tyr Phe Ser Asn Asp Gln Glu Ser Arg Cys Arg Gln Leu Glu
            20                  25                  30

Leu Tyr Ala Thr Lys Ser Ile Ile Pro Thr Thr Pro Ala Met Ser Ser
        35                  40                  45

Phe Asn Thr Ile Ala Thr Pro His Gly Ala Leu Thr Ile Pro Val Asn
    50                  55                  60

Trp Leu Tyr Pro Glu Val Pro Lys Val Thr Ser Ala His Thr Asn Cys
65                  70                  75                  80

Leu Phe Ile Ala Ala Ala Leu Gln Val Asp Thr Trp Glu His Ser Arg
                85                  90                  95

Pro Leu Lys Gln Ser Cys His Ala Gln Asp Leu Pro Glu His Gly Gln
            100                 105                 110

Cys His Gln Gly Arg Val Ala His Tyr Ser Ala Tyr Val Asn Ser Val
        115                 120                 125

Ser Ala Val Gln Gln Val Ile Gln Phe Ala Ala Ser His Arg Leu Arg
```

```
    130                 135                 140

Leu Ala Ile Arg Asn Thr Gly His Asp Leu Ala Gly Arg Ser Ser Ala
145                 150                 155                 160

Pro Asn Ser Leu Gln Leu His Thr Ala Gly Leu Lys Gly Ile Asp Tyr
                165                 170                 175

Val Glu Ser Phe Thr Pro Gln Ala Pro Ala Gly Gln Ser Val Pro Ser
            180                 185                 190

Asp Gly Pro Ala Val Thr Val Gly Ala Gly Val Leu Thr Gly Glu Leu
        195                 200                 205

Tyr Ser Ala Ala Ala Glu Ala Gly Tyr Thr Val Val Gly Gly Ser Cys
    210                 215                 220

Ser Thr Val Gly Ile Ala Gly Gly Trp Met Gln Gly Gly Gly Tyr Gly
225                 230                 235                 240

Ile Leu Thr Pro Ser Arg Gly Leu Gly Val Asp Asn Val Leu Glu Ile
                245                 250                 255

Gly Val Val Thr Ala Gln Gly Val Tyr Val Thr Ala Asn Gln Tyr Gln
            260                 265                 270

Asn Gln Asp Leu Phe Trp Ala Ile Arg Gly Gly Gly Gly Gly Thr Phe
        275                 280                 285

Gly Ala Val Val His Val Thr Phe Arg Thr Tyr Pro Asp Ser Pro Ala
    290                 295                 300

Thr Val Ser Lys Leu Asn Val Val Ser Pro His Gly Leu Asn Ser Ala
305                 310                 315                 320

Phe Trp Glu Ala Ile Thr Asp Leu Leu Arg Ala Ile Pro Val Leu Val
                325                 330                 335

Asp Arg Gly Asp Ala Val Gln Ala Phe Val Met Pro Val Met Pro Gly
            340                 345                 350

Asn Thr Thr Phe Leu Thr Ile Glu Ser Tyr Leu Ile Asn Glu Thr His
        355                 360                 365

Val Ser Gly Leu Asp Val Ile Arg Glu Leu Lys Lys Ser Met Glu Ala
    370                 375                 380

Arg Gly Leu Ser Val Glu Ser Ser Glu Glu Ser Phe Asp Trp Leu Ser
385                 390                 395                 400

Ala Tyr Leu Ala Ile Pro Lys Gly Leu Asp Gln Ala Gly Met Gly Met
                405                 410                 415

Met Thr Ala Ser Arg Leu Val Ser Arg Glu Leu Met Thr Ser Ala Gln
            420                 425                 430

Gly Pro Ser Leu Ile Ser Gln Thr Leu Ala Gln Leu Ser Tyr Asp Pro
        435                 440                 445

Gly Asn Val Leu Ser Leu Glu Gly Met Val Gly Gly Pro Ala Val Arg
    450                 455                 460

Gly Arg Glu Thr Ala Asp Arg Ala Thr His Pro Ser Trp Gln Ser Ala
465                 470                 475                 480

Val Met Ser Leu Thr Leu Gly His Ser Leu Pro Ser Ala Pro Asp Trp
                485                 490                 495

Thr Ala Tyr Ser Arg Ala Gln Arg Glu Leu Ala Met Thr Gln Leu Pro
            500                 505                 510

Ala Leu Gln Ala Leu Glu Gln Gly Thr Met Gly Gly Tyr Leu Gly Ile
        515                 520                 525

Pro Phe Pro Tyr Glu Ser His Pro Ser Arg Val Phe Trp Gly Ser His
    530                 535                 540

Tyr Asp Arg Leu Leu Thr Leu Lys Gly Arg Trp Asp Pro Asp Asp Leu
545                 550                 555                 560
```

```
Phe Leu Thr Arg Leu Gly Val Gly Ser Glu Arg Trp Asp Glu Glu Gly
                565                 570                 575

Met Cys Arg Val Gly Arg Ala Gln Ala Phe Leu Trp Trp Tyr Ser Ser
            580                 585                 590

Ile Val Asp Arg Val Lys Ser Trp Thr Ala
        595                 600


<210> SEQ ID NO 70
<211> LENGTH: 1389
<212> TYPE: DNA
<213> ORGANISM: Penicillium fellutanum ATCC20841

<400> SEQUENCE: 70

tcaattaatc tcctctaatt ccaaccatgg atactcatca gaggaatggt agtatacact     60

caggtaaacc cccgtctttt ccgtgtacgc aaaagaaatc cacgatgtca gacgagcagt    120

tttgcttagg tctctctcgg ggctgtcaaa gttagcaatt gaatcatttt tacaggggac    180

aggagaagta gagaagtcat acaaatagtg ccgtaccgtc gcctcgtaat tgtcaccata    240

cttagacaag ccgatacggg acaagaattg agctaggcca ccaatgacgt tttgatcact    300

ctcgccatgg attggaaaat agaacttcgt gagtgggaag gcctcgccaa ttttcatctc    360

gtaattccat accatcgggg ttgcggtggc atctttgccg tcgtcgaagc cgccattgaa    420

ttcacggtgc ccttcggata gcttagttaa ctcccacagc tcctttagat acactagacc    480

ctcttggaca acaggcgact tggcccgccc tccaagtgtc caaatctcct ctaccttgga    540

ccagaccacg ctgttgtgag agctatagag cttgaggcgt gattgggcag ggtcaacaca    600

gtcaaacgac caaaaggcaa actggctata tccattcgtt ccttccagat aagagtggac    660

catatcaaac gaggggatgg ggcccatttg cgccgcaaga ggctgaattg attcagaaat    720

gaagttccca aatcctttct cgttgagggt gcatttgata gcggggaatg tgtagccctt    780

gactgagata gctttttcct tcagatcaaa cccaaaagca ctctgggagg ttaactcgct    840

gccttcaatc ttcttctcct tcagcagccc tttctcgtgg ccattgacgg tatgagcgtc    900

caggaaatat cggaacagtg atgggtcgaa tgccggtata ttgagcactt caagctggtt    960

caagagatca acaactggga tttggttgta gggatcaatt tctgtcccag acgctgcagc   1020

aactggttca aatccgatgc gaaccaccgg gtcgatatct ccccgttgct ggtagttgac   1080

gctgaactcc agcggcagcc cacttcgggt aattgcgctg cggaattgat gcgggtgcgg   1140

gcccagaaat ggaatcagca cctgaatgta aaacgtgaga gcctccaagc gacgggcagg   1200

gttatagcct gctgaagcta ggattttgtc gagcagctgg ccggtcctct cccaccagac   1260

cttctggtgg ctatcaacga agacatggtc tcggctcagt acgtcgaaaa ttgtgggaat   1320

gggagaagtg gaatccccct tagccagcat gcctttggat acatggccct cggtcgcttc   1380

aatcgtcat                                                           1389


<210> SEQ ID NO 71
<211> LENGTH: 462
<212> TYPE: PRT
<213> ORGANISM: Penicillium fellutanum ATCC20841

<400> SEQUENCE: 71

Met Thr Ile Glu Ala Thr Glu Gly His Val Ser Lys Gly Met Leu Ala
1               5                   10                  15

Lys Gly Asp Ser Thr Ser Pro Ile Pro Thr Ile Phe Asp Val Leu Ser
            20                  25                  30
```

```
Arg Asp His Val Phe Val Asp Ser His Gln Lys Val Trp Trp Glu Arg
        35                  40                  45

Thr Gly Gln Leu Leu Asp Lys Ile Leu Ala Ser Ala Gly Tyr Asn Pro
    50                  55                  60

Ala Arg Arg Leu Glu Ala Leu Thr Phe Tyr Ile Gln Val Leu Ile Pro
65                  70                  75                  80

Phe Leu Gly Pro His Pro His Gln Phe Arg Ser Ala Ile Thr Arg Ser
                85                  90                  95

Gly Leu Pro Leu Glu Phe Ser Val Asn Tyr Gln Gln Arg Gly Asp Ile
            100                 105                 110

Asp Pro Val Val Arg Ile Gly Phe Glu Pro Val Ala Ala Ala Ser Gly
        115                 120                 125

Thr Glu Ile Asp Pro Tyr Asn Gln Ile Pro Val Val Asp Leu Leu Asn
    130                 135                 140

Gln Leu Glu Val Leu Asn Ile Pro Ala Phe Asp Pro Ser Leu Phe Arg
145                 150                 155                 160

Tyr Phe Leu Asp Ala His Thr Val Asn Gly His Glu Lys Gly Leu Leu
                165                 170                 175

Lys Glu Lys Lys Ile Glu Gly Ser Glu Leu Thr Ser Gln Ser Ala Phe
            180                 185                 190

Gly Phe Asp Leu Lys Glu Lys Ala Ile Ser Val Lys Gly Tyr Thr Phe
        195                 200                 205

Pro Ala Ile Lys Cys Thr Leu Asn Glu Lys Gly Phe Gly Asn Phe Ile
    210                 215                 220

Ser Glu Ser Ile Gln Pro Leu Ala Ala Gln Met Gly Pro Ile Pro Ser
225                 230                 235                 240

Phe Asp Met Val His Ser Tyr Leu Glu Gly Thr Asn Gly Tyr Ser Gln
                245                 250                 255

Phe Ala Phe Trp Ser Phe Asp Cys Val Asp Pro Ala Gln Ser Arg Leu
            260                 265                 270

Lys Leu Tyr Ser Ser His Asn Ser Val Val Trp Ser Lys Val Glu Glu
        275                 280                 285

Ile Trp Thr Leu Gly Gly Arg Ala Lys Ser Pro Val Val Gln Glu Gly
    290                 295                 300

Leu Val Tyr Leu Lys Glu Leu Trp Glu Leu Thr Lys Leu Ser Glu Gly
305                 310                 315                 320

His Arg Glu Phe Asn Gly Gly Phe Asp Asp Gly Lys Asp Ala Thr Ala
                325                 330                 335

Thr Pro Met Val Trp Asn Tyr Glu Met Lys Ile Gly Glu Ala Phe Pro
            340                 345                 350

Leu Thr Lys Phe Tyr Phe Pro Ile His Gly Glu Ser Asp Gln Asn Val
        355                 360                 365

Ile Gly Gly Leu Ala Gln Phe Leu Ser Arg Ile Gly Leu Ser Lys Tyr
    370                 375                 380

Gly Asp Asn Tyr Glu Ala Thr Val Arg His Tyr Leu Tyr Asp Phe Ser
385                 390                 395                 400

Thr Ser Pro Val Pro Cys Lys Asn Asp Ser Ile Ala Asn Phe Asp Ser
                405                 410                 415

Pro Glu Arg Asp Leu Ser Lys Thr Ala Arg Leu Thr Ser Trp Ile Ser
            420                 425                 430

Phe Ala Tyr Thr Glu Lys Thr Gly Val Tyr Leu Ser Val Tyr Tyr His
        435                 440                 445
```

```
Ser Ser Asp Glu Tyr Pro Trp Leu Glu Leu Glu Glu Ile Asn
    450                 455                 460
```

<210> SEQ ID NO 72
<211> LENGTH: 1272
<212> TYPE: DNA
<213> ORGANISM: Penicillium fellutanum ATCC20841

<400> SEQUENCE: 72

```
atgaccgtct caactgaatc aaatttccca catggggcga gcactcagaa acctcagagc      60
gcggaaccag agatatactc ctccctaaca aaatctttgg acttcagcaa cgatgcagaa     120
gagaaatggt ggacgcgaac agctcctctc ctttccagaa tcctcgattc agccggctac     180
acgcttcccc agcaatgcca gttcctcacc ctcttcaaca cgcttatgat cccgaacttt     240
gggccccatc ctcacatatg gcactcctct attacgcact ccgggcttcc cgtggaattt     300
agcgtcaatt accaacccgg aaagcaaccg accgtgcgca ttggttttga accggcttcg     360
tccatatcgg gcactgcgcg ggatccatac aatatggtca ccgtgttaaa cgtcctgaac     420
aaaatgtcca ggctgaactt caagggcttc gacccatctc tgttccacac tttgattagt     480
tcactcgccc tctcgaagaa cgaaagtgac ctgctccaag gagcgaagct tgaaggctcc     540
aagttcaaga cacaggcggc ctttgggctg gatctgaagg gagatgctgt gacggtcaaa     600
acttatctct atcctgcatt gaaatgcaag gtgtctggac ttgcatttag cgagcttctg     660
gaggccgcac ttgctaagca ccagaacgct cacgactttt ctcgggtgct cccattggtc     720
caaagttata tggaggaagg gcagtgctac aatcagtact cttttgttgg atttgactgt     780
gttgactctt caaagtcccg gttgaagatc tacggagctc tgttggatat atcttggaag     840
aaggtggagg aggtatggac gcttggtgct cggttggtaa atagtgagac caacaaggag     900
ggccttaggt atatgcgggc cctgtgggag tacctgacac ccggaaaggt gagatcaata     960
ccccgtaacc tcctttcaag aggcttacca agacaatagg aacgacgacc tgtgggaatc    1020
tggaactacg agctattacc cgggagtgaa gagccgatgc ctaagttcta tgtggacatg    1080
aatggcgaga acgattttca aaatgcgctg ggcataacca agttcttgca tcatatcgga    1140
ttgacgacaa cggctgaagg cttgatcagc aaaatccagg agtacttgta cggagtcccc    1200
cactaccctt tgtcgcaaac acatgtgctc tttgctaacc aaggtcccat gcagccccgg    1260
tgtgaacctt ga                                                        1272
```

<210> SEQ ID NO 73
<211> LENGTH: 406
<212> TYPE: PRT
<213> ORGANISM: Penicillium fellutanum ATCC20841

<400> SEQUENCE: 73

```
Met Thr Val Ser Thr Glu Ser Asn Phe Pro His Gly Ala Ser Thr Gln
1               5                   10                  15

Lys Pro Gln Ser Ala Glu Pro Glu Ile Tyr Ser Ser Leu Thr Lys Ser
            20                  25                  30

Leu Asp Phe Ser Asn Asp Ala Glu Glu Lys Trp Trp Thr Arg Thr Ala
        35                  40                  45

Pro Leu Leu Ser Arg Ile Leu Asp Ser Ala Gly Tyr Thr Leu Pro Gln
    50                  55                  60

Gln Cys Gln Phe Leu Thr Leu Phe Asn Thr Leu Met Ile Pro Asn Phe
65                  70                  75                  80

Gly Pro His Pro His Ile Trp His Ser Ser Ile Thr His Ser Gly Leu
```

```
                85                  90                  95

Pro Val Glu Phe Ser Val Asn Tyr Gln Pro Gly Lys Gln Pro Thr Val
            100                 105                 110

Arg Ile Gly Phe Glu Pro Ala Ser Ser Ile Ser Gly Thr Ala Arg Asp
        115                 120                 125

Pro Tyr Asn Met Val Thr Val Leu Asn Val Leu Asn Lys Met Ser Arg
    130                 135                 140

Leu Asn Phe Lys Gly Phe Asp Pro Ser Leu Phe His Thr Leu Ile Ser
145                 150                 155                 160

Ser Leu Ala Leu Ser Lys Asn Glu Ser Asp Leu Leu Gln Gly Ala Lys
                165                 170                 175

Leu Glu Gly Ser Lys Phe Lys Thr Gln Ala Ala Phe Gly Leu Asp Leu
            180                 185                 190

Lys Gly Asp Ala Val Thr Val Lys Thr Tyr Leu Tyr Pro Ala Leu Lys
        195                 200                 205

Cys Lys Val Ser Gly Leu Ala Phe Ser Glu Leu Leu Glu Ala Ala Leu
    210                 215                 220

Ala Lys His Gln Asn Ala His Asp Phe Ser Arg Val Leu Pro Leu Val
225                 230                 235                 240

Gln Ser Tyr Met Glu Glu Gly Gln Cys Tyr Asn Gln Tyr Ser Phe Val
                245                 250                 255

Gly Phe Asp Cys Val Asp Ser Ser Lys Ser Arg Leu Lys Ile Tyr Gly
            260                 265                 270

Ala Leu Leu Asp Ile Ser Trp Lys Lys Val Glu Glu Val Trp Thr Leu
        275                 280                 285

Gly Ala Arg Leu Val Asn Ser Glu Thr Asn Lys Glu Gly Leu Arg Tyr
    290                 295                 300

Met Arg Ala Leu Trp Glu Tyr Leu Thr Pro Gly Lys Glu Arg Arg Pro
305                 310                 315                 320

Val Gly Ile Trp Asn Tyr Glu Leu Leu Pro Gly Ser Glu Glu Pro Met
                325                 330                 335

Pro Lys Phe Tyr Val Asp Met Asn Gly Glu Asn Asp Phe Gln Asn Ala
            340                 345                 350

Leu Gly Ile Thr Lys Phe Leu His His Ile Gly Leu Thr Thr Thr Ala
        355                 360                 365

Glu Gly Leu Ile Ser Lys Ile Gln Glu Tyr Leu Tyr Gly Val Pro His
    370                 375                 380

Tyr Pro Leu Ser Gln Thr His Val Leu Phe Ala Asn Gln Gly Pro Met
385                 390                 395                 400

Gln Pro Arg Cys Glu Pro
                405
```

<210> SEQ ID NO 74
<211> LENGTH: 1492
<212> TYPE: DNA
<213> ORGANISM: Penicillium fellutanum ATCC20841

<400> SEQUENCE: 74

```
ctagggtgac ttgttctgca atggctcctt aacgtcaaca ttccgaatcc ccagttgtac      60

ccgtaacttg tcaggcaggt tcgttgcgtg atattcctct ccttcctgga ctgccctcac     120

caccatctca aactcctgct cagtataagc ctggctgtca tgaccataga tccaggtctc     180

aagtgggaga gaggcaatat tctgctcatt tggctcataa gcatcccagt cctgattccg     240

ccagccttcg ttcacgcgat ggcttatcag ctgtacagct gaggctcgag catagcgtat     300
```

```
ccgttcagcg acgtgaagag ccagggagac tcgttgtcgt ccggccagag acagactagt    360

agctaggaca tttgcgtctt caattccctg ggatgcacct tgccctgcgg caggggagag    420

tgggtgggcc gcgtccccta taagaatcaa tcgaccatgg ctggataccc aatggtctaa    480

gggcttgtgg ttcaataacg ggtagttgat gaacttttga ggctgggtat gtcggattac    540

ggaccagagg cgctgcccaa tgggccagac tttgatcaga tccagcattt cgttggggtc    600

ggcaggggac gtccagacgt ctaggagatt tcttgtatcc tacacgcttc gttagctcag    660

atcatttgta ctggatggaa ttcaacatac ctgatgaatg cagaaccacg aaaagacttt    720

ccctttatta caagactgca gggcgatctg agcaccagaa aggaagaaga catcaaaccg    780

atcgttttct tccactccct caaacaccca gctcgcttcc gggtcacctt taagtgtctc    840

cgtatctacc agtgcccgaa aggccgcgta tccagacgga cgaggctcaa caggttgcgg    900

catgatcgcc ttccgcattt tgctgtgcac cccgtcgctg cagataataa agtcacctcg    960

tactatctgt cgttcgccat ctcgggtaag ggcaacaaca ctggcgccct cctcgtcctc   1020

ggaaggctca caaacttcca caccgaggct tatctccacc ccgatcttga gcgcatgctc   1080

atacatcact cggataagct ctgaccgtgg gaggaggtag tttggctgct cgcacacctc   1140

cgagaggtcc tgtcggatta tcagacggcc ggatgagttg tgtatacgga tttccttgga   1200

tgagactatc cagggtcgga gggcttcgtg aacagcacca tcgccccatc gtttgatgat   1260

gcgcgtggcg ttgctttgaa gaccaataca gtctcctaca cgaagggcag tcgcactatt   1320

agcttctacc accaaagttg cggggcacag tcttaccgat ggacttcagt atattgcttt   1380

tctcaaaagc gtggacacta tgtcccttct cgcgacactc gatcgctgcg gcaagtccga   1440

cgatgcccag gccgacaatt attacttgaa cttcttcacc taaagagccc at           1492
```

```
<210> SEQ ID NO 75
<211> LENGTH: 459
<212> TYPE: PRT
<213> ORGANISM: Penicillium fellutanum ATCC20841

<400> SEQUENCE: 75

Met Gly Ser Leu Gly Glu Glu Val Gln Val Ile Ile Val Gly Leu Gly
1               5                   10                  15

Ile Val Gly Leu Ala Ala Ala Ile Glu Cys Arg Glu Lys Gly His Ser
            20                  25                  30

Val His Ala Phe Glu Lys Ser Asn Ile Leu Lys Ser Ile Gly Asp Cys
        35                  40                  45

Ile Gly Leu Gln Ser Asn Ala Thr Arg Ile Ile Lys Arg Trp Gly Asp
    50                  55                  60

Gly Ala Val His Glu Ala Leu Arg Pro Trp Ile Val Ser Ser Lys Glu
65                  70                  75                  80

Ile Arg Ile His Asn Ser Ser Gly Arg Leu Ile Ile Arg Gln Asp Leu
                85                  90                  95

Ser Glu Val Cys Glu Gln Pro Asn Tyr Leu Leu Pro Arg Ser Glu Leu
            100                 105                 110

Ile Arg Val Met Tyr Glu His Ala Leu Lys Ile Gly Val Glu Ile Ser
        115                 120                 125

Leu Gly Val Glu Val Cys Glu Pro Ser Glu Asp Glu Glu Gly Ala Ser
    130                 135                 140

Val Val Ala Leu Thr Arg Asp Gly Glu Arg Gln Ile Val Arg Gly Asp
145                 150                 155                 160
```

```
Phe Ile Ile Cys Ser Asp Gly Val His Ser Lys Met Arg Lys Ala Ile
                165                 170                 175

Met Pro Gln Pro Val Glu Pro Arg Pro Ser Gly Tyr Ala Ala Phe Arg
            180                 185                 190

Ala Leu Val Asp Thr Glu Thr Leu Lys Gly Asp Pro Glu Ala Ser Trp
        195                 200                 205

Val Phe Glu Gly Val Glu Glu Asn Asp Arg Phe Asp Val Phe Phe Leu
    210                 215                 220

Ser Gly Ala Gln Ile Ala Leu Gln Ser Cys Asn Lys Gly Lys Val Phe
225                 230                 235                 240

Ser Trp Phe Cys Ile His Gln Asp Thr Arg Asn Leu Leu Asp Val Trp
                245                 250                 255

Thr Ser Pro Ala Asp Pro Asn Glu Met Leu Asp Leu Ile Lys Val Trp
            260                 265                 270

Pro Ile Gly Gln Arg Leu Trp Ser Val Ile Arg His Thr Gln Pro Gln
        275                 280                 285

Lys Phe Ile Asn Tyr Pro Leu Leu Asn His Lys Pro Leu Asp His Trp
    290                 295                 300

Val Ser Ser His Gly Arg Leu Ile Leu Ile Gly Asp Ala Ala His Pro
305                 310                 315                 320

Leu Ser Pro Ala Ala Gly Gln Gly Ala Ser Gln Gly Ile Glu Asp Ala
                325                 330                 335

Asn Val Leu Ala Thr Ser Leu Ser Leu Ala Gly Arg Gln Arg Val Ser
            340                 345                 350

Leu Ala Leu His Val Ala Glu Arg Ile Arg Tyr Ala Arg Ala Ser Ala
        355                 360                 365

Val Gln Leu Ile Ser His Arg Val Asn Glu Gly Trp Arg Asn Gln Asp
    370                 375                 380

Trp Asp Ala Tyr Glu Pro Asn Glu Gln Asn Ile Ala Ser Leu Pro Leu
385                 390                 395                 400

Glu Thr Trp Ile Tyr Gly His Asp Ser Gln Ala Tyr Thr Glu Gln Glu
                405                 410                 415

Phe Glu Met Val Val Arg Ala Val Gln Glu Gly Glu Glu Tyr His Ala
            420                 425                 430

Thr Asn Leu Pro Asp Lys Leu Arg Val Gln Leu Gly Ile Arg Asn Val
        435                 440                 445

Asp Val Lys Glu Pro Leu Gln Asn Lys Ser Pro
    450                 455
```

<210> SEQ ID NO 76
<211> LENGTH: 1862
<212> TYPE: DNA
<213> ORGANISM: Penicillium fellutanum ATCC20841

<400> SEQUENCE: 76

```
ctagaaccca gccatttccc tctccgtaaa cgccaagtcc aacggggcca accccatcac      60

aaacccatcc gtcctctccc tccaatactt ctccggatct gcaccgggcg caagcacaat     120

ttcatagcgc cgaatcaact ccacaagcac atgtctcacc tgcataagcg ccaaactttt     180

gccgagacaa ttgtacgggc ccagtaaaaa cggcgcgaag gcctcgggat tcttcaccaa     240

ctcctttctt gttgtccagc gctcggggat gaacttttct ggctctgcaa agttacgctc     300

gtctaggaag agtgtgtaga aggggatctt gatgttggtg tttcctggga tgtaccgtcc     360

agcgatgtgg agaccccctg gggtgtttg gcgttggaag ccggagaggg cagggtagtg      420
```

```
gaggcggagg gtttcgttga tgacggcgtt gagcgtttgg actttagaaa gggtatgcga    480
gttgatttcg tctagtgtgt cgagctcttg tctgatttgg gtgaggtagt ctggggaggt    540
ggaggtgagg aagtagaggc agccaatgat tgtgacggcg accgttccac tggagaagag    600
cgtcagggtc tattgtctgg taggggatgg atgagaaagg attgtactaa cctgcctgcg    660
aagatgacga gggatgcatc agccaccaga tcaagtttcg actgcggcgt ctccatcccc    720
tgctccttaa aatcctccca cagccacgaa aagacatccc gttgcccgga tgtctgcatc    780
ttctgtctgt tctgaacctg ttcctcggaa aacccaataa gggccttcat attcgcattc    840
aagcctggcg tcgctttgat gaaggagatg agccaaacaa cgtggctgac gacaccggtg    900
actaggttgg acgagtcgtt gatctccata atgggatgtc ttttgttgtg tttcacgcat    960
tcgtattctt ggctgaatgc gactcggccg gtcaactacc agtttgatta gtttggtgac   1020
gtggctggtg tagtagaggc ggatgcatac atcaaatgta aatagattga tccagtaagt   1080
catatccata gacttcccct tgcgcctctc gacctgttcc aagagctcat tggtaccctt   1140
ctccagcgca ggcaggtact cgagaaccgc tatctaccat tagcgcggcc attcgaggga   1200
aaagtttatc gagatcatct accattcggt cgaaatgcaa gctcccaagg cttccggcgt   1260
cggctatgtt ccgccttgtc tctaatcgca aagagagaga tgaacgggtg gagcatacta   1320
taccatggcc ccttcgtaca ctccgaccgg ccggagtgga cagcttgcag ggcatcagga   1380
tggttcaccg aaagctccgt cggtcctgtg cgcacgaaat cgccgtactg ctgatgcagc   1440
ccacgcacgg tattgaaggc atccgggttc tgcgcgtata ggctggtcac ataccacatt   1500
gagaggcgag cgggaaaggg gccagggaag ctgttgagtc ggtggaagaa tgctcggtag   1560
gagagaatgc tgacggtggt tccggctatg aagccaaggg tgatttggcc taccaaccat   1620
agcgcagtgt agattgaagt tggagggccg gggacgaaga ggtagtagct gaataggcag   1680
ctttggagga taaacagacc gactgggatc ctggcagcag cgatatccca ttctccccgc   1740
ctgaatatga tgatatgtgc cgctattccg gccacgaagg cggtcgttag acgtgagaag   1800
ttctcgttcg aggcaagcat gggtagcact ttcaggatgt gcccgtcatg atgaggctcc   1860
at                                                                  1862
```

```
<210> SEQ ID NO 77
<211> LENGTH: 563
<212> TYPE: PRT
<213> ORGANISM: Penicillium fellutanum ATCC20841

<400> SEQUENCE: 77

Met Glu Pro His His Asp Gly His Ile Leu Lys Val Leu Pro Met Leu
1               5                   10                  15

Ala Ser Asn Glu Asn Phe Ser Arg Leu Thr Thr Ala Phe Val Ala Gly
            20                  25                  30

Ile Ala Ala His Ile Ile Ile Phe Arg Arg Gly Glu Trp Asp Ile Ala
        35                  40                  45

Ala Ala Arg Ile Pro Val Gly Leu Phe Ile Leu Gln Ser Cys Leu Phe
    50                  55                  60

Ser Tyr Tyr Leu Phe Val Pro Gly Pro Pro Thr Ser Ile Tyr Thr Ala
65                  70                  75                  80

Leu Trp Leu Val Gly Gln Ile Thr Leu Gly Phe Ile Ala Gly Thr Thr
                85                  90                  95

Val Ser Ile Leu Ser Tyr Arg Ala Phe Phe His Arg Leu Asn Ser Phe
            100                 105                 110
```

```
Pro Gly Pro Phe Pro Ala Arg Leu Ser Met Trp Tyr Val Thr Ser Leu
        115                 120                 125

Tyr Ala Gln Asn Pro Asp Ala Phe Asn Thr Val Arg Gly Leu His Gln
    130                 135                 140

Gln Tyr Gly Asp Phe Val Arg Thr Gly Pro Thr Glu Leu Ser Val Asn
145                 150                 155                 160

His Pro Asp Ala Leu Gln Ala Val His Ser Gly Arg Ser Glu Cys Thr
                165                 170                 175

Lys Gly Pro Trp Tyr Ser Met Leu His Pro Phe Ile Ser Leu Phe Ala
            180                 185                 190

Ile Arg Asp Lys Ala Glu His Ser Arg Arg Arg Lys Pro Trp Glu Leu
        195                 200                 205

Ala Phe Arg Pro Asn Ala Val Leu Glu Tyr Leu Pro Ala Leu Glu Lys
    210                 215                 220

Gly Thr Asn Glu Leu Leu Glu Gln Val Glu Arg Arg Lys Gly Lys Ser
225                 230                 235                 240

Met Asp Met Thr Tyr Trp Ile Asn Leu Phe Thr Phe Asp Leu Thr Gly
                245                 250                 255

Arg Val Ala Phe Ser Gln Glu Tyr Glu Cys Val Lys His Asn Lys Arg
            260                 265                 270

His Pro Ile Met Glu Ile Asn Asp Ser Ser Asn Leu Val Thr Gly Val
        275                 280                 285

Val Ser His Val Val Trp Leu Ile Ser Phe Ile Lys Ala Thr Pro Gly
    290                 295                 300

Leu Asn Ala Asn Met Lys Ala Leu Ile Gly Phe Ser Glu Glu Gln Val
305                 310                 315                 320

Gln Asn Arg Gln Lys Met Gln Thr Ser Gly Gln Arg Asp Val Phe Ser
                325                 330                 335

Trp Leu Trp Glu Asp Phe Lys Glu Gln Gly Met Glu Thr Pro Gln Ser
            340                 345                 350

Lys Leu Asp Leu Val Ala Asp Ala Ser Leu Val Ile Phe Ala Gly Ser
        355                 360                 365

Gly Thr Val Ala Val Thr Ile Ile Gly Cys Leu Tyr Phe Leu Thr Ser
    370                 375                 380

Thr Ser Pro Asp Tyr Leu Thr Gln Ile Arg Gln Glu Leu Asp Thr Leu
385                 390                 395                 400

Asp Glu Ile Asn Ser His Thr Leu Ser Lys Val Gln Thr Leu Asn Ala
                405                 410                 415

Val Ile Asn Glu Thr Leu Arg Leu His Tyr Pro Ala Leu Ser Gly Phe
            420                 425                 430

Gln Arg Gln Thr Pro Pro Gly Gly Leu His Ile Ala Gly Arg Tyr Ile
        435                 440                 445

Pro Gly Asn Thr Asn Ile Lys Ile Pro Phe Tyr Thr Leu Phe Leu Asp
    450                 455                 460

Glu Arg Asn Phe Ala Glu Pro Glu Lys Phe Ile Pro Glu Arg Trp Thr
465                 470                 475                 480

Thr Arg Lys Glu Leu Val Lys Asn Pro Glu Ala Phe Ala Pro Phe Leu
                485                 490                 495

Leu Gly Pro Tyr Asn Cys Leu Gly Lys Ser Leu Ala Leu Met Gln Val
            500                 505                 510

Arg His Val Leu Val Glu Leu Ile Arg Arg Tyr Glu Ile Val Leu Ala
        515                 520                 525

Pro Gly Ala Asp Pro Glu Lys Tyr Trp Arg Glu Arg Thr Asp Gly Phe
```

```
    530                 535                 540

Val Met Gly Leu Ala Pro Leu Asp Leu Ala Phe Thr Glu Arg Glu Met
545                 550                 555                 560

Ala Gly Phe


<210> SEQ ID NO 78
<211> LENGTH: 2282
<212> TYPE: DNA
<213> ORGANISM: Penicillium fellutanum ATCC20841

<400> SEQUENCE: 78

ctactcctcc ttaagcaaag taccaccggc tatggaatgc gcctccttct cccaccgatc     60

agacaatatc ctgacctgga catccttcct attccgtgca ctaatccgat ctacccactg    120

catgctgctc tcatccgtct caaacaacga catttcaaac cgtgaaaata cgtatgctgt    180

aacacaaaat agttctaggt atgcaaggct gcgatatcat tagtgctcgc gctgcatggc    240

ataaaattcg cctcgtggcc taggatatag gggtatacta acctgctccc aatgcatcgc    300

cgagggcccc ggctgaaccc gacatgccat ctctcaagat ccttgccctc ttcacccagc    360

caacgctctg gtttaaactt gtaggggtcg tggaagatgg tgtcgtttgt gataattgac    420

agatggctgg aggatacaat agtctgctga gggtaagtct tgataataca ataacgataa    480

gcaaataggg caggacatac gccttcagga agatagacag atcccaccgt gacgcctccg    540

gggggaacca gtcggggaag gttgccgggc accgctgttg atagtcgcat ggtctccttg    600

agcacggctc cctgtcgagt agtgttacgg tcagcagaga accgaaaaca aaaacggaaa    660

cctggggtcc ctataggaaa acgtaccaga tacggtagag cctgaatctg cttcgcattg    720

aagtcattcc gtatgaagtc gaccgaagca tccagctcct cgtgcagctt tttgaaaacc    780

tgcggattat tcaagatatg gaatgccgta gaagagagag tataggccgt tgactcggta    840

cctgctgtca ggaaattgaa agcatcctcg acaggctgag ccacgccgct cacagcggtc    900

tcagggccag cgcccagctc cgcgtagtag tcaaagagat tcttttgccc tacctgcacg    960

cccgactcac gtttgagttg ggcttttgcc tcccaggttt cacattgctc gtgccagtca   1020

gcaagtggaa gagcttagta caggggcagt actcactcgt ttgaaatcgt taaattccgg   1080

ggccagcttg tcgccaagac caaagggtag gtggaattgg attgacttga cccaaggaaa   1140

atagaccact gtcagcaaca ttagtaacct tcctggcatt agcctcagat atctcatacc   1200

gagccaggaa aacgcagtaa accgatccag tgccgcaaca aatggatgat atccattgcc   1260

gtcgccaatg aagtccggac tttcgccaaa aagtagctcg cataccatat ctgactatgc   1320

tcacgaagta taccgtcagc actaccatct gcagaaccac ccaatttggc aaggaaatac   1380

ataccgtgaa ggagcgatac agtgcctgta tattcaacgg atgataatcc ttccggtgca   1440

tatcaaagat gcgtgttgct ttctcgagct caagtttcaa acgaggtacc actccatcaa   1500

cggcacggct ggcgaagagt ggtcgcaggt ggttccggta catgcggtgg tgtttagggt   1560

ctaggattga ggccattgcc ccttctgctc cgagcgcttt gtagaactcg ggctccttat   1620

agtacttcgt tgtcatggaa aacatcctgt gagtacgtta gctgcgtgct tacatctgct   1680

caatgtattt gaggctcact cctggtagaa actcgggtca tcgacatgga cagcattggg   1740

gccgattcgg atgactgggg agtctataaa acgaacactc atttagaccc aagcgatact   1800

gacgaaacca atgttcaacg taccgtattt cttgtgaagt gaagaaaaag atagactgta   1860

ttggccatcc cgaataacat tgtggtaaaa gccgtaccac ttggtcaatg cagctagctt   1920
```

```
cgggcccggc actttgctga gaggctggaa gaatattctg ttgacggcaa tgaagaaccc   1980

ataagagata attgccagaa gaaatgatcc cagcactgta tttatgcttg gcggtttact   2040

ccccaactgt atgcaacccg tctggtggca gtccatcgct cgcagatgtg ataatttagc   2100

aattgatgga tgagactgag gtcgtcaagc ttccctctta cgagattatg ccctcttgtt   2160

ctacaaacgc ggacagtggg cggcttggcg tagcccgggg gccgtagaca aggggagtgg   2220

gcatccttgg cgttcgtgca ggggcctact tcacagtaca tgccagttgt cccttgcttc   2280

at                                                                  2282
```

<210> SEQ ID NO 79
<211> LENGTH: 536
<212> TYPE: PRT
<213> ORGANISM: Penicillium fellutanum ATCC20841

<400> SEQUENCE: 79

```
Met Lys Gln Gly Thr Thr Gly Met Tyr Cys Glu Val Gly Pro Cys Thr
1               5                   10                  15

Asn Ala Lys Asp Ala His Ser Pro Cys Leu Arg Pro Pro Gly Tyr Ala
            20                  25                  30

Lys Pro Pro Thr Val Arg Val Cys Arg Thr Arg Gly His Asn Leu Pro
        35                  40                  45

Leu Ser Lys Val Pro Gly Pro Lys Leu Ala Ala Leu Thr Lys Trp Tyr
    50                  55                  60

Gly Phe Tyr His Asn Val Ile Arg Asp Gly Gln Tyr Ser Leu Ser Phe
65                  70                  75                  80

Ser Ser Leu His Lys Lys Tyr Asp Ser Pro Val Ile Arg Ile Gly Pro
                85                  90                  95

Asn Ala Val His Val Asp Asp Pro Ser Phe Tyr Gln Glu Met Phe Ser
            100                 105                 110

Met Thr Thr Lys Tyr Tyr Lys Glu Pro Glu Phe Tyr Lys Ala Leu Gly
        115                 120                 125

Ala Glu Gly Ala Met Ala Ser Ile Leu Asp Pro Lys His His Arg Met
    130                 135                 140

Tyr Arg Asn His Leu Arg Pro Leu Phe Ala Ser Arg Ala Val Asp Gly
145                 150                 155                 160

Val Val Pro Arg Leu Lys Leu Glu Leu Glu Lys Ala Thr Arg Ile Phe
                165                 170                 175

Asp Met His Arg Lys Asp Tyr His Pro Leu Asn Ile Gln Ala Leu Tyr
            180                 185                 190

Arg Ser Phe Thr Ser Asp Met Val Cys Glu Leu Leu Phe Gly Glu Ser
        195                 200                 205

Pro Asp Phe Ile Gly Asp Gly Asn Gly Tyr His Pro Phe Val Ala Ala
    210                 215                 220

Leu Asp Arg Phe Thr Ala Phe Ser Trp Leu Val Val Tyr Phe Pro Trp
225                 230                 235                 240

Val Lys Ser Ile Gln Phe His Leu Pro Phe Gly Leu Gly Asp Lys Leu
                245                 250                 255

Ala Pro Glu Phe Asn Asp Phe Lys Arg Gln Cys Glu Thr Trp Glu Ala
            260                 265                 270

Lys Ala Gln Leu Lys Arg Glu Ser Gly Val Gln Val Gly Gln Lys Asn
        275                 280                 285

Leu Phe Asp Tyr Tyr Ala Glu Leu Gly Ala Gly Pro Glu Thr Ala Val
    290                 295                 300
```

```
Ser Gly Val Ala Gln Pro Val Glu Asp Ala Phe Asn Phe Leu Thr Ala
305                 310                 315                 320

Gly Thr Glu Ser Thr Ala Tyr Thr Leu Ser Ser Thr Ala Phe His Ile
                325                 330                 335

Leu Asn Asn Pro Gln Val Phe Lys Lys Leu His Glu Glu Leu Asp Ala
            340                 345                 350

Ser Val Asp Phe Ile Arg Asn Asp Phe Asn Ala Lys Gln Ile Gln Ala
        355                 360                 365

Leu Pro Tyr Leu Gly Ala Val Leu Lys Glu Thr Met Arg Leu Ser Thr
    370                 375                 380

Ala Val Pro Gly Asn Leu Pro Arg Leu Val Pro Pro Gly Gly Val Thr
385                 390                 395                 400

Val Gly Ser Val Tyr Leu Pro Glu Gly Thr Tyr Pro Gln Gln Thr Ile
                405                 410                 415

Val Ser Ser Ser His Leu Ser Ile Ile Thr Asn Asp Thr Ile Phe His
            420                 425                 430

Asp Pro Tyr Lys Phe Lys Pro Glu Arg Trp Leu Gly Glu Glu Gly Lys
        435                 440                 445

Asp Leu Glu Arg Trp His Val Gly Phe Ser Arg Gly Pro Arg Arg Cys
    450                 455                 460

Ile Gly Ser Ser Leu Ala Tyr Leu Glu Leu Phe Cys Val Thr Ala Tyr
465                 470                 475                 480

Val Phe Ser Arg Phe Glu Met Ser Leu Phe Glu Thr Asp Glu Ser Ser
                485                 490                 495

Met Gln Trp Val Asp Arg Ile Ser Ala Arg Asn Arg Lys Asp Val Gln
            500                 505                 510

Val Arg Ile Leu Ser Asp Arg Trp Glu Lys Glu Ala His Ser Ile Ala
        515                 520                 525

Gly Gly Thr Leu Leu Lys Glu Glu
    530                 535
```

<210> SEQ ID NO 80
<211> LENGTH: 879
<212> TYPE: DNA
<213> ORGANISM: Penicillium fellutanum ATCC20841

<400> SEQUENCE: 80

```
ctatgcctcc ggctttctag cgactatcaa aaacattggc gaaaaaattc ccaattcacc      60

accacggtac attccatcca gaatcgtcac cacaagatcg acaaccttct gcgaacccgc     120

agggaaaacc gtcatctgct ccagcttccc aacaacggcc tgcaagcccc ggttaataag     180

cggcatggcc ctcgccgcaa agaaaacact cagcagcgca aatgacaata gcccctgctt     240

ctccaaaaac gggtcagaca gctgcgtctc ccaggggatc tggtcgggtc gagcaccgag     300

gtcgtcaatc gccagtacct cgaagccgac agctttcatt gcggcaatgg cctcagccga     360

ggtgtgaatc ctagccaggc cgccgccgcg ctcgatgttg gtcttcacct cccggtgcat     420

ggggttgttg tcgtcgtact tgtctgttag aactgcttcg tacactccga atcttgcgcc     480

cggttttagc acgcggaaga tctcgctgta gacctcgaca aggtctgggg cgtaacaagt     540

cgactcaatg gcgtacgccc cgtcaaatgt atcatctgca aattctatct ttaggaagtt     600

ctgctcaaca aagttgacct ggtagctaag gccggcttcc tgagtcaact gacgcgcctg     660

ccggagttgc tgcgcgttga tgttcaagcc tgtgatgttt gctccggtga atcgcgcgat     720

tgaccgggct gggttcccga tgccgcatcc caggtcgata attcgttggc cctcttggat     780
```

```
attgacgcgg tgggcaaggt agtgttcatg gcggacgagg gactgggcca tgggttcgtt     840

cggggagagg cggcagaggt gtccgcacat acgaccgga                            879


<210> SEQ ID NO 81
<211> LENGTH: 292
<212> TYPE: PRT
<213> ORGANISM: Penicillium fellutanum ATCC20841

<400> SEQUENCE: 81

Ser Gly Arg Met Cys Gly His Leu Cys Arg Leu Ser Pro Asn Glu Pro
1               5                   10                  15

Met Ala Gln Ser Leu Val Arg His Glu His Tyr Leu Ala His Arg Val
            20                  25                  30

Asn Ile Gln Glu Gly Gln Arg Ile Ile Asp Leu Gly Cys Gly Ile Gly
        35                  40                  45

Asn Pro Ala Arg Ser Ile Ala Arg Phe Thr Gly Ala Asn Ile Thr Gly
    50                  55                  60

Leu Asn Ile Asn Ala Gln Gln Leu Arg Gln Ala Arg Gln Leu Thr Gln
65                  70                  75                  80

Glu Ala Gly Leu Ser Tyr Gln Val Asn Phe Val Glu Gln Asn Phe Leu
                85                  90                  95

Lys Ile Glu Phe Ala Asp Asp Thr Phe Asp Gly Ala Tyr Ala Ile Glu
            100                 105                 110

Ser Thr Cys Tyr Ala Pro Asp Leu Val Glu Val Tyr Ser Glu Ile Phe
        115                 120                 125

Arg Val Leu Lys Pro Gly Ala Arg Phe Gly Val Tyr Glu Ala Val Leu
    130                 135                 140

Thr Asp Lys Tyr Asp Asp Asn Asn Pro Met His Arg Glu Val Lys Thr
145                 150                 155                 160

Asn Ile Glu Arg Gly Gly Gly Leu Ala Arg Ile His Thr Ser Ala Glu
                165                 170                 175

Ala Ile Ala Ala Met Lys Ala Val Gly Phe Glu Val Leu Ala Ile Asp
            180                 185                 190

Asp Leu Gly Ala Arg Pro Asp Gln Ile Pro Trp Glu Thr Gln Leu Ser
        195                 200                 205

Asp Pro Phe Leu Glu Lys Gln Gly Leu Leu Ser Phe Ala Leu Leu Ser
    210                 215                 220

Val Phe Phe Ala Ala Arg Ala Met Pro Leu Ile Asn Arg Gly Leu Gln
225                 230                 235                 240

Ala Val Val Gly Lys Leu Glu Gln Met Thr Val Phe Pro Ala Gly Ser
                245                 250                 255

Gln Lys Val Val Asp Leu Val Val Thr Ile Leu Asp Gly Met Tyr Arg
            260                 265                 270

Gly Gly Glu Leu Gly Ile Phe Ser Pro Met Phe Leu Ile Val Ala Arg
        275                 280                 285

Lys Pro Glu Ala
    290


<210> SEQ ID NO 82
<211> LENGTH: 1837
<212> TYPE: DNA
<213> ORGANISM: Penicillium fellutanum ATCC20841

<400> SEQUENCE: 82

atgtcaaagt acttgttaat gtcgttcacc gaaggatcca tgtcaacatg gcattatcta      60
```

```
gccatgctca ccacaatatg gctagtctat caatatctga agcctgtacc aatagtcccc    120

gggcttccgg taatcaatcg ggcagagcgc tgggacttct tctcgatcaa aatgaagcga    180

cgtttcctaa ataacgccgc tgcactcatg aaagaaggct tcgaacaggt gagttgcatt    240

ggaacacctc tccccatcac ttgagatgca gtttctcaga gcttgaagtc accgaggggt    300

ttcacgatca tgtctgtaaa tggacctaaa ttggtcttgt caccggacta tgcagacgaa    360

ctcaagaatg atgcacgttt ttctttggag gatgctggac tgagggtaag cactctgaat    420

gagtttccga tgatggttca gattcaaatg ctcatgtctc ataataggac tatccacgca    480

gtattgactg cttgaagcct ataagtggtg gaaatttaca ggtactacgg ggatgcatcg    540

caaagattac aagaaacctc ggtatcgcct ggactgtgta aatcgattga tggacaatgt    600

gtgctaatat tgtgggattt atagcctctt tgacagcgcc actatcggat gaaaccagca    660

agtcttttca agatcattgg acagacgacc ccggttagta gcagttcact gggctaattg    720

aaggcgctct tattctcggt cgctggctaa tttgcgagat actagactgg catcctgtcc    780

cactaggtag cggcttgcaa aggatggtat tgcagatatc tggtcgcgcc tttctggggc    840

cggaggtttg cggcgacatc agatggattg aggcaactat gggatatctg gaaatggggg    900

tcagaactgc tttccttctc caggtctttc ctcgcttcct gtttccactc cagaggtggt    960

tccctttgtg tcgcaaagtc cggaagcata ttgacatggc tggaaccatt ctgcgtcccg   1020

taattgatag ccgtcgggca gacggaaggc cagcacagga tgcgatcagt tggtttgatg   1080

aagcagccgc tggggaaacg tacaaccctg tttattctca gctctccctc tccttcgcat   1140

caactcacac cactgccgat acaatgacca aagtcataat tcacctggcc gaaaacccag   1200

ctgtggttac ggaccttcga aaggaagttg tcgaggcaat tgccaaacat ggtgaattga   1260

cgaagaccgc tctatctcaa atgaatctat tggacagcac cttgaaggaa tcccagcgac   1320

tagagccctt agcatcaggt atctccaagc catctgtctc ctttcgaatt atgtgctctg   1380

gcatcttgct gacaatacct ttcttccatg agcagcaacg atgaaccggg tgacgaggga   1440

agaagtgacc ctctcgaacg gcctatggat tccacggaac atgtatgtat tggtgtcggg   1500

tcatcgcatg agagatccaa ccctatatcc agacccggaa aagttcgacg cataccgatt   1560

cgtcaagatg cgcgagattg agaagaagaa aagcgattgt gcatacacag cagccacggt   1620

ggaccacatg ggatttggct acgggaagca ctcttgccct ggccgattct ttgccgctca   1680

tgaggtaaag attatcctgt gccacttgat cttgaagtat gagttcaaat taccagaaga   1740

tcaagcacgt acgtatttgc ttgccggatt cttcacatcc gctgggcccg aaaacgagct   1800

tcttgttcgc aggcgcgtcg aggaaattgc actctga                            1837
```

<210> SEQ ID NO 83
<211> LENGTH: 436
<212> TYPE: PRT
<213> ORGANISM: Penicillium fellutanum ATCC20841

<400> SEQUENCE: 83

```
Met Ser Lys Tyr Leu Leu Met Ser Phe Thr Glu Gly Ser Met Ser Thr
1               5                   10                  15

Trp His Tyr Leu Ala Met Leu Thr Thr Ile Trp Leu Val Tyr Gln Tyr
            20                  25                  30

Leu Lys Pro Val Pro Ile Val Pro Gly Leu Pro Val Ile Asn Arg Ala
        35                  40                  45

Glu Arg Trp Asp Phe Phe Ser Ile Lys Met Lys Arg Arg Phe Leu Asn
    50                  55                  60
```

```
Asn Ala Ala Ala Leu Met Lys Glu Gly Phe Glu Gln Pro Lys Leu Val
65                  70                  75                  80

Leu Ser Pro Asp Tyr Ala Asp Glu Leu Lys Asn Asp Ala Arg Phe Ser
                85                  90                  95

Leu Glu Asp Ala Gly Leu Arg Arg His Tyr Arg Met Lys Pro Ala Ser
            100                 105                 110

Leu Phe Lys Ile Ile Gly Gln Thr Thr Pro Ile Ser Gly Arg Ala Phe
        115                 120                 125

Leu Gly Pro Glu Val Cys Gly Asp Ile Arg Trp Ile Glu Ala Thr Met
    130                 135                 140

Gly Tyr Leu Glu Met Gly Val Arg Thr Ala Phe Leu Leu Gln Val Phe
145                 150                 155                 160

Pro Arg Phe Leu Phe Pro Leu Gln Arg Trp Phe Pro Leu Cys Arg Lys
                165                 170                 175

Val Arg Lys His Ile Asp Met Ala Gly Thr Ile Leu Arg Pro Val Ile
            180                 185                 190

Asp Ser Arg Arg Ala Asp Gly Arg Pro Ala Gln Asp Ala Ile Ser Trp
        195                 200                 205

Phe Asp Glu Ala Ala Ala Gly Glu Thr Tyr Asn Pro Val Tyr Ser Gln
    210                 215                 220

Leu Ser Leu Ser Phe Ala Ser Thr His Thr Thr Ala Asp Thr Met Thr
225                 230                 235                 240

Lys Val Ile Ile His Leu Ala Glu Asn Pro Ala Val Val Thr Asp Leu
                245                 250                 255

Arg Lys Glu Val Val Glu Ala Ile Ala Lys His Gly Glu Leu Thr Lys
            260                 265                 270

Thr Ala Leu Ser Gln Met Asn Leu Leu Asp Ser Thr Leu Lys Glu Ser
        275                 280                 285

Gln Arg Leu Glu Pro Leu Ala Ser Ala Thr Met Asn Arg Val Thr Arg
    290                 295                 300

Glu Glu Val Thr Leu Ser Asn Gly Leu Trp Ile Pro Arg Asn Met Tyr
305                 310                 315                 320

Val Leu Val Ser Gly His Arg Met Arg Asp Pro Thr Leu Tyr Pro Asp
                325                 330                 335

Pro Glu Lys Phe Asp Ala Tyr Arg Phe Val Lys Met Arg Glu Ile Glu
            340                 345                 350

Lys Lys Lys Ser Asp Cys Ala Tyr Thr Ala Ala Thr Val Asp His Met
        355                 360                 365

Gly Phe Gly Tyr Gly Lys His Ser Cys Pro Gly Arg Phe Phe Ala Ala
    370                 375                 380

His Glu Val Lys Ile Ile Leu Cys His Leu Ile Leu Lys Tyr Glu Phe
385                 390                 395                 400

Lys Leu Pro Glu Asp Gln Ala Arg Thr Tyr Leu Leu Ala Gly Phe Phe
                405                 410                 415

Thr Ser Ala Gly Pro Glu Asn Glu Leu Leu Val Arg Arg Arg Val Glu
            420                 425                 430

Glu Ile Ala Leu
        435
```